United States Patent
El-Deiry et al.

(10) Patent No.: US 11,535,608 B2
(45) Date of Patent: *Dec. 27, 2022

(54) PRODIGIOSIN ANALOGS AND METHODS OF USE

(71) Applicant: Institute For Cancer Research, Philadelphia, PA (US)

(72) Inventors: Wafik S. El-Deiry, Philadelphia, PA (US); Xiaobing Tian, Philadelphia, PA (US)

(73) Assignee: Institute For Cancer Research, Philadelphia, PA (US)

(*) Notice: Subject to any disclaimer, the term of this patent is extended or adjusted under 35 U.S.C. 154(b) by 87 days.

This patent is subject to a terminal disclaimer.

(21) Appl. No.: 17/076,469

(22) Filed: Oct. 21, 2020

(65) Prior Publication Data

US 2021/0139465 A1 May 13, 2021
US 2022/0033382 A9 Feb. 3, 2022

Related U.S. Application Data

(63) Continuation of application No. 16/396,669, filed on Apr. 27, 2019, now Pat. No. 10,870,640, which is a continuation-in-part of application No. 16/091,701, filed as application No. PCT/US2017/026748 on Apr. 10, 2017, now Pat. No. 10,654,801.

(60) Provisional application No. 62/778,978, filed on Dec. 13, 2018, provisional application No. 62/319,882, filed on Apr. 8, 2016.

(51) Int. Cl.
*C07D 403/14* (2006.01)
*A61P 35/00* (2006.01)

(52) U.S. Cl.
CPC ............ *C07D 403/14* (2013.01); *A61P 35/00* (2018.01)

(58) Field of Classification Search
CPC ................................ C07D 403/14; A61P 35/00
See application file for complete search history.

(56) References Cited

U.S. PATENT DOCUMENTS

| | | |
|---|---|---|
| 6,638,968 B1 | 10/2003 | Kim et al. |
| 2005/0267073 A1 | 12/2005 | Dairi et al. |
| 2008/0076739 A1 | 3/2008 | Viallet et al. |
| 2008/0318902 A1 | 12/2008 | Attardo et al. |

OTHER PUBLICATIONS

Baldino et al., "Indoloprodigiosins from the C-10 bipyrrolic precursor: new antiproliferative prodigiosin analogs", Bioorg Med Chem Lett, 2006, 16(3), pp. 701-704.
Chaikuad et al., "A unique inhibitor binding site in ERK1/2 is associated with slow binding kinetics", Nat Chem Biol, 2014, 10(10), pp. 853-860.
Chen et al., "Regorafenib inhibits colorectal tumor growth through PUMA-mediated apoptosis", Clin Cancer Res, 2014, 20(13), pp. 3472-3484.
Fischer et al., "Census and evaluation of P53 target genes", Oncogene, 2017, 36(28), pp. 3943-3956.
Hong et al., "Prodigiosin rescues deficient p53 signaling and anti-tumor effects via up-regulating p73 and disrupting its interaction with mutant p53", Cancer Res, 2014, 74(4), pp. 1153-1165.
Montaner et al., "DNA interaction and dual topoisomerase I and II inhibition properties of the anti-tumor drug prodigiosin", Toxicol Sci, 2005, 85(2), pp. 870-879.
Prabhu et al., "Small-molecule Prodigiosin Restores p53 Tumor Suppressor Activity in Chemoresistant Colorectal Cancer Stem Cells via c-Jun-Mediated delta Np73 Inhibition and p73 Activation", Caner Res, 2016, 76(7), pp. 1989-1999.

*Primary Examiner* — Kamal A Saeed
(74) *Attorney, Agent, or Firm* — Armstrong Teasdale LLP

(57) ABSTRACT

Prodigiosin analogs which reactivate the p53 pathway are provided, as well as compositions of these compounds, and methods for reactivation of the p53 pathway using these compounds are provided. The prodigiosin analogs may be used to treat cancer in which p53 mutation plays a role, including prostate cancer, breast cancer, kidney cancer, ovarian cancer, lymphoma, leukemia, and glioblastoma, among others.

18 Claims, 107 Drawing Sheets

Specification includes a Sequence Listing.

| | IC 50 (µM) of the analogs | | | | | |
|---|---|---|---|---|---|---|
| cell lines | HCT116 | HCT116-P53null | SW480 | DLD-1 | Wi38 | MRC5 |
| P01 | 0.05599 | 0.05196 | 0.03877 | 0.04108 | 0.09716 | 0.2338 |
| P301 | 0.1966 | 0.2606 | 0.1598 | 0.2192 | 0.3524 | 0.6382 |
| P303 | 0.4628 | 0.7936 | 0.2877 | | | |

|  | HT29 | MB468 | SW480 | DLD1 | HCT116 p53-null |
|---|---|---|---|---|---|
| IC50(nM) | 66.26 | 97.6 | 95.28 | 53.98 | 41.14 |

|  | FaDu | CAL-27 | PANC-1 | ASPC-1 | U251 | H1975 | MB-231 | MRC5 |
|---|---|---|---|---|---|---|---|---|
| IC50(nM) | 66.02 | 33.88 | 135.5 | 39.19 | 100.2 | 190.4 | 242.3 | 172.6 |

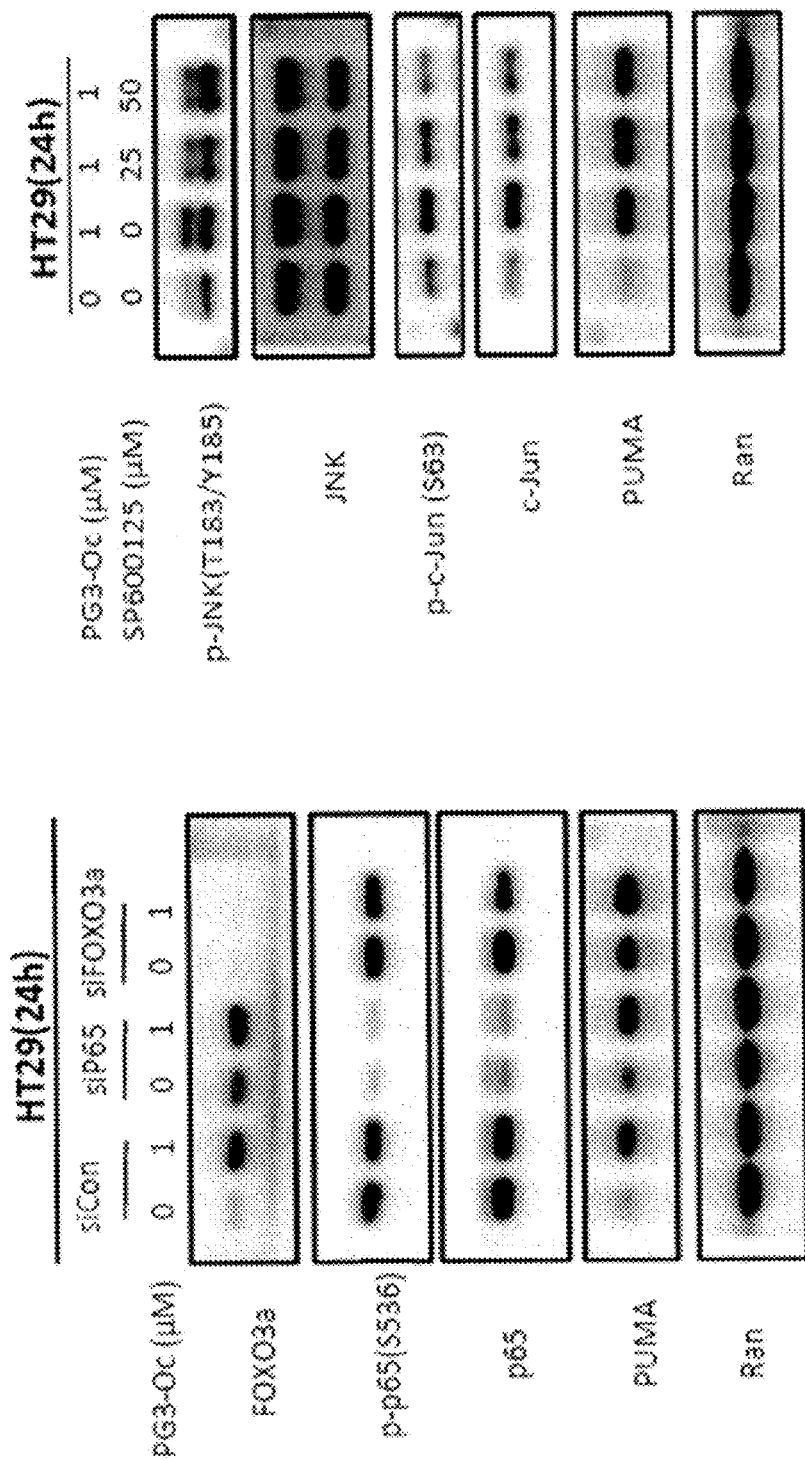

P2A

5'-GCCGCTCGTACTGTGCGTTG-3'

HT29-P2A

Decomposition window

HT29-P2A

Indel Spectrum

HT29(72h)

Ctrl

1µM

PRODIGIOSIN ANALOGS AND METHODS OF USE

REFERENCE TO GOVERNMENT GRANTS

This invention was made with government support under Grant No. CA176289 awarded by the National Institutes of Health. The government has certain rights in the invention.

FIELD

The present disclosure relates generally to the field of formulation chemistry. More particularly, the present disclosure relates to compounds, compositions, and methods for treating cancer, specifically by restoring the p53 pathway and inducing the expression of the p73 protein.

BACKGROUND

Prodigiosin (represented by tautomeric Formulas (A1) and (A2)) is the parent member of the tripyrrole alkaloid family of natural products that shows potent anti-cancer activity against tumors with mutated p53 proteins.

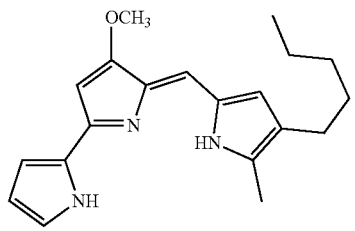

(A1)

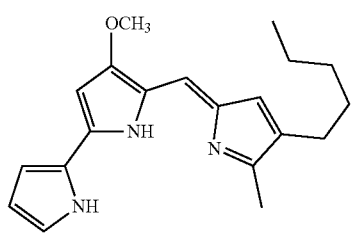

(A2)

Activation of p53 can induce cell-cycle arrest and apoptosis through transcriptional regulation of specific target genes. However, p53 is mutated in more than 50% of tumors, making functional reactivation of the p53 pathway an attractive strategy for cancer therapy development. Prodigiosin is further able to induce the expression of the p73 protein and disrupt its interaction with mutant p53, thereby rescuing p53 pathway deficiency and promoting anti-tumor effects. Accordingly, it is desirable to identify and synthesize prodigiosin analogs that are suitable as cancer treatments through restoration of the p53 pathway and inducing the expression of the p73 protein.

SUMMARY

The present disclosure provides compounds of Formula XIV:

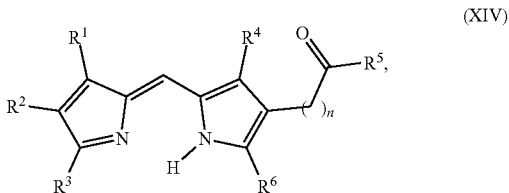

(XIV)

wherein: $R^1$ and $R^2$ are, independently, selected from the group consisting of H, OH, halogen, —$C_{1-6}$alkyl, —$C_{1-6}$fluoroalkyl, —CN, —$NO_2$, —$OR^7$, —$SR^7$, —S(=O)$R^7$, —S(=O)$_2R^7$, —NHS(=O)$_2R^7$, —C(=O)$R^7$, —OC(=O)$R^7$, —$CO_2R^7$, —$OCO_2R^7$, —CH($R^7$)$_2$, —N($R^7$)$_2$, —C(=O)N($R^7$)$_2$, —NHC(=O)NH$R^7$, —NHC(=O)$R^7$, —NHC(=O)O$R^7$, —C(OH)($R^7$)$_2$, and —C($NH_2$)($R^7$)$_2$; each $R^7$ is, independently, H, halogen, or $C_1$-$C_6$alkyl, wherein the alkyl group is optionally substituted by 1, 2, 3, 4, or 5 substituents independently selected from, OH, CN, and $NO_2$; $R^3$ is an optionally substituted aryl or an optionally substituted heteroaryl; $R^4$, $R^5$, and $R^6$ are, independently, OH, —$C_{1-10}$alkyl, —$OC_{1-10}$alkyl, or —$SC_{1-10}$alkyl, wherein each alkyl group is, independently, optionally substituted by 1, 2, 3, 4, or 5 substituents independently selected from halogen, OH, CN, and $NO_2$; and n is an integer from 0 to 5; or an isomer, tautomer, or solvate thereof, or a pharmaceutically acceptable salt thereof; provided that: if n is 0, then $R^3$ is not an optionally substituted pyrrolyl; and if n is 2, then the compound is not

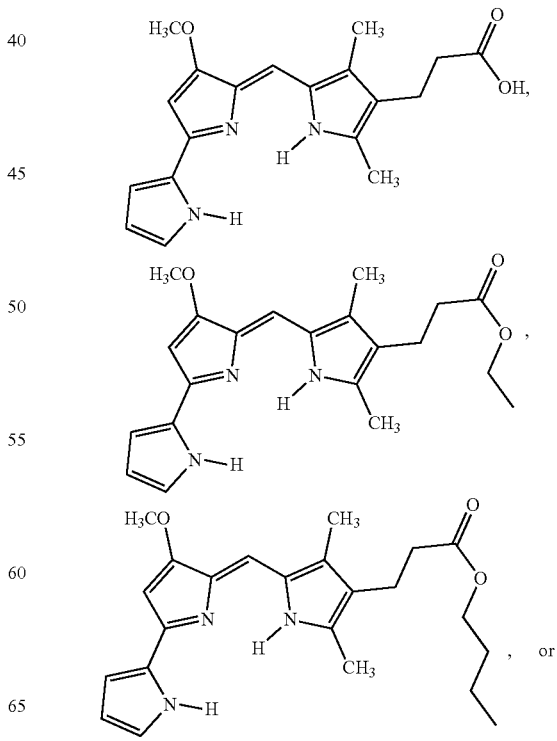

-continued

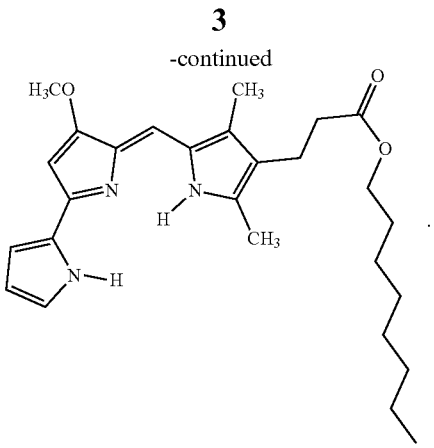

The present disclosure also provides pharmaceutical compositions comprising the compounds, or an isomer, tautomer, or solvate thereof, or a pharmaceutically acceptable salt thereof, of Formula XIV and a pharmaceutically acceptable carrier.

The present disclosure also provides methods of treating cancer in a subject comprising administering to the subject in need thereof the compound, or isomer, tautomer, or solvate thereof, or pharmaceutically acceptable salt thereof, of Formula XIV.

The present disclosure also provides methods of preparing a compound of Formula XIV:

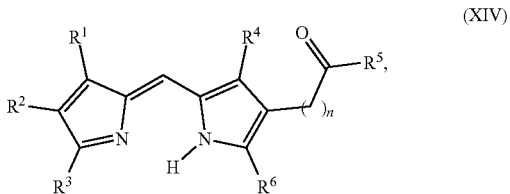

wherein: $R^1$ and $R^2$ are, independently, selected from the group consisting of H, OH, halogen, —$C_{1-6}$alkyl, —$C_{1-6}$fluoroalkyl, —CN, —$NO_2$, —$SR^7$, —S(=O)$R^7$, —S(=O)$_2R^7$, —NHS(=O)$_2R^7$, —C(=O)$R^7$, —OC(=O)$R^7$, —$CO_2R^7$, —$OCO_2R^7$, —CH($R^7$)$_2$, —N($R^7$)$_2$, —C(=O)N($R^7$)$_2$, —NHC(=O)NH$R^7$, —NHC(=O)$R^7$, —NHC(=O)O$R^7$, —C(OH)($R^7$)$_2$, and —C(NH$_2$)($R^7$)$_2$; each $R^7$ is, independently, H, halogen, or $C_1$-$C_6$alkyl, wherein the alkyl group is optionally substituted by 1, 2, 3, 4, or 5 substituents independently selected from halogen, OH, CN, and $NO_2$; $R^3$ is an optionally substituted aryl or an optionally substituted heteroaryl; $R^4$, $R^5$, and $R^6$ are, independently, —OH, —O$C_{1-10}$alkyl, or —S$C_{1-10}$alkyl, wherein each alkyl group is, independently, optionally substituted by 1, 2, 3, 4, or 5 substituents independently selected from halogen, OH, CN, and $NO_2$; and n is an integer from 0 to 5; wherein the method comprises: admixing a solvent, an acid, a compound of Formula XII

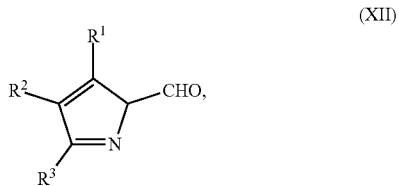

and a compound of Formula XIII

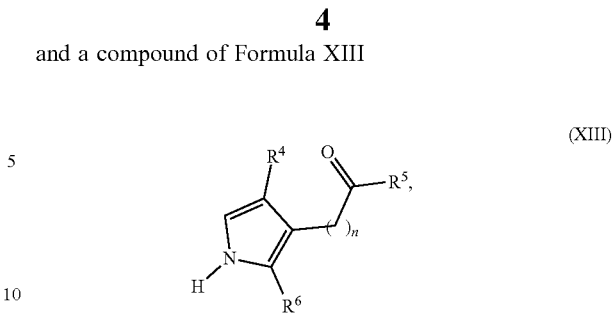

at a temperature sufficient to result in the formation of the compound of Formula XIV; the acid is selected from the group consisting of hydrochloric acid, hydrobromic acid, hydrofluoric acid, acetic acid, phosphoric acid, toluenesulfonic acid, sulfuric acid, and nitric acid; and the temperature is about from about 0° C. to about 100° C.

BRIEF DESCRIPTION OF THE DRAWINGS

FIGS. 31A, 31B, 31C, 31D, and 31E depict the exploration of the molecular mechanism of PG3-Oc-induced up-regulation of PUMA.

DESCRIPTION OF EMBODIMENTS

Figure 1:
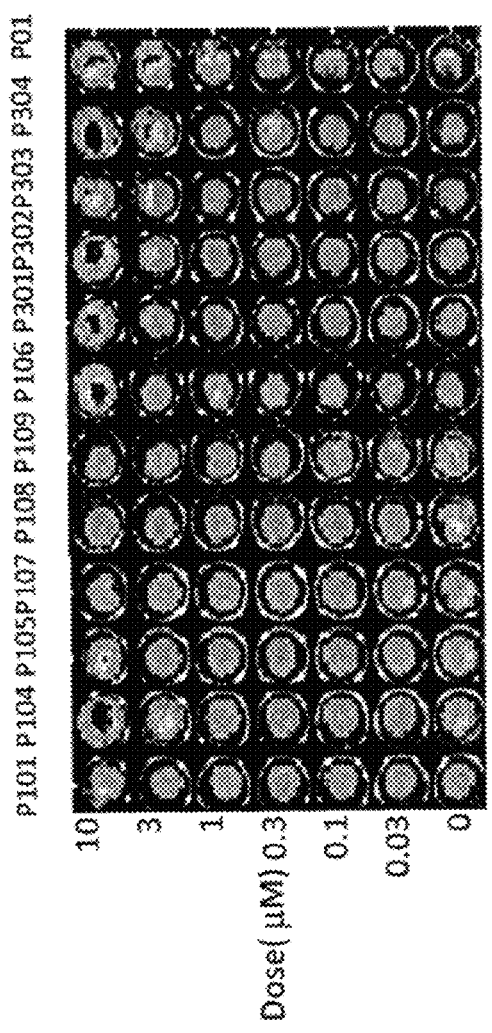
FIG. 1 depicts various aspects of a p53-responsive Luciferase Reporter Assay experiment conducted using prodigiosin analogs.

Various terms relating to aspects of the present disclosure are used throughout the specification and claims. Such terms are to be given their ordinary meaning in the art, unless otherwise indicated. Other specifically defined terms are to be construed in a manner consistent with the definition provided herein. Unless defined otherwise, all technical and scientific terms have the same meaning as is commonly understood by one of ordinary skill in the art to which the disclosed embodiments belong.

As used herein, the singular forms "a," "an," and "the" include plural referents unless expressly stated otherwise.

As used herein, the term "about" means that the recited numerical value is approximate and small variations would not significantly affect the practice of the disclosed embodiments. Where a numerical value is used, unless indicated otherwise by the context, "about" means the numerical value can vary by ±10% and remain within the scope of the disclosed embodiments.

As used herein, the term "alkoxy" means a straight or branched —O-alkyl group having 1 to 20 carbon atoms. In some embodiments, the alkoxy group has from 1 to 10 carbon atoms, from 1 to 8 carbon atoms, from 1 to 6 carbon atoms, from 1 to 4 carbon atoms, from 2 to 10 carbon atoms, from 2 to 8 carbon atoms, from 2 to 6 carbon atoms, or from 2 to 4 carbon atoms. Examples of alkoxy groups include, but are not limited to, methoxy, ethoxy, n-propoxy, isopropoxy, t-butoxy, and the like.

As used herein, "alkyl" refers to a saturated straight or branched hydrocarbon, such as a straight or branched group of 1-12, 1-10, or 1-6 carbon atoms, referred to herein as $C_1$-$C_{12}$alkyl, $C_1$-$C_{10}$alkyl, and $C_1$-$C_6$alkyl, respectively.

Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc. An alkyl group can be substituted (i.e., optionally substituted) with one or more substituents or can be multi-cyclic as set forth below.

As used herein, "ether" and "ether group" refer to a functional group comprising two hydrocarbon groups covalently linked by an oxygen.

As used herein, the term "amino" means —NH2.

As used herein, "ring structure" includes aryl, cycloalkyl, heteroaryl, and heterocyclyl.

As used herein, "aryl" is art-recognized and refers to a carbocyclic aromatic group. Representative aryl groups include, but are not limited to, phenyl, naphthyl, anthracenyl, and the like. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, heteroaryl, —CF$_3$, —CN, or the like. "Aryl" also includes polycyclic ring systems having two or more carbocyclic rings in which two or more carbons are common to two adjoining rings (the rings are "fused rings") wherein at least one of the rings is aromatic, and the other ring(s) may be, for example, cycloalkyl, cycloalkenyl, cycloalkynyl, and/or aryl. "Haloaryl" refers to an aryl group that is substituted with at least one halogen. In some embodiments, the aromatic group is not substituted (i.e., it is unsubstituted).

As used herein, "cycloalkyl" means a non-aromatic mono- or multi-cyclic ring system of about 3 to about 10 carbon atoms, or about 5 to about 10 carbon atoms. Suitable cycloalkyl rings contain about 5 to about 6 ring atoms. The cycloalkyl can be optionally substituted with one or more "ring system substituents" which may be the same or different, and are as defined herein. Representative monocyclic cycloalkyls include, but are not limited to, cyclopentyl, cyclohexyl, cycloheptyl, and the like. Representative multicyclic cycloalkyl include, but are not limited to, 1-decalin, norbornyl, adamantyl, and the like. In such cycloalkyl groups and, including the $C_5$-$C_7$ cycloalkyl groups, one or two of the carbon atoms forming the ring can optionally be replaced with a hetero atom, such as sulfur, oxygen or nitrogen. Examples of such groups include, but are not limited to, piperidinyl, piperazinyl, morpholinyl, pyrrolidinyl, imidazolidinyl, oxazolidinyl, perhydroazepinyl, perhydrooxazapinyl, oxepanyl, perhydrooxepanyl, tetrahydrofuranyl, and tetrahydropyranyl. $C_3$ and $C_4$ cycloalkyl groups having a member replaced by nitrogen or oxygen include, but are not limited to, aziridinyl, azetidinyl, oxetanyl, and oxiranyl.

As used herein, "heteroaryl" is art-recognized and refers to aromatic groups that include at least one ring heteroatom. In some embodiments, a heteroaryl group contains 1, 2, 3, or 4 ring heteroatoms. Representative examples of heteroaryl groups includes, but are not limited to, pyridyl, pyrimidinyl, pyrazinyl, pyridazinyl, pyridinyl (including 2-aminopyridine), triazinyl, furyl, quinolyl, isoquinolyl, thienyl, imidazolyl, thiazolyl, indolyl (such as indol-3-yl), pyrryl, oxazolyl, benzofuryl, benzothienyl, pyrazolyl, benzthiazolyl, isoxazolyl, triazolyl (including 1,2,4-triazole, 1,2,3-triazole, and 5-amino-1,2,4-triazole), tetrazolyl, indazolyl, isothiazolyl, 1,2,4-thiadiazolyl, benzothienyl, purinyl, carbazolyl, isoxazolyl, benzimidazolyl, indolinyl, pyranyl, pyrazolyl, triazolyl, oxadiazolyl (including 1,2,3-oxadiazole, 1,2,4-oxadiazole, 1,2,5-oxadiazole, 3-amino-1,2,4-oxadiazole, 1,3,4-oxadiazole), thianthrenyl, indolizinyl, isoindolyl, isobenzofuranyl, pyrrolyl, benzoxazolyl, xanthenyl, 2H-pyrrolyl, 3H-indolyl, 4H-quinolizinyl, phthalazinyl, acridinyl, naphthyridinyl, quinazolinyl, phenanthridinyl, perimidinyl, phenanthrolinyl, phenazinyl, isothiazolyl, phenothiazinyl, isoxazolyl, furazanyl, phenoxazinyl groups, and the like. Unless specified otherwise, the heteroaryl ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl, —CF$_3$, —CN, or the like. "Heteroaryl" also includes polycyclic ring systems having two or more rings in which two or more carbons are common to two adjoining rings (the rings are "fused rings") wherein at least one of the rings is heteroaromatic, and the other ring(s) may be, for example, cycloalkyl, cycloalkenyl, cycloalkynyl, and/or aryl.

As used herein, "heterocyclyl" and "heterocyclic group" are art-recognized and refer to saturated, partially unsaturated, or aromatic 3- to 10-membered ring structures, alternatively 3- to 7-membered rings, whose ring structures include one to four heteroatoms, such as nitrogen, oxygen, and sulfur. Heterocycles may also be mono-, bi-, or other multi-cyclic ring systems. A heterocycle may be fused to one or more aryl, partially unsaturated, or saturated rings. Heterocyclyl groups include, but are not limited to, biotinyl, chromenyl, dihydrofuryl, dihydroindolyl, dihydropyranyl, dihydrothienyl, dithiazolyl, homopiperidinyl, imidazolidinyl, isoquinolyl, isothiazolidinyl, isoxazolidinyl, morpholinyl, oxolanyl, oxazolidinyl, phenoxanthenyl, piperazinyl, piperidinyl, pyranyl, pyrazolidinyl, pyrazolinyl, pyridyl, pyrimidinyl, pyrrolidinyl, pyrrolidin-2-onyl, pyrrolinyl, tetrahydrofuryl, tetrahydroisoquinolyl, tetrahydropyranyl, tetrahydroquinolyl, thiazolidinyl, thiolanyl, thiomorpholinyl, thiopyranyl, xanthenyl, lactones, lactams such as azetidinones and pyrrolidinones, sultams, sultones, and the like. Unless specified otherwise, the heterocyclic ring is optionally substituted at one or more positions with substituents such as alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl and thiocarbonyl. In some embodiments, the heterocyclyl group is not substituted (i.e., it is unsubstituted).

As used herein, "in need thereof" means that the "individual," "subject," or "patient" has been identified as having a need for the particular method, prevention, or treatment. In some embodiments, the identification can be by any means of diagnosis. In any of the methods, preventions, and treatments described herein, the "individual," "subject," or "patient" can be in need thereof.

As used herein, "subject" and "patient" are used interchangeably. A subject may be any animal, including mammals such as companion animals, laboratory animals, and non-human primates. In some embodiments, the subject is a human.

As used herein, the terms "treat," "treated," or "treating" mean both therapeutic treatment and prophylactic or preventative measures wherein the object is to prevent or slow down (lessen) an undesired physiological condition, disorder or disease, or obtain beneficial or desired clinical results. For purposes herein, beneficial or desired clinical results include, but are not limited to, alleviation of symptoms; diminishment of extent of condition, disorder or disease; stabilized (i.e., not worsening) state of condition, disorder or disease; delay in onset or slowing of condition, disorder or disease progression; amelioration of the condition, disorder or disease state or remission (whether partial or total), whether detectable or undetectable; an amelioration of at least one measurable physical parameter, not necessarily discernible by the patient; or enhancement or improvement of condition, disorder or disease. Treatment includes eliciting a clinically significant response, optionally without excessive levels of side effects. Treatment also includes prolonging survival as compared to expected survival if not receiving treatment.

As used herein, the term, "compound" means all stereoisomers, tautomers, isotopes, and polymorphs of the compounds described herein.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive and open-ended and include the options following the terms, and do not exclude additional, unrecited elements or method steps.

As used herein, the term "halo" means halogen groups and includes, but is not limited to, fluoro, chloro, bromo, and iodo.

As used herein, the term "haloalkyl" means a $C_{1-6}$alkyl group having one or more halogen substituents. Examples of haloalkyl groups include, but are not limited to, —CF$_3$, —C$_2$F$_5$, —CHF$_2$, —CCl$_3$, —CHCl$_2$, —C$_2$Cl$_5$, —CH$_2$CF$_3$, and the like.

As used herein, the term "integer" means a numerical value that is a whole number. For example, an "integer from 1 to 5" means 1, 2, 3, 4, or 5.

As used used herein, the phrase "optionally substituted" means that a substitution is optional and, therefore, includes both unsubstituted and substituted atoms and moieties. A "substituted" atom or moiety indicates that any hydrogen atom on the designated compound or moiety can be replaced with a selection from the indicated substituent groups, provided that the normal valency of the designated compound or moiety is not exceeded, and that the substitution results in a stable compound. For example, if a methyl group is optionally substituted, then 1, 2, or 3 hydrogen atoms on the carbon atom within the methyl group can be replaced with 1, 2, or 3 of the recited substituent groups.

The compounds described herein also include hydrates and solvates, as well as anhydrous and non-solvated forms.

Embodiments of the present disclosure include prodigiosin analogs which have anti-cancer activity against tumors with mutated p53 proteins. Without intending to be bound to any particular theory or mechanism of action, it is believed that the prodigiosin analogs result in functional reactivation of the p53 pathway in cells with mutated p53 proteins as well as induced expression of the p73 protein and disruption of the interaction between p73 and mutant p53.

Prodigiosin analogs have been developed including various side groups on the three rings of the Prodigiosin core molecule: the A-ring, the B-ring, and the C-ring, as depicted in Formula (B).

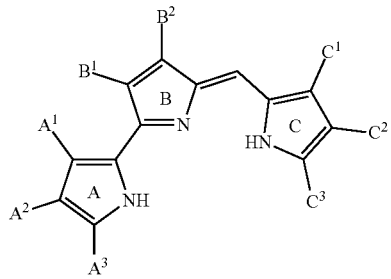
(B)

Prodigiosin analogs may include side groups attached to the core molecule at positions $A^1$, $A^2$, or $A^3$ of the A-Ring, $B^1$ or $B^2$ of the B-Ring, and $C^1$, $C^2$, or $C^3$ of the C-Ring. Embodiments of the present disclosure include prodigiosin analogs with side groups on at least the C-ring of the prodigiosin core molecule, particularly at position $C^2$. In some embodiments, the side group includes a carbonyl group. In some embodiments, the carbonyl side group is an ethyl ester ($CH_2CH_2COR$) or an ethyl secondary amide ($CH_2CH_2CONHR$).

In some embodiments, the prodigiosin analog has the structure of Formula (I) or Formula (II)

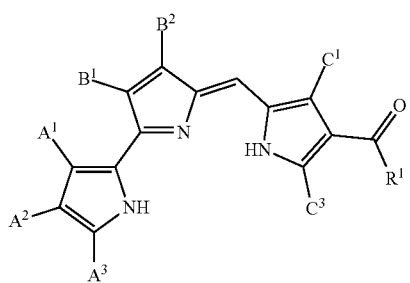
(I)

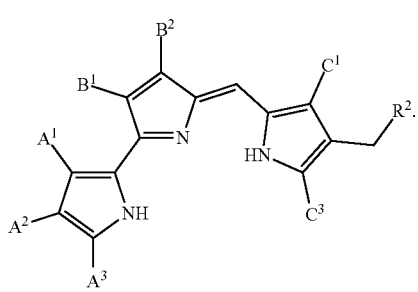
(II)

Formula (I) and Formula (II) are prodigiosin analogs according to Formula (B) wherein $C^2$ is $COR^1$ and $CH_2R^2$, respectively. Formula (I) and Formula (II) may also be represented by tautomeric Formulas (Ia) and (IIa), respectively.

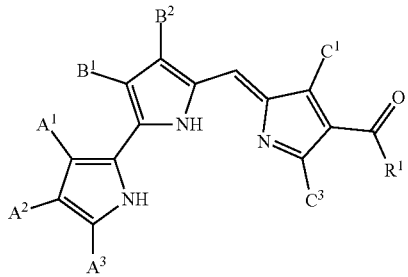
(Ia)

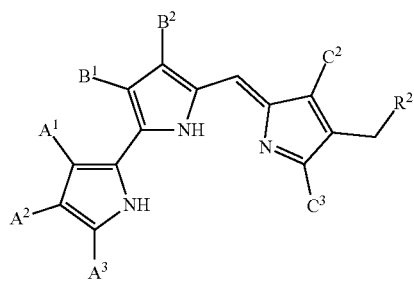
(IIa)

Further prodigiosin analogs according to embodiments of the disclosure are described with respect to Formula (I) and Formula (II). However, one of ordinary skill in the art will understand that each analog could also be expressed as a form of Formula (Ia) or Formula (IIa), the respective tautomers of Formula (I) and Formula (II).

$A^1$, $A^2$, and $A^3$ in Formulas (I) and (II) are, independently, hydrogen, phenyl, $C_1$-$C_{20}$ alkyl or $C_2$-$C_{20}$ alkenyl, wherein the alkyl and alkenyl groups are unsubstituted or substituted by 1 to 3 substituents chosen, independently, from halogen, $C_1$-$C_6$ alkoxy, hydroxy, aryl, and aryloxy. In some embodiments, $A^1$, $A^2$, and $A^3$ are hydrogen. In some embodiments, $B^1$ is hydrogen, $C_1$-$C_6$ alkyl, cyano, carboxy or ($C_1$-$C_6$ alkoxy) carbonyl. In some embodiments, $B^2$ is halogen, hydroxy or $C_1$-$C_{11}$ alkoxy unsubstituted or substituted by phenyl. In some embodiments, $B^1$ is hydrogen and $B^2$ is methoxy. In some embodiments, $C^1$ and $C^3$ are, independently, hydrogen, phenyl, $C_1$-$C_{20}$ alkyl, $C_2$-$C_{20}$ alkenyl, $C_2$-$C_{20}$ alkynyl, or $C_1$-$C_{20}$ alkoxy. In some embodiments, $C^1$ and $C^3$ are methyl.

In some embodiments, the prodigiosin analog has the structure of Formula (III) or Formula (IV)

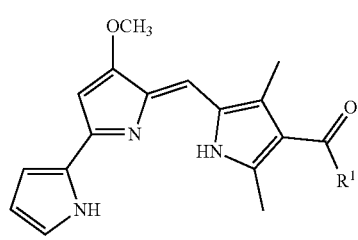
(III)

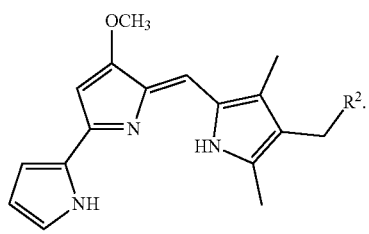
(IV)

Formula (III) and Formula (IV) are Formula (I) and Formula (II), respectively, where $A^1$, $A^2$, $A^3$, and $B^1$ are hydrogen, $B^2$ is methoxy, and $C^1$ and $C^3$ are methyl.

In some embodiments, the prodigiosin analog has the structure of Formula (V) or Formula (VI)

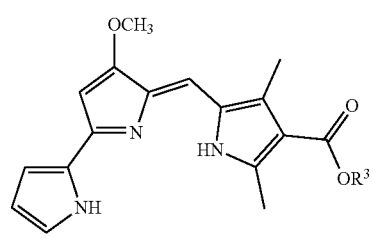
(V)

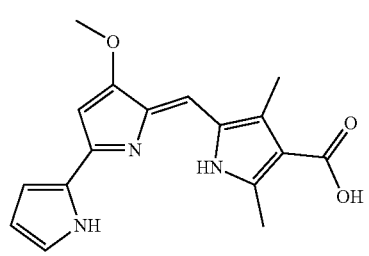
(VI)

Formula (V) and Formula (VI) are Formula (III), where $R_1$ is $OR_3$ and $NR_4R_5$, respectively.

In some embodiments, the prodigiosin analog has the structure of Formula (Va), (Vb), (Vc), (Vd), or (Ve)

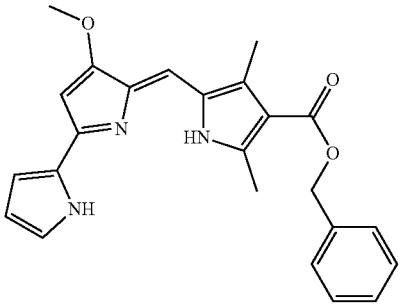
(Va)

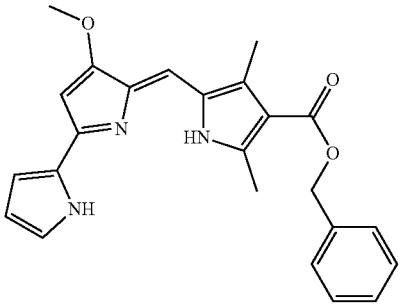
(Vb)

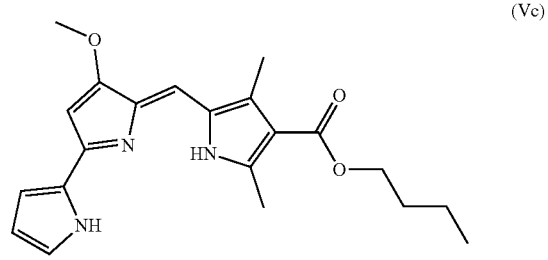
(Vc)

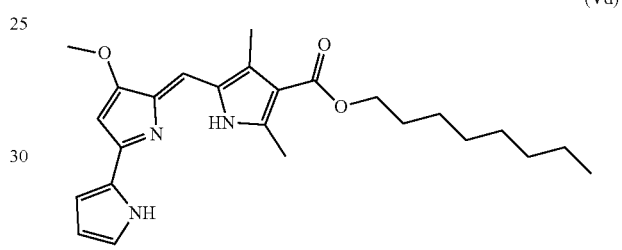
(Vd)

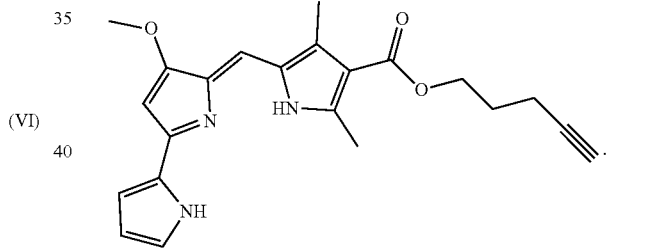
(Ve)

Formula (Va) is Formula (V) where $R^3$ is hydrogen. Formula (Vb) is Formula (V) where $R^3$ is benyzl. Formula (Vc) is Formula (V) where $R^3$ is n-butyl. Formula (Vd) is Formula (V) where $R_3$ is n-octyl. Formula (Ve) is Formula (V) where $R^3$ is 1-pentyne.

In some embodiments, the prodigiosin analog has the structure of Formula (VIa)

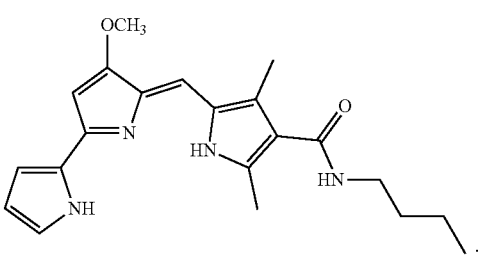
(VIa)

Formula (VIa) is Formula (VI), where $R^4$ is hydrogen and $R^5$ is n-butyl.

In some embodiments, the prodigiosin analog has the structure of Formula (VII)

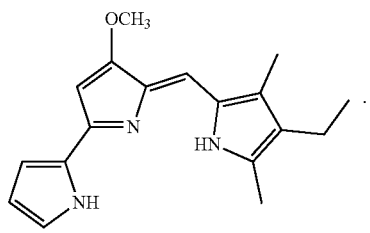
(VII)

Formula (VII) is Formula (III) where $R_2$ is hydrogen.

In some embodiments, the prodigiosin analog has the structure of Formula (VIII)

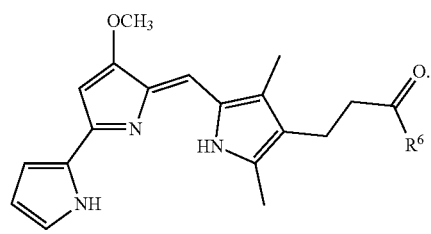
(VIII)

Formula (VIII) is Formula (III) where $R_2$ is $COR_6$.

In some embodiments, the prodigiosin analog has the structure of Formula (IX) or Formula (X)

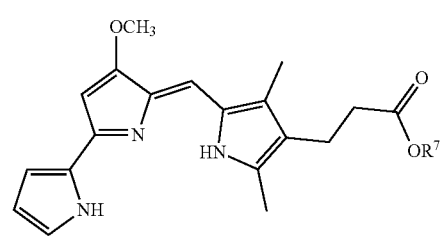
(IX)

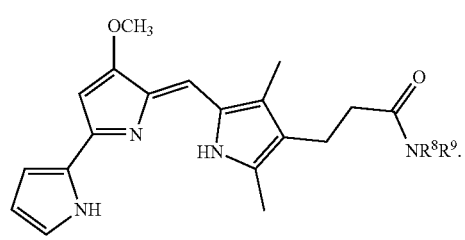
(X)

Formula (IX) and Formula (X) are Formula (VIII) where $R^6$ is $OR^7$ or $NR^8R^9$, respectively.

In some embodiments, the prodigiosin analog has the structure of Formula (IXa), Formula (IXb), Formula (IXc), or Formula (IXd)

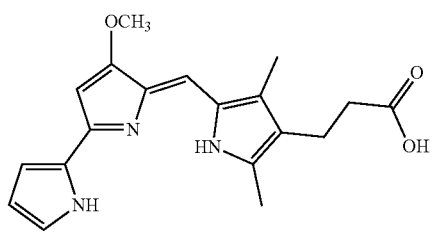
(IXa)

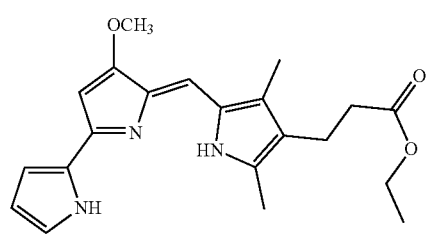
(IXb)

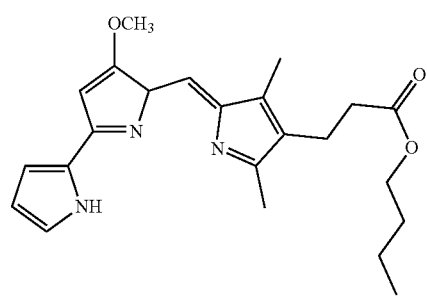
(IXc)

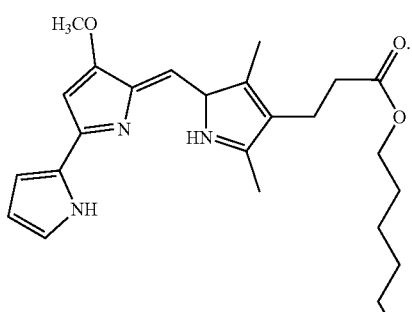
(IXd)

Formula (IXa) is Formula (IX) where $R^7$ is hydrogen. Formula (IXb) is Formula (IX) where $R^7$ is ethyl. Formula (IXc) is Formula (IX) where $R^7$ is n-butyl. Formula (IXd) (PG3-Oc) is Formula (IX) where $R^7$ is n-octyl.

In some embodiments, the prodigiosin analog has the structure of Formula (Xa)

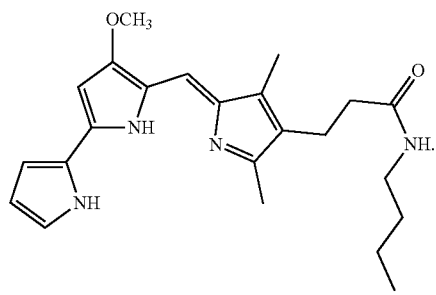

Formula (Xa) is Formula (X) where $R^8$ is hydrogen and $R^9$ is n-butyl.

The compounds may be formulated as a composition, for example, with a carrier. Compositions may comprise a compound of Formulas (I), (II), (III), (IV), (V), (Va), (Vb), (Vc), (Vd), (Ve), (VI), (VIa), (VII), (VIII), (IX), (IXa), (IXb), (IXc), (IXd), (X), (Xa), and (XIV), or a pharmaceutically acceptable salt thereof. Compositions may comprise a compound of Formula (XIV), or a pharmaceutically acceptable salt thereof. The composition may include more than one compound, including any combination, of Formulas (I), (II), (III), (IV), (V), (Va), (Vb), (Vc), (Vd), (Ve), (VI), (VIa), (VII), (VIII), (IX), (IXa), (IXb), (IXc), (IXd), (X), (Xa), and (XIV). The composition may include more than one compound, including any combination, of compounds within Formula (XIV). The composition may also include one or more other anti-cancer drugs.

The present disclosure also provides compounds of Formula XIV

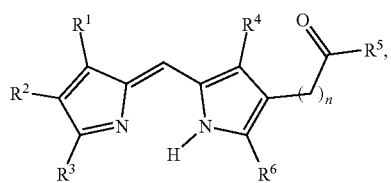

wherein:

$R^1$ and $R^2$ are, independently, selected from the group consisting of H, OH, halogen, —$C_{1-6}$alkyl, —$C_{1-6}$fluoroalkyl, —CN, —$NO_2$, —$SR^7$, —S(=O)$R^7$, —S(=O)$_2R^7$, —NHS(=O)$_2R^7$, —C(=O)$R^7$, —OC(=O)$R^7$, —$CO_2R^7$, —$OCO_2R^7$, —CH($R^7$)$_2$, —N($R^7$)$_2$, —C(=O)N($R^7$)$_2$, —NHC(=O)NH$R^7$, —NHC(=O)$R^7$, —NHC(=O)O$R^7$, —C(OH)($R^7$)$_2$, and —C(NH$_2$)($R^7$)$_2$;

each $R^7$ is, independently, H, halogen, or $C_1$-$C_6$alkyl, wherein the alkyl group is optionally substituted by 1, 2, 3, 4, or 5 substituents independently selected from halogen, OH, CN, and $NO_2$;

$R^3$ is an optionally substituted aryl or an optionally substituted heteroaryl;

$R^4$, $R^5$, and $R^6$ are, independently, OH, —$C_{1-10}$alkyl, —$OC_{1-10}$alkyl, or —$SC_{1-10}$alkyl, wherein each alkyl group is, independently, optionally substituted by 1, 2, 3, 4, or 5 substituents independently selected from halogen, OH, CN, and $NO_2$; and n is an integer from 0 to 5; provided that if n is 0, then $R^3$ is not an optionally substituted pyrrolyl; and if n is 2, then the compound is not

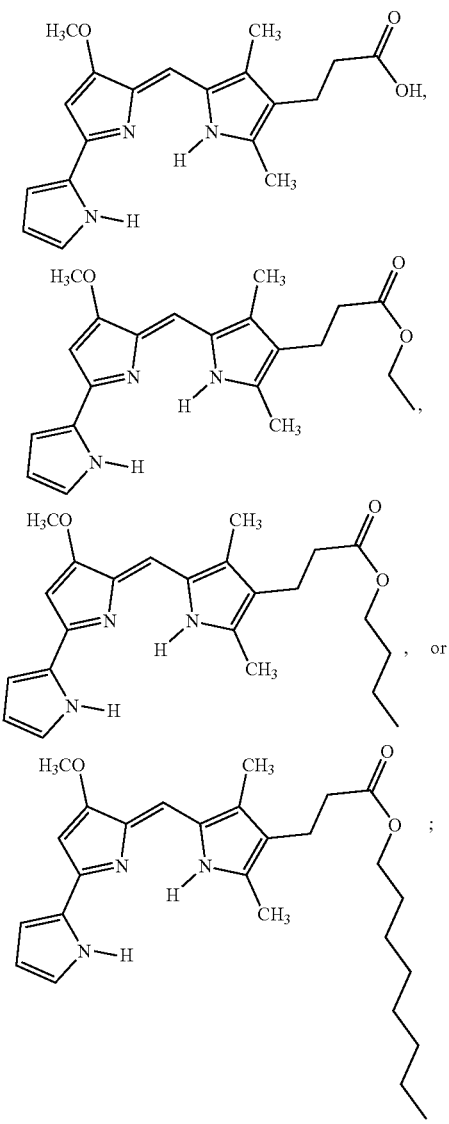

or an isomer, tautomer, or solvate thereof, or a pharmaceutically acceptable salt thereof.

In some embodiments, $R^1$ and $R^2$ are, independently, selected from the group consisting of H, halogen, —$C_{1-6}$alkyl, —$C_{1-6}$fluoroalkyl, —O$R^7$, —S$R^7$, —S(=O)$R^7$, —C(=O)$R^7$, —OC(=O)$R^7$, —$CO_2R^7$, —$OCO_2R^7$, —CH(R)$_2$, —C(=O)N($R^7$)$_2$, —C(OH)($R^7$)$_2$, and —C(NH$_2$)($R^7$)$_2$. In some embodiments, $R^1$ and $R^2$ are, independently, selected from the group consisting of H, halogen, —$C_{1-6}$alkyl, —O$R^7$, —S$R^7$, —S(=O)$R^7$, —C(=O)$R^7$, —OC(=O)$R^7$, —$CO_2R^7$, —$OCO_2R^7$, —CH($R^7$)$_2$, and —C(OH)($R^7$)$_2$. In some embodiments, $R^1$ and $R^2$ are, independently, selected from the group consisting of H, —$C_{1-6}$alkyl, —O$R^7$, —C(=O)$R^7$, and OC(=O)$R^7$. In some embodiments, $R^1$ and $R^2$ are, independently, selected from the group consisting of H, —$C_{1-6}$alkyl, and —O$R^7$. In some embodiments, $R^1$ is —O$R^7$ and $R^2$ is H. In some embodiments, $R^1$ is —$OCH_3$ and $R^2$ is H.

In some embodiments, $R^3$ is an optionally substituted heteroaryl. In some embodiments, $R^3$ is an optionally substituted heteroaryl selected from the group consisting of pyridyl, pyrimidinyl, pyrazinyl, pyridazinyl, pyridinyl, triazinyl, furyl, quinolyl, isoquinolyl, thienyl, imidazolyl, thiazolyl, indolyl, pyrryl, oxazolyl, pyrazolyl, isoxazolyl, triazolyl, tetrazolyl, indazolyl, isothiazolyl, purinyl, carbazolyl, isoxazolyl, indolinyl, pyranyl, pyrazolyl, triazolyl, oxadiazolyl, thianthrenyl, indolizinyl, isoindolyl, pyrrolyl, and xanthenyl. In some embodiments, $R^3$ is an optionally substituted heteroaryl selected from the group consisting of pyridyl, pyrimidinyl, pyrazinyl, pyridazinyl, pyridinyl, furyl, thienyl, imidazolyl, thiazolyl, indolyl, pyrryl, oxazolyl, pyrazolyl, isoxazolyl, indazolyl, isothiazolyl, purinyl, carbazolyl, isoxazolyl, indolinyl, pyranyl, pyrazolyl, oxadiazolyl, and pyrrolyl. In some embodiments, $R^3$ is an optionally substituted heteroaryl selected from the group consisting of pyridyl, pyrimidinyl, pyridinyl, imidazolyl, indolyl, pyrryl, purinyl, pyranyl, and pyrrolyl. In some embodiments, $R^3$ is an optionally substituted heteroaryl selected from the group consisting of pyridyl, pyrimidinyl, pyridinyl, pyrryl, and pyrrolyl. In some embodiments, $R^3$ is an optionally substituted pyrrolyl.

In some embodiments, $R^4$, $R^5$, and $R^6$ are, independently, OH, —$C_{1-6}$alkyl or —$OC_{1-10}$alkyl, wherein each alkyl group is, independently, optionally substituted by 1, 2, or 3 substituents independently selected from halogen, OH, CN, and $NO_2$. In some embodiments, $R^4$, $R^5$, and $R^6$ are, independently, OH, —$C_{1-6}$alkyl or —$OC_{1-8}$alkyl, wherein each alkyl group is, independently, optionally substituted by 1 or 2 substituents independently selected from halogen and OH. In some embodiments, $R^4$ and $R^6$ are, independently, —$C_{1-3}$alkyl, and $R^5$ is OH or —$OC_{1-8}$alkyl, wherein each alkyl group is, independently, optionally substituted by 1 or 2 halogens. In some embodiments, $R^4$ and $R^6$ are, independently, —$C_{1-3}$alkyl, and $R^5$ is —$OC_{6-8}$alkyl. In some embodiments, n is 2 or 3. In some embodiments, n is 2.

In some embodiments, $R^1$ and $R^2$ are, independently, selected from the group consisting of H, —$C_{1-6}$alkyl, —$C_{1-6}$fluoroalkyl, halogen, —$OR^7$, —$SR^7$, —$S(=O)R^7$, —$C(=O)R^7$, —$OC(=O)R^7$, —$CO_2R^7$, —$OCO_2R^7$, —CH$(R^7)_2$, —$C(=O)N(R^7)_2$, —$C(OH)(R^7)_2$, and —$C(NH_2)(R^7)_2$; each $R^7$ is, independently, H, halogen, or $C_1$-$C_6$alkyl; $R^3$ is an optionally substituted heteroaryl; $R^4$, $R^5$, and $R^6$ are, independently, OH, —$C_{1-6}$alkyl or —$OC_{1-10}$alkyl, wherein each alkyl group is, independently, optionally substituted by 1, 2, or 3 substituents independently selected from halogen, OH, CN, and $NO_2$; and n is an integer from 1 to 3.

In some embodiments, $R^1$ and $R^2$ are, independently, selected from the group consisting of H, —$C_{1-6}$alkyl, halogen, —$OR^7$, —$SR^7$, —$S(=O)R^7$, —$C(=O)R^7$, —$OC(=O)R^7$, —$CO_2R^7$, —$OCO_2R^7$, —CH$(R^7)_2$, and —$C(OH)(R^7)_2$; each $R^7$ is, independently, H, halogen, or $C_1$-$C_3$alkyl; $R^3$ is an optionally substituted heteroaryl selected from the group consisting of pyridyl, pyrimidinyl, pyrazinyl, pyridazinyl, pyridinyl, furyl, thienyl, imidazolyl, thiazolyl, indolyl, pyrryl, oxazolyl, pyrazolyl, isoxazolyl, indazolyl, isothiazolyl, purinyl, carbazolyl, isoxazolyl, indolinyl, pyranyl, pyrazolyl, oxadiazolyl, and pyrrolyl; $R^4$, $R^5$, and $R^6$ are, independently, OH, —$C_{1-6}$alkyl or —$OC_{1-8}$alkyl, wherein each alkyl group is, independently, optionally substituted by 1 or 2 substituents independently selected from halogen and OH; and n is an integer from 1 to 3.

In some embodiments, $R^1$ and $R^2$ are, independently, selected from the group consisting of H, —$C_{1-6}$alkyl, —$OR^7$, —$C(=O)R^7$, and —$OC(=O)R^7$; each $R^7$ is, independently, halogen or $C_1$-$C_3$alkyl; $R^3$ is an optionally substituted heteroaryl selected from the group consisting of pyridyl, pyrimidinyl, pyrazinyl, pyridazinyl, pyridinyl, furyl, thienyl, imidazolyl, indolyl, pyrryl, purinyl, pyranyl, pyrazolyl, oxadiazolyl, and pyrrolyl; $R^4$ and $R^6$ are, independently, —$C_{1-3}$alkyl, and $R^5$ is OH or —$OC_{1-8}$alkyl, wherein each alkyl group is, independently, optionally substituted by 1 or 2 halogens; and n is 2 or 3.

In some embodiments, $R^1$ and $R^2$ are, independently, selected from the group consisting of H, —$C_{1-6}$alkyl, and —$OR^7$; each $R^7$ is, independently, halogen or $C_1$-$C_3$alkyl; $R^3$ is an optionally substituted heteroaryl selected from the group consisting of pyridyl, pyrimidinyl, pyridinyl, imidazolyl, indolyl, pyrryl, purinyl, pyranyl, and pyrrolyl; $R^4$ and $R^6$ are, independently, —$C_{1-3}$alkyl; $R^5$ is —$OC_{6-8}$alkyl; and n is 2 or 3.

In some embodiments, $R^1$ is —$OR^7$; $R^2$ is H; each $R^7$ is, independently, halogen, or $C_1$-$C_3$alkyl; $R^3$ is an optionally substituted heteroaryl selected from the group consisting of pyridyl, pyrimidinyl, pyridinyl, pyrryl, and pyrrolyl; $R^4$ and $R^6$ are, independently, —$C_{1-3}$alkyl; $R^5$ is —$OC_{6-8}$alkyl; and n is 2.

In some embodiments, the compound(s) having Formulas (I), (II), (III), (IV), (V), (Va), (Vb), (Vc), (Vd), (Ve), (VI), (VIa), (VII), (VIII), (IX), (IXa), (IXb), (IXc), (IXd), (X), (Xa), and (XIV) or an isomer, tautomer, or solvate thereof, or a pharmaceutically acceptable salt thereof, are a component of a pharmaceutical composition comprising a pharmaceutically acceptable carrier. In some embodiments, the compound(s) having Formula (XIV) or an isomer, tautomer, or solvate thereof, or a pharmaceutically acceptable salt thereof, are a component of a pharmaceutical composition comprising a pharmaceutically acceptable carrier.

In some embodiments, the pharmaceutical composition further comprises an anti-cancer agent. As used herein, the phrase "anti-cancer agent" is meant to include all forms of treatment of cancer including, but not limited to, traditional chemotherapy (i.e., chemotherapeutic agents, whether they are administered parenterally or orally), immunotherapeutic agents, small molecule enzyme or kinase inhibitors, intravesical therapeutic agents, antibody inhibitors of receptors or kinases, antibody-drug conjugates, and radiation therapy.

Examples of chemotherapeutic agents include, but are not limited to, cisplatin, carboplatin, oxaliplatin, nedaplatin, triplatin tetranitrate, phenanthriplatin, picoplatin, satraplatin, methotrexate, vincristine, doxorubicin, tunicamycin, oligomycin, bortezomib, MG132, 5-flurouracil, sorafenib, flavopiridol, gemcitabine, taxol, mercaptopurine, thioguanine, hydroxyurea, cytarabine, mitomycin, cyclophosphamide, ifosfamide, nitrosourea, dacarbazine, procarbizine, an etoposide, a campathecin, bleomycin, idarubicin, daunorubicin, dactinomycin, distamycin A, etidium, netropsin, auristatin, amsacrine, prodigiosin, bortexomib, pibenzimol, tomaymycin, duocarmycin SA, plicamycin, mitoxantrone, asparaginase, vinblastine, vinorelbine, paclitaxel, docetaxel, CPT-11, gleevec, erlotinib, gefitinib, ibrutinib, crizotinib, ceritinib, lapatinib, navitoclax, and regorafenib, or any combination thereof. In some embodiments, the chemotherapeutic agent is a combination of agents, such as, for example, methotrexate/vincristine/doxorubicin/cisplatin (MVAC) or gemcitabine/cisplatin.

Examples of immunotherapeutic agents include, but are not limited to, OPDIVO® (nivolumab), KEYTRUDA® (pembrolizumab), TECENTRIQ® (atezolizumab), IMFINZI® (durvalab), YERVOY® (ipilumumab), or BAVENCIO® (avelumab), or any combination thereof.

In some embodiments, the ratio of the compound(s) having Formulas (I), (II), (III), (IV), (V), (Va), (Vb), (Vc), (Vd), (Ve), (VI), (VIa), (VII), (VIII), (IX), (IXa), (IXb), (IXc), (IXd), (X), (Xa), and (XIV) to the anti-cancer agent in the pharmaceutical compositon is from about 0.01:1 to about 100:1 w/w. In some embodiments, the ratio of the compound(s) within Formula (XIV) to the anti-cancer agent in the pharmaceutical compositon is from about 0.01:1 to about 100:1 w/w.

The pharmaceutical compostons described herein can be administered to a patient in need thereof in an oral formulation, an intravenous formulation, a topical formulation, an intraperitoneal formulation, an intrapleural formulation, an intravesical formulation, or an intrathecal formulation. The compositions may be formulated in a suitable controlled-release vehicle, with an adjuvant, or as a depot formulation.

Pharmaceutically acceptable salts may be acid or base salts. Non-limiting examples of pharmaceutically acceptable salts include sulfates, methosulfates, methanesulfates, pyrosulfates, bisulfates, sulfites, bisulfites, nitrates, besylates, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, dioates, benzoates, chlorobenzoates, methylbenzoates, dinitromenzoates, hydroxybenzoates, methoxybenzoates, phthalates, sulfonates, toluenesulfonates, xylenesulfonates, pheylacetates, phenylpropionates, phenylbutyrates, citrates, lactates, γ-hydroxybutyrates, glycollates, tartrates, methanesulfonates, propanesulfonates, mandelates, and other salts customarily used or otherwise FDA-approved.

In some embodiments, the carrier is a pharmaceutically acceptable carrier. Pharmaceutically acceptable carriers include, but are not limited to, aqueous vehicles such as water, alcohol (e.g., ethanol or glycol), saline solutions, dextrose solutions, and balanced salt solutions, as well as nonaqueous vehicles such as alcohols and oils, including plant or vegetable-derived oils such as olive oil, cottonseed oil, corn oil, canola oil, sesame oil, and other non-toxic oils. The compositions may also comprise one or more pharmaceutically acceptable excipients.

In some embodiments, the compositions comprise an effective amount of the compound such as a compound having Formulas (I), (II), (III), (IV), (V), (Va), (Vb), (Vc), (Vd), (Ve), (VI), (VIa), (VII), (VIII), (IX), (IXa), (IXb), (IXc), (IXd), (X), (Xa), and (XIV), or any combination thereof. In some embodiments, the compositions comprise an effective amount of the compound such as a compound having Formula (XIV), or any combination of compounds therein.

The compositions may be formulated for administration to a subject in any suitable dosage form. The compositions may be formulated for oral, buccal, nasal, transdermal, parenteral, injectable, intravenous, subcutaneous, intramuscular, rectal, or vaginal administration. The compositions may be formulated in a suitable controlled-release vehicle, with an adjuvant, or as a depot formulation.

Preparations for parenteral administration include, but are not limited to, sterile solutions ready for injection, sterile dry soluble products ready to be combined with a solvent just prior to use, including, but not limited to, hypodermic tablets, sterile suspensions ready for injection, sterile dry insoluble products ready to be combined with a vehicle just prior to use and sterile emulsions.

Solid dosage forms include, but are not limited to, tablets, pills, powders, bulk powders, capsules, granules, and combinations thereof. Solid dosage forms may be prepared as compressed, chewable lozenges and tablets which may be enteric-coated, sugar coated or film-coated. Solid dosage forms may be hard or encased in soft gelatin, and granules and powders may be provided in non-effervescent or effervescent form. Solid dosage forms may be prepared for dissolution or suspension in a liquid or semi-liquid vehicle prior to administration. Solid dosage forms may be prepared for immediate release, controlled release, or any combination thereof. Controlled release includes, but is not limited to, delayed release, sustained release, timed pulsatile release, and location-specific pulsatile release, and combinations thereof.

Liquid dosage forms include, but are not limited to, aqueous solutions, emulsions, suspensions, solutions and/or suspensions reconstituted from non-effervescent granules and effervescent preparations reconstituted from effervescent granules. Aqueous solutions include, but are not limited to, elixirs and syrups. Emulsions may be oil-in water or water-in-oil emulsions.

Pharmaceutically acceptable excipients utilized in solid dosage forms include, but are not limited to, coatings, binders, lubricants, diluents, disintegrating agents, coloring agents, flavoring agents, preservatives, sweeteners, and wetting agents. Enteric-coated tablets, due to their enteric-coating, resist the action of stomach acid and dissolve or disintegrate in the neutral or alkaline intestines. Other examples of coatings include, but are not limited to, sugar coatings and polymer coatings. Sweetening agents are useful in the formation of chewable tablets and lozenges. Pharmaceutically acceptable excipients used in liquid dosage forms include, but are not limited to, solvents, suspending agents, dispersing agents, emulsifying agents, surfactants, emollients, coloring agents, flavoring agents, preservatives, and sweeteners.

Suitable examples of binders include, but are not limited to, glucose solution, acacia mucilage, gelatin solution, sucrose and starch paste. Suitable examples of lubricants include, but are not limited to, talc, starch, magnesium or calcium stearate, lycopodium and stearic acid. Suitable examples of diluents include, but are not limited to, lactose, sucrose, starch, kaolin, salt, mannitol and dicalcium phosphate. Suitable examples of disintegrating agents include, but are not limited to, corn starch, potato starch, bentonite, methylcellulose, agar and carboxymethylcellulose. Suitable examples of emulsifying agents include, but are not limited to, gelatin, acacia, tragacanth, bentonite, and surfactants such as polyoxyethylene sorbitan monooleate. Suitable examples of suspending agents include, but are not limited to, sodium carboxymethylcellulose, pectin, tragacanth, veegum and acacia.

Suitable examples of coloring agents include, but are not limited to, any of the approved certified water soluble FD and C dyes, mixtures thereof, and water insoluble FD and D dyes suspended on alumina hydrate. Suitable examples of sweetening agents include, but are not limited to, dextrose, sucrose, fructose, lactose, mannitol and artificial sweetening agents such as saccharin, aspartame, sucralose, acelsulfame potassium, and other artificial sweeteners. Suitable examples of flavoring agents include, but are not limited to, synthetic flavors and natural flavors extracted from plants such as fruits and mints, and synthetic blends of compounds which produce a pleasant sensation. Suitable examples of wetting agents include, but are not limited to, propylene glycol monostearate, sorbitan monooleate, diethylene glycol monolaurate and polyoxyethylene laural ether. Suitable examples of enteric-coatings include, but are not limited to, fatty acids, fats, waxes, shellac, ammoniated shellac and cellulose acetate phthalates. Suitable examples of film coatings include, but are not limited to, hydroxyethylcellulose, sodium carboxymethylcellulose, polyethylene glycol 4000 and cellulose acetate phthalate. Suitable examples of preservatives include, but are not limited to, glycerin, methyl and propylparaben, ethylparaben, butylparaben, isobutylparaben, isopropylparaben, benzylparaben, citrate, benzoic acid, sodium benzoate and alcohol.

Suitable examples of elixirs include, but are not limited to, clear, sweetened, hydroalcoholic preparations. Pharmaceutically acceptable carriers used in elixirs include solvents. Suiatbel examples of syrups include, but are not limited to, concentrated aqueous solutions of a sugar, for example, sucrose, and may contain a preservative. An emulsion is a two-phase system in which one liquid is dispersed throughout another liquid. Pharmaceutically acceptable carriers used in emulsions can also include emulsifying agents and preservatives. Suspensions may use pharmaceutically acceptable suspending agents and preservatives. Pharmaceutically acceptable substances used in non-effervescent granules, to be reconstituted into a liquid oral dosage form, include, but are not limited to, diluents, sweeteners, and wetting agents. Pharmaceutically acceptable substances used in effervescent granules, to be reconstituted into a liquid oral dosage form, include, but are not limited to, organic acids and a source of carbon dioxide. Sources of carbon dioxide include, but are not limited to, sodium bicarbonate and sodium carbonate. Coloring and flavoring agents may be used in all such dosage forms.

Additional excipients that may be included in any dosage forms include, but are not limited to, antimicrobial agents, isotonic agents, buffers, antioxidants, local anesthetic agents, sequestering or chelating agents, analgesic agents, antiemetic agents, and other agents to enhance selected characteristics of the formulation.

Antimicrobial agents may be cidal or static, and may be antimicrobial, antifungal, antiparasitic, or antiviral. Suitable examples of commonly used antimicrobial agents include, but are not limited to, phenols or cresols, mercurials, benzyl alcohol, chlorobutanol, methyl and propyl p-hydroxybenzoic acid esters, thimerosal, benzalkonium chloride and benzethonium chloride. Acidic or basic pH may be used for antimicrobial effects in some aspects. Suitable examples of isotonic agents include, but are not limited to, sodium chloride and dextrose. Suitable examples of buffers include, but are not limited to, phosphate and citrate buffers. A non-limiting example of a chelating agent for metal ions is EDTA.

The amount of the compound(s) having Formulas (I), (II), (III), (IV), (V), (Va), (Vb), (Vc), (Vd), (Ve), (VI), (VIa), (VII), (VIII), (IX), (IXa), (IXb), (IXc), (IXd), (X), (Xa), and (XIV) to be administered may be that amount which is therapeutically effective. The dosage to be administered may depend on the characteristics of the subject being treated, e.g., the particular animal treated, age, weight, health, types of concurrent treatment, if any, and frequency of treatments, and on the nature and extent of the cancer, and can be easily determined by one skilled in the art (e.g., by the clinician). The selection of the specific dose regimen can be selected or adjusted or titrated by the clinician according to methods known to the clinician to obtain the desired clinical response. In addition, in vitro or in vivo assays may optionally be employed to help identify optimal dosage ranges. The precise dose to be employed in the compositions may also depend on the route of administration, and should be decided according to the judgment of the practitioner and each patient's circumstances.

The compositions may be prepared to provide from about 0.05 mg to about 500 mg of the compound of any of the formulas disclosed herein, such as Formula (XIV), or pharmaceutically acceptable salt thereof. In some embodiments, the compositions may comprise from about 1 mg to about 200 mg, from about 10 mg to about 200 mg, from about 10 mg to about 100 mg, from about 50 mg to about 100 mg, from about 20 mg to about 400 mg, from about 100 mg to about 300 mg, or from about 50 mg to about 250 mg of the compound of any of the formulas disclosed herein, such as Formula (XIV), or an isomer, tautomer, or solvate thereof, or a pharmaceutically acceptable salt thereof.

Suitable dosage ranges for oral administration include, but are not limited to, from about 0.001 mg/kg body weight to about 200 mg/kg body weight, from about 0.01 mg/kg body weight to about 100 mg/kg body weight, from about 0.01 mg/kg body weight to about 70 mg/kg body weight, from about 0.1 mg/kg body weight to about 50 mg/kg body weight, from 0.5 mg/kg body weight to about 20 mg/kg body weight, or from about 1 mg/kg body weight to about 10 mg/kg body weight. In some embodiments, the oral dose is about 5 mg/kg body weight.

Suitable dosage ranges for intravenous administration include, but are not limited to, from about 0.01 mg/kg body weight to about 500 mg/kg body weight, from about 0.1 mg/kg body weight to about 100 mg/kg body weight, from about 1 mg/kg body weight to about 50 mg/kg body weight, or from about 10 mg/kg body weight to about 35 mg/kg body weight.

Suitable dosage ranges for other routes of administration can be calculated based on the forgoing dosages as known by one skilled in the art. For example, recommended dosages for intradermal, intramuscular, intraperitoneal, subcutaneous, epidural, sublingual, intracerebral, transdermal, or inhalation are in the range from about 0.001 mg/kg body weight to about 200 mg/kg body weight, from about 0.01 mg/kg body weight to about 100 mg/kg body weight, from about 0.1 mg/kg body weight to about 50 mg/kg body weight, or from about 1 mg/kg body weight to about 20 mg/kg body weight. Effective doses may be extrapolated from dose-response curves derived from in vitro or animal model test systems. Such animal models and systems are well known in the art.

The disclosure also provides methods for reactivation of the p53 pathway. Such methods may comprise treatment methods, by which reactivation of the p53 pathway treats any condition in which the p53 pathway plays a role, including cancer.

In some embodiments, the methods of treatment further comprise administering another therapy to the subject. In some embodiments, the another therapy is radiation therapy, chemotherapy, immunotherapy, or a combination thereof. In some embodiments, the another therapy is administered to the subject at a lower level compared to the level when administered in the absence of the compound(s) of Formulas (I), (II), (III), (IV), (V), (Va), (Vb), (Vc), (Vd), (Ve), (VI), (VIa), (VII), (VIII), (IX), (IXa), (IXb), (IXc), (IXd), (X), (Xa), and (XIV). In some embodiments, the another therapy is administered to the subject at a lower level compared to the level when administered in the absence of the compound(s) of Formula (XIV).

In some embodiments, the methods comprise contacting a cell with mutated p53 with an effective amount of a compound or composition comprising any of the formulas described herein, such as Formula (XIV), or any combination thereof, or any pharmaceutically acceptable salt thereof.

The composition may comprise any dosage form and/or any excipients, including those described or exemplified herein.

In some embodiments, the methods comprise contacting a cancer cell with an effective amount of a compound or composition comprising any one of Formulas (I), (II), (III), (IV), (V), (Va), (Vb), (Vc), (Vd), (Ve), (VI), (VIa), (VII), (VIII), (IX), (IXa), (IXb), (IXc), (IXd), (X), (Xa), and (XIV), or any combination thereof, or any pharmaceutically acceptable salt thereof. In some embodiments, the methods comprise contacting a cancer cell with an effective amount of a compound or composition comprising Formula (XIV), or any pharmaceutically acceptable salt thereof. The composition may comprise any dosage form and/or any excipients, including those described or exemplified herein.

In some embodiments, the methods comprise contacting a cell having a p53 mutation with an effective amount of a compound or composition comprising any one of Formulas (I), (II), (III), (IV), (V), (Va), (Vb), (Vc), (Vd), (Ve), (VI), (VIa), (VII), (VIII), (IX), (IXa), (IXb), (IXc), (IXd), (X), (Xa), and (XIV), or any combination thereof, or any pharmaceutically acceptable salt thereof. In some embodiments, the methods comprise contacting a cell having a p53 mutation with an effective amount of a compound or composition comprising any one of the compounds within Formula (XIV), or any pharmaceutically acceptable salt thereof. The composition may comprise any dosage form and/or any excipients, including those described or exemplified herein. In contacting the cell in this manner, the compound or composition reactivates the p53 pathway. The cell may be within the body of a subject. The cell may be a cancer cell, such as a prostate cancer cell, a breast cancer cell, a kidney cancer cell, an ovarian cancer cell, a lymphoma cell, a melanoma cell, a leukemia cell, or a glioblastoma cell.

In some embodiments, methods for treating a cancer patient comprise administering to the patient a compound or composition comprising any one of Formulas (I), (II), (III), (IV), (V), (Va), (Vb), (Vc), (Vd), (Ve), (VI), (VIa), (VII), (VIII), (IX), (IXa), (IXb), (IXc), (IXd), (X), (Xa), and (XIV), or any combination thereof, or any pharmaceutically acceptable salt thereof, in an amount effective to treat the cancer. In some embodiments, methods for treating a cancer patient comprise administering to the patient a compound or composition comprising any of the compounds within Formula (XIV), or any pharmaceutically acceptable salt thereof, in an amount effective to treat the cancer. In some embodiments, the effective amount is an amount effective to reactivate the p53 pathway in cancer cells within the patient's body. In some embodiments, the patient is a human cancer patient. In some embodiments, the cancer is associated with a p53 gain of function (GOF) mutation. The cancer may be any cancer in which the p53 pathway is mutated including, but are not limited to, prostate cancer, breast cancer, kidney cancer, ovarian cancer, lymphoma, leukemia, melanoma, or glioblastoma.

In some embodiments, the cancer is selected from the group consisting of a carcinoma, a sarcoma, a colorectal cancer, a lymphoma, a leukemia, a blastoma, a germ cell cancer, a breast cancer, a lung cancer, a pancreatic cancer, a stomach cancer, a bone cancer, an ovarian cancer, a prostate cancer, a head and neck cancer, a bladder cancer, a cervical cancer, a colon cancer, a skin cancer, a gliobastoma cancer, an esophageal cancer, an oral cancer, a gallbladder cancer, a liver cancer, a testicular cancer, a uterine cancer, a thyroid cancer, and a throat cancer. In some embodiments, the cancer is a colorectal cancer, a head and neck cancer, a pancreatic cancer, a breast cancer, a colon cancer, a lung cancer, or a gliobastoma cancer.

Administration may be according to any technique or route suitable to the cancer being treated or the patient's needs. Administration may be, for example, oral, parenteral, or via direct injection. Administration may be directly to the tumor or to a location proximal to the tumor. Delivery may be via the bloodstream. Delivery may include active targeting, for example, by conjugating the compound to an antibody that binds to an antigen on the tumor being treated. Delivery may also be passive.

Uses of one or more compounds which reactivate the p53 pathway according to any one of Formulas (I), (II), (III), (IV), (V), (Va), (Vb), (Vc), (Vd), (Ve), (VI), (VIa), (VII), (VIII), (IX), (IXa), (IXb), (IXc), (IXd), (X), (Xa), and (XIV), or a pharmaceutically acceptable salt thereof, or a composition thereof, in the treatment of cancer or tumors are also provided. The disclosure provides compounds which reactivates the p53 pathway according to any one of Formulas (I), (II), (III), (IV), (V), (Va), (Vb), (Vc), (Vd), (Ve), (VI), (VIa), (VII), (VIII), (IX), (IXa), (IXb), (IXc), (IXd), (X), (Xa), and (XIV), or a pharmaceutically acceptable salt thereof, or a composition thereof, in the treatment of prostate cancer. The disclosure provides compounds which reactivate the p53 pathway according to any one of Formulas (I), (II), (III), (IV), (V), (Va), (Vb), (Vc), (Vd), (Ve), (VI), (VIa), (VII), (VIII), (IX), (IXa), (IXb), (IXc), (IXd), (X), (Xa), and (XIV), or a pharmaceutically acceptable salt thereof, or a composition thereof, in the treatment of kidney cancer. The disclosure provides uses of compounds which reactivate the p53 pathway according to any one of Formulas (I), (II), (III), (IV), (V), (Va), (Vb), (Vc), (Vd), (Ve), (VI), (VIa), (VII), (VIII), (IX), (IXa), (IXb), (IXc), (IXd), (X), (Xa), and (XIV), or a pharmaceutically acceptable salt thereof, or a composition thereof, in the treatment of breast cancer. The disclosure provides uses of compounds which reactivate the p53 pathway according to any one of Formulas (I), (II), (III), (IV), (V), (Va), (Vb), (Vc), (Vd), (Ve), (VI), (VIa), (VII), (VIII), (IX), (IXa), (IXb), (IXc), (IXd), (X), (Xa), and (XIV), or a pharmaceutically acceptable salt thereof, or a composition thereof, in the treatment of ovarian cancer. The disclosure provides uses of compounds which reactivates the p53 pathway according to any one of Formulas (I), (II), (III), (IV), (V), (Va), (Vb), (Vc), (Vd), (Ve), (VI), (VIa), (VII), (VIII), (IX), (IXa), (IXb), (IXc), (IXd), (X), (Xa), and (XIV), or a pharmaceutically acceptable salt thereof, or a composition thereof, in the treatment of melanoma. The disclosure provides uses of compounds which reactivate the p53 pathway according to any one of Formulas (I), (II), (III), (IV), (V), (Va), (Vb), (Vc), (Vd), (Ve), (VI), (VIa), (VII), (VIII), (IX), (IXa), (IXb), (IXc), (IXd), (X), (Xa), and (XIV), or a pharmaceutically acceptable salt thereof, or a composition thereof, in the treatment of lymphoma. The disclosure provides uses of compounds which reactivate the p53 pathway according to any one of Formulas (I), (II), (III), (IV), (V), (Va), (Vb), (Vc), (Vd), (Ve), (VI), (VIa), (VII), (VIII), (IX), (IXa), (IXb), (IXc), (IXd), (X), (Xa), and (XIV), or a pharmaceutically acceptable salt thereof, or a composition thereof, in the treatment of leukemia. The disclosure provides uses of compounds which reactivate the p53 pathway according to any one of Formulas (I), (II), (III), (IV), (V), (Va), (Vb), (Vc), (Vd), (Ve), (VI), (VIa), (VII), (VIII), (IX), (IXa), (IXb), (IXc), (IXd), (X), (Xa), and (XIV), or a pharmaceutically acceptable salt thereof, or a composition thereof, in the treatment of glioblastoma. Uses may be in the manufacture of a medicament for cancer treatment as provided.

The present disclosure also provides methods of preparing a compound of Formula XIV

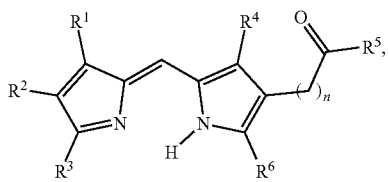

(XIV)

wherein:

R$^1$ and R$^2$ are, independently, selected from the group consisting of H, OH, halogen, —C$_{1-6}$fluoroalkyl, —CN, —NO$_2$, —OR$^7$, —SR$^7$, —S(=O)R$^7$, —S(=O)$_2$R$^7$, —NHS(=O)$_2$R$^7$, —C(=O)R$^7$, —OC(=O)R$^7$, —CO$_2$R$^7$, —OCO$_2$R$^7$, —CH(R$^7$)$_2$, —N(R$^7$)$_2$, —C(=O)N(R$^7$)$_2$, —NHC(=O)NHR$^7$, —NHC(=O)R$^7$, —NHC(=O)OR$^7$, —C(OH)(R$^7$)$_2$, and —C(NH$_2$)(R$^7$)$_2$;

each R$^7$ is, independently, H, halogen, or C$_1$-C$_6$alkyl, wherein the alkyl group is optionally substituted by 1, 2, 3, 4, or 5 substituents independently selected from halogen, OH, CN, and NO$_2$;

R$^3$ is an optionally substituted aryl or an optionally substituted heteroaryl;

R$^4$, R$^5$, and R$^6$ are, independently, —OH, —C$_{1-10}$alkyl, —OC$_{1-10}$alkyl, or —SC$_{1-10}$alkyl, wherein each alkyl group is, independently, optionally substituted by 1, 2, 3, 4, or 5 substituents independently selected from halogen, OH, CN, and NO$_2$; and n is an integer from 0 to 5;

wherein the method comprises:

admixing a solvent, an acid, a compound of Formula XII

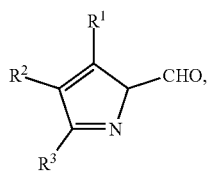

(XII)

and a compound of Formula XIII

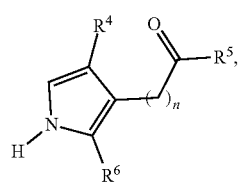

(XIII)

at a temperature sufficient to result in the formation of the compound of Formula XIV.

In some embodiments, the acid is selected from the group consisting of hydrochloric acid, hydrobromic acid, hydrofluoric acid, acetic acid, phosphoric acid, toluenesulfonic acid, sulfuric acid, and nitric acid.

In some embodiments, the temperature is about from about 0° C. to about 100° C.

In some embodiments, the solvent is a protic solvent. In some embodiments, the solvent is an aprotic solvent.

In some embodiments, the method set forth above further comprises alkylating the compound of Formula XIII, when R$^5$ is OH, prior to reacting with the compound of Formula XII, by admixing the compound of Formula XIII with an alkylating agent, a base, a nucleophilic catalyst salt, and a solvent at a temperature sufficient to result in the formation of the compound of Formula XIV. In some embodiments, the alkylating agent is selected from the group consisting of a linear —C$_{1-6}$haloalkyl, a linear —C$_{1-20}$haloalkyl, a branched —C$_{1-6}$haloalkyl, and a branched —C$_{1-20}$haloalkyl. In some embodiments, the base is selected from the group consisting of potassium carbonate, cesium carbonate, sodium carbonate, and calcium carbonate. In some embodiments, the nucleophilic catalyst salt is selected from the group consisting of potassium iodide, sodium iodide, calcium iodide, and tetra-n-butyl ammonium iodide. In some embodiments, the solvent is a protic solvent. In some embodiments, the solvent is an aprotic solvent. In some embodiments, the temperature is from about 0° C. to about 100° C.

In some embodiments, the method set forth above further comprises alkylating the compound of Formula XIV, when R$^5$ is OH, after reacting the compound of Formula XIII with the compound of Formula XII, by admixing the compound of Formula XIV with an alkylating agent, a base, a nucleophilic catalyst salt, and a solvent at a temperature sufficient to result in the formation of the compound of Formula XIV. In some embodiments, the alkylating agent is selected from the group consisting of a linear —C$_{1-6}$haloalkyl, a linear —C$_{1-20}$haloalkyl, a branched —C$_{1-6}$haloalkyl, and a branched —C$_{1-20}$haloalkyl. In some embodiments, the base is selected from the group consisting of potassium carbonate, cesium carbonate, sodium carbonate, and calcium carbonate. In some embodiments, the nucleophilic catalyst salt is selected from the group consisting of potassium iodide, sodium iodide, calcium iodide, and tetra-n-butyl ammonium iodide. In some embodiments, the solvent is a protic solvent. In some embodiments, the solvent is an aprotic solvent. In some embodiments, the temperature is from about 0° C. to about 100° C.

The following examples are provided to further describe the disclosed embodiments in even greater detail. The examples are intended to illustrate, and not to limit, the embodiments disclosed herein.

Example 1: Prodigiosin Analogs and Cell Lines

As used herein, P01 is prodigiosin, P104 is the prodigiosin analog of Formula (VIa), P105 is the prodigiosin analog of Formula (Vb), P107 is the prodigiosin analog of Formula (Vd), P108 is the prodigiosin analog of Formula (Ve), P109 is the prodigiosin analog of Formula (Va), P106 is the prodigiosin analog of Formula (Vc), P301 is the prodigiosin analog of Formula (VII), P302 is the prodigiosin analog of Formula (Xa), P303 is the prodigiosin analog of Formula (IXb), P304 is the prodigiosin analog of Formula (IXa), P305 is the prodigiosin analog of Formula (IXc), P306 is the prodigiosin analog of Formula (IXd), and P01RC is Obatoclax. P101 is another prodigiosin analog of Formula (XI).

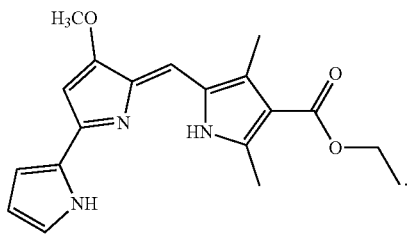

(XI)

Various cell lines were obtained for testing the anti-cancer properties of the prodigiosin analogs described above. SW480, DLD-1, DLD1-p73KD, HCT116, and p53-null HCT116 were generated in the laboratory and each cell stably expressed a p-53 regulated luciferase reporter. MRCS and Wi38 were obtained from the ATCC and cultured as recommended. Cells were regularly authenticated by bioluminescence, growth, and morphologic observation.

p53-Responsive Luciferase Reporter Assay

Figures 2A, 2B:
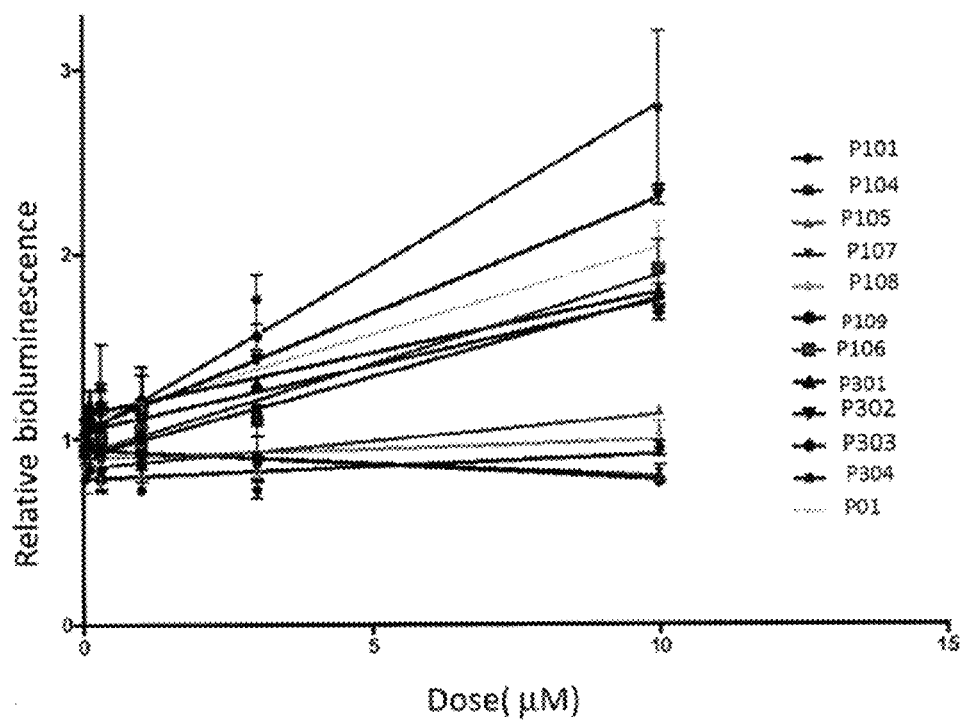
FIGS. 2A and 2B depict various aspects of a p53-responsive Luciferase Reporter Assay experiment conducted using prodigiosin analogs.

The p53-mutant SW480 human colon cancer cells, stably expressing a p53-responsive luciferase reporter, were used for compound screening. The SW480 cells were treated with P01, P101, P104, P105, P106, P107, P108, P109, P301, P302, P303, and P304 in concentrations ranging from 0.03 µM to 10 µM for 4 hours. After the treatment, cells were imaged by using an IVIS Imaging System (Xenogen) to detect luciferase activity (see, FIGS. 1, 2A, and 2B). Positive hits with strong activity for luciferase induction were selected for additional testing.

Western Blotting

Figure 3:
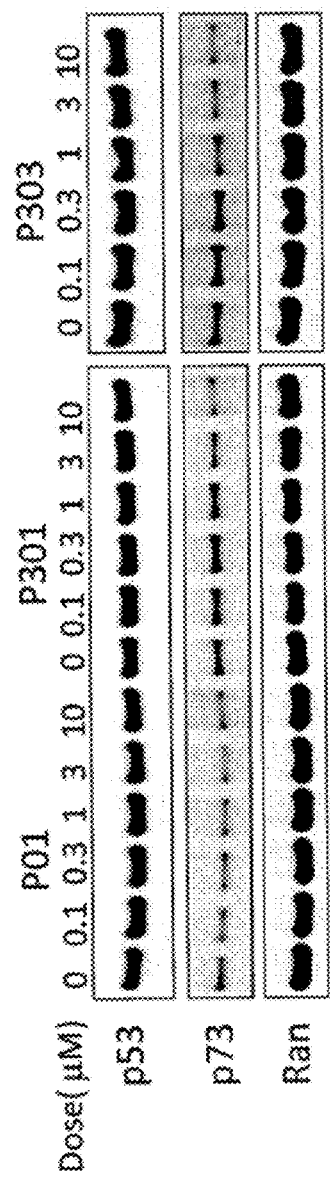
FIG. 3 depicts various aspects of a western blotting experiment conducted using prodigiosin analogs.
Figure 4:
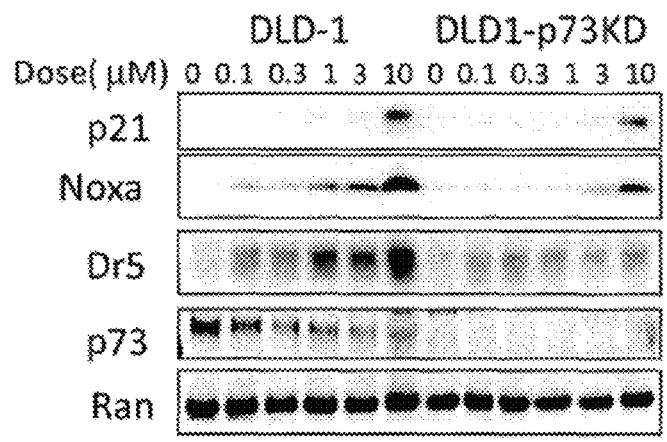
FIG. 4 depicts various aspects of a western blotting experiment conducted using prodigiosin analogs.
Figure 5:
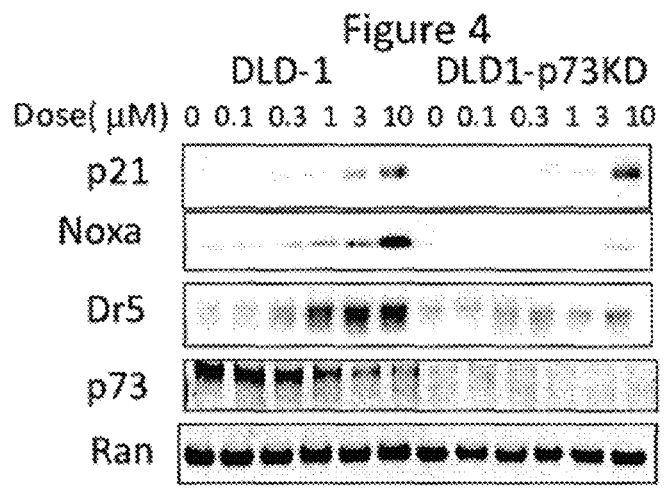
FIG. 5 depicts various aspects of a western blotting experiment conducted using prodigiosin analogs.
Figure 6:
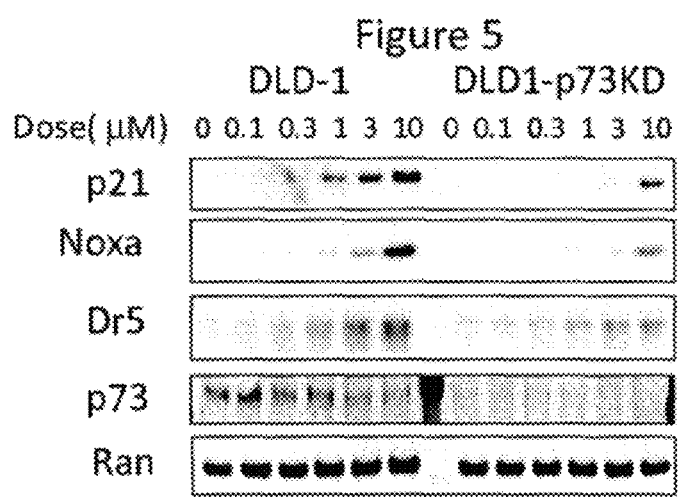
FIG. 6 depicts various aspects of a western blotting experiment conducted using prodigiosin analogs.
Figure 7:
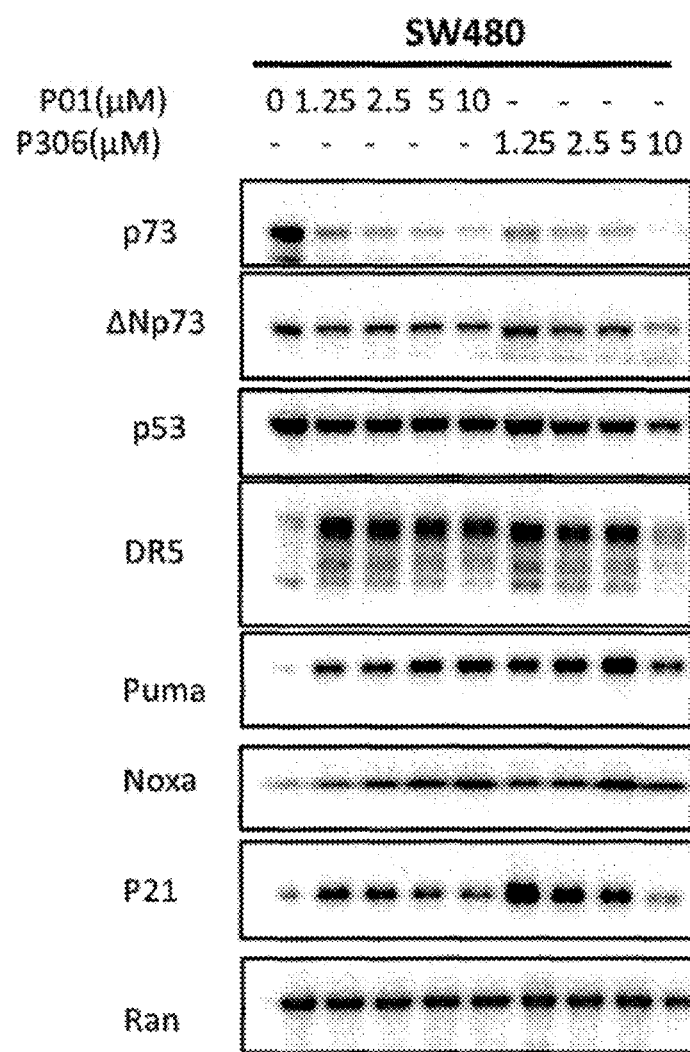
FIG. 7 depicts various aspects of a western blotting experiment conducted using prodigiosin analogs.
Figure 8:
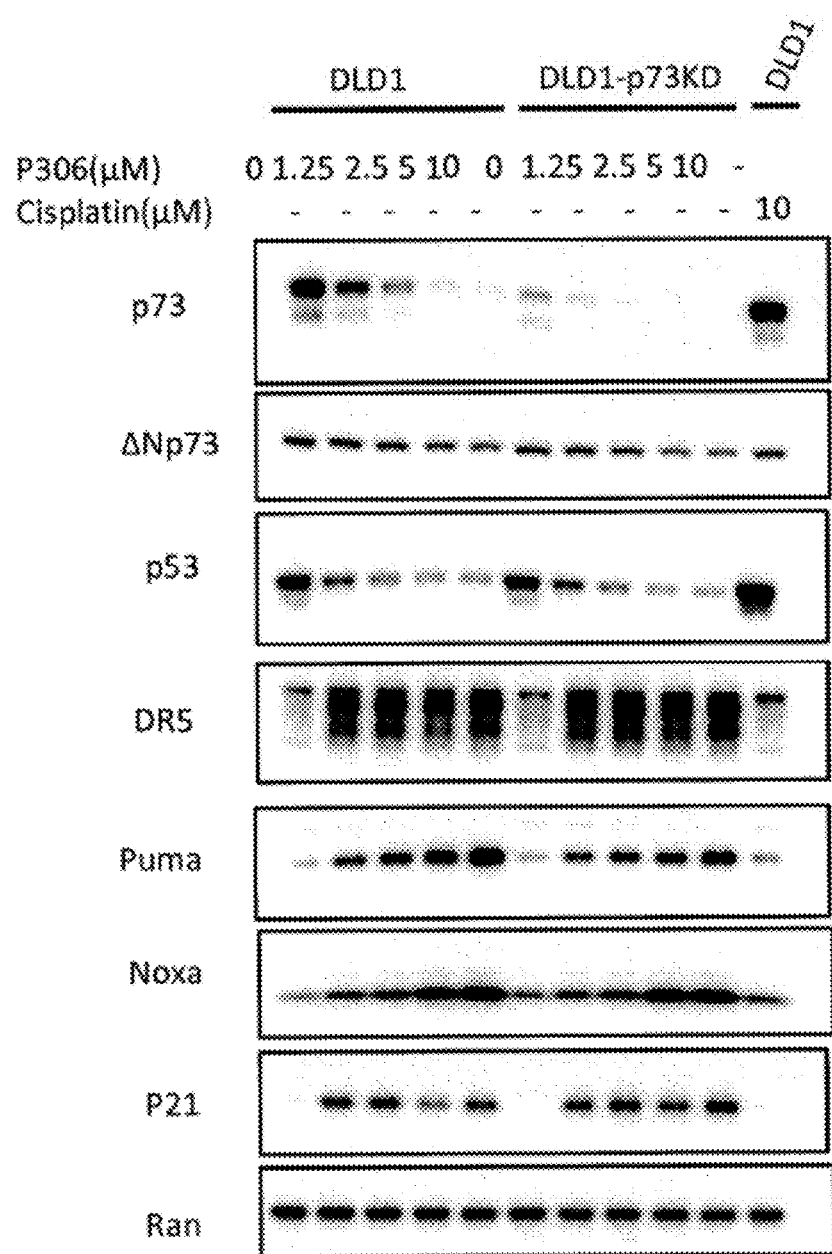
FIG. 8 depicts various aspects of a western blotting experiment conducted using prodigiosin analogs.
Figure 9:
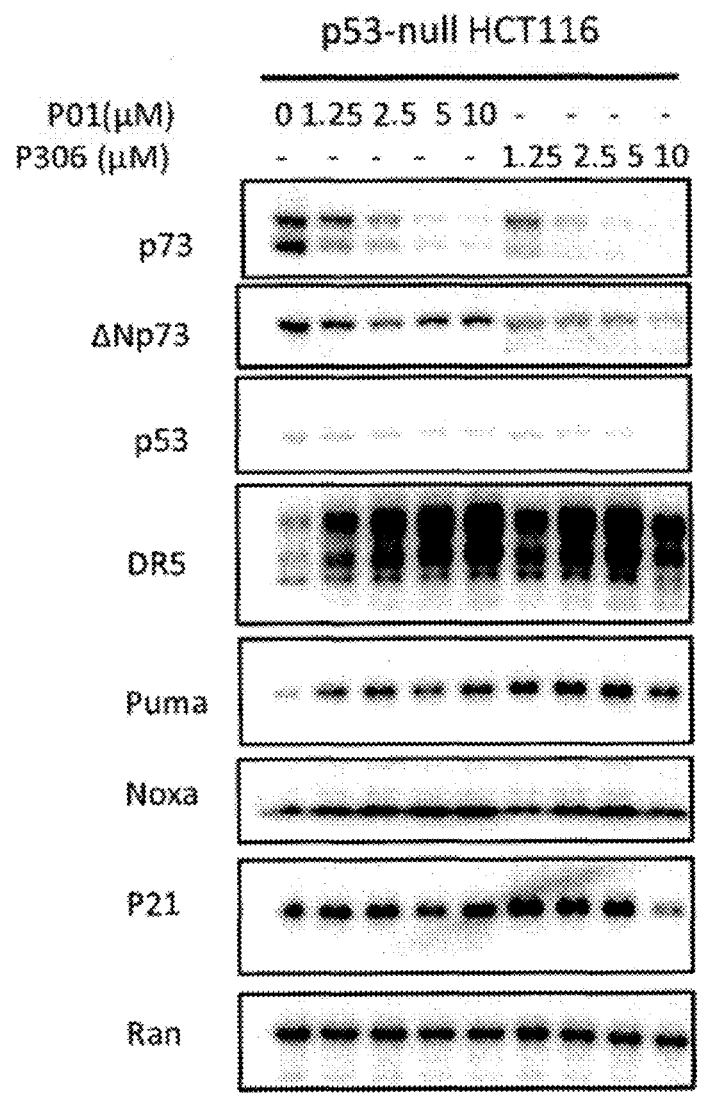
FIG. 9 depicts various aspects of a western blotting experiment conducted using prodigiosin analogs.
Figure 10:
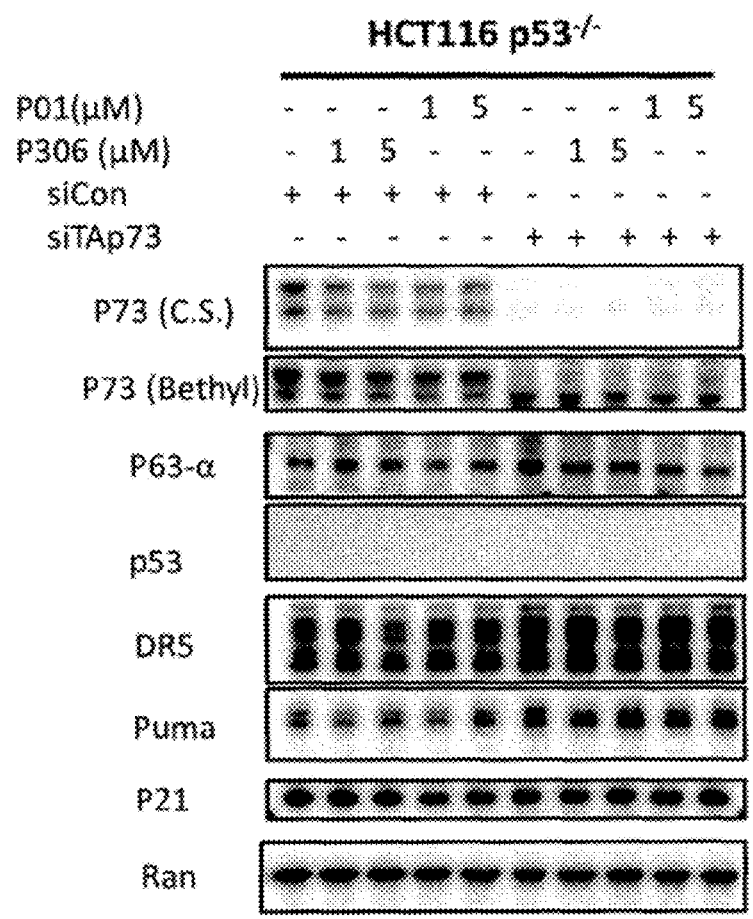
FIG. 10 depicts various aspects of a western blotting experiment conducted using prodigiosin analogs.
Figure 11:
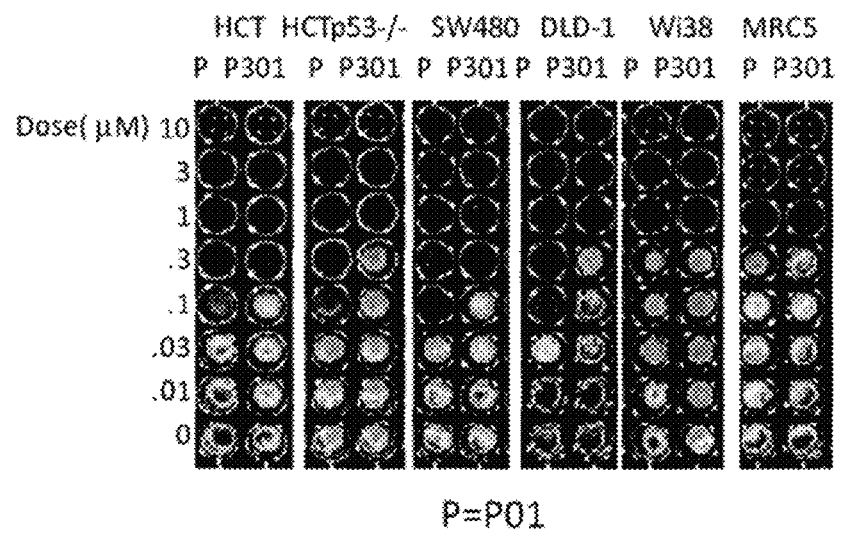
FIG. 11 depicts various aspects of a CellTiter-Glo luminescent cell viability assay experiment conducted using prodigiosin analogs.
Figure 12:
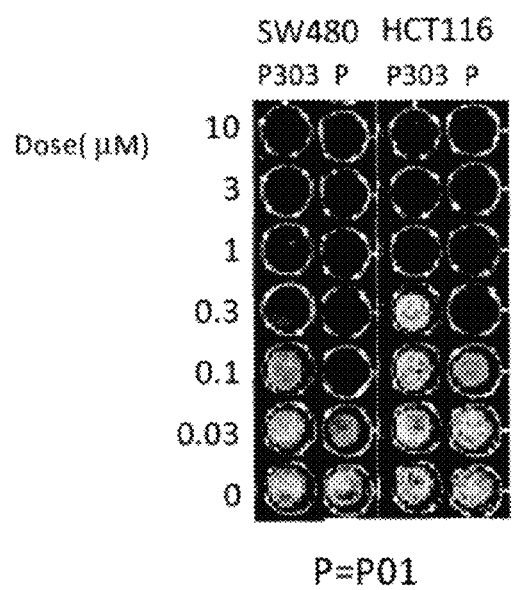
FIG. 12 depicts various aspects of a CellTiter-Glo luminescent cell viability assay experiment conducted using prodigiosin analogs.
Figure 13:
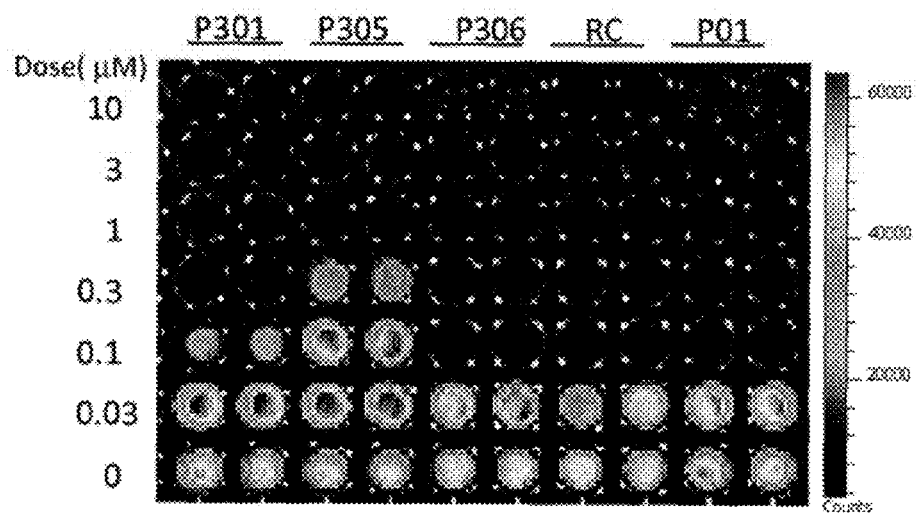
FIG. 13 depicts various aspects of a CellTiter-Glo luminescent cell viability assay experiment conducted using prodigiosin analogs.
Figure 14:
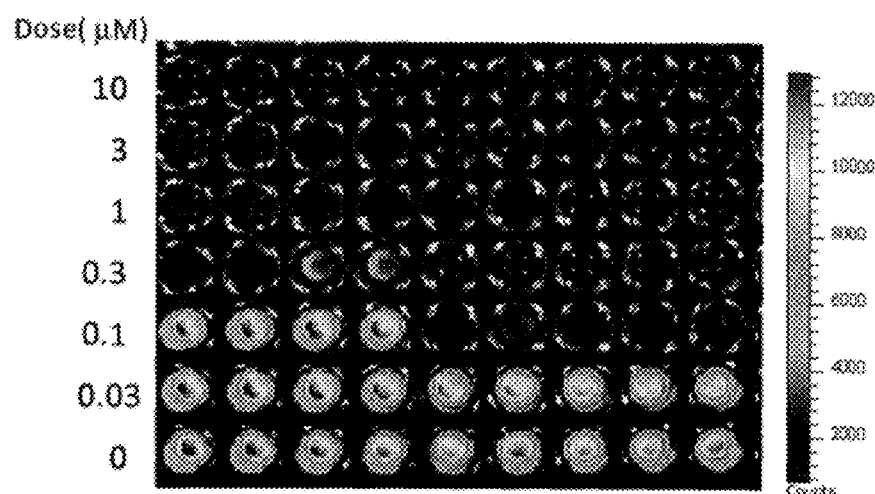
FIG. 14 depicts various aspects of a CellTiter-Glo luminescent cell viability assay experiment conducted using prodigiosin analogs.
Figures 15, 16:
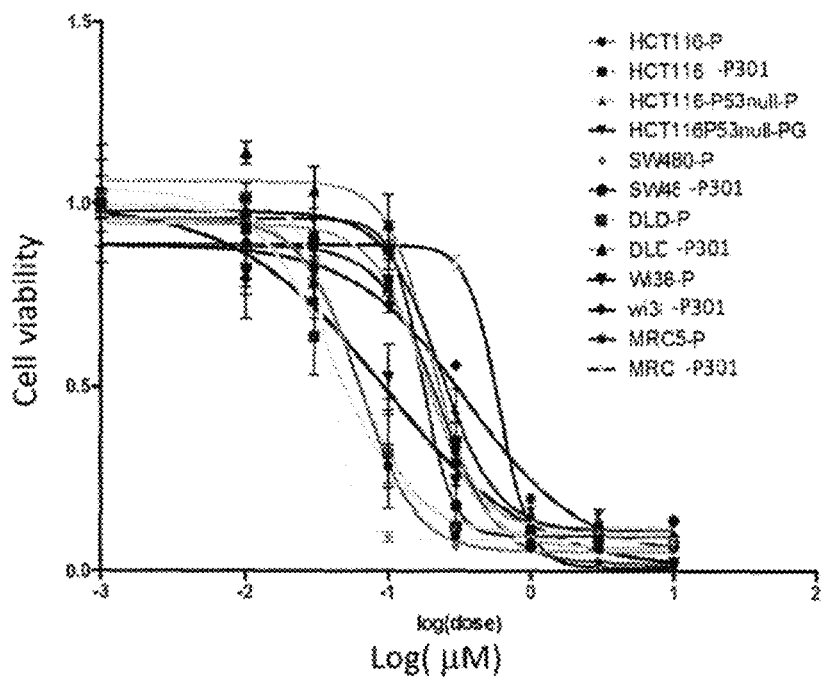
FIG. 15 depicts various aspects of a CellTiter-Glo luminescent cell viability assay experiment conducted using prodigiosin analogs.
FIG. 16 depicts various aspects of a CellTiter-Glo luminescent cell viability assay experiment conducted using prodigiosin analogs.

After treatment, protein lysates were collected for Western blot analysis. Twenty-five micrograms of protein were used for SDS-PAGE. After primary and secondary antibody incubations, the signal was detected with a chemiluminescent detection kit, followed by autoradiography or Syngen. In FIG. 3, SW480 cells were treated with P01, P301, and P303 in various concentrations for 16 hours, and tested for p 53, p'73, and Ran proteins. In FIGS. 4-6, DLD-1 and DLD1-p73KD cells were treated with P01 (see, FIG. 4), P301 (see, FIG. 5), and P303 (see, FIG. 6) in various concentrations for 18 hours, and tested for p21, Noxa, DR5, p'73, and Ran proteins. In FIG. 7, SW480 cells were treated with P01 and P306 in various concentrations for 18 hours and tested for p'73, ΔNp73, p53, DR5, Puma, Noxa, P21, and Ran proteins. In FIG. 8, DLD1 and DLD1-p73KD cells were treated with P306 and Cispatlin for 18 hours, and tested for p'73, ΔNp73, p53, DR5, Puma, Noxa, P21, and Ran proteins. In FIG. 9, p53-null HCT116 cells were treated with P01 and P306 in various concentrations for 18 hours, and tested for p'73, ΔNp73, p53, DR5, Puma, Noxa, P21, and Ran proteins. In FIG. 10, p53-null HCT116 cells were treated with P01 and P306, alone or in combination with SiCon or SiTAp73, in various concentrations for 6 hours, and tested for p73 (C.S.), p73 (Bethyl), P63-α, p53, DR5, Puma, P21, and Ran proteins.

CellTiter-Glo® Luminescent Cell Viability Assay

SW480, DLD-1, DLD1-p73KD, HCT116, and p53-null HCT116, MRCS and Wi38 cells were seeded at 5,000 cells per well on 96-well plates. The cells were treated for 72 hours with P01, P301, P303, P305, P306, and P01RC in various concentrations. Then, cells were mixed with an equal volume of CellTiterGlo® reagents (Promega), following the manufacturer's protocol, and bioluminescence imaging was measured using the IVIS imager. The results of the luminescent cell viability assay are presented in FIGS. 11-16.

Flow Cytometry Assay

Figure 17:
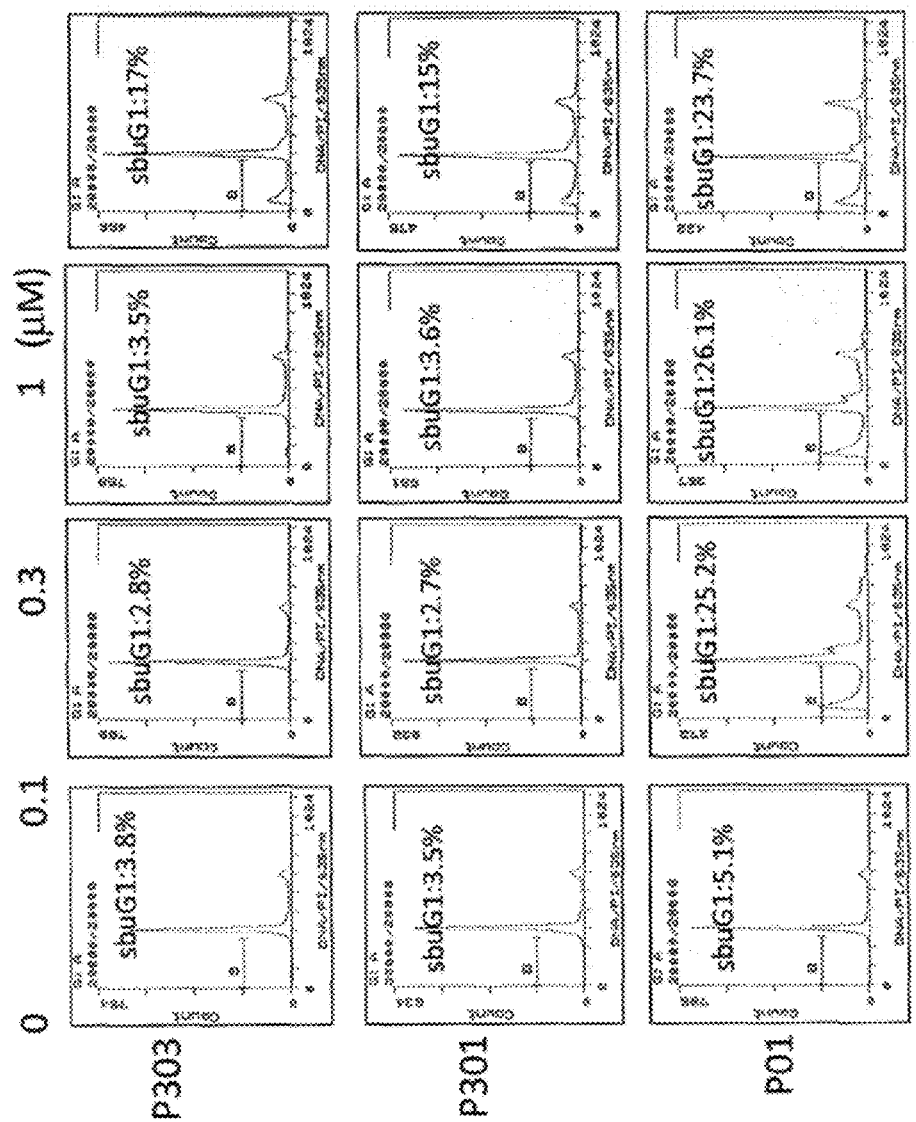
FIG. 17 depicts various aspects of a flow cytometry assay experiment conducted using prodigiosin analogs.
Figure 18:
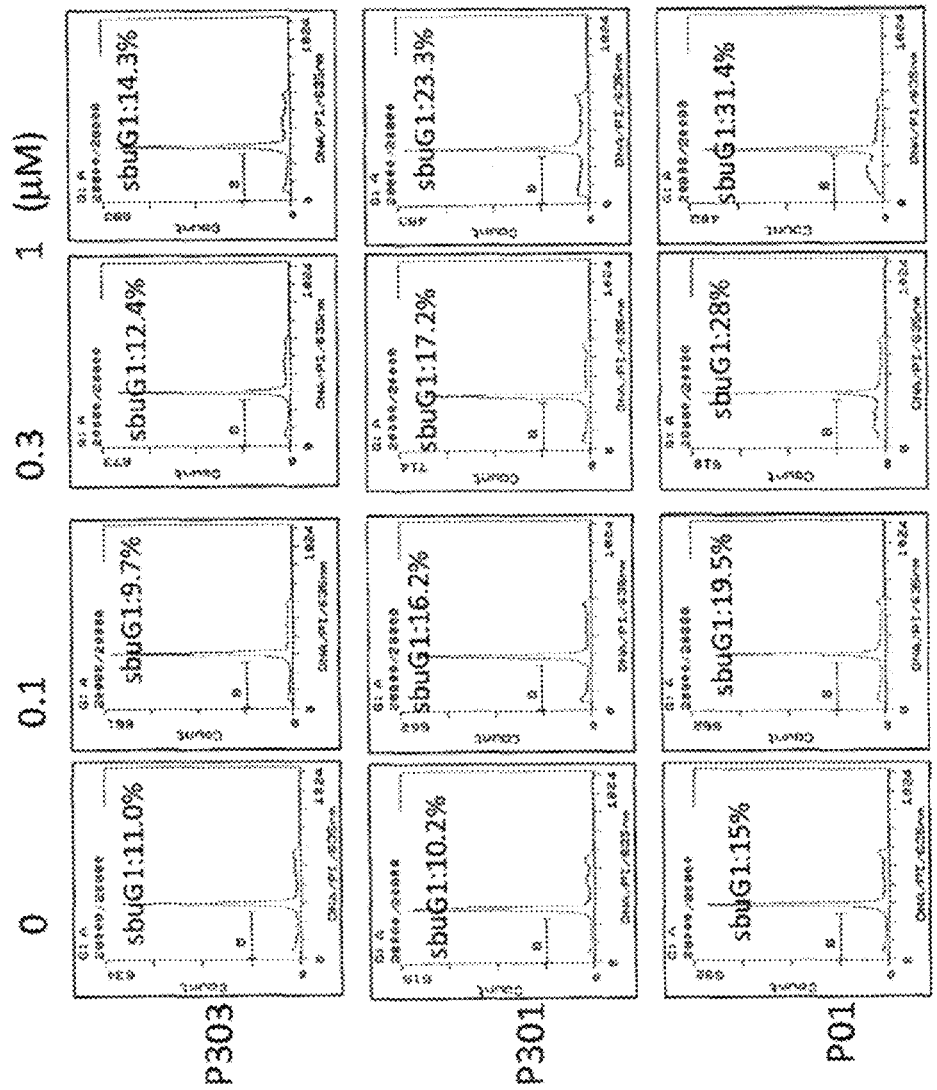
FIG. 18 depicts various aspects of a flow cytometry assay experiment conducted using prodigiosin analogs.
Figure 19:
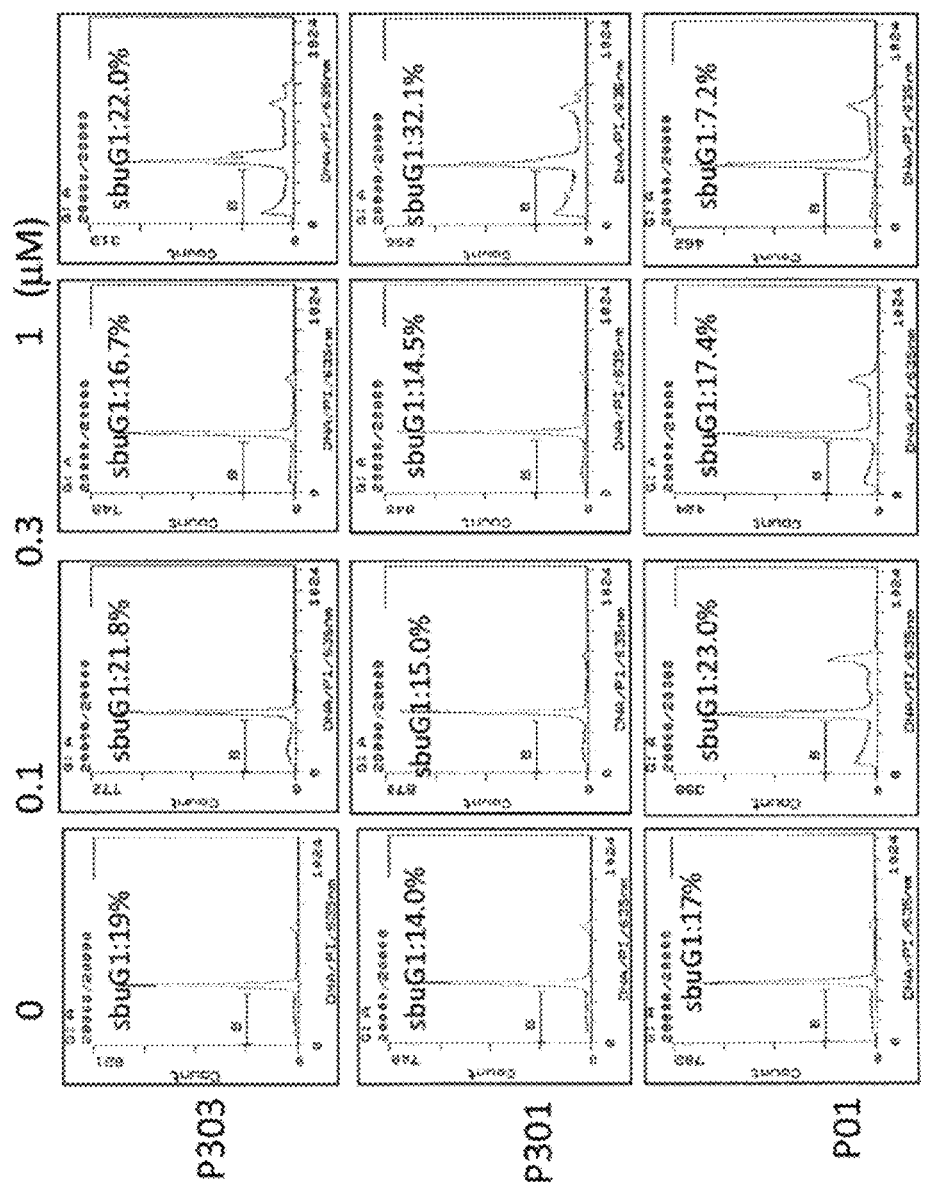
FIG. 19 depicts various aspects of a flow cytometry assay experiment conducted using prodigiosin analogs.

After treatment with P01, P301, and P303 in various concentrations for 72 hours, SW480 (see, FIG. 17), HT29 (see, FIG. 18), and DLD-1 (see, FIG. 19) cells were harvested, fixed by ethanol, and stained by propidium iodide. Flow cytometry was then performed on the resulting cells.

Colony Formation Assay 6-well plates were filled with 500 cells per well of SW480 (see, FIG. 20) and HT29 (see, FIG. 21) cells. The cells were then treated with P01, P301, and P303 in various concentrations for 72 hours. The cells were then cultured with drug-free complete medium for 2 weeks with fresh medium changed every 3 days. Cells were fixed with 10% formalin and stained with 0.05% crystal violet at the end of 2 weeks period of cell culture.

Immunofluorescence

Figure 22:
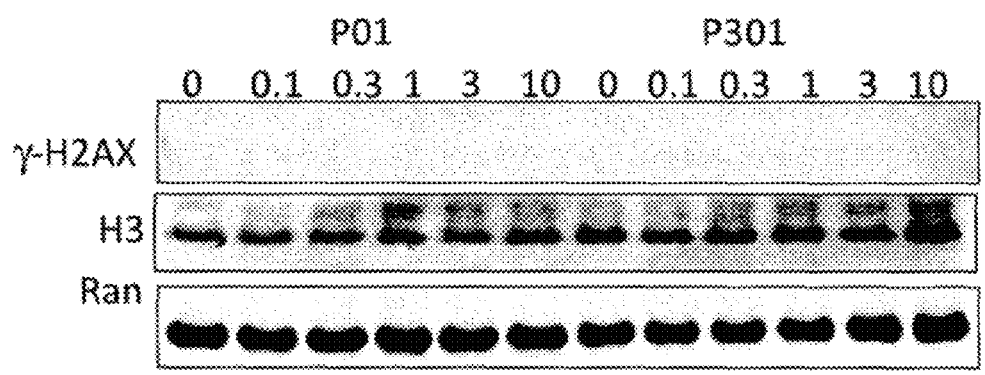
FIG. 22 depicts various aspects of an immunofluorescence experiment conducted using prodigiosin analogs.
Figure 23:
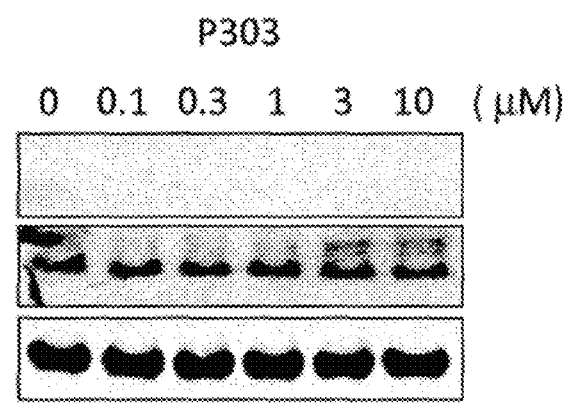
FIG. 23 depicts various aspects of an immunofluorescence experiment conducted using prodigiosin analogs.
Figure 24:
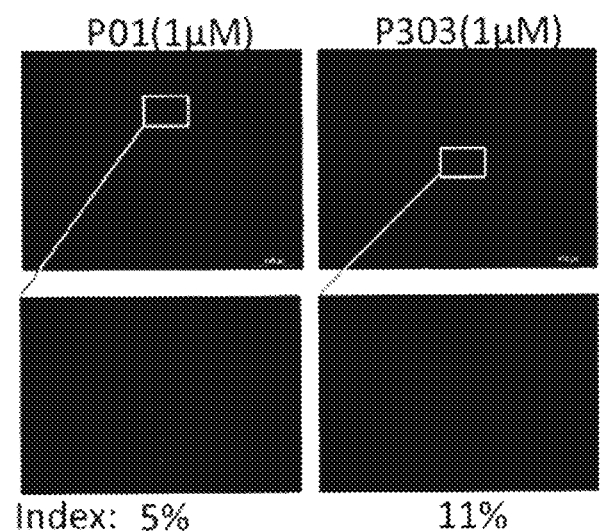
FIG. 24 depicts various aspects of an immunofluorescence experiment conducted using prodigiosin analogs.
Figure 25:
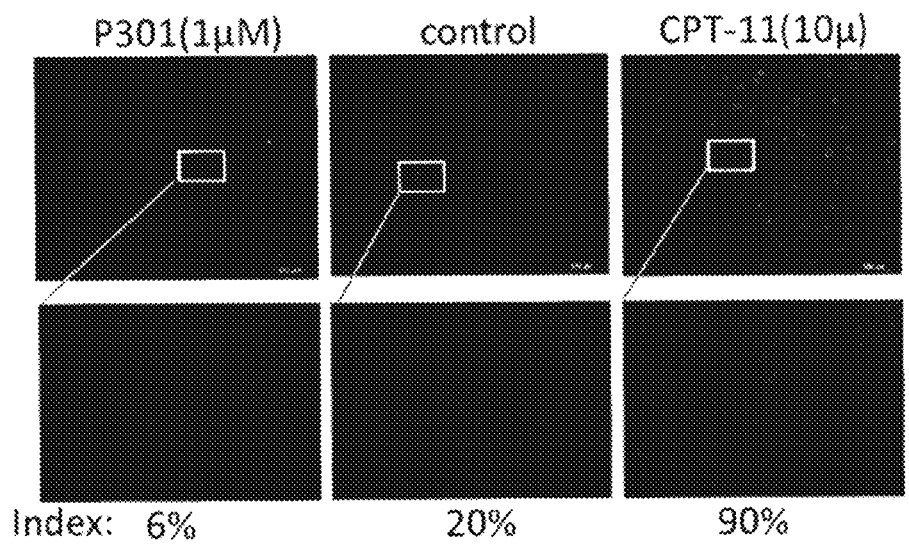
FIG. 25 depicts various aspects of an immunofluorescence experiment conducted using prodigiosin analogs.

SW480 cells were seeded in four-chamber slides. After treatment with P01, P301, P303, and Irinotecan (CPT-11) at various concentrations for 8 hours, cells were fixed by Cytofix/Cytoperm (BD Biosciences) for 30 minutes. Untreated cells were also fixed as a control. Western blotting was used to test for γ-H2AX, H3, and Ran proteins in the cells treated with P01, P301, P303 (see, FIGS. 22 and 23). Fixed cells were blocked for 2 hours, followed by primary antibody incubation for 2 hours and secondary antibody incubation for 2 hours at room temperature. After washing, samples mounted and were examined by fluorescence microscopy (see, FIGS. 24 and 25).

As can be seen from the experimental results, at least prodigiosin analogs P301 (i.e., Formula (VII)), P303 (i.e., Formula (Xa)), and P306 (i.e., Formula (IXd)) potently induced cell death of p53 mutant colon cancer cell line SW480, DLD1 and p53-null cell line HCT116. The $IC_{50}$ values are within nanomolar range. The prodigiosin analogs induced cell death in cancer cells with no genotoxicity. P301 and P303 induced the expression of p53-target genes via p73. P306 induced mutant p53 and ΔNp73 degradation and the expression of p53-target genes.

Example 2: PG3-Oc (Formula (IXd))

Materials and Methods

1) Cell lines: HT29, SW480, DLD-1, HCT116, and p53-null HCT116 cells, H1975, MDA-MD-231, U251, FaDu, CAL-27, PANC-1, Aspc-1, and MRCS were obtained from the ATCC and cultured as recommended. Cells were regularly authenticated by bioluminescence, growth, and morphologic observation. The cells were routinely examined for *Mycoplasma* and all cell lines underwent STR authentication.

2) Western blotting: After treatment, protein lysates were collected for Western blot analysis. 15 µg of protein was used for SDS-PAGE. After primary and secondary antibody incubations, the signal was detected by chemiluminescent detection kit, imaged by Syngene (Imgen Technologies). Antibodies for Puma, $FLIP_{L/S}$ and p53 (Santa Cruz Biotechnology), cleaved caspase 8, caspase 9, caspase 3, cleavage PARP, eIF2α, p-eIF2α(Ser51), CHOP, ATF4, DR5, FOXO3a, p-FOXO3a(Ser253), NF-κB p65, p-NF-κB p65 (Ser536), c-Jun, p-c-Jun(Ser63), JNK, p-JNK(Thr183/Tyr185) (Cell Signaling Technology), Noxa, p21 (Calbiochem), p73 (Bethyl laboratories Inc), Ran (BD Biosciences), β-actin (Sigma).

3) Cell viability assay: Cells were seeded in 96-well plate ($6\times10^3$ cells/well). Cells were treated with different concentrations of compounds or dimethyl sulfoxide (DMSO) control for 72 hours. The cell viability was assessed by CellTiterGlo bioluminescent cell proliferation assay (Promega), following the manufacturer's protocol. Bioluminescence imaging was measured using the IVIS imager. Percentage of cell viability (mean±SEM) at each dose was calculated against the respective DMSO control. The $IC_{50}$ values were determined from the sigmoidal dose-response curves using GraphPad Prims4.

4) Caspase activity assay: Cells were seeded in 96-well plate ($1\times10^4$ cells/well). Cells were treated with different concentrations of compounds or DMSO control for 24 hours. The caspase 3/7 activity was assessed by Caspase-Glo® 3/7 Assay kit (Promega), following the manufacturer's protocol. Bioluminescence imaging was measured using the IVIS imager. Caspase activity was normalized to cell numbers and compared to those of DMSO treatment as control in each cell line. Data is reported as mean RLU+ SEM (n=3).

5) Colony formation assays: Five hundred cells were seeded per well on 6-well plates and treated with different concentrations of compounds for 24 hours, then, cells were cultured with drug-free complete medium for 2 weeks with fresh medium changed every 7 days. Cells were fixed with 10% formalin and stained with 0.05% crystal violet at the end of 2 weeks period of cell culture.

6) Flow cytometry assay:

a) Cell Cycle Analysis: Propidium iodide (PI) staining and flow cytometry were used to determine the degree of cellular apoptosis. Cells were seeded at $3\times10^5$ cells/well in six-well plates. Cells were treated with PG3-Oc for 48 hours. Cells were harvested, fixed by 70% ethanol, and stained by propidium iodide, then flow cytometry was performed as previously described (Smithen et al., Org. Biomol. Chem., 2013, 11, 62-68). The percentage of hypodiploid cells (sub-G1) was used to quantify dead cells in apoptosis assays.

b) Early apoptosis detection: Cells were seeded at $3\times10^5$ cells/well in six-well plates. Cells were treated with PG3-Oc for 48 hours. Cells were harvested and prepared using Alex Fluor 488 Annexin V/Dead Cell Apoptosis Kit following manufacturer's protocol (Thermo Scientific Invitrogen).

7) Real-time reverse transcriptase PCR: Total RNA was isolated from PG3-Oc-treated cells using Qick-RNA mini prep kit (Zymo Research, Irvine, Calif.) according to the manufacturer's protocol. 500 ng of total RNA was used to generate cDNA using SuperScript III first-strand synthesis system with random primers (Invitrogen), following the manufacturer's protocol. Real-time PCR was performed using POWER SYBR GREEN mast mix (Applied Biosystem) for DR5, p21, PUMA and GAPDH on 7900HT Sequence Detection System (Applied Biosystem). PUMA primer (forward, 5'-GACGACCTCAACGCACAGTA-3' (SEQ ID NO:1); reverse, 5'-AGGAGTCCCATGAT-GAGATTGT-3' (SEQ ID NO:2)), DR5 primer (forward, 5'-ACAGTTGCAGCCGTAGTCTTG-3' (SEQ ID NO:3); reverse, 5'-CCAGGTCGTTGTGAGCT TCT-3' (SEQ ID NO:4)), GAPDH primer (forward, 5'-TCGACAGTCAGCCGCATCTTCTTT-3' (SEQ ID NO:5); reverse, 5'-ACCAAATCCGTTGACTCCGACCTT-3' (SEQ ID NO:6)). ΔΔCt method was used to analyze and report fold change of indicated genes.

8) siRNA knockdown: Knockdown experiments were performed by transfecting either 80 pmole of indicated siRNA(s), or scramble siRNA using RNAiMAX (Invitrogen). Transfected cells were treated with PG3-Oc, 24 hours post-transfection. The control scrambled siRNA and siRNA for human ATF4, CHOP, DR5, Puma, NF-κB p65 were purchased from Santa Cruz Biotechnology. p73 siRNA was from Ambion, and FOXO3a siRNA from Thermo Scientific Dharmacon.

9) Knock-out of PUMA by CRISPR/Cas9 gene editing:

a) sgRNA design and plasmid construction: sgRNA targets the exon 3 of PUMA gene, which contains sequence code for BH3 domain of PUMA. Two sgDNAs (Guide 1 and Guide 2) were introduced into lentiviral vectors (pLentiCRISPR-E) which contain eSpCas9 and puromycin cassette. Guide1 DNA (forward, 5'-CACCGGCGGGCGGTCC-CACCCAGG-3' (SEQ ID NO:7); reverse, 5'-AAACCCTGGGTGGGACCGCCCGCC-3' (SEQ ID NO:8)) and Guide 2 DNA (forward, 5'-CACCGCCGCTCGTACTGTGCGTTG-3' (SEQ ID NO:9); reverse, 5'-AAAC-CAACGCACAGTACGAGCGGC-3' (SEQ ID NO:10)) were annealed and linked to the restriction enzyme-cut plasmid by T4 ligase. Stb13 strain (Invitrogen C7373-03) was transformed by the guides-containing plasmids. LB-amp plates were streaked and incubated on a shaker at 37 C overnight. The bacteria colonies were selected and mixed up with LB (Terrific Broth) and 100 µg/mL ampicillin, and were incubated on a shaker at 37 C overnight. Plasmids from different colonies were isolated and purified using QIAprep Spin Miniprep Kit (Qiagen). To screen plucks, plasmids were digested with EcoR I HF and Bam HI in Cut Smart Buffer (New England BioLabs, Inc.) at 37 C for 1 hour and then analyzed by 1% agarose gel. Sequencing was performed by GENEWIZ (South Plainfield, N.J.; see, FIGS. 30A-30E and FIGS. 34A-34I).

b) Cell culture, DNA transfection: Lentivirus were generated with psPAX2, pVSV-G and the pLentiCRISPR plasmids that contain the guides and Cas9 in 293T cells. 48 hours later, all the supernatant was transferred to a 1.5 mL tube. The debris was removed by centrifugation and the supernatant was ransferred to a new 1.5 mL tube, and stored at 4 C. HT29 cells were transfected with the lentivirus supernatant and polybrene was added to enhance the transfection. Puromycin at a final concentration of 1 µg/mL was added to medium to select positive cells.

c) Mutation screens by Sanger sequencing and TIDE analysis: DNA was extracted and purified from positive HT29 cells using DNeasy Blood & Tissue kit (Qiagen). PCR primers that flank both sides of the exon 3 of PUMA gene were used to amplify the target region (forward, 5'-CACAGTCTCTGGCCTTCTGG-3' (SEQ ID NO:11); reverse, 5'-AGCTGCCGCACATCT GG-3' (SEQ ID NO:12)). The amplicon is GC-rich region, to improve PCR specificity. Temperature gradient PCR was performed to optimize annealing temperature. A hot-start and touch-down PCR with accuPrime™ Pfx DNA Polymerase (ThermoFisher Scientific) and 2.5% DMSO and 1M betaine, was performed to achieve specific amplification of target region. The PCR products were purified by QIAquick PCR purification kit (Qiagen) for Sanger sequencing.

TIDE analysis was performed using an online tool (TIDE: Tracking of Indels by Decomposition (see, world wide web at "tide-calculator.nki.nl/")). Sequencing was performed by GENEWIZ (South Plainfield, N.J.; see, FIGS. 30A-30E and FIGS. 34A-34I).

d) Single cell colonies. 300 positive HT29 cells were placed into a 10 cm dish and incubated at 37 C. After 2 weeks, single cell colonies were selected and expanded.

Western blotting using PUMA antibody was performed to screen the colonies (see, FIGS. 30A-30E and FIGS. 34A-34I).

10) Statistical analysis: All results were obtained from triplicate experiments, unless other indicated. Statistical analyses were performed using PRISM4 Software (GraphPad Software, Inc.), and the Student t test. Statistical significances were determined by P<0.05. Combination indices were calculated using the Chou-Talalay method with CalcuSyn software (Biosoft).

Results

1) PG3-Oc Inhibits Growth in a Broad Panel of p53-Mutant Cancer Cell Lines:

Efficacy of the newly synthesized analogs was assayed by measuring cell viability, at 72 hours post-treatment. Of the 15 compounds screened, PG3-Oc (see, FIG. 26A) was identified as the most potent inhibitor of cell growth in a broad spectrum of human cancer cells with mutant p53. These included colorectal cancer cell lines (HT29, SW480, DLD1, HCT116 and HCT116 p53$^{-/-}$) and head and neck squamous cell lines (FaDu and CAL-27) (see, FIGS. 26B, 26C and 26D). $IC_{50}$ values for pancreatic cancer cell lines (PANC-1 and ASPC-1), glioblastoma (U251), non-small cell lung cancer (H1975), and triple-negative breast cancer cells (MDA-MB-231 and MDA-MB-468) were within the nanomolar range (see, FIG. 26B). The potency of PG3-Oc (Oc) for inhibition of cancer cell growth was found to be comparable with prodigiosin (P) and obatoclax (Ob) (see, FIG. 26D). PG3-Oc showed similar toxicity for normal cell MRCS as obatoclax (see, FIG. 26E). For colorectal and head and neck squamous cancer cells, the $IC_{50}$ for normal cells was found to be about 3-fold higher than the values in colorectal and head-neck cancer cells. These data indicate that PG3-Oc can be a suitable compound in the treatment of human colorectal cancers.

Figure 26A:
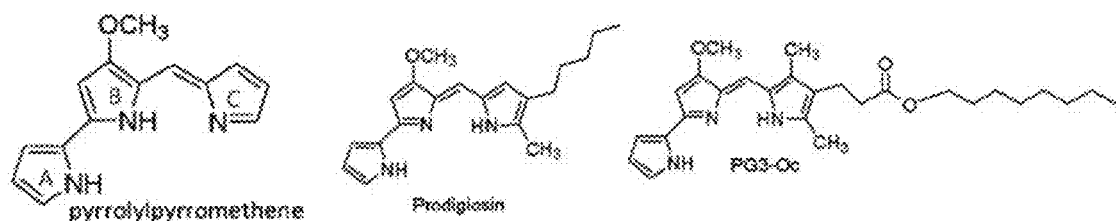
FIGS. 26A, 26B, 26C, 26D, and 26E depict PG3-Oc inhibition of the growth of p53-mutant cancer cell lines.
Figure 26B:
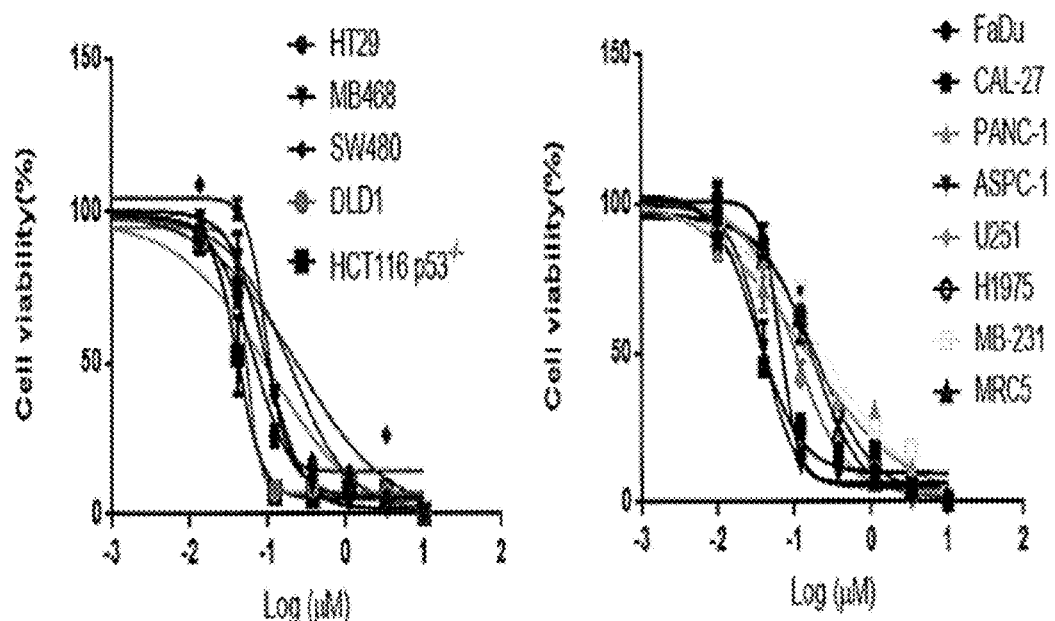
Figure 26C:
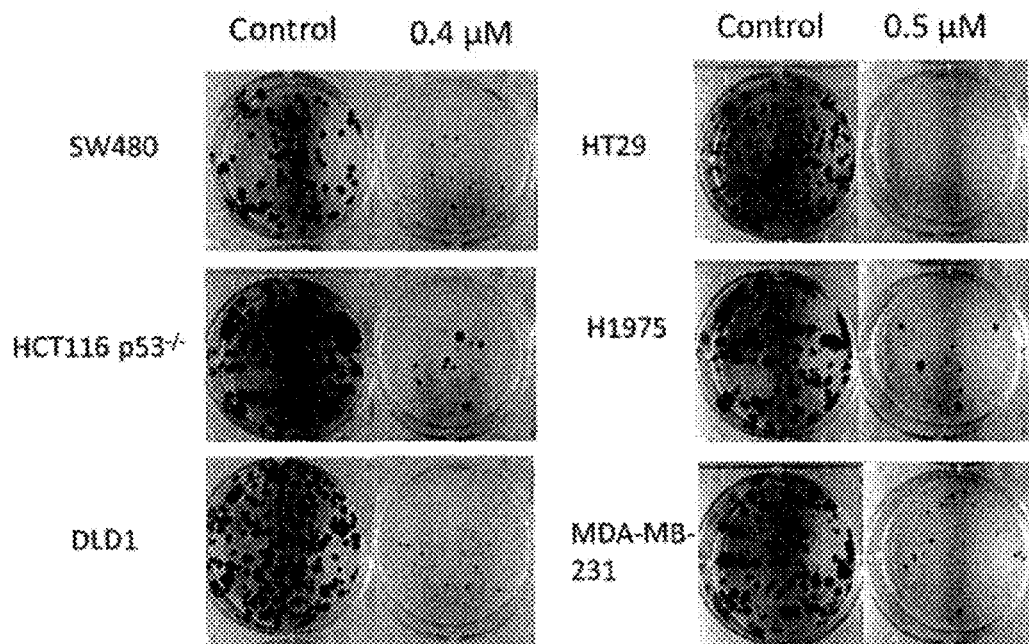
Figure 26D:
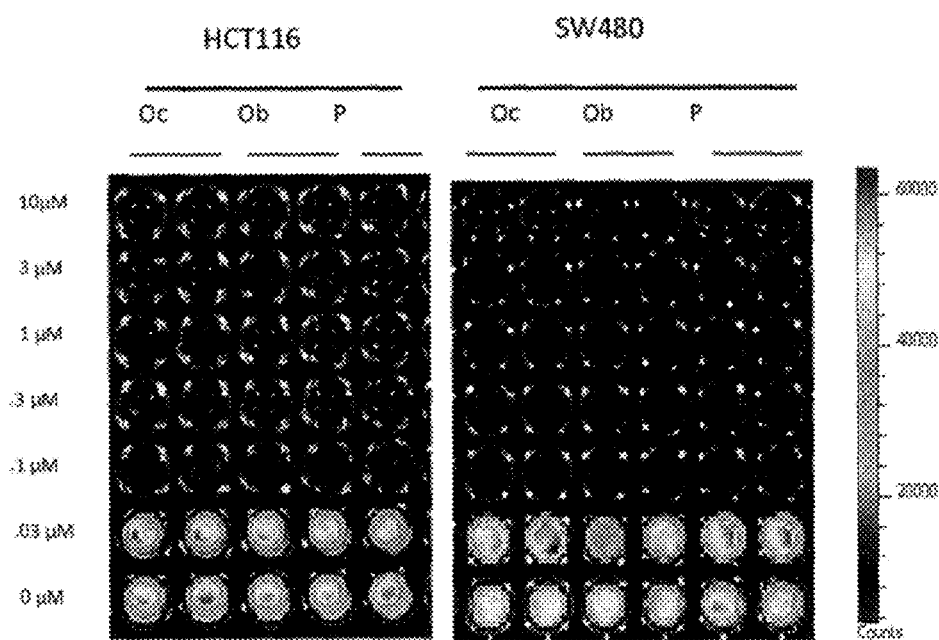
Figure 26E:
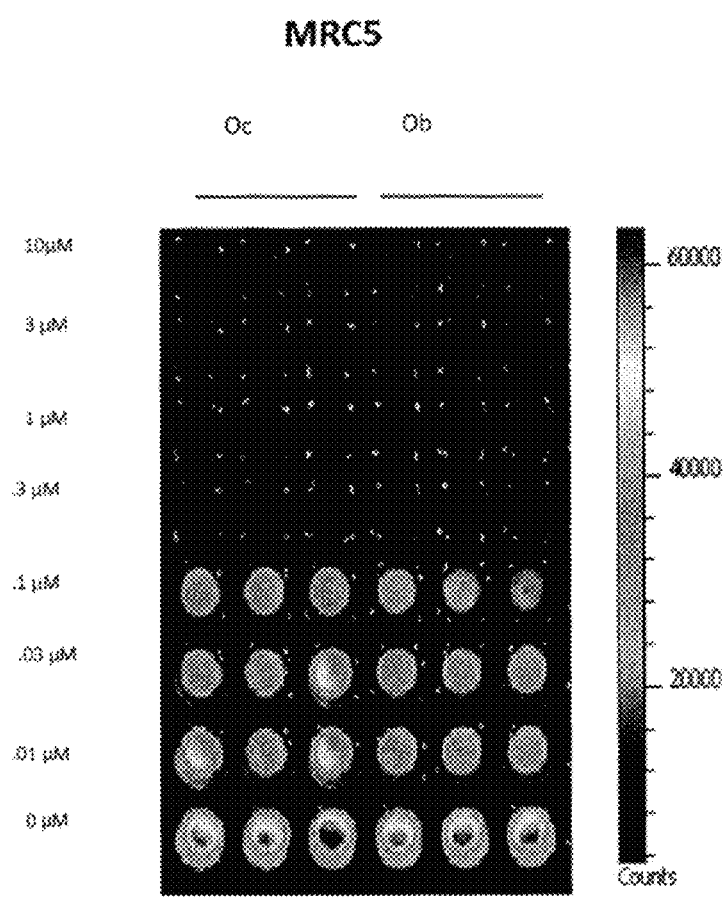

In particular, referring to FIGS. 26A-26E, PG3-Oc inhibition of the growth of p53-mutant cancer cell lines is shown. FIG. 26A shows the structure of PG3-Oc. FIG. 26B shows dose response curves and $EC_{50}$ values of PG3-Oc in a panel of cancer cell lines with p53 mutation, comparing to normal human cells MRCS. FIG. 26C shows colony formation assay of p53-mutant and p53-null human cancer cells. Cells were treated with indicated concentrations of PG3-Oc for 24 hours, and then cultured in drug-free medium for 14 days following crystal violet staining of attached cells. FIG. 26D shows cell viability assay, comparing potency of PG3-Oc (Oc) to obatoclax (Ob) and prodigiosin (P) in p53 wild type cell line HCT116 and p53 mutant cell line SW480. Cells were treated with different concentration of PG3-Oc or DMSO control for 72 hours. Luciferase activity was imaged by the IVIS Imaging System after treatment. Cell viability data were normalized to those of DMSO treatment as control in each cell line and data analyses were performed using PRISM4 software. $EC_{50}$ data are expressed as mean±SD in normal fibroblast cells (normal; n=3). FIG. 26E shows cell viability assay, comparing toxicity of PG3-Oc (Oc) to obatoclax (Ob) in MRCS cells.

Figure 20:
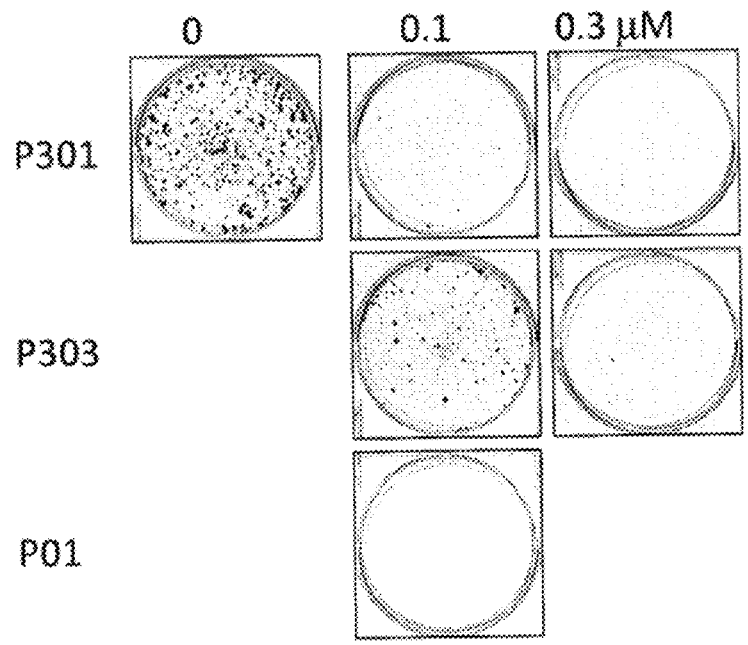
FIG. 20 depicts various aspects of a colony formation assay experiment conducted using prodigiosin analogs.
Figure 21:
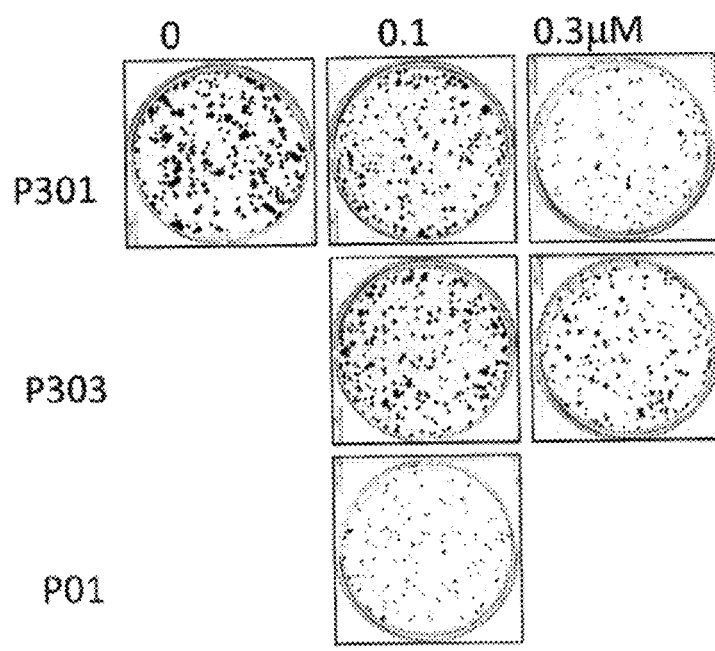
FIG. 21 depicts various aspects of a colony formation assay experiment conducted using prodigiosin analogs.
Figure 27A:
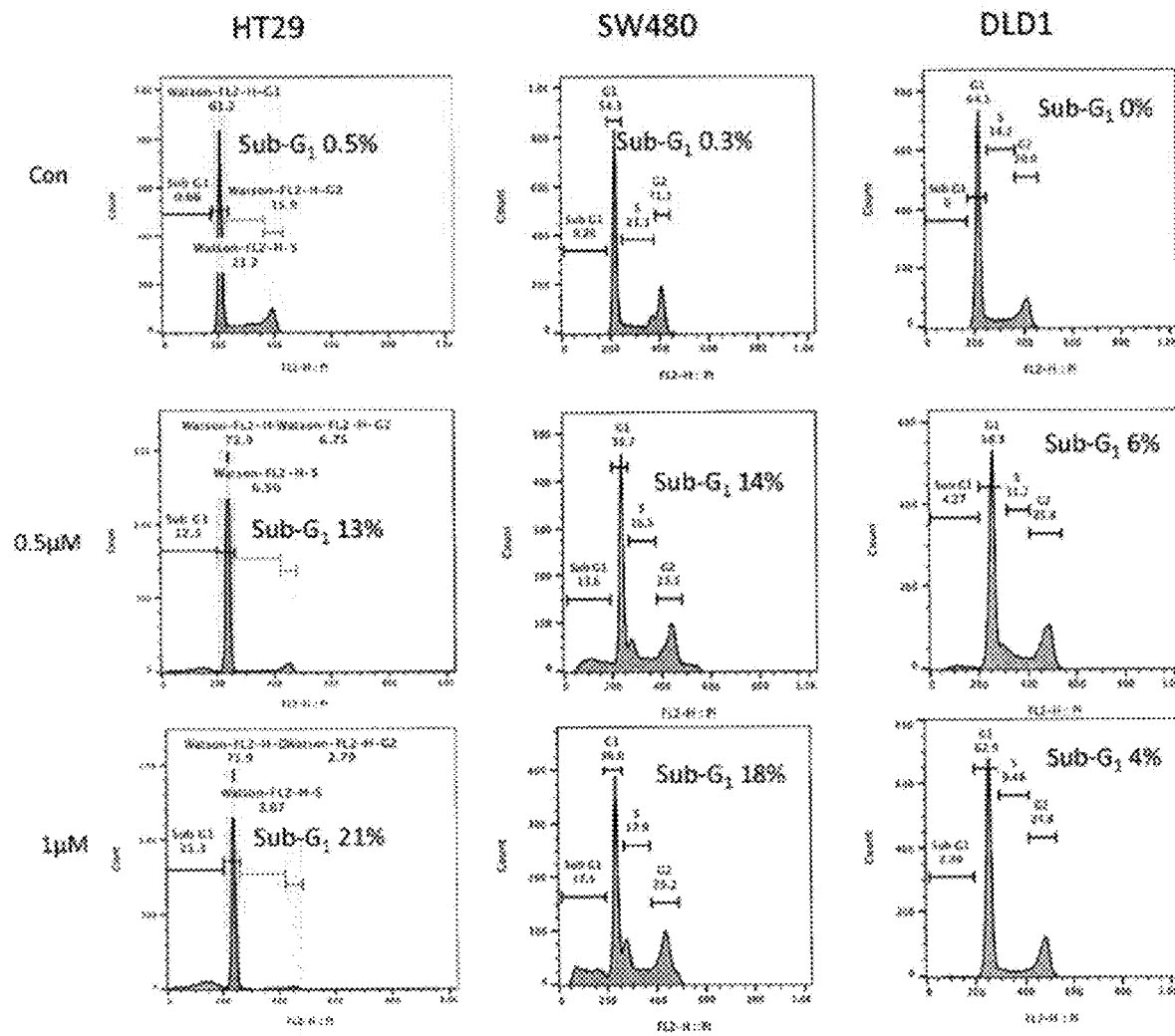
FIGS. 27A, 27B, 27C, 27D, and 27E depict PG3-Oc induction of apoptosis in p53 mutant cancer cell lines, Caspase 3/7 activity assay, HT29 cells co-treated with 1 µM PG3-Oc and pan-caspase inhibitor Z-VAD-fmk, and Western blotting analysis of active caspase-8, active caspase-3 and cleaved PARP in HT29 cells and SW480 cells.

2) PG3-Oc Induces Apoptosis in Mutant p53-Expressing Human Cancer Cell Lines:

Treatment of colorectal cancer cell lines HT29 and SW480 with 1 µM PG3-Oc for 48 hours induced cancer cell death as demonstrated by sub-G1 analysis (see, FIG. 27A). To evaluate if the cell death was caspase-dependent, Caspase 3/7 activity was measured. Treatment with PG3-Oc induced a 2-fold increase in caspase 3/7 activity as compared to untreated cells using mutant p53 and p53-null expressing cancer cells (see, FIG. 27B). Induction of apoptosis was further confirmed by pan-caspase inhibitor (Z-VAD-FMK) co-treatment experiments with PG3-Oc. As seen in FIG. 27C, 20 µM Z-VAD-FMK completely blocked the formation of a sub-G1 population as compared to the untreated control. Under similar experiment conditions, western blot analysis showed that Z-VAD-FMK (20 µM) completely inhibits the cleavage of caspase-8 and caspase-3 in both HT29 and SW480 cells (see, FIGS. 27D and 27E). Taken together, these data indicate that PG3-Oc treatment induces capase-8 and caspase-3 activation in colorectal cancer cell lines, and caspase activation may be required for PG3-Oc-induced cell death.

Figure 27B:
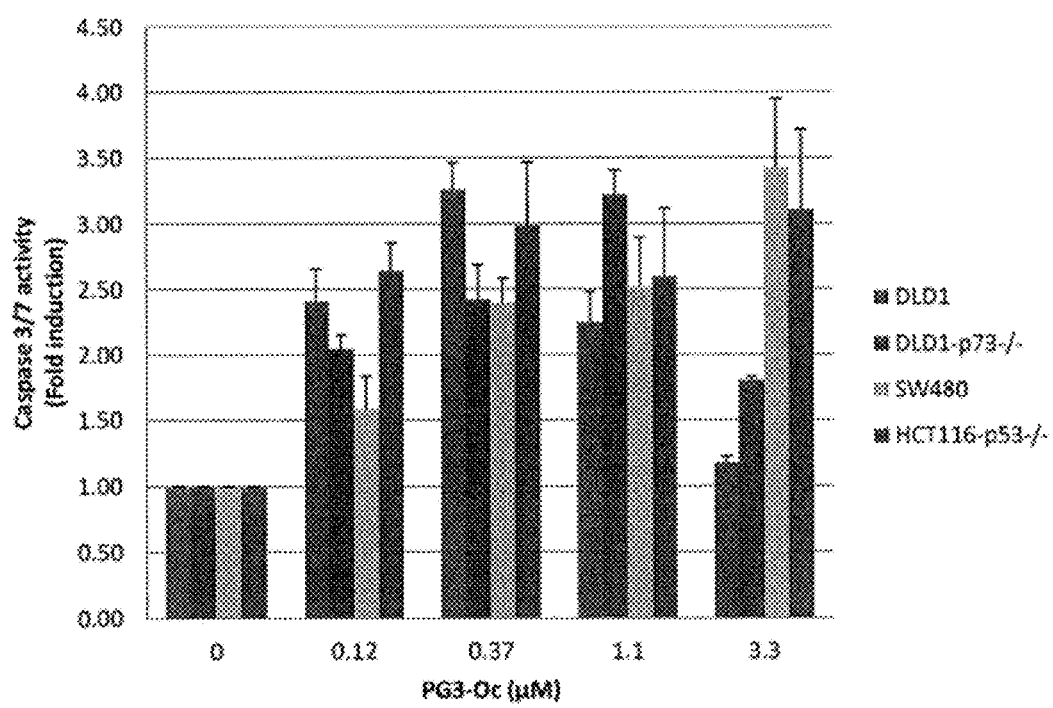
Figure 27C:
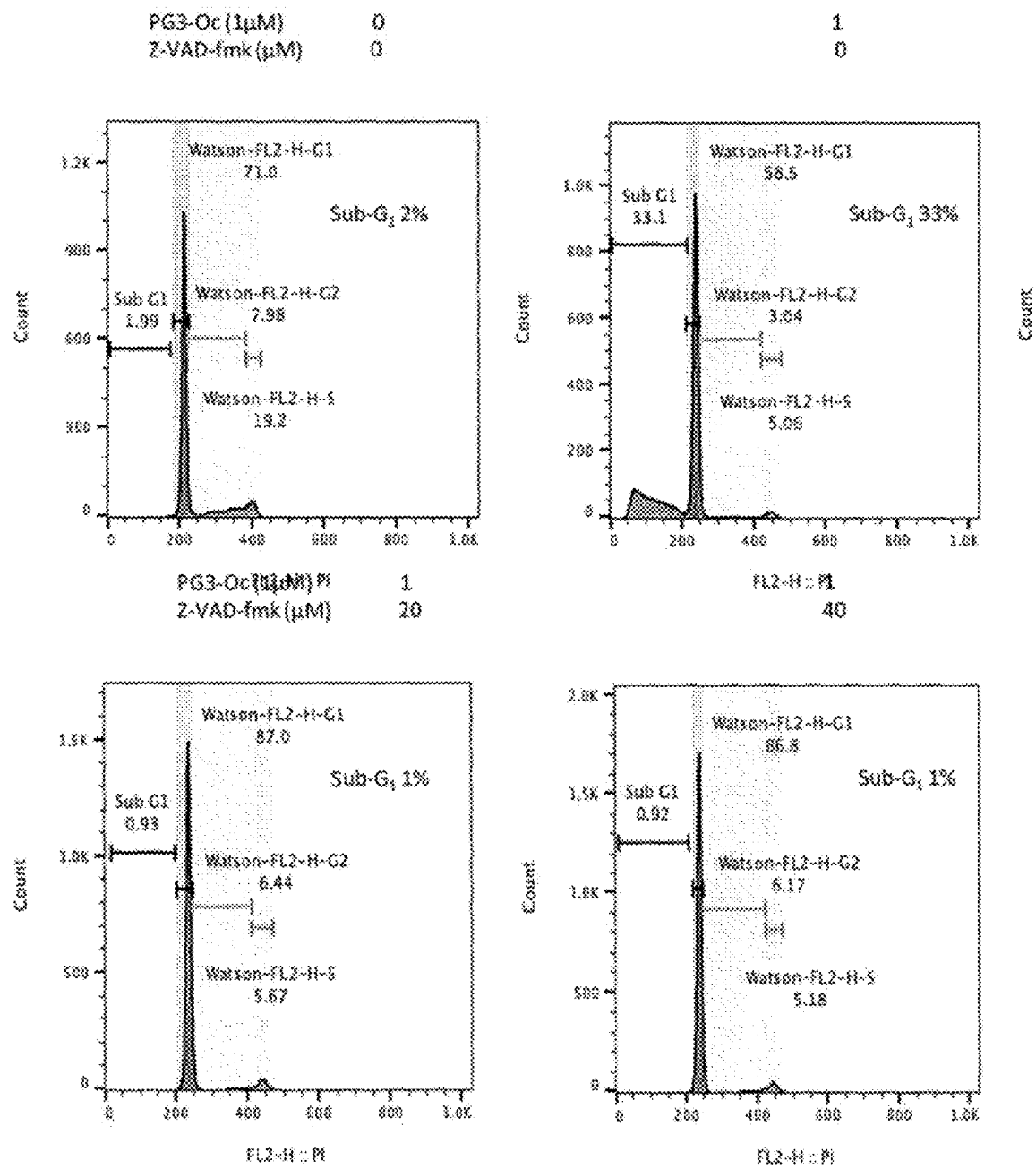
Figure 27D:
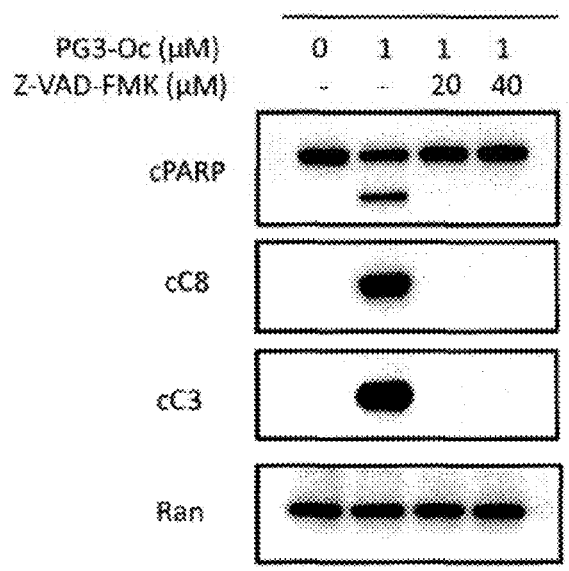

In particular, referring to FIGS. 27A-27E, PG3-Oc-induced apoptosis in p53 mutant cancer cell lines is shown. FIG. 27A shows cell-cycle profiles of cells at 48 hours after PG3-Oc treatment. Apoptosis was analyzed by nuclear PI-staining using flow cytometry. HT29 and SW480 cells were treated with PG3-Oc at indicated concentration for 48 hours, DLD1 cells were treated for 72 hours. FIG. 27B shows caspase 3/7 activity assay. Cells were treated with PG3-Oc at the indicated concentrations for 24 hours. Luciferase activity was imaged by the IVIS Imaging System after treatment. Caspases activity data (triplicate) were normalized to cell numbers and then those of DMSO treatment as control in each cell line and data analyses were performed using Excel. FIG. 27C shows HT29 cells were co-treated with 1 µM PG3-Oc and pan-caspase inhibitor Z-VAD-fmk for 48 hours. Cell cycle analysis was performed as before. Western blotting analysis of active caspase-8, active caspase-3 and cleaved PARP in HT29 cells (see, FIG. 27D) and SW480 cells (see, FIG. 27E).

Figure 28A:
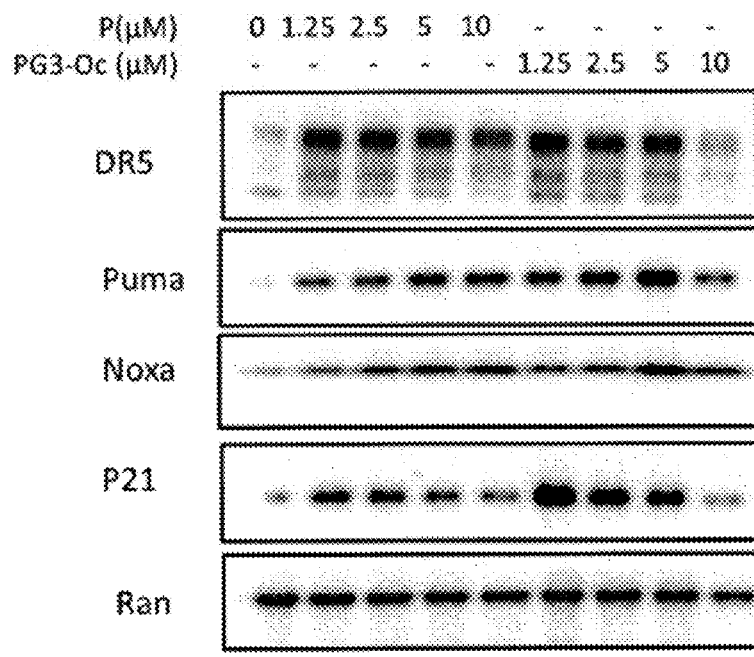
FIGS. 28A, 28B, 28C, and 28D depict PG3-Oc restoration of p53 pathway in p53 mutant cancer cell lines.
Figure 28B:
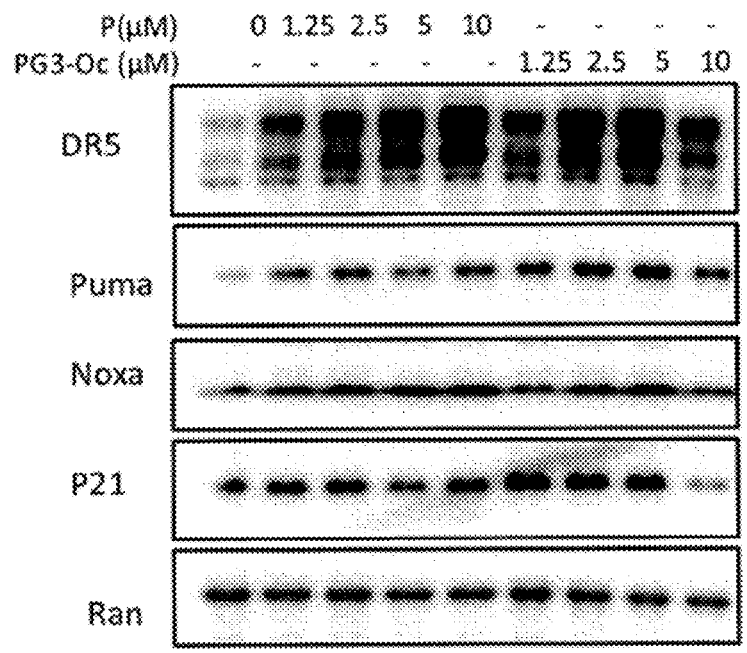

3) PG3-Oc Restores p53 Pathway in p53 Mutant Cancer Cell Lines:

Similar to prodigision, treatment of p53 mutant containing SW480 and p53-null HCT116 colon cancer cells with PG3-Oc also potently induced up-regulation of p53 target genes, such as DR5, PUMA, Noxa and p21 (see, FIGS. 28A and 28B). However, the magnitude of induction of target genes was much higher in PG3-Oc treated cells as compared to prodigiosin, especially for p21 and PUMA (see, FIGS. 28A and 28B). To investigate whether the up-regulation of p53 target genes occurs at the transcriptional level, after cells were treated with 1 µM PG3-Oc at different time points, real-time PCR analysis of mRNA level of DR5, p21 and PUMA was performed in HT29 and HCT116 p53$^{-/-}$ cells (see, FIGS. 28C and 28D). At 8 and 19 hour time points, robust up-regulation of both p21 and PUMA mRNAs were observed in the cell lines tested. For DR5 mRNA level, more than 2-fold up-regulation was observed at 19 hours post-treatment in HT29 cells. Contrary to that, DR5 protein level was potently up-regulated in HCT116 p53$^{-/-}$ cells with no significant change of DR5 mRNA. This indicates that PG3-Oc treatment may lead to DR5 protein stabilization depending on cell type. Taken together, these data indicate that PG3-Oc can restore the p53 pathway at the transcriptional level, especially for p21 and PUMA.

Figure 28C:
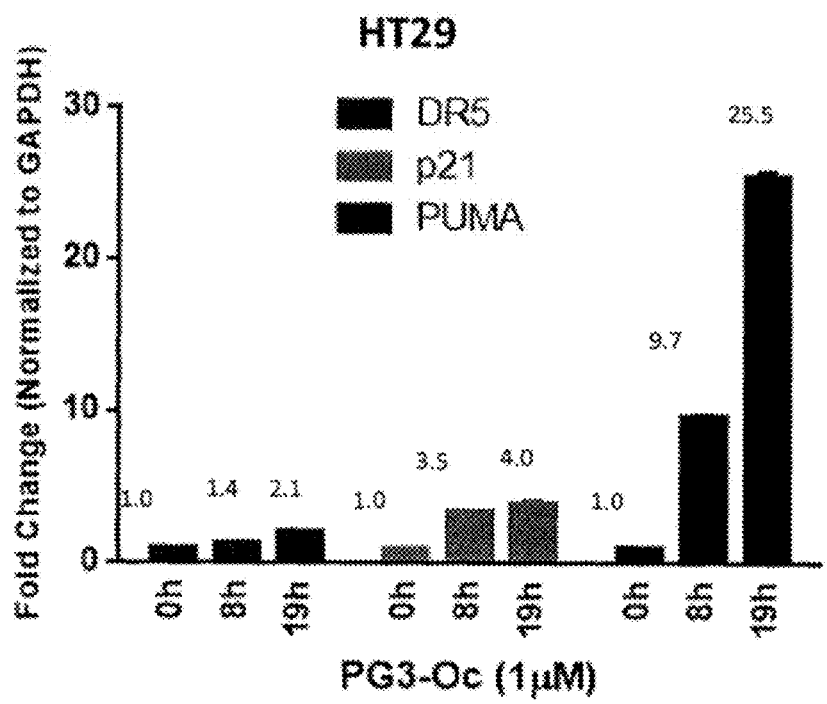
Figure 28D:
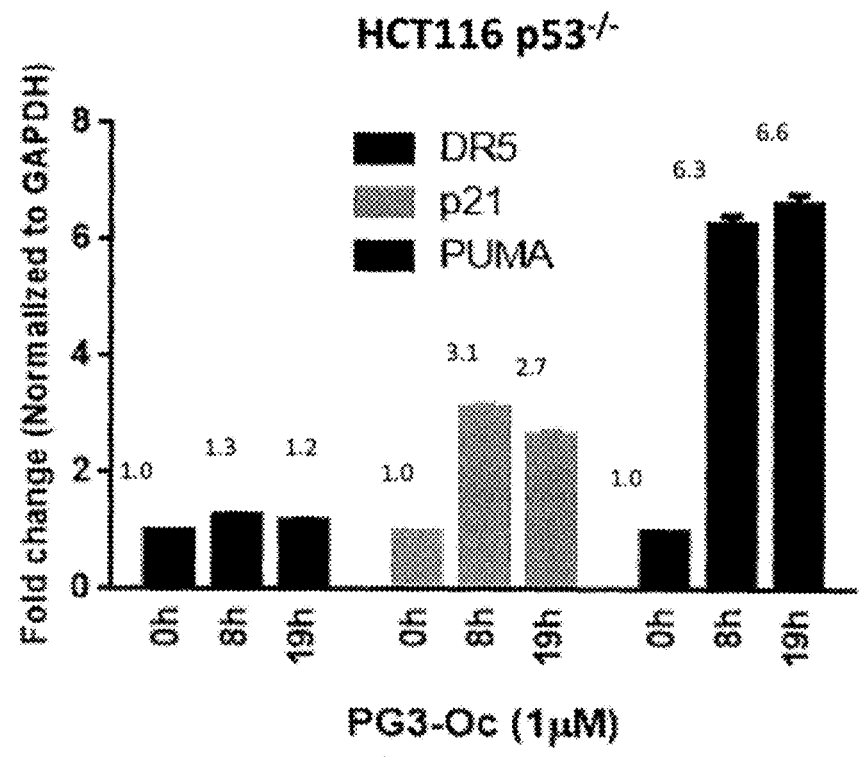

In particular, referring to FIGS. 28A-28D, PG3-Oc restoration of the p53 pathway in p53 mutant cancer cell lines is shown. FIGS. 28A and 28B show PG3-Oc induced expression of p53-target genes in p53-mutant cell lines. PG3-Oc induced more up-regulation of Puma and p21 than prodigiosin (P) in both p53-muant SW480 (see, FIG. 28A) and p53-null HCT 116 cancer cell lines (see, FIG. 28B). Western blot analysis of p53-target gene expression of DR5, Puma, Noxa and p21 in p53-mutat and p53-null cancer cells. Cells were treated with PG3-Oc at indicated concentrations for 18 hours. FIGS. 28C and 28D show qPCR analysis of the change of mRNA level in HT29 and HCT116 p53−/−. Cells were treated with PG3-Oc (1 µM) for 8 hours and 19 hours. mRNA samples were prepared and RT-PCR was performed to prepare cDNAs.

4) PUMA is Required for PG3-Oc Mediated Cell Death:

Whether PUMA and DR5 are dispensable for PG3-Oc mediated cell death in mutant p53 cells was examined. Since PUMA was most dramatically induced by PG3-Oc in HT29 cells, this cell line was selected to dissect out the role of PUMA. Time-course experiments indicated that PUMA protein was first induced at 16 hours post PG3-Oc treatment and this induction was sustained even at 48 hours. At 48 hours, induction of cleaved PARP was observed, as well as cleaved caspase-8 and -3 occurred (see, FIG. 29B). Therefore, 48 hours as a time period was selected for a subsequent dose-response study of PG3-Oc (see, FIGS. 29A and 29C). These data indicate that PG3-Oc induces up-regulation of PUMA in a time-and-dose dependent manner. A similar time- and dose-dependent induction of DR5 was observed in PG3-Oc treated cells.

Having optimized the time and dose of PG3-Oc using different apoptosis markers, siRNA studies were subsequently performed. As shown in FIGS. 29D and 29E, knockdown of PUMA by siRNA reduced the sub-G1 population to 11.1% as compared to 25.8% in siControl, in PG3-Oc treated cells. However, knockdown of DR5 by siRNA did not protect cells from death induced by PG3-Oc (see, FIG. 29D). Similar results were observed by Western Blot analysis when PUMA was knocked down alone or together with DR5 using siRNA. As shown in FIG. 29E, PUMA knockdown completely blunted PARP cleavage and cleavage of caspases post PG3-Oc treatment. However, DR5 knockdown had no impact on the same apoptotic markers. Taken together, this indicates that DR5 is dispensable for PG3-Oc mediated cell death. However, PUMA protein is required and is a key player in cell death induced by PG3-Oc treatment in HT29 cancer cells.

Figures 29A, 29B, 29C:
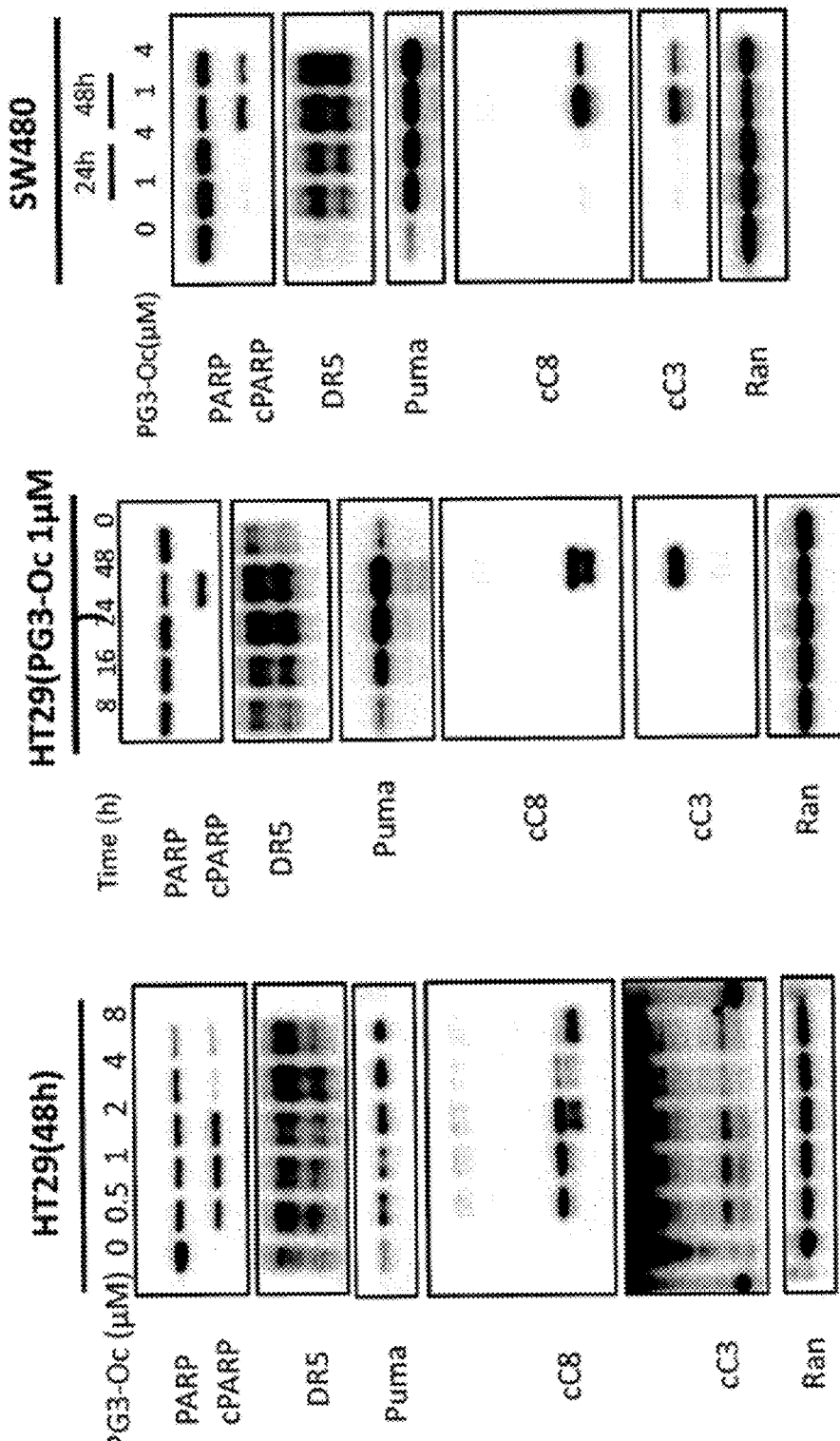
FIGS. 29A, 29B, 29C, 29D, and 29E depict the induction of PUMA is correlated with cell death.
Figure 29D:
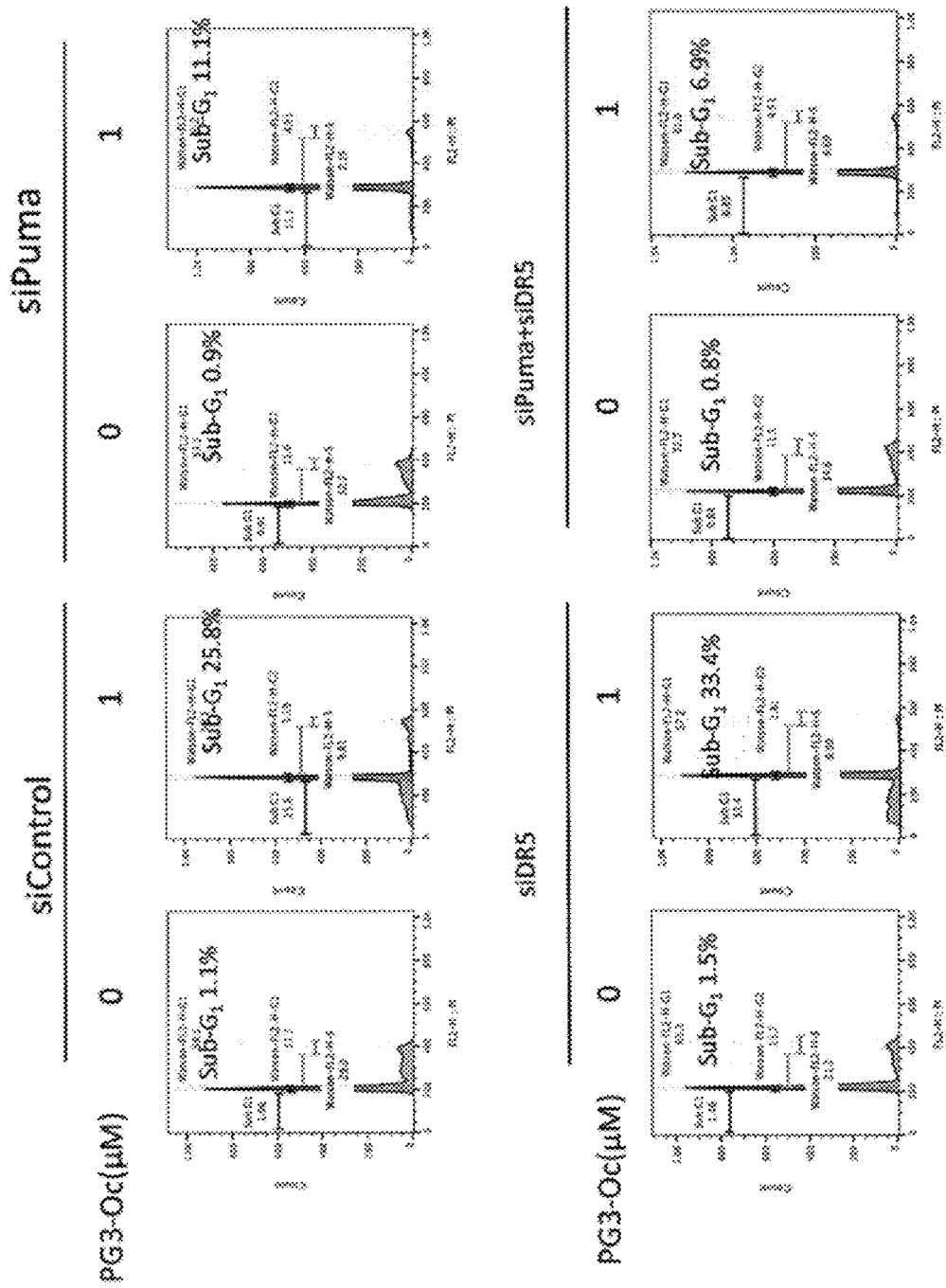
Figure 29E:
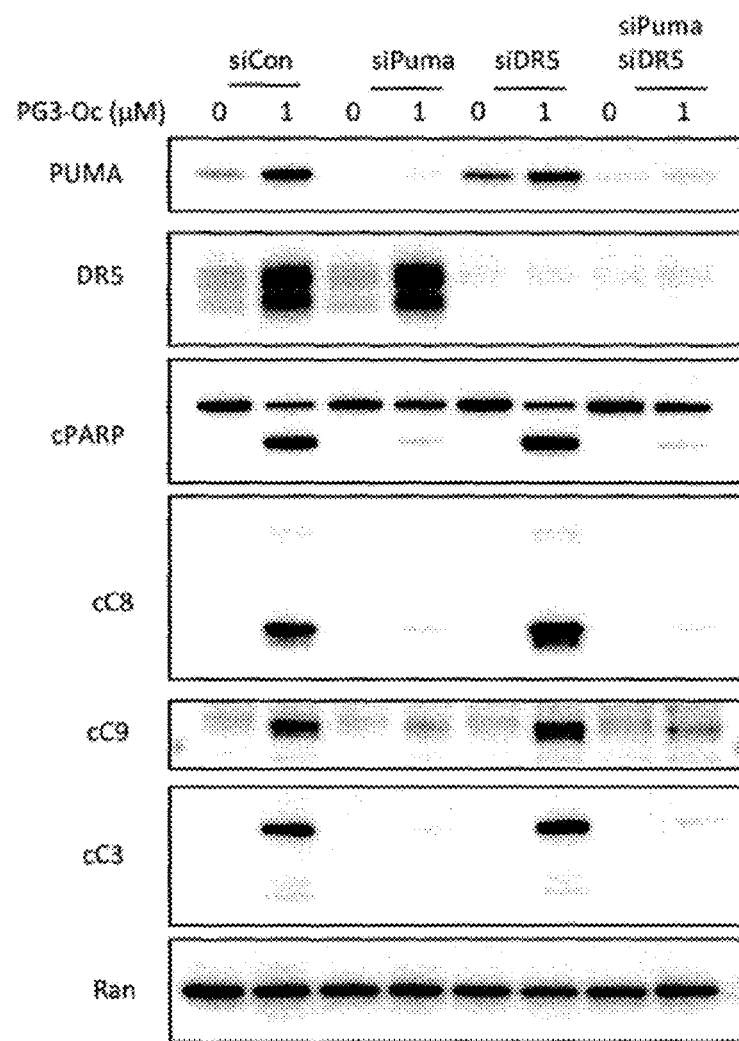

In particular, referring to FIGS. 29A-29E, the correlation of induction of PUMA with cell death is shown. FIGS. 29A, 29B, and 29C show dose-response and time-course analysis of active caspase-3, active caspase-8, active caspase-9, cleaved PARP (cPARP), Puma, and DR5 in PG3-Oc-treated HT29 cells (see, FIGS. 29A and 29B) or SW480 cells (see, FIG. 29C) by Western Blot. FIG. 29D shows HT29 cells transfected with Control, Puma, DR5 and Puma/DR5 siRNAs, after 24 hours transfection, the cells were treated with 1 µM PG3-Oc for 48 hours. After treatment, apoptosis was analyzed by nuclear PI-staining using flow cytometry. FIG. 29E shows Western blotting analysis of Puma, DR5, active caspase-8, caspase-9 caspase-3 and cleaved PARP.

PUMA siRNA studies were validated by creating PUMA gene knockout HT29 cells line via CRISPR/Cas9 gene editing technology (see, FIGS. 30A-30E). The guide was designed to target the DNA sequence that encodes amino-acid residues for the BH3-domain of PUMA (see, FIG. 30A). Knockout of the PUMA gene was found to abolish PG3-Oc-induced sub-G1 population, as well as cleavage of PARP and caspases (see, FIGS. 30F and 30G). This further indicates that binding of PUMA to anti-apoptotic Bcl-2 family members (Bcl-2, Mcl-1) may be important for PG3-Oc-mediated cell death. This may be due to disruption of the BH3-domain of PUMA and abrogation of the downstream mediators of apoptosis.

Usually activation of caspase-8 involves the extrinsic pathway of apoptosis. Of note, both knockout of the PUMA gene and knockdown of PUMA mRNAs not only abolished caspase-8 cleavage induced by PG3-Oc treatment, but also inhibited the cleavage of caspase-9, caspase-3 and PARP (see, FIGS. 29E and 30G). Further, blockage of caspase-8 by the caspase-8 inhibitor Z-IETD-FMK not only inhibited caspase 8 cleavage, but also resulted in inhibition of cleavage of caspase-9, caspase-3 and PARP. In addition, the caspase-8 inhibitor completely blocked the sub-G1 population induced by PG3-Oc treatment (see, FIGS. 30F and 30G). By contrast, the caspase-9 inhibitor Z-LEHD-FMK partially abrogated PG3-Oc-induced activation of caspase 3 and cleavage of PARP (see, FIGS. 30F and 30G). Combined treatment of caspase-8 and 9 inhibitors prevented cleavage of both caspase-3 and PARP, and reduced the sub-G1 population to the same level as untreated control cells. The pan-caspase inhibitor Z-VAD-FMK inhibited the formation of a sub-G1 population and blocked the cleavage of caspase-8, caspase-3, caspase-9 and PARP, similar to knockout of PUMA or knockdown of PUMA (see, FIGS. 30F and 30G).

Figure 30A:
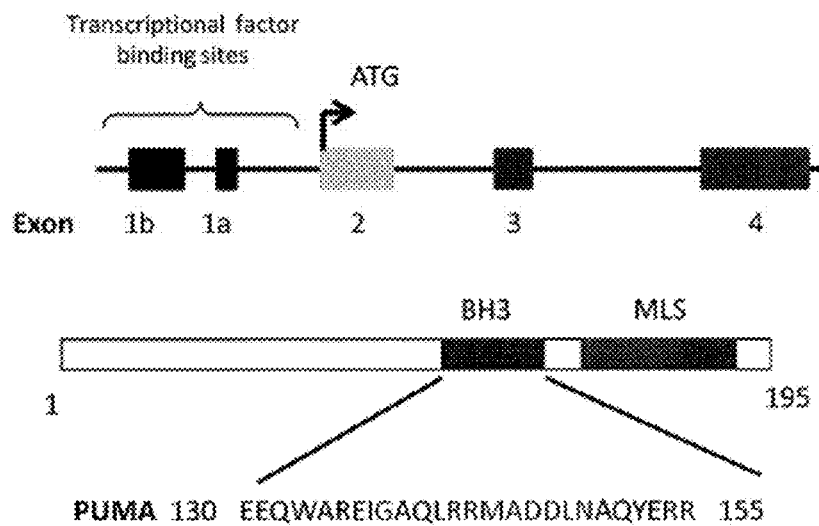
FIGS. 30A, 30B, 30C, 30D, 30E, 30F, 30G, and 30H depict that PUMA is a key effector of PG3-Oc-mediated apoptosis in mutant p53 cell lines.
Figure 30B:
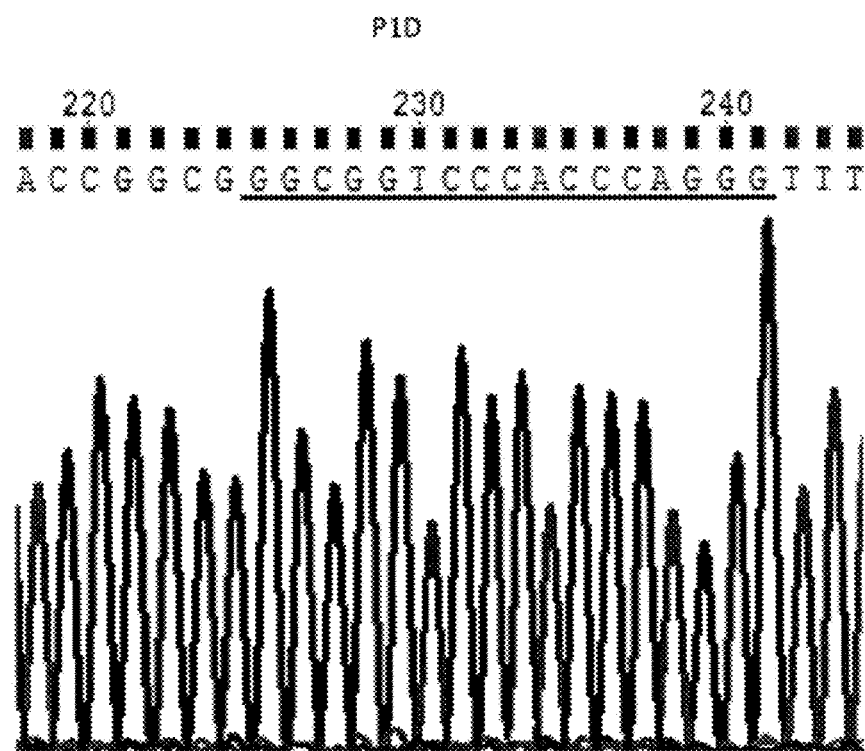
Figure 30C:
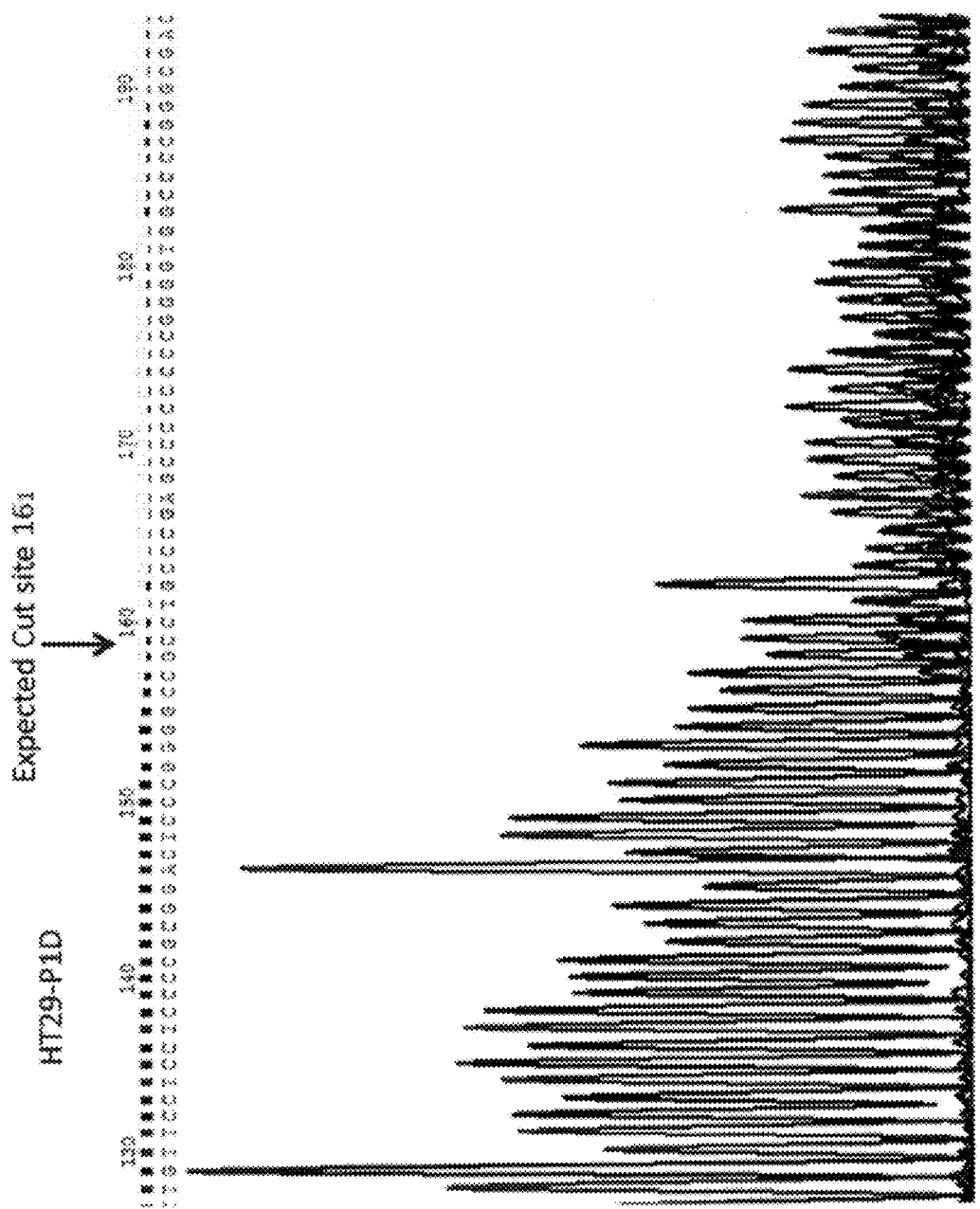
Figure 30D:
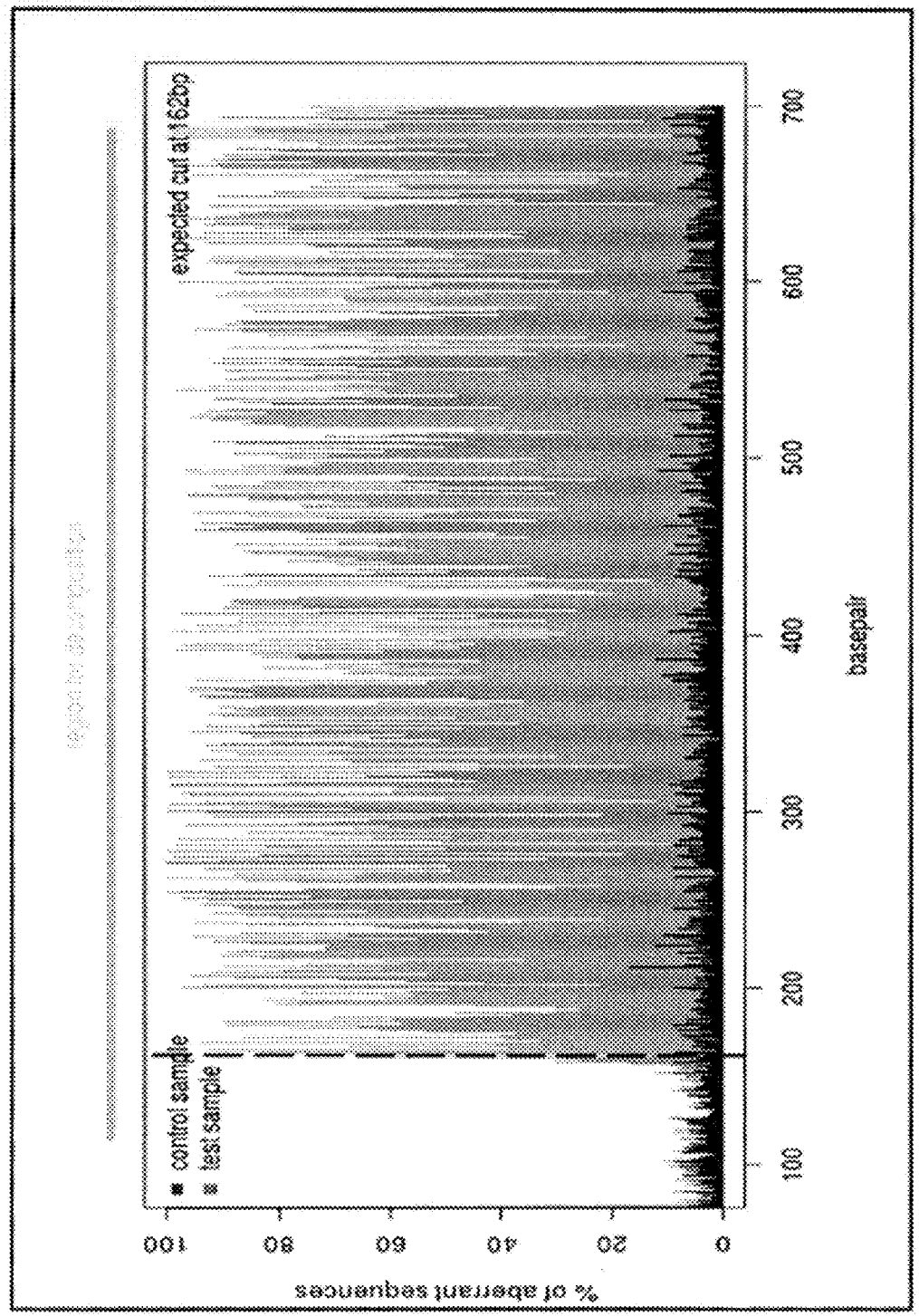
Figure 30E:
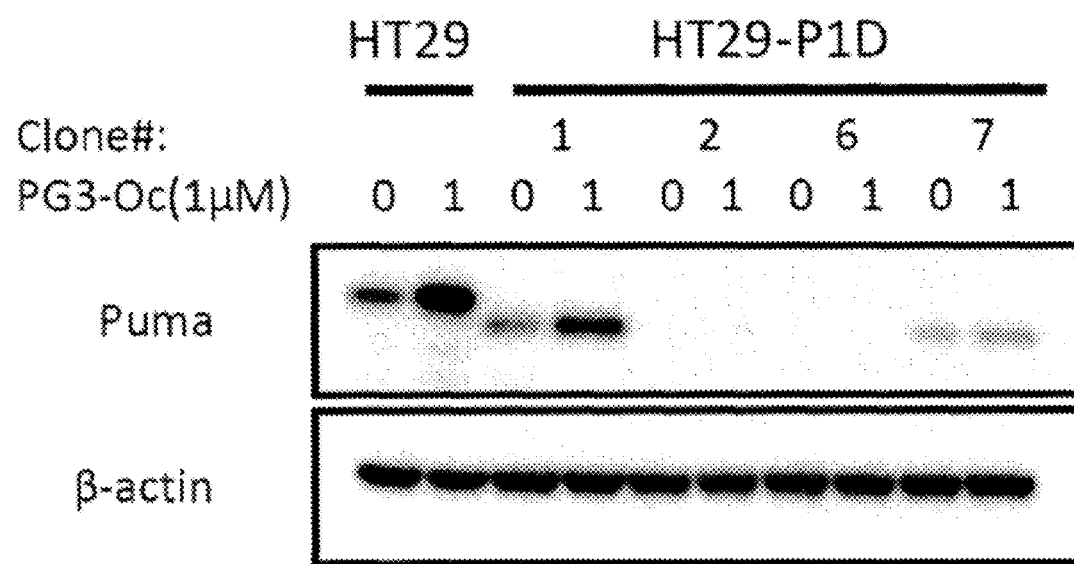
Figure 30F:
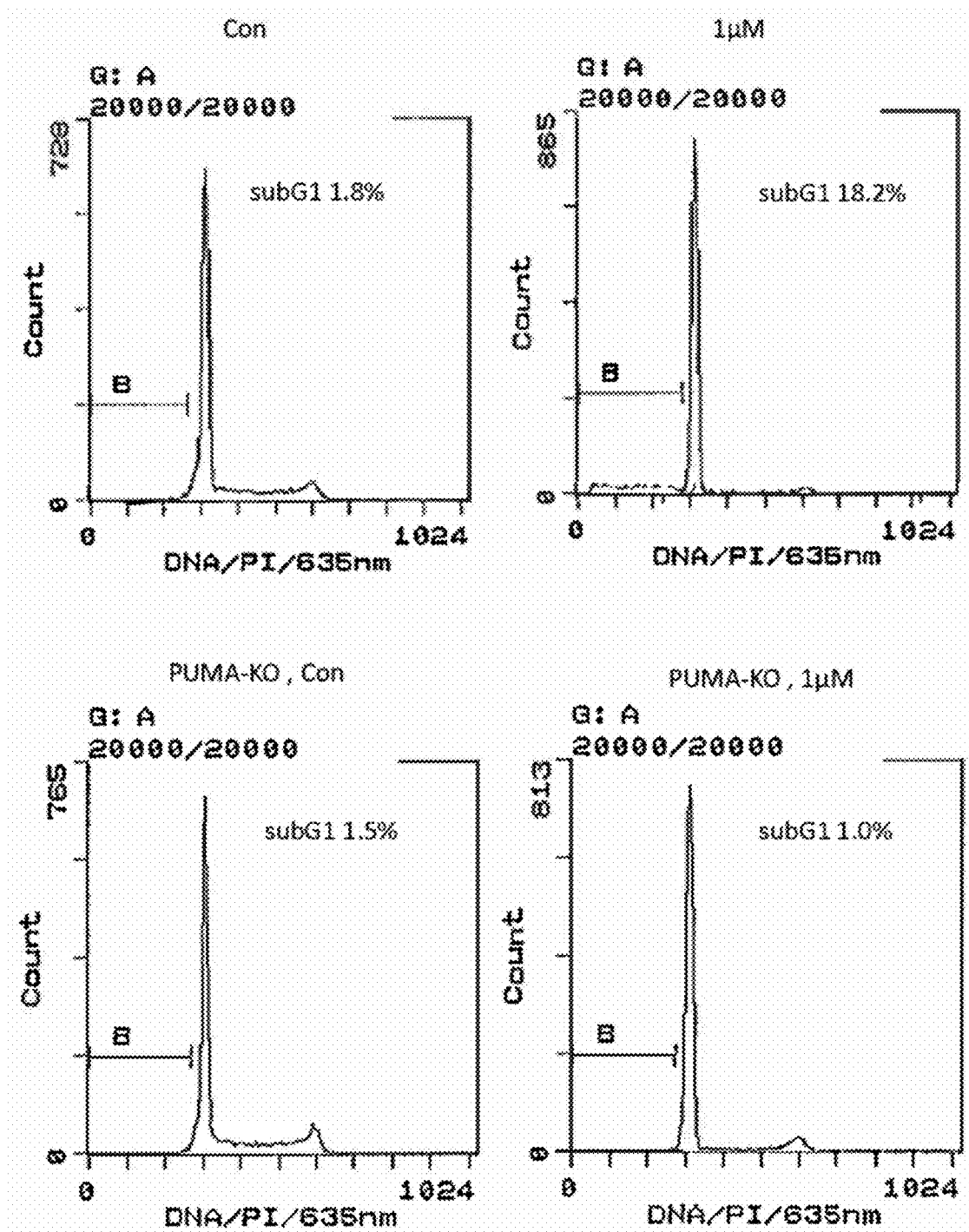
Figure 30F:
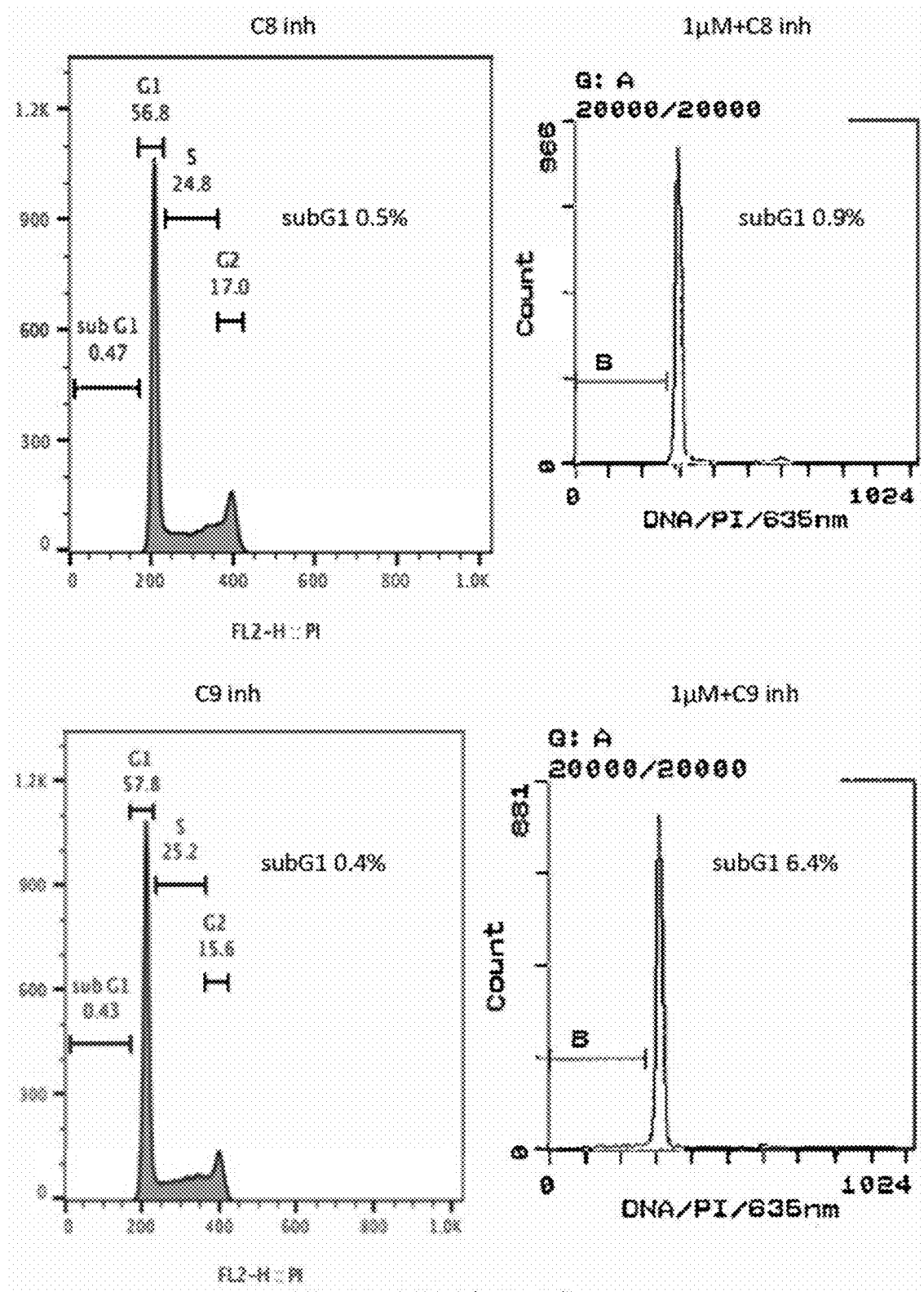
Figure 30F:
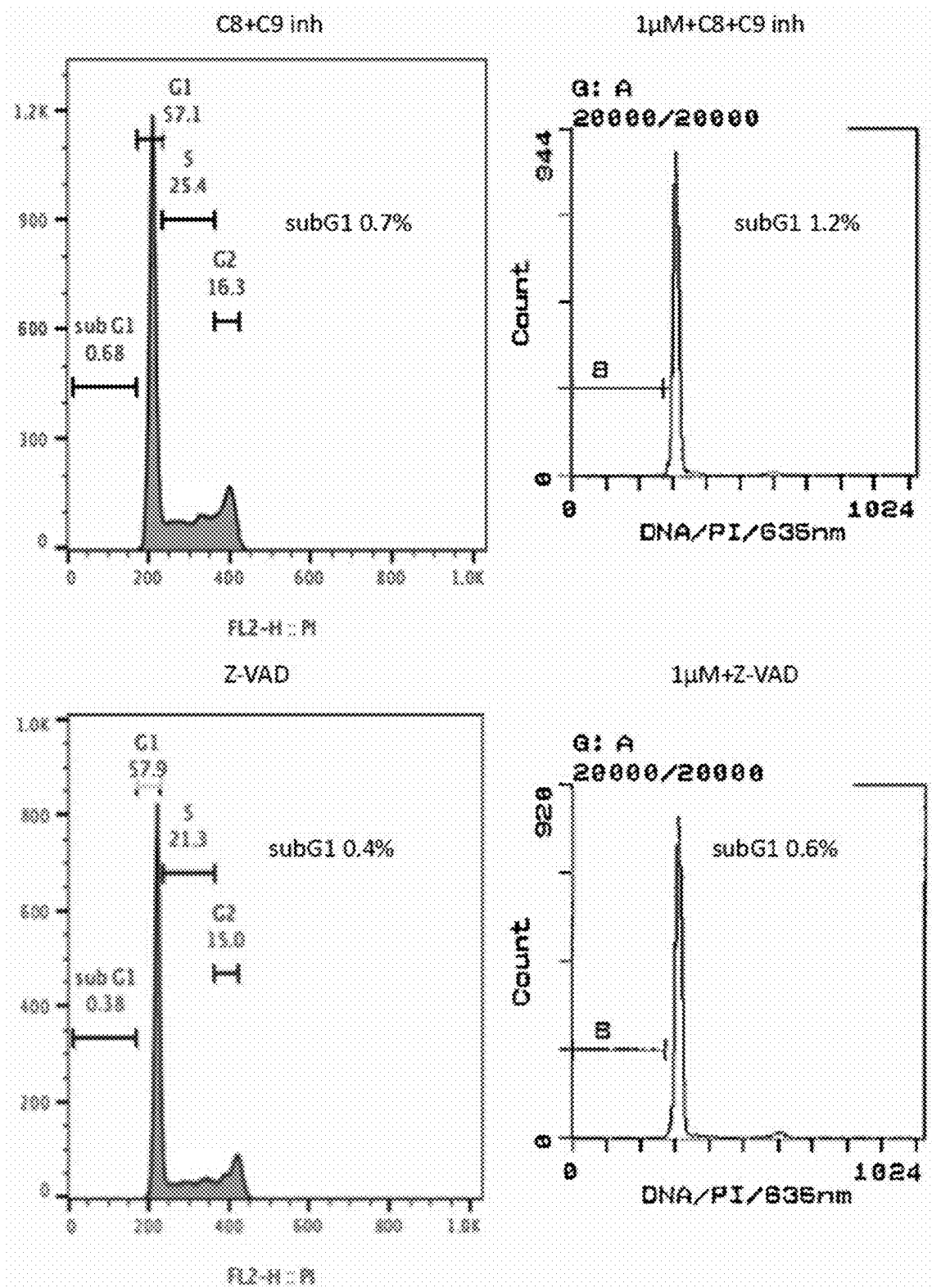
Figure 30G:
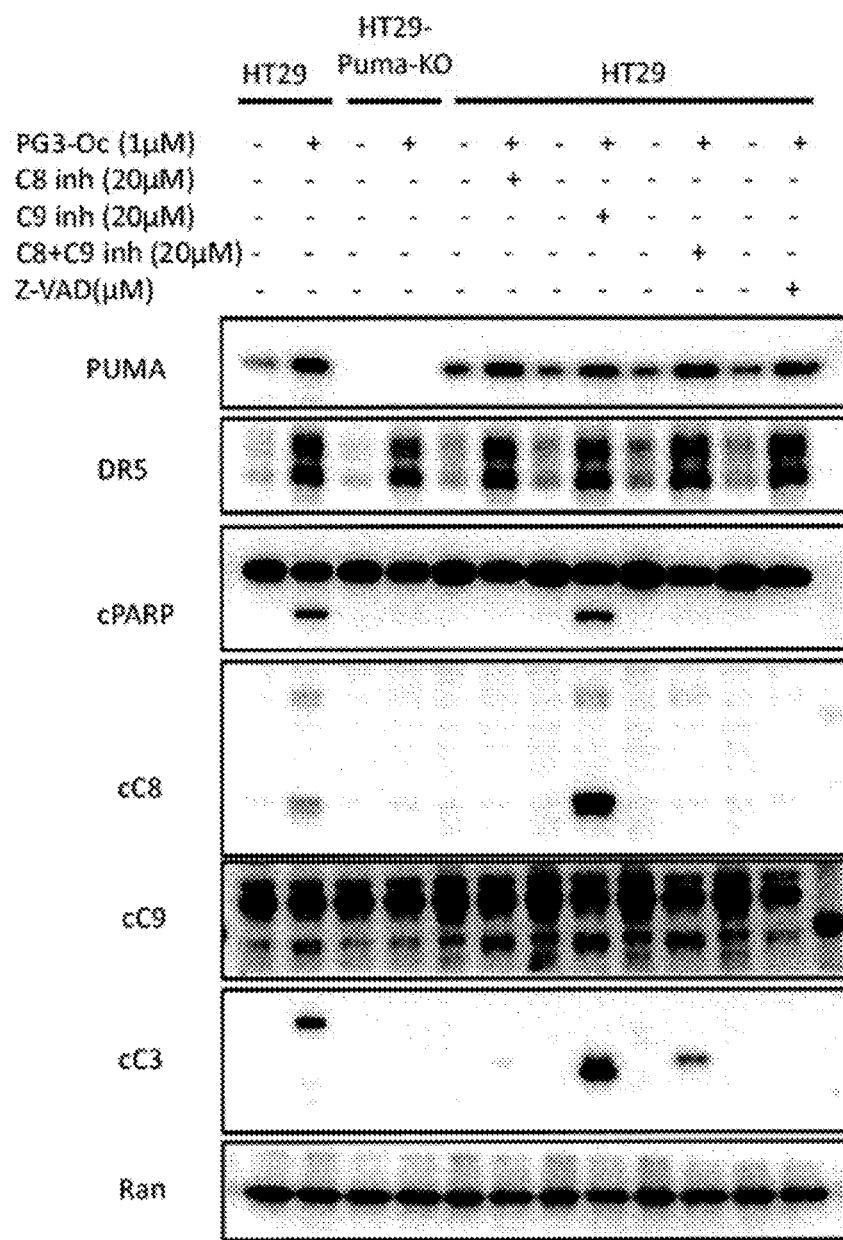
Figure 30H:
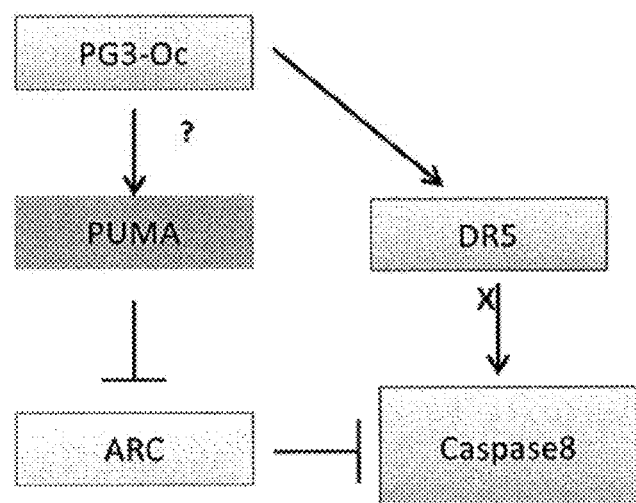

In particular, referring to FIGS. 30A-30H, it is shown that PUMA is a key effector of PG3-Oc mediated apoptosis in mutant p53 cell lines. FIG. 30A shows the human PUMA gene contains three coding exons (exons-2-4) and two non-coding exons (exons 1a and 1b). PUMA protein has two functional domains, the BH3 and C-terminal mitochondria-localizaion signal (MLS). The red-colored residues are conserved within other proapoptotic Bcl-2 family members. FIG. 30B shows sequencing result of guide 1-containing plasmid P1D. FIG. 30C shows DNA sequencing results of HT29-P1D, which are pools of lentivirus-infected and puromycin-selected cells. FIG. 30D shows the decomposition window of TIDE analysis for HT29-P1D. FIG. 30E shows Western blotting analysis of the express of PUMA protein from single cell colonies of HT29-P1D cells. FIG. 30F shows HT29 and HT29-Puma-KO cells were treated with PG3-Oc or co-treated with caspase 8(cas8 inh), caspase-9 (cas9 inh) and pan-caspase (Z-VAD-FMK) inhibitors for 48 hours, subG1 populations were analyzed by flow cytometry. FIG. 30G shows the activation of caspases and PARP cleavage were detected by western blotting using indicated antibodies. FIG. 30H shows a model for PUMA mediated activation of caspase-8.

Taken together, these data indicate that caspase-8 cleavage is an up-stream event of the activation of caspase-9 and caspase-3, and that PUMA mediates the apoptotic effects of PG3-Oc through activation caspase-8.

5) The Molecular Mechanism of PG3-Oc-Induced Up-Regulation of PUMA May Involve the UPR:

The molecular mechanisms responsible for up-regulation of p53 target genes by PG3-Oc in p53 mutant colorectal cancer cells was investigated. Transcription factors p73, p63, ATF4, CHOP, FOXO3a, NF-κB, and JNK/c-Jun can mediate induction of PUMA in a p53-independent manner depending on cell types and stimuli.

Figure 31A:
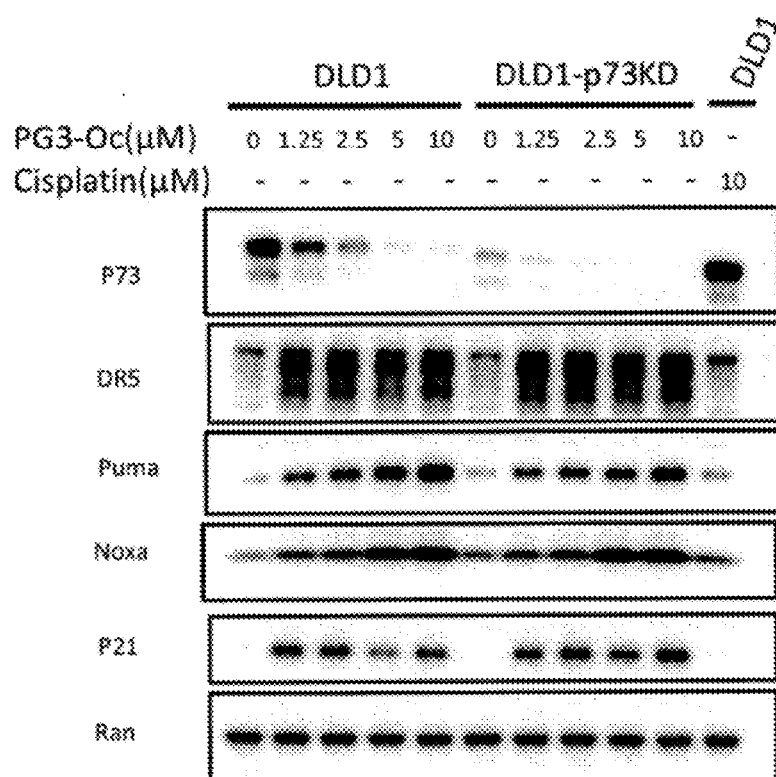
Figure 31C:
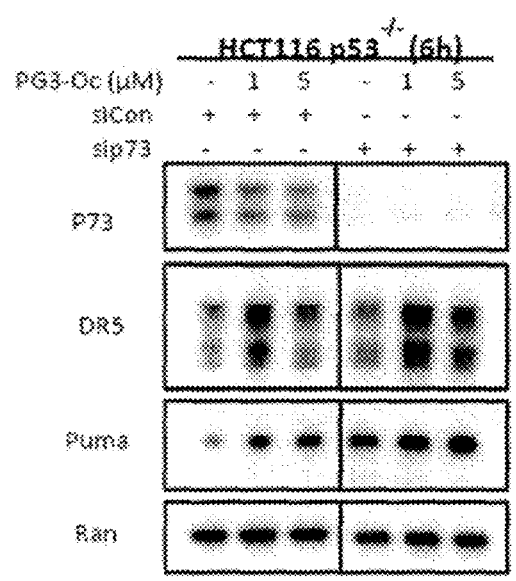
Figure 32A:
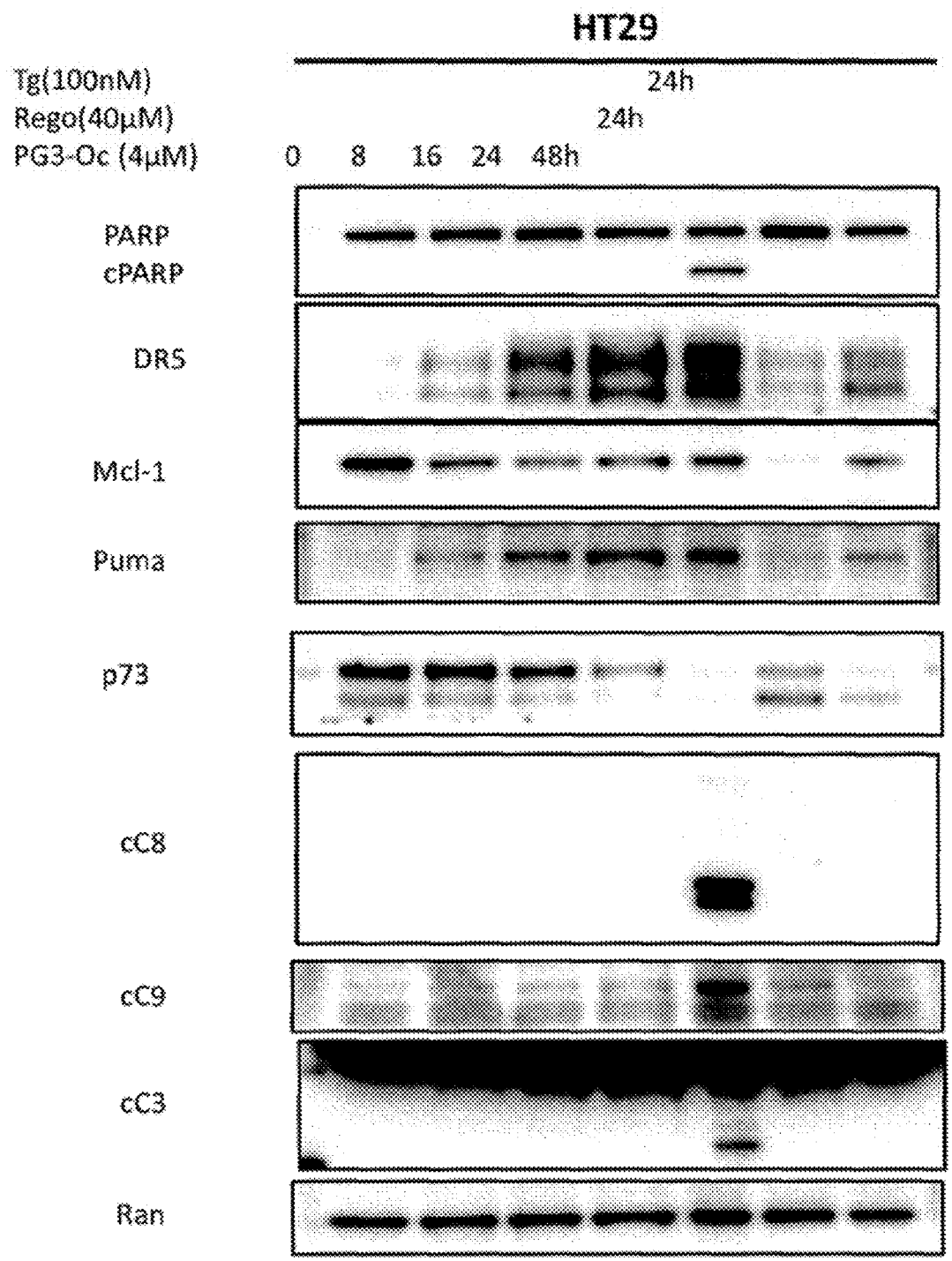
FIGS. 32A and 32B depict time-course analysis of caspase activation.
Figure 32B:
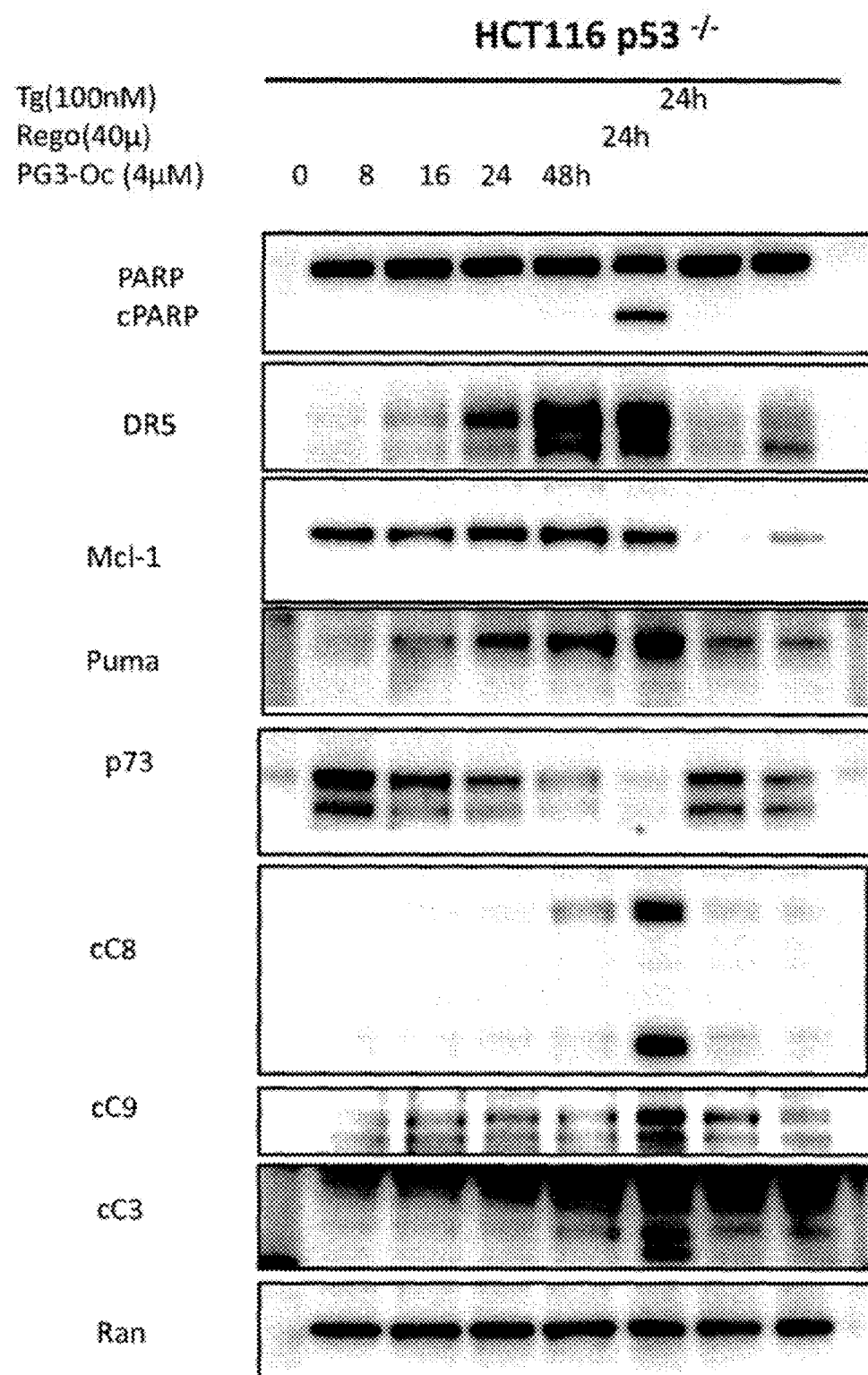

PG3-Oc treatment resulted in a decrease of p73 protein in DLD1, HCT116 p53$^{-/-}$ (see, FIGS. 31A and 31C), SW480 and HT29 (FIGS. 32A and 32B). Knockdown of p73 did not affect PG3-Oc-induced up-regulation of p53 target genes, DR5, p21, Noxa and PUMA (see, FIGS. 31A and 31C). These data indicate that p73 is not involved in PG3-Oc-induced up-regulation of these p53 target genes in these colorectal cancer cell lines.

In particular, referring to FIGS. 32A and 32B, the time-course analysis of active caspase-3, active caspase-8, active caspase-9, cleaved PARP(cPARP), Puma, and DR5 in PG3-Oc-treated HT29 cells (see, FIG. 32A) or HCT116 p53$^{-/-}$ cells (see, FIG. 32B) by Western Blot. Regorafenib (Rego) is a positive control for Puma, and thapsigargin(Tg) is a positive control for DR5.

Figure 33A:
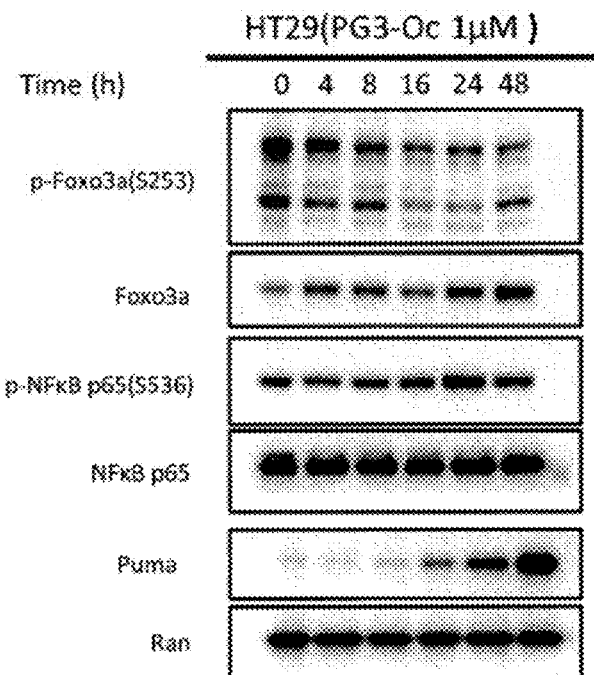
FIGS. 33A, 33B, 33C, and 33D depict the exploration of the molecular mechanism of PG3-Oc-induced up-regulation of PUMA.
Figure 33B:
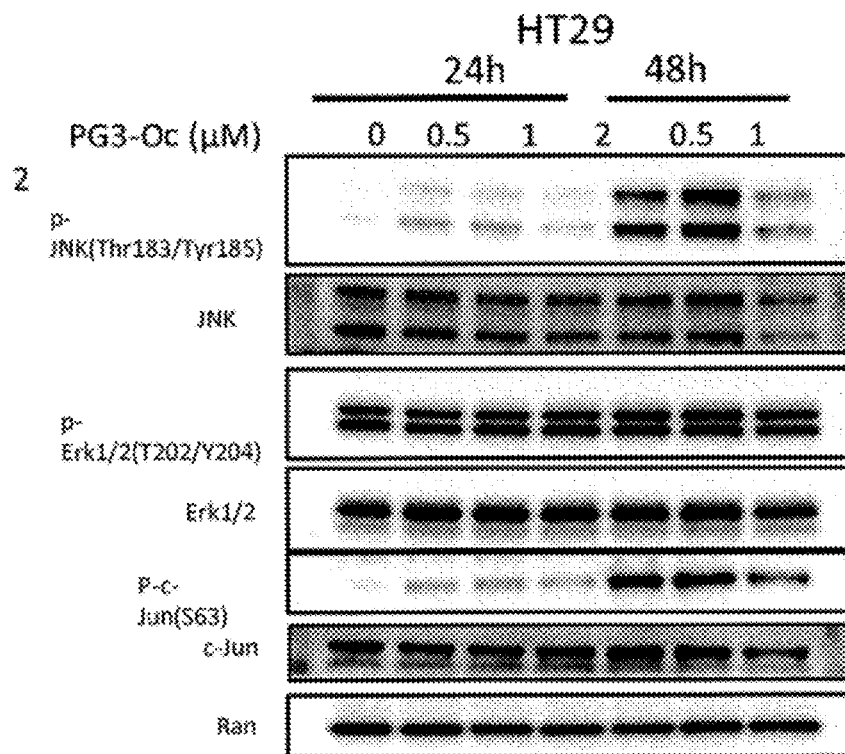
Figures 33C, 33D:
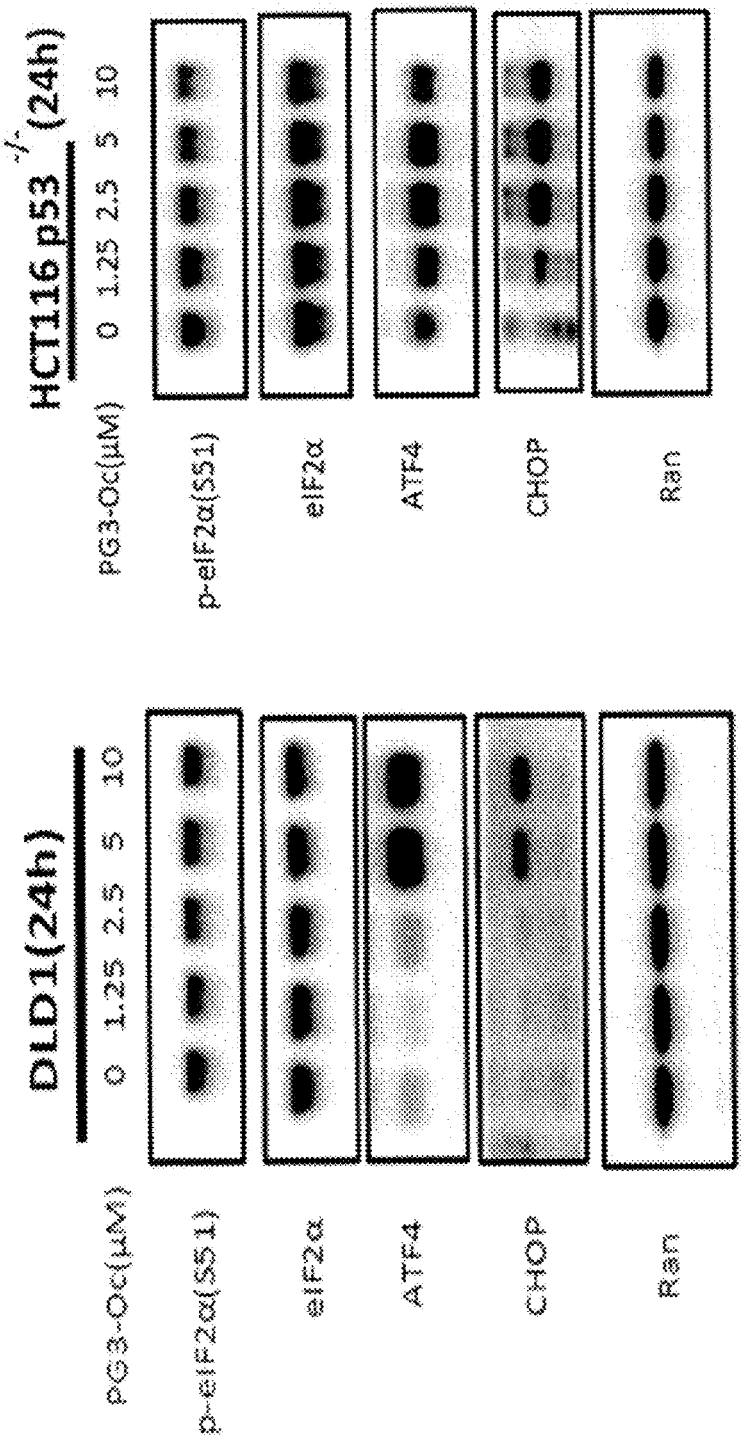

PG3-Oc treatment resulted in up-regulation of ATF4 and CHOP in both DLD1 and HCT116 p53$^{-/-}$ cell lines. However, induction of ATF4 and CHOP occurred at a significantly lower concentration in HCT116 p53$^{-/-}$ cells at 1.25 µM as compared to 5 µM in DLD1 cells (see, FIGS. 33C and 33D). HCT116 p53$^{-/-}$ cells were selected for studying whether ATF4 and/or CHOP may be responsible for PUMA up-regulation. Knockdown of ATF4 or CHOP by siRNAs, respectively, did not blunt up-regulation of PUMA and p21, but blocked the up-regulation of DR5. These data indicate that ATF4 and CHOP are not involved in regulation of PUMA and p21, but may be responsible for DR5 induction (see, FIG. 31B), indicating that PG3-Oc treatment may trigger the UPR signaling pathway.

PG3-Oc treatment leads to decreased phosphorylation of Ser-253 of FOXO3a, increased phosphorylation of Ser-536 of NF-κB p56 and phosphorylation of JNK and c-Jun (see, FIGS. 33A and 33B); however, knockdown of FOXO3a and NF-κB p56, inhibition of JNK by JNK inhibitor SP600125 did not abolish up-regulation of PUMA (see, FIGS. 31D and 31E). These data indicate that NF-κB, FOXO3a and JNK/c-Jun do not involved in the regulation of Puma.

In particular, referring to FIGS. 33A-33D, the exploration of the molecular mechanism of PG3-Oc-induced up-regulation of PUMA is shown. HT29 cells were treated with indicated doses and time points, phosphorylation of FOXO3a, NF-κB, JNK, c-Jun and Erk1/2 were detected by Weston blotting using corresponding antibodies.

Figure 31B:
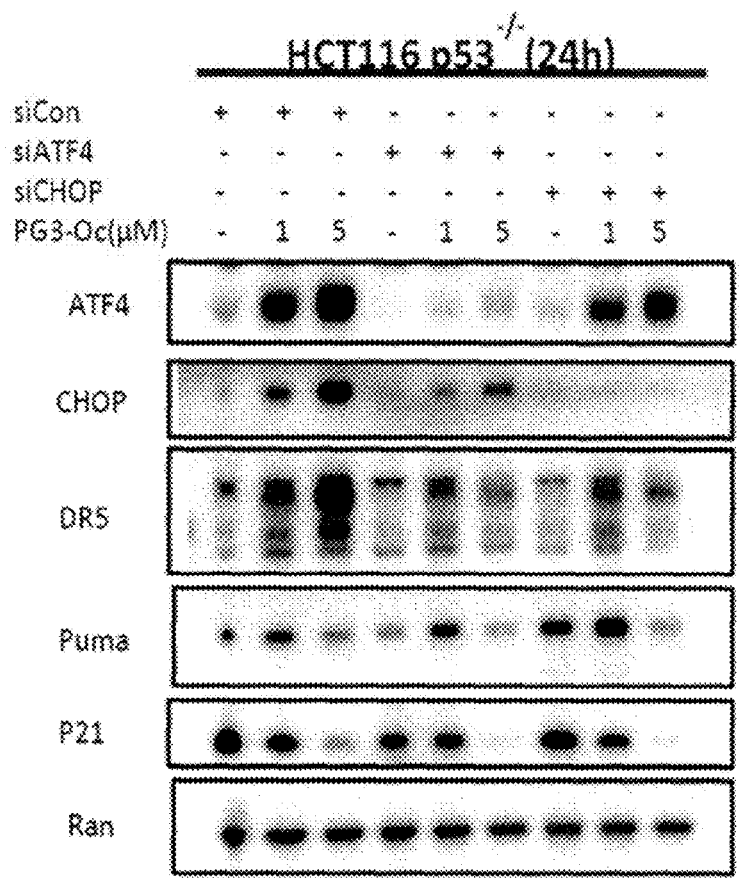

In particular, referring to FIGS. 31A-31E, the exploration of the molecular mechanism of PG3-Oc-induced up-regulation of PUMA is shown. FIG. 31A shows p53 mutant DLD1(S241F) and p73 stable-knockdown DLD1-p73KD were treated with indicated concentration of PG3-Oc for 18 hours, Cisplatin was used as a positive control for p73. FIG. 31B shows HCT116 p53$^{-/-}$ cells were transfected with ATF4 or CHOP siRNAs, after 24 hours transfection the cells were treated with PG3-Oc for 24 hours. Protein levels of p53 target genes in cells were detected by Western Blot. FIG. 31C shows HCT116 p53$^{-/-}$ cells were transfected with p73 siRNA, after 24 hours transfection the cells were treated with PG3-Oc for 6 hours. Protein levels of p53 target genes in cells after PG3-Oc treatment were detected by Western Blot. Knockdown of p73 does not prevent PG3-Oc-induced expression of p53-target genes. FIG. 31D shows HT29 cells were transfected with Control, NF-κB and FOXO3a siRNAs respectively. After 24 hours of transfection, the cells were treated with 1 µM PG3-Oc for 24 hours and protein levels in cells were detected by Western Blot. FIG. 31E shows T29 cells were pre-treated for 1 hour with JNK inhibitor SP600125, and then treated with 1 µM PG3-Oc for 24 hours. Protein levels in cells were detected by western blot using indicated antibodies.

Figure 34A:
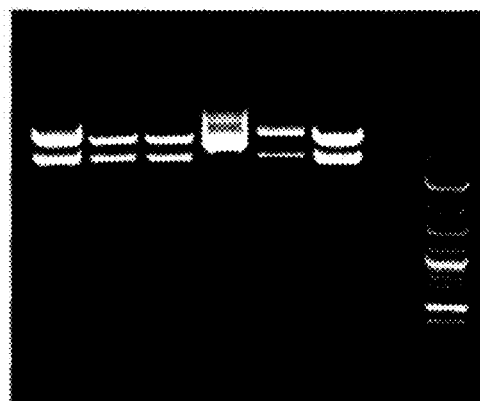
FIGS. 34A, 34B, 34C, 34D, 34E, 34F, 34G, 34H, and 34I depict knock-out of PUMA by CRISPR/Cas9 gene editing.
Figure 34B:
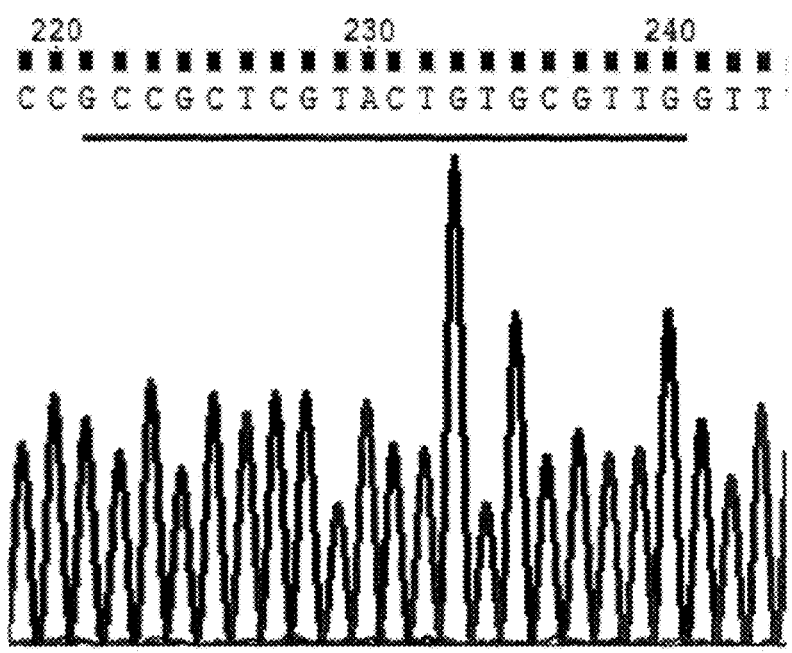
Figure 34C:
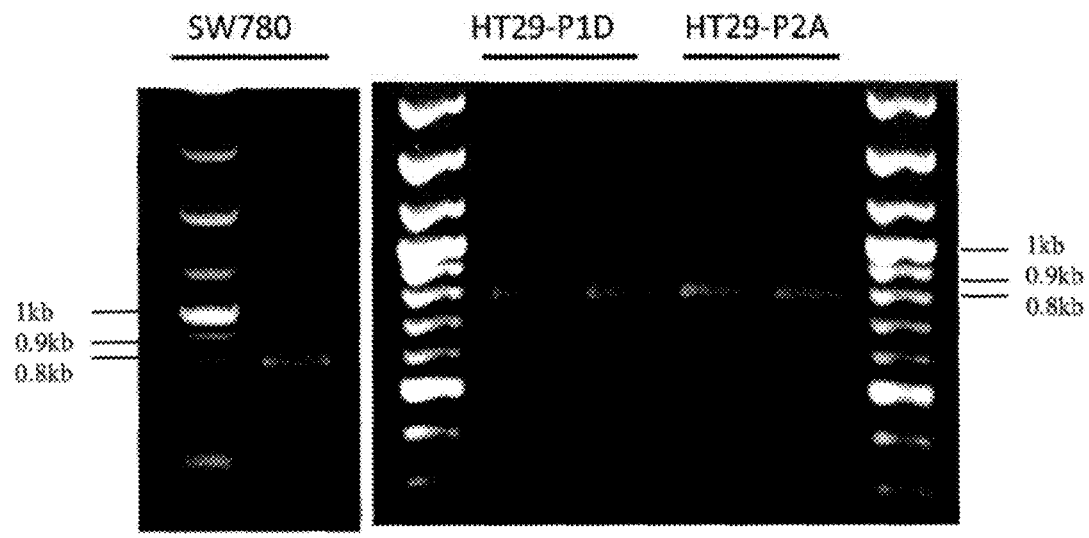
Figure 34D:
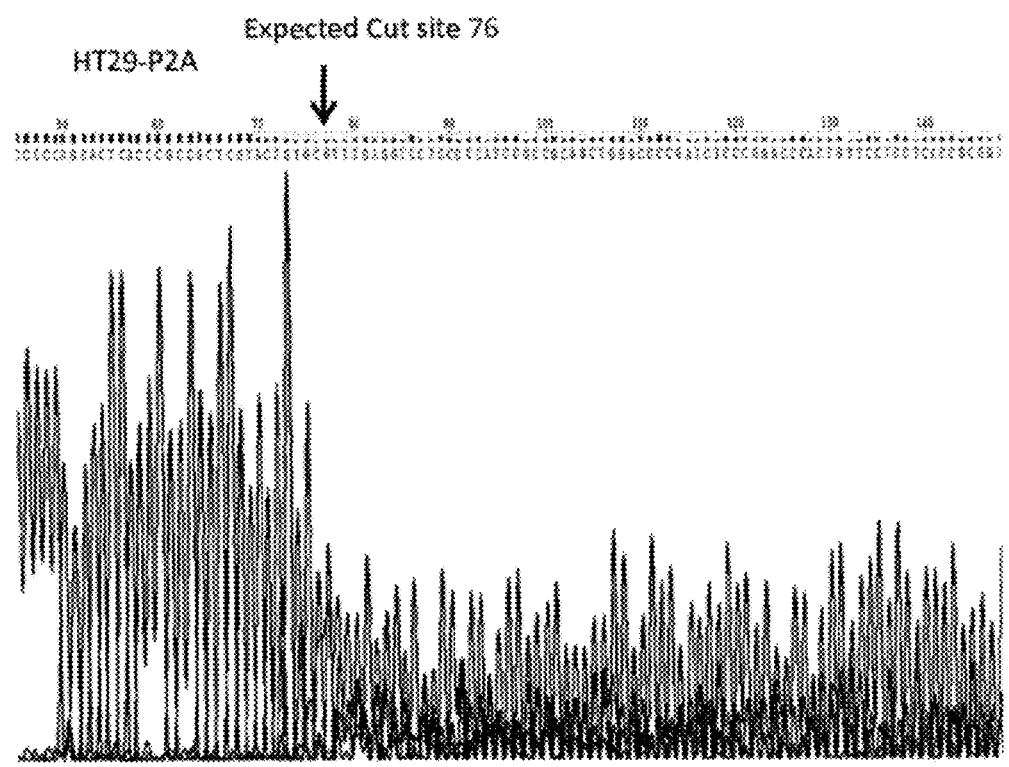
Figure 34E:
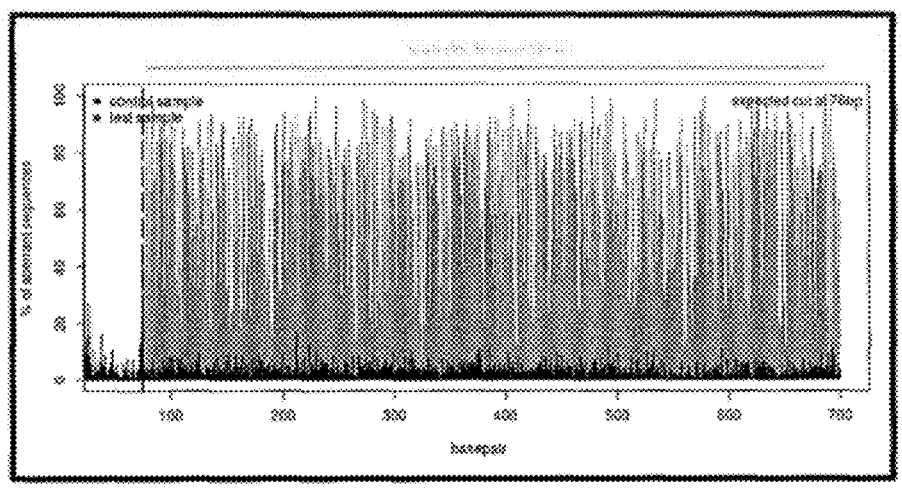
Figure 34F:
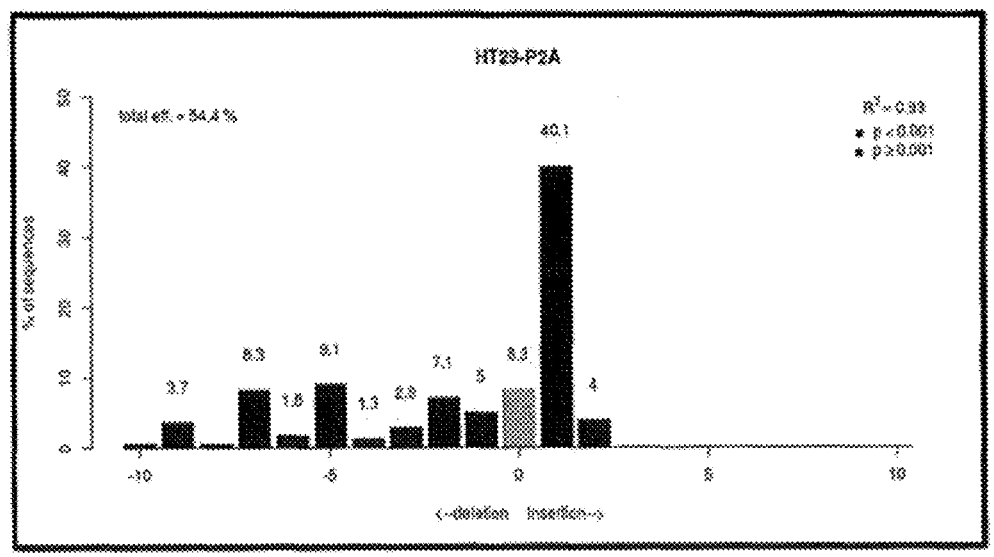
Figure 34G:
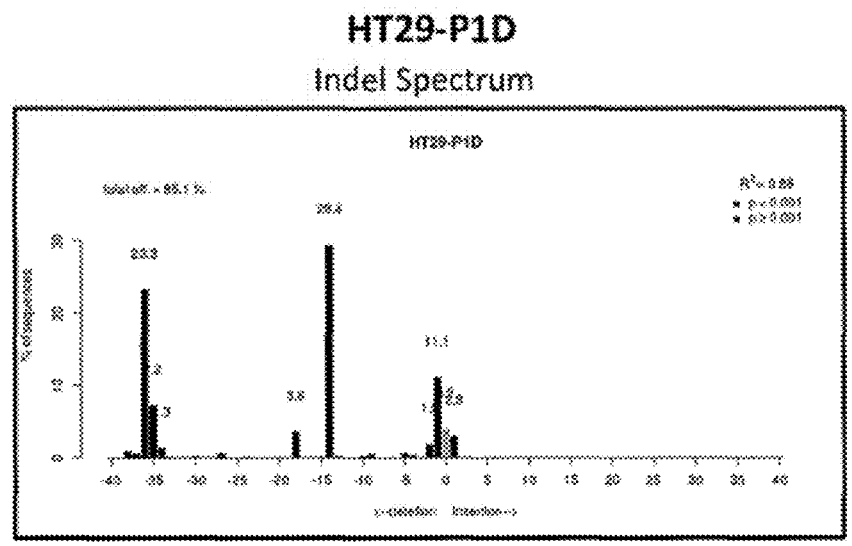
Figure 34H:
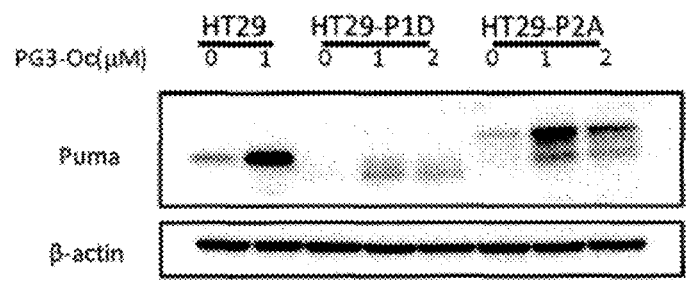
Figure 34I:
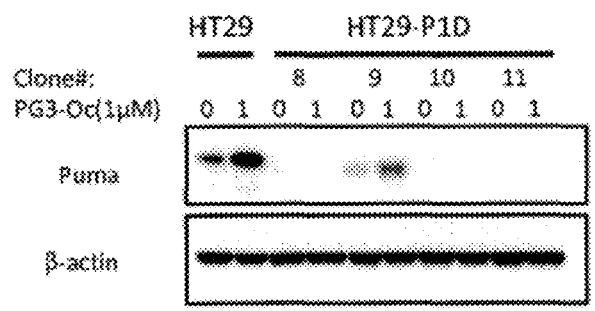

In particular, referring to FIGS. 34A-34I, the knock-out of PUMA by CRISPR/Cas9 gene editing is shown. FIG. 34A shows P1A, P1D, P2A and P2B are plasmids containing guide 1 or guide 2 purified from corresponding bacteria colonies (P1A, P1D, P2A and P2B), respectively. Plcve is a negative control plasmid, and KDM6A is a positive control plasmid. FIG. 34B shows sequence of guide 2 and sequencing result of guide 2-containing plasmid P2A. FIG. 34C shows PCR results of HT29-P1D, HT29-P2A and SW780 (wild-type DNA) using primers that cover the exon 3 of PUMA gene. FIG. 34D shows DNA sequencing results of HT29-P2A, which is a pool of lentivirus-infected and puromycin-selected cells. FIG. 34E shows the decomposition window and indel spectrum of TIDE analysis for HT29-P2A. FIG. 34F shows indel spectrum of TIDE analysis for HT29-P2A. FIG. 34G shows indel spectrum of TIDE analysis for HT29-P1D. FIG. 34H shows Western blotting analysis of the express of PUMA protein in HT29-P1D and HT29-P2A cells. FIG. 34I shows Western blotting analysis of the express of PUMA protein from single cell colonies of HT29-P1D cells.

Discussion:

Apoptosis repressor with caspase recruitment domain (ARC) is an endogenous inhibitor of apoptosis which binds and suppresses caspase-8. Expression of ARC protein is predominantly seen in terminally differentiated cells (cardiac, skeletal myocytes and neurons) under normal conditions and is markedly induced in a variety of cancers including pancreatic, colorectal, breast, lung, glioblastoma, liver, kidney, melanoma, and acute myeloid leukemia. ARC is a primary target of p53, and p53 transcriptionally represses the express of ARC, which can initiate apoptosis. Phosphorylation of ARC at T149 by CK2 (casein kinase 2) leads to ARC translocation from cytosol to mitochondria where it binds to death domain of caspase-8 and inhibits caspase-8 activation.

PUMA localizes in mitochondria and induces apoptosis by activating caspases via activating BAK and BAX to cause mitochondrial dysfunction. ARC binds to caspase-8 death domain through its N-terminal CARD (caspase recruitment domain) domain. PUMA via its BH3 domain binds to the CARD domain of ARC tightly, resulting in releasing of caspase-8 from ARC, and then activation of caspase-8. Vice versa, up-regulation of ARC protein level in cancer cells can suppress PUMA-mediated caspase activation and apoptosis by sequestering PUMA and releasing anti-apoptotic Bcl-2 family members. Based on the data, a model of PG3-Oc-induced and PUMA-mediated apoptosis in colorectal cancer cells is disclosed in FIG. 30H.

The results indicate that a prodigiosin analog, PG3-Oc, has comparable efficacy as obatoclax and prodigiosin in p53 mutant cancer cell lines. PG3-Oc is a more potent inducer than prodigiosin in restoration of the p53 signaling pathway.

Example 3: Synthesis of PG3-Oc (Formula (IXd))

Figure 35:
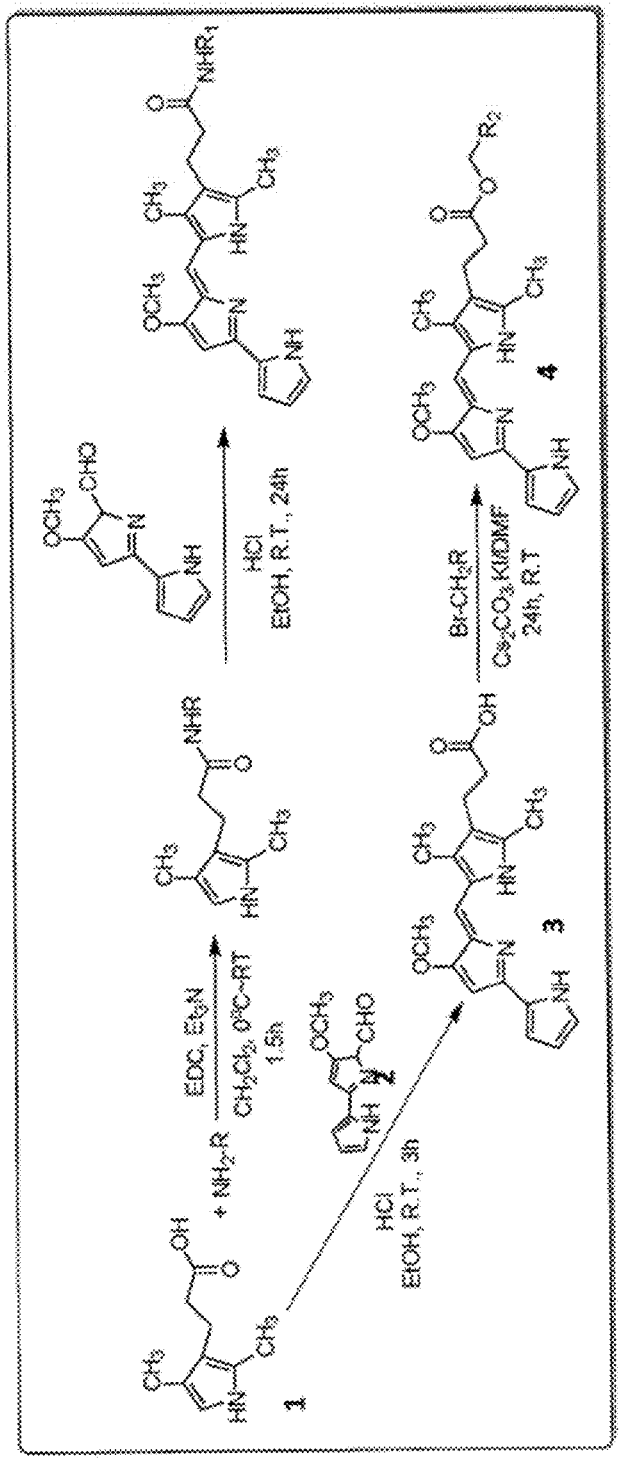
FIG. 35 depicts a representative synthetic scheme for PG3-Oc.
Figure 39:
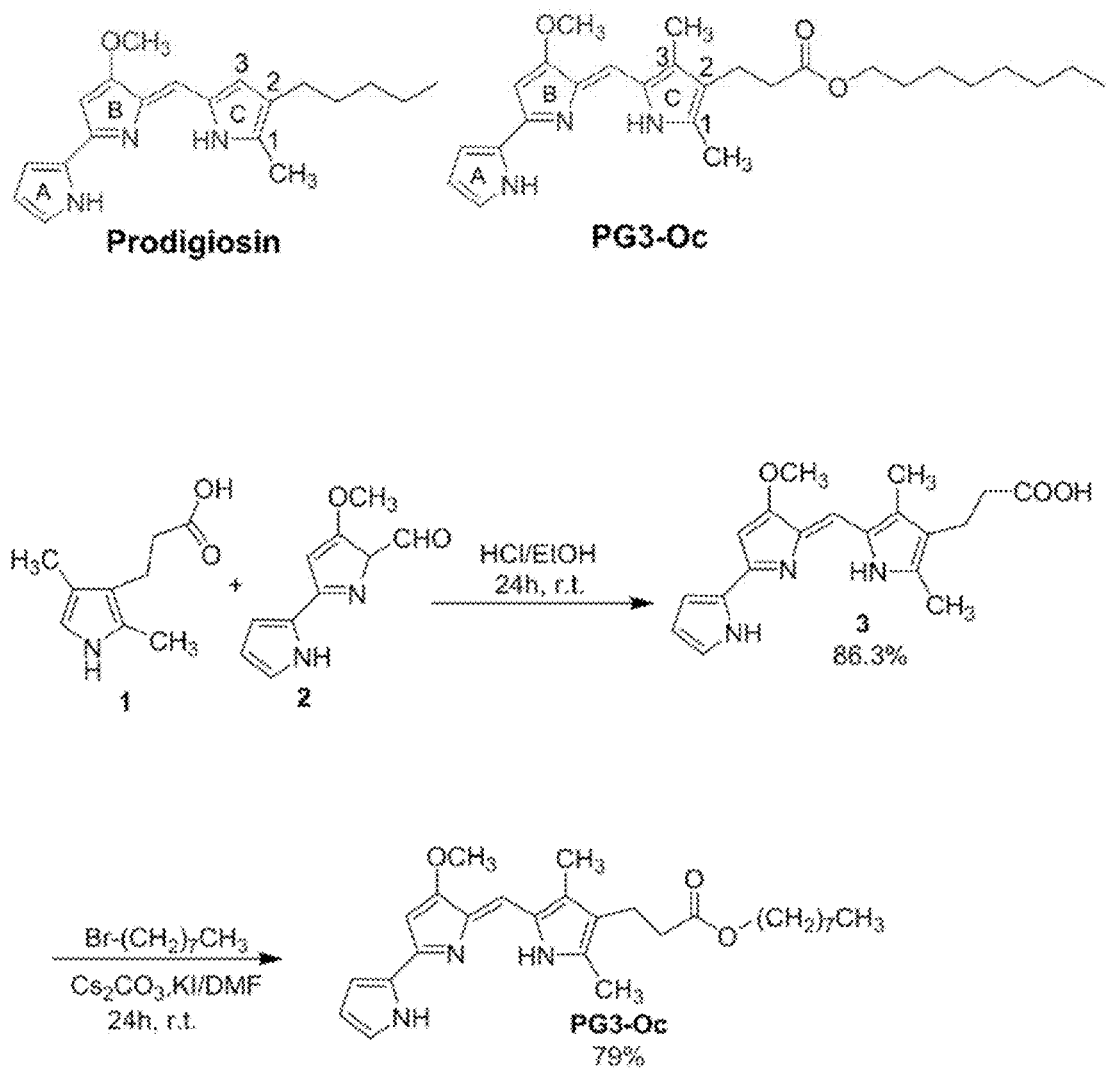
FIG. 39 shows progigiosin and PG3-Oc structures and a representative synthetic preparation of PG3-Oc.

A representative synthesis of PG3-Oc and related compounds is shown in FIGS. 35 and 39. Compound 1 and Compound 2 (see, FIG. 39) were purchased from AstaTech Inc. (Bristal, Pa. 19007).

Figure 36:
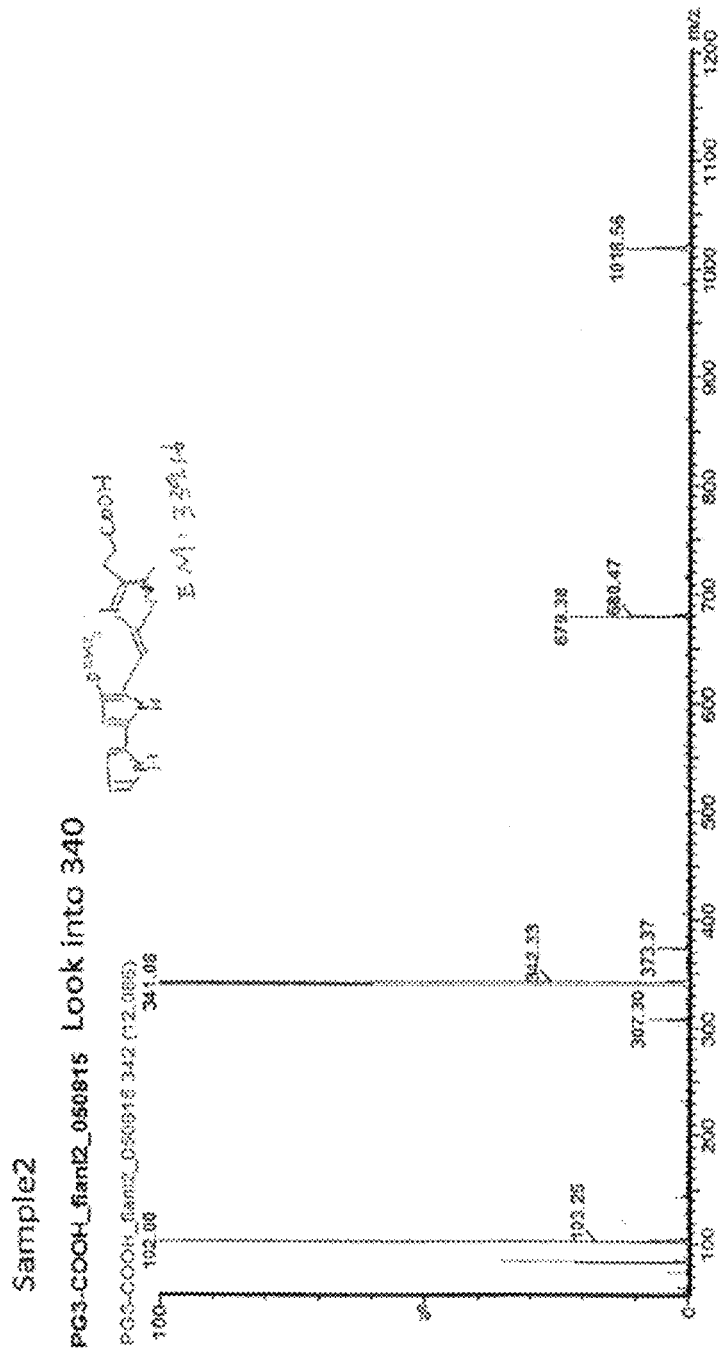
FIG. 36 depicts Mass spectrum analysis of Compound 3 in FIG. 35.
Figure 37:
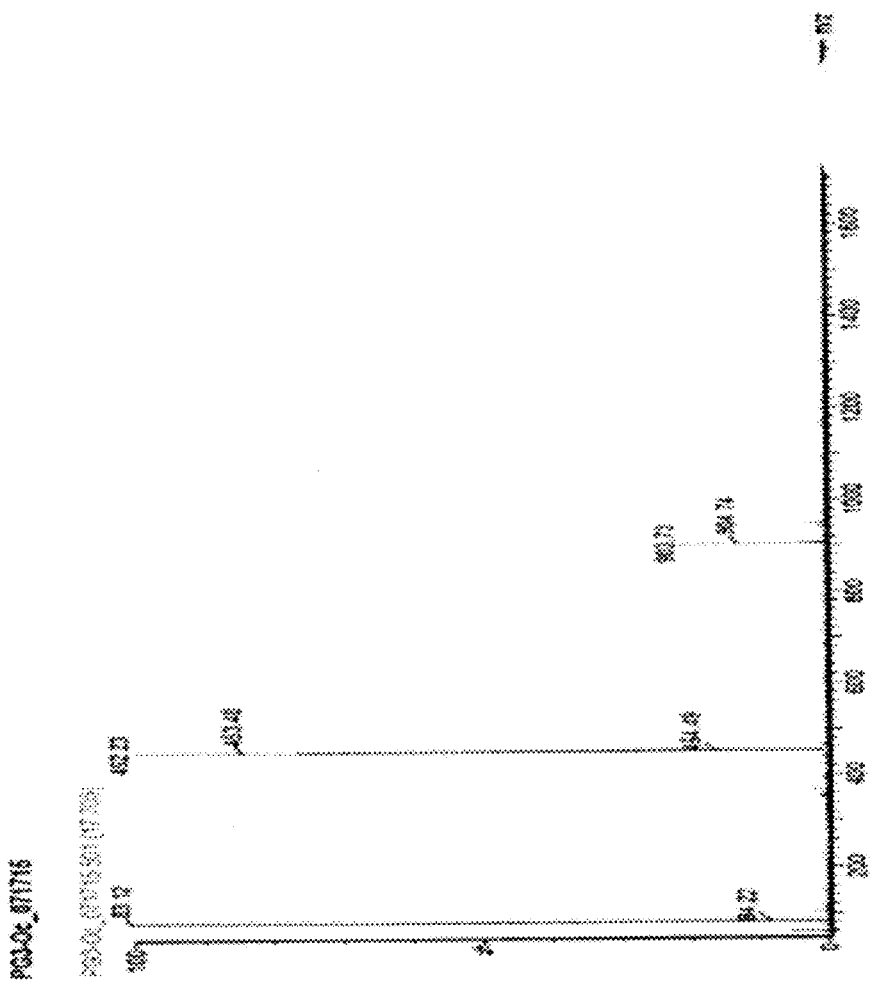
FIG. 37 depicts Mass spectrum analysis of PG3-Oc.
Figure 38:
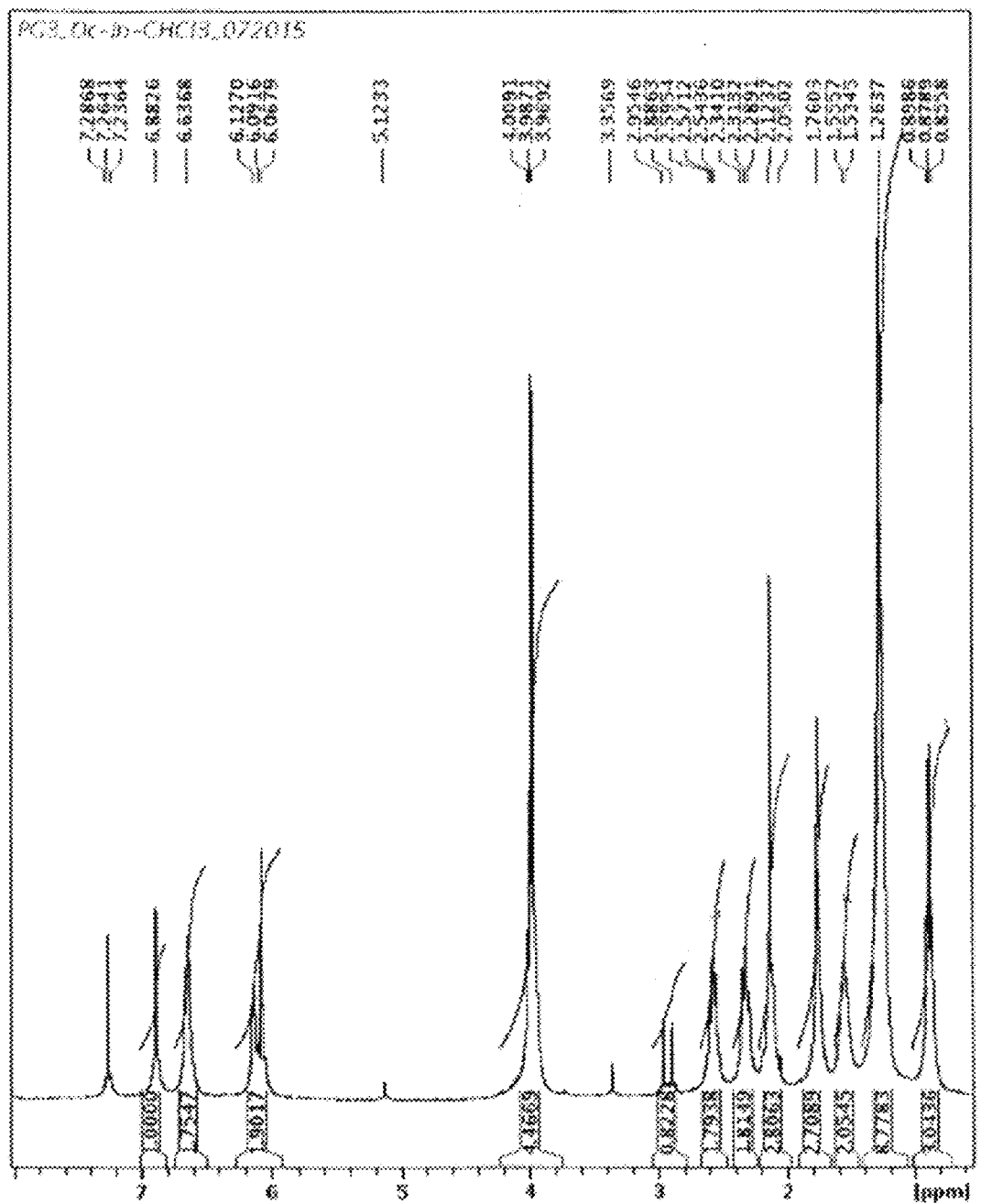
FIG. 38 depicts $^1$H NMR analysis of PG3-Oc.

Synthesis of compound 4 (PG3-0c): Mass spectrum analysis was performed with Waters LC-MS system which includes a Waters single quadrupole 3100 MS (mass detector using electrospray and chemical ionization). $^1$H NMR analysis was performed on a Bruker Advance 300 MHz instrument (see, FIGS. 36, 37, and 38 MS and NMR spectrums).

Compound 3, (Z)-3-(5-((4'-methoxy-1H,5'H-[2,2'-bipyrrol]-5'-ylidene)methyl)-2,4-dimethyl-1H-pyrrol-3-yl)propanoic acid (Compound 3)

2,4-Dimethyl-1H-pyrrole-3-carboxylic acid 131.9 mg (compound 1, 0.79 mmol) and 4-methoxy-1H,1'H-2,2'-bipyrrole-5-carbaldehyde 100 mg (compound 2, 0.53 mmol) were dissolved in 10 mL ethanol, and then 90 µL concentrated hydrochloric acid was added to the mixture. The reaction was stirred at room temperature for 3 hours. The reaction mixture was concentrated. The crude material was chromatographed 63-200 µM aluminum oxide (activity II) eluting with ethyl acetate/hexane 30:70 to produce the desired compound 3, giving a correct molecular weight 339.91. $^1$H NMR (300 MHz, DMSO-d6): δ=11.4 (1H, bs), 7.66 (1H, s), 7.59 (1H, s), 7.21 (1H, s), 6.95 (1H, s), 4.22 (3H, s), 2.83 (2H, t), 2.64 (3H, s), 2.55 (2H, t), 2.38 (3H, s).

Compound 4 (PG3-Oc), Octyl (Z)-3-(5-((4'-methoxy-1H,5'H-[2,2'-bipyrrol]-5'-ylidene)methyl)-2,4-dimethyl-1H-pyrrol-3-yl)propanoate KI (18.7 mg), $Cs_2CO_3$ (169.3 mg) and compound 3 (75 mg) were added to 0.75 ml anhydrous DMF, stirred for 5 minutes at room temperature. Then 1-Bromooctane (39 μL) was added to the mixture, which was stirred at room temperature for 24 hours. 20 ml of PBS w/o $Ca^{2+}$—$Mg^{2+}$ buffer was added to the reaction mixture. The mixture was extracted with 20 mL×2 dichloromethane, and combined organic layer was washed with 50 ml of saturated NaCl. The organic layer was dried over anhydrous $Na_2SO_4$ overnight. The next day, the dried organic layer was concentrated and crude product was separated on aluminum oxide column. The desired compound 4 was eluted with ethyl acetate/hexane gradient from 10% to 20%. MS analysis gave the correct molecular weight [M+H⁺] 452.23. ¹H NMR (300 MHz, $CDCl_3$): δ=6.88 (1H, s), 6.63 (2H, s), 6.12 (1H, s), 6.06 (1H, s), 4.00 (2H, s), 3.98 (3H, s), 2.57 (2H, t), 2.31 (2H, s), 2.12 (3H, s), 1.76 (3H, s), 1.55 (3H, m), 1.26 (10H, m), 0.87 (3H, t).

Example 4: Materials and Methods of Cell-Based Biological Evaluation of PG3-Oc

Cell Lines

P53-mutant cell lines: HT29 (R273H), SW480 (R273H/P309S), DLD-1 (S241F), H1975 (R273H), MDA-MD-231 (R280K), U251 (R273H), FaDu (R248L), CAL-27 (H193L), PANC-1 (R273H), Aspc-1 (frameshift mutation), Jurkat (multiple p53 mutations, including truncation); P53 wild-type cell lines: HCT116, and CCD 841 Con; P53-null cell line: HCT116 p53⁻/⁻. All cell lines were obtained from the ATCC and cultured as recommended. Cells were regularly authenticated by bioluminescence, growth, and morphologic observation. Cells were routinely checked for *mycoplasma* and all cell lines underwent STR authentication.

Western Blotting

After treatment, protein lysates were collected for Western blot analysis. A total of 15 μg of protein was used for SDS-PAGE. After primary and secondary antibody incubations, the signal was detected by a chemiluminescence detection kit, imaged by Syngene (Imgen Technologies). Antibodies for PUMA (for IHC), p53 (Santa Cruz Biotechnology), caspase 8, cleaved caspase 8, caspase 9, caspase 3, cleavage PARP, eIF2a, p-eIF2a (Ser51), CHOP, ATF4, DR5, FOXO3a, p-FOXO3a (Ser253), NF-κB p65, p-NF-κB p65 (Ser536), c-Jun, p-c-Jun (Ser63), JNK, p-JNK (Thr183/Tyr185), PUMA (for WB), c-Myc, phosphor-S62-cMyc (Cell Signaling Technology), Noxa, p21 (Calbiochem), p73 (Bethyl laboratories Inc), Ran (BD Biosciences), β-actin (Sigma).

Cell Viability Assay

Cells were seeded in 96-well plates (6×10³ cells/well). Cells were treated with different concentrations of compounds or dimethyl sulfoxide (DMSO) as a control for 72 hours.

The cell viability was assessed by CellTiterGlo bioluminescent cell proliferation assay (Promega), following the manufacturer's protocol. Bioluminescence imaging was measured using the IVIS imager. Percentage of cell viability (mean±SEM) at each dose was calculated against the respective DMSO control. The IC50 values were determined from the sigmoidal dose-response curves using GraphPad Prism.

Caspase Activity Assay

Cells were seeded in 96-well plate (1×10⁴ cells/well). Cells were treated with different concentrations of compounds or dimethyl sulfoxide (DMSO) as a control for 24 hours. Caspase 3/7 activity was assessed by the Caspase-Glo® 3/7 Assay kit (Promega), following the manufacturer's protocol. Bioluminescence imaging was measured using the IVIS imager. Caspase activity was normalized to cell numbers and compared to those of the DMSO treatment control in each cell line. Data is reported as mean RLU+SEM (n=3).

Colony Formation Assays

Five hundred cells were seeded per well in 6-well plates and treated with different concentrations of compounds for 24 hours, then, cells were cultured with drug-free complete medium for 2 weeks with fresh medium changed every 7 days. Cells were fixed with 10% formalin and stained with 0.05% crystal violet at the end of 2 weeks period of cell culture (Franken et al., Nat. Protoc., 2006, 1, 2315-9).

Cell Uptake and Localization

A total of 5×10⁴ cells were seeded in each well of 8-well chamber slides. Cells were incubated with PG3-Oc for 2 and 8 hours respectively, washed and fixed by 4% paraformaldehyde for 15 minutes at room temperature, washed, stained with DAPI for 10 minutes, mounted, and examined by fluorescence microscopy.

Immunofluorescence Staining

A total of 5×10⁴ cells were seeded in each well of 8-well chamber slides. After treatment, cells were fixed and permeabilized by methanol:acetone (1:1) for 20 minutes at −20° C. Fixed cells were blocked by 2% BSA for 1 hour, followed by primary antibody incubation for 1 hours and Cy3-conjuated secondary antibody incubation for 1 hour at room temperature. After washing, cells were stained with DAPI for 10 minutes at room temperature. Cells were mounted, and examined by fluorescence microscopy.

Flow Cytometry Assay

Cell Cycle Analysis: Propidium iodide (PI) staining and flow cytometry were used to determine the degree of cellular apoptosis. Cells were seeded at 3×10⁵ cells/well in six-well plates. Cells were treated with PG3-Oc for 48 hours. Cells were harvested, fixed by 70% ethanol, and stained by propidium iodide, then flow cytometry was performed as previously described (Smithen et al., Org. Biomol. Chem., 2013, 11, 62-68). The percentage of hypo-diploid cells (sub-G1) was used to quantify dead cells in apoptosis assays.

qRT-PCR

Total RNA was isolated from PG3-Oc-treated cells using the Quick-RNA mini prep kit (Zymo Research, Irvine, Calif.) according to the manufacturer's protocol. 500 ng of total RNA was used to generate cDNA using SuperScript III first-strand synthesis system with random primers (Invitrogen), following the manufacturer's protocol. Real-time PCR was performed using POWER SYBR GREEN mast mix (Applied Biosystem) for DR5, p21, PUMA, GAPDH, and TaqMan primer-probes for detection of c-Myc mRNA levels on 7900HT Sequence Detection System (Applied Biosystem). Primers having SEQ ID NOs:1-6 (see above) were used. Taq Prob IDs for c-Myc (HS 00153408) and GAPDH (HA 99999905). ΔΔCt method was used to analyze and report fold changes of the indicated genes.

siRNA Knockdown

Knockdown experiments were performed by transfecting either 80 pmoles of indicated siRNA(s), or scramble siRNA using RNAiMAX (Invitrogen). Transfected cells were treated with PG3-Oc, 24 hours post-transfection. The control scrambled siRNA and siRNA for human ATF4, CHOP, DR5, Puma, NF-κB p65, and c-Myc were purchased from Santa Cruz Biotechnology. p73 siRNA was obtained from Ambion, and FOXO3a siRNA was obtained from Thermo Scientific Dharmacon.

Transfection of Plasmids

Cells were transfected with c-Myc expression plasmids (Ricci et al., Mol. Cell. Biol., 2004, 24, 8541-55) and vector pcDNA3 (Invitrogen) using Lipofectamine 2000 (Invitrogen) according to the manufacturer's instruction.

Immunoprecipitation of PUMA with ARC

After 48 hours of co-transfection of PUMA and ARC plasmids using Lipofectamine 2000, HEK 293 cells were lysed with immunoprecipitation lysis buffer. 300 μg whole-cell lysate were incubated with 5 μg ARC antibody for 6 hours at 4° C. and followed by adding 10 μL of protein A/G Sepharose beads, and the samples were rocked at 4° C. for overnight and then washed three times with 200 μL washing buffer. Samples were eluted with elution buffer, followed by SDS-PAGE to detect ARC and PUMA.

Knock-Out of PUMA by CRISPR/Cas9 Gene Editing sgRNA design and plasmid construction: sgRNA targets the exon 3 of PUMA gene, which contains sequence code for BH3 domain of PUMA. Two sgDNAs (Guide) was introduced into lentiviral vectors (pLentiCRISPR-E) which contain eSpCas9 and puromycin cassette. Guide1 DNA primers (SEQ ID NO:7-8) and Guide 2 DNA primers (SEQ ID NO:9-10) (see above) were annealed and linked to the restriction enzyme-cut plasmid by T4 ligase. Stbl3 strain (Invitrogen C7373-03) was transformed by the guides-containing plasmids. LB-amp plates were streaked and incubated on a shaker at 37 C overnight. The bacterial colonies were selected and mixed with LB (Terrific Broth) and 100 μg/mL of ampicillin, and were incubated on a shaker at 37 C overnight. Plasmids from different colonies were isolated and purified using QIAprep Spin Miniprep Kit (Qiagen). Plasmids were digested with EcoRI HF and BamHI in Cut Smart Buffer (New England BioLabs, Inc.) at 37 C for 1 hour and then analyzed by 1% agarose gel. Sequencing was performed by GENEWIZ (South Plainfield, N.J.; see FIGS. 11 A-F).

Cell Culture, DNA Transfection

Lentivirus was generated with psPAX2, pVSV-G and the pLentiCRISPR plasmids that contain the guides and Cas9 in 293T cells. 48 hours later, all supernatant was transferred to a 1.5 mL tube. Debris was removed by centifugation, and the supernatant was transferred to a new 1.5 mL tube, and stored at 4 C. HT29 cells were transfected with the lentivirus supernatant and polybrene was added to enhance the transfection. Puromycin (final concentration is 1 μg/mL) was added to medium to select positive cells.

Mutation Screens by Sanger Sequencing and TIDE Analysis

DNA was extracted and purified from positive HT29 cells using DNeasy Blood & Tissue kit (Qiagen). PCR primers that flank both sides of the exon 3 of PUMA gene were used to amplify the target region (using primers with SEQ ID NO:1112; see above). The amplicon was GC-rich. Thus, to improve PCR specificity, temperature gradient PCR was performed to optimize annealing temperature. A hot-start and touch-down PCR with accuPrime™ Pfx DNA Polymerase (ThermoFisher Scientific) and 2.5% DMSO and 1M betaine, was performed to achieve specific amplification of target region. The PCR products were purified by QIAquick PCR purification kit (Qiagen) for Sanger sequencing. TIDE analysis was performed using an online tool (TIDE: Tracking of Indels by DEcomposition, world wide web at "tide-calculator.nki.nl/"). Sequencing was performed by GENEWIZ (South Plainfield, N.J.; see FIG. 30C).

Figure 95:
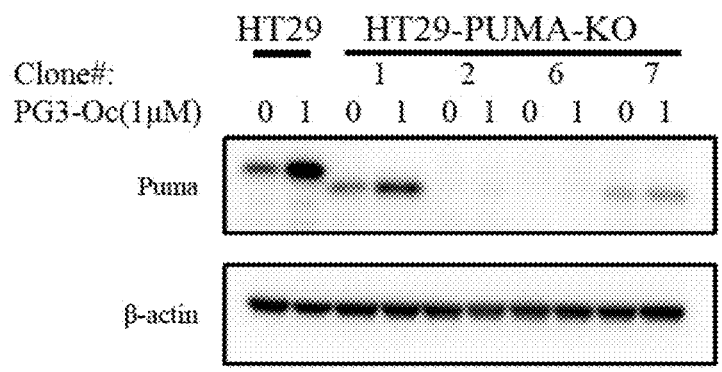
FIG. 95 shows the Western blot analysis of the expression of PUMA protein from single cell colonies isolated from a pool of HT29-PUMA-KO cells.
Figure 96:
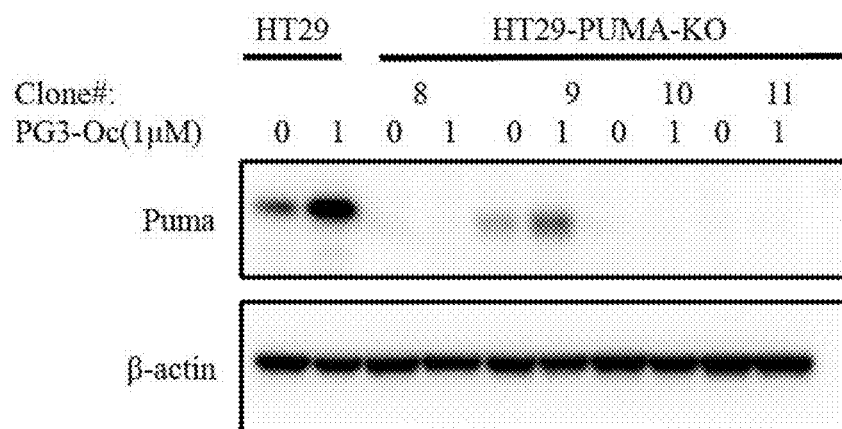
FIG. 96 shows the Western blot analysis of the expression of PUMA protein from single cell colonies isolated from a pool of HT29-PUMA-KO cells.

Single Cell Colonies 300 positive HT29 cells were placed into a 10 cm dish and incubated at 37 C. After 2 weeks, single cell colonies were selected and expanded. Western blotting using PUMA antibody was performed to screen the colonies (see, FIGS. 95 and 96).

In Vivo Anti-Tumor Assay

One million HT29 were implanted subcutaneously in the flanks in each athymic nude mouse (female, 4-6 weeks old). The mice were divided at random into two groups and treated with the vehicle (10% DMSO, 20% Kollipher EL in PBS) and PG3-Oc (5 mg/kg, 3 times/week) by intraperitoneal injection when the tumor masses reached a size of 5 to 6 mm. Subsequently, tumor volumes were measured with a caliper and calculated using V=0.5×Length×Width. Twenty three days after treatment, the mice were euthanized and tumors were excised. H & E staining and Immunohistochemistry (IHC) of paraffin-embedded tumor and tissue sections were performed at the Fox Chase Cancer Center Histopathology Facility.

Statistical Analysis

All results were obtained from triplicate experiments, unless other indicated. Statistical analyses were performed using PRISM4 Software (GraphPad Software, Inc.), and the Student t test. Statistical significances were determined by P<0.05. Combination indices were calculated using the Chou-Talalay method with CalcuSyn software (Biosoft).

Figure 40:
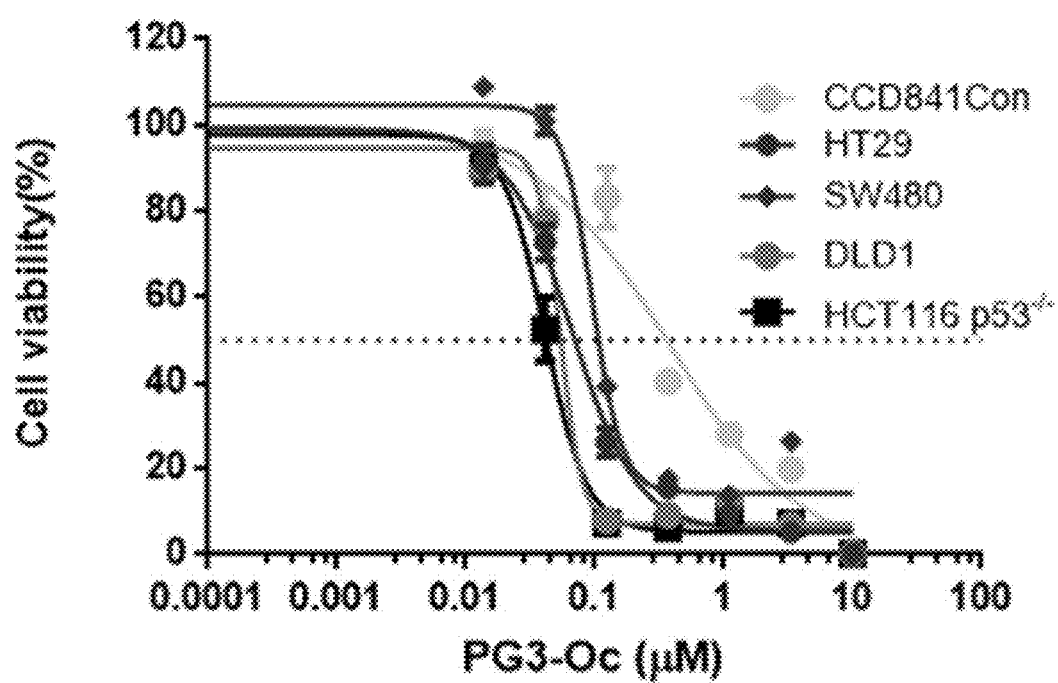
FIGS. 40 and 41 show cell viability assay, dose response curves, and IC50 value measurement of PG3-Oc in a panel of cancer cell lines.
Figure 41:
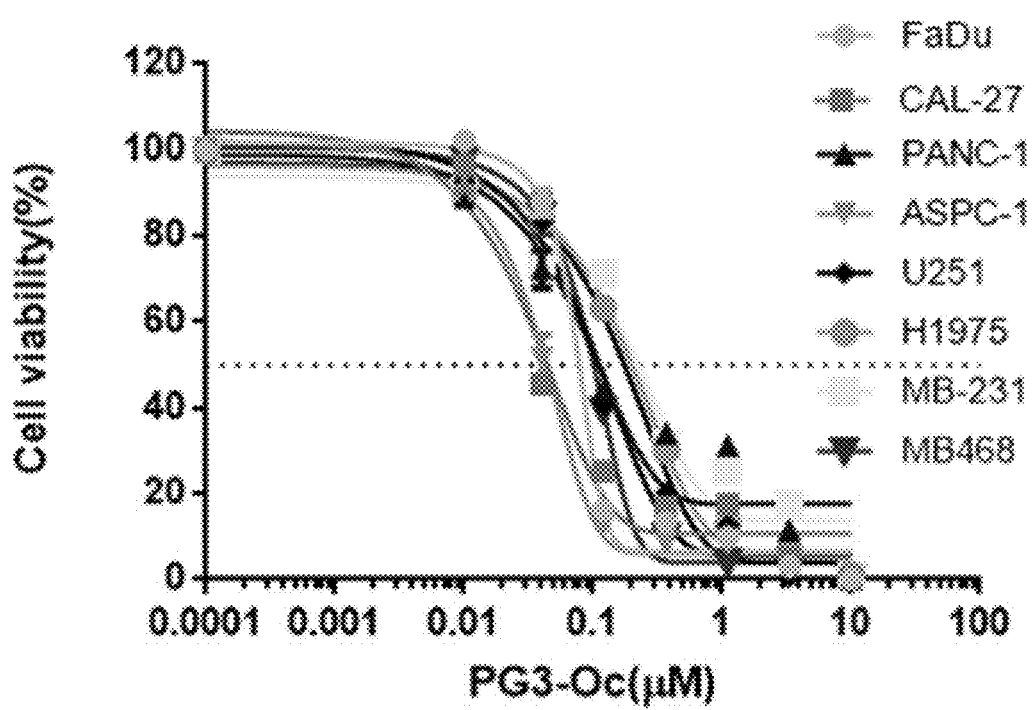
Figure 84:
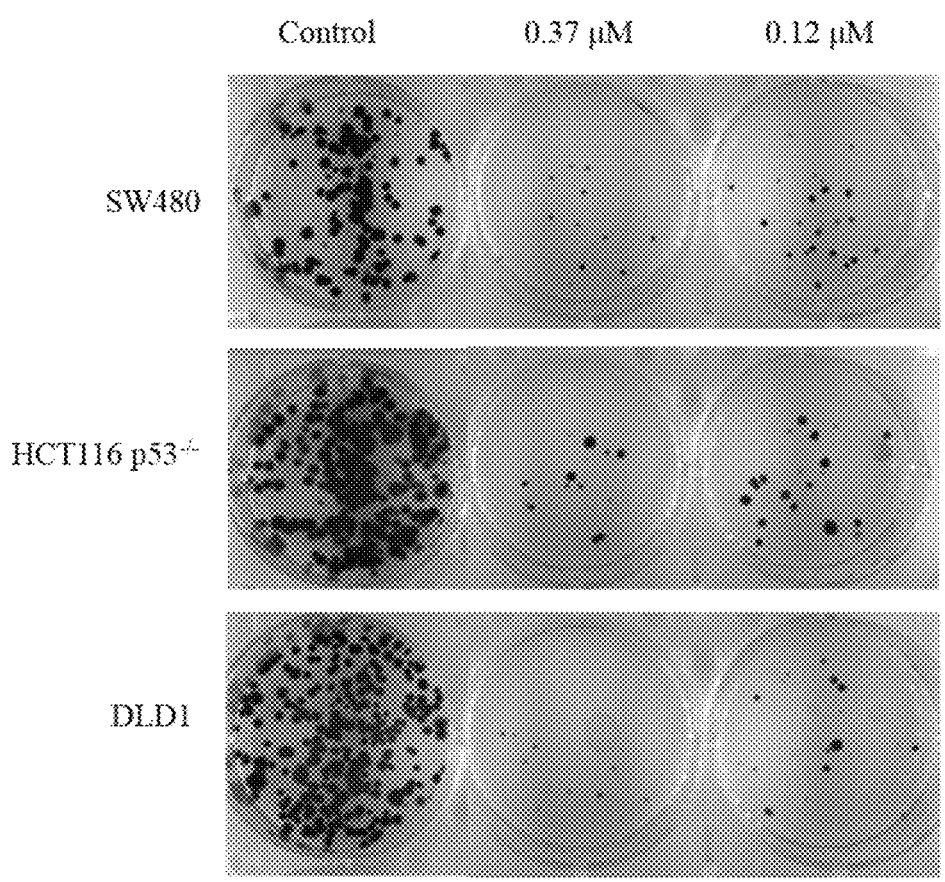
FIGS. 84 and 85 show colony formation assays of p53-mutant and p53-null human cancer cells.
Figure 85:
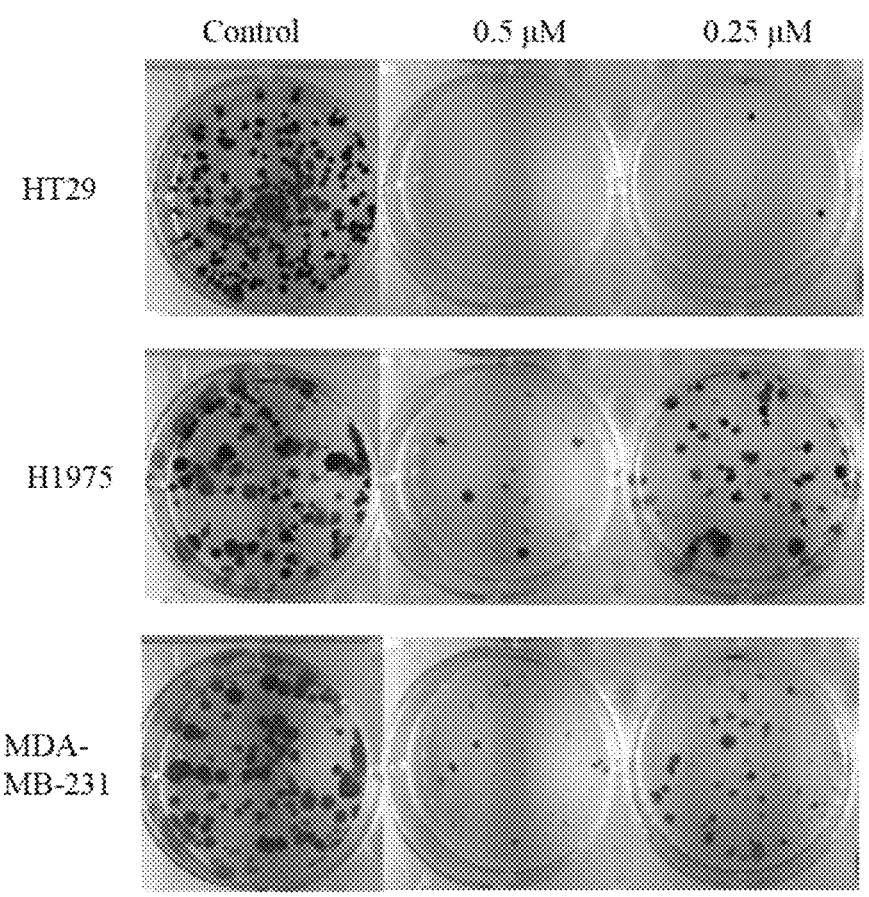

Example 5: PG3-Oc Inhibits Cell Proliferation and Induces Apoptosis in Mutant p53-Expressing Cancer Cell Lines PG3-Oc was a potent inhibitor of cell proliferation, and its potency was found to be comparable to prodigiosin and obatoclax (FIGS. 39 and 26D). PG3-Oc was efficacious in a broad spectrum of human cancer cells with mutant p53. $IC_{50}$ values were within the nano-molar range (Table 1). PG3-Oc had a 4- to 9-fold therapeutic index in colorectal cancer (CRC) cell lines as compared to normal colon cells CCD 841 Con (FIG. 40 and Table 1). In addition, PG3-Oc had anti-proliferative effects on other tumor types, including head and neck squamous cancer cell lines, pancreatic cancer, breast cancer, glioblastoma multiforme and non-small cell lung cancer cells (NSCLC) (FIG. 41 and Table 1). Like CRC, the $IC_{50}$ in additional tumor types was also in the sub-micromolar range (Table 1). Over 90% inhibition in long-term cell proliferation was also observed in a panel of CRC cell lines treated with low dose PG3-Oc (FIGS. 84 and 85). These data suggest that PG3-Oc is a promising lead compound for further evaluation of efficacy in the treatment of human colorectal cancers and other solid tumors.

Figure 42:
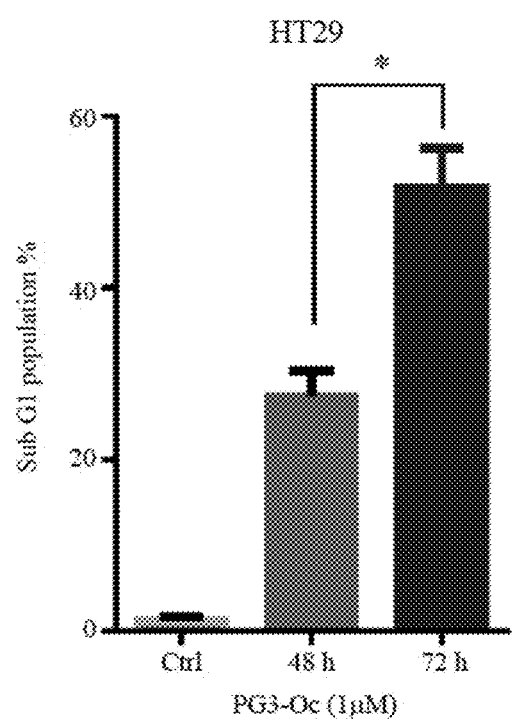
FIG. 42 shows HT29 cells treated with PG3-Oc.
Figure 43:
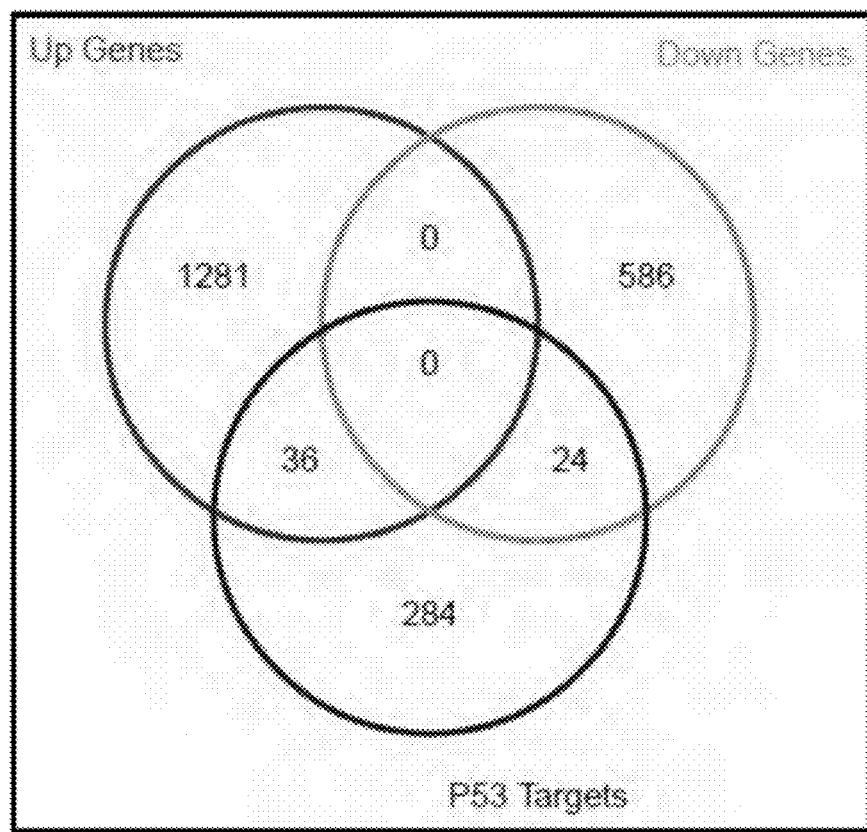
FIG. 43 shows that PG3-Oc restores p53 target gene expression.
Figure 86:
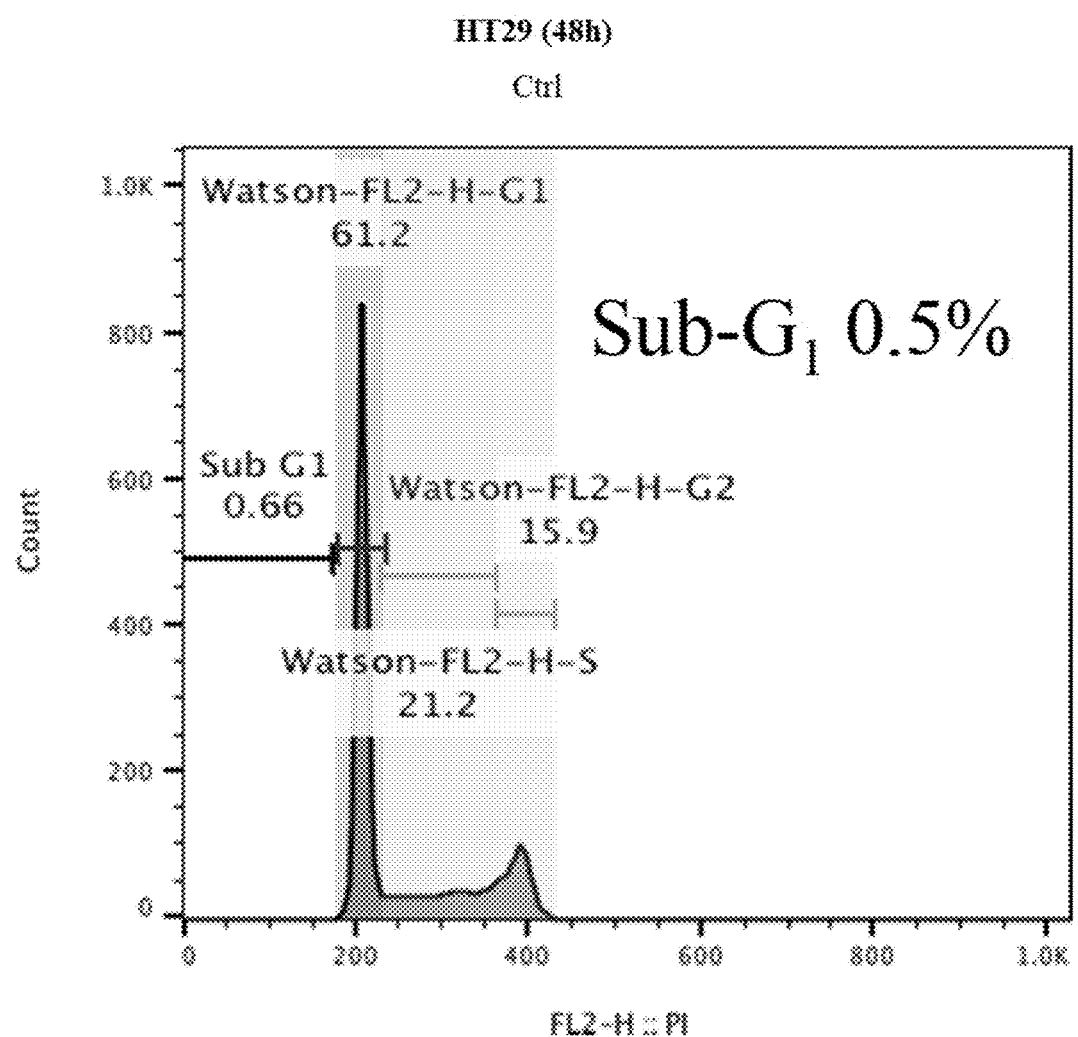
FIG. 86 shows cell-cycle profiles after PG3-Oc treatment.
Figure 86:
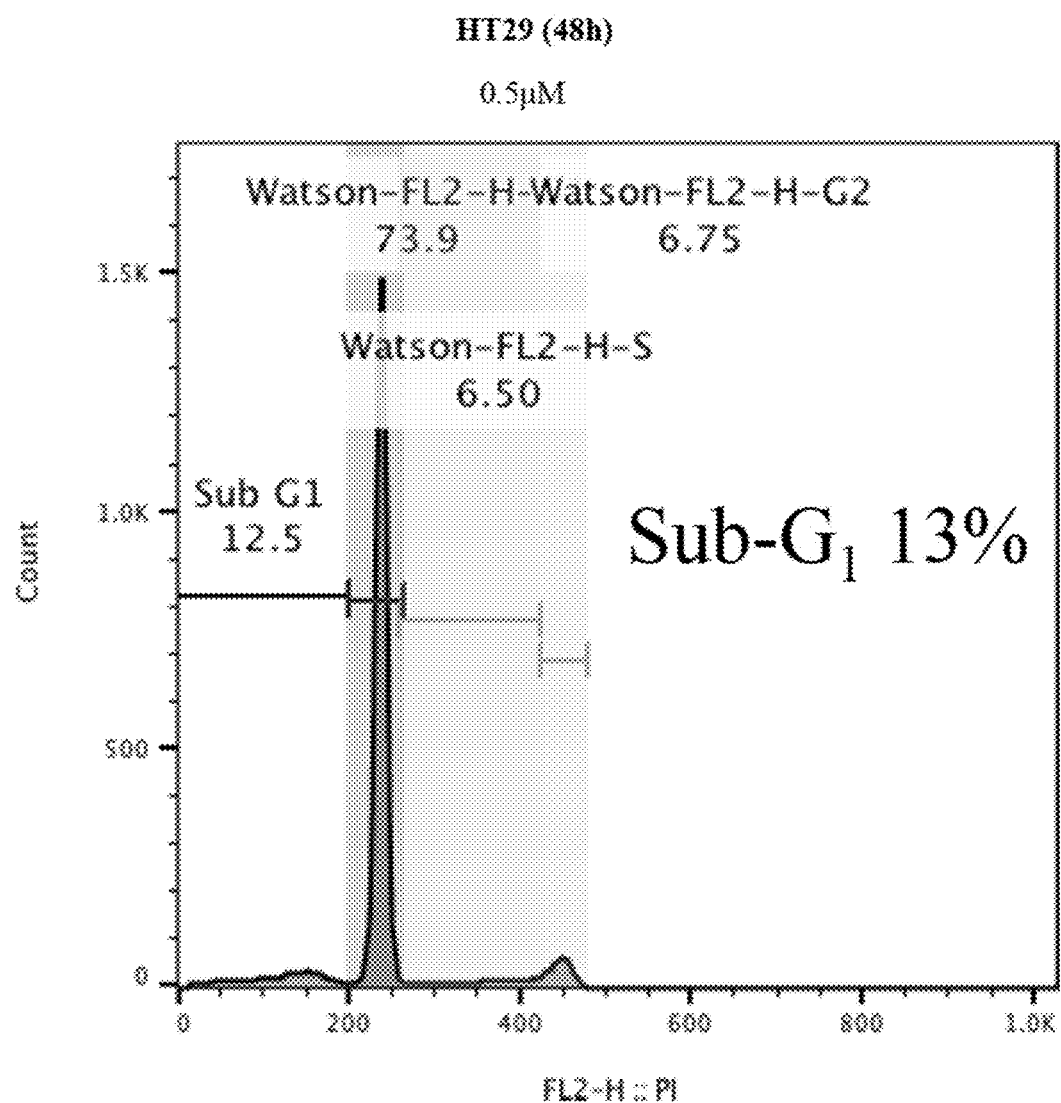
Figure 86:
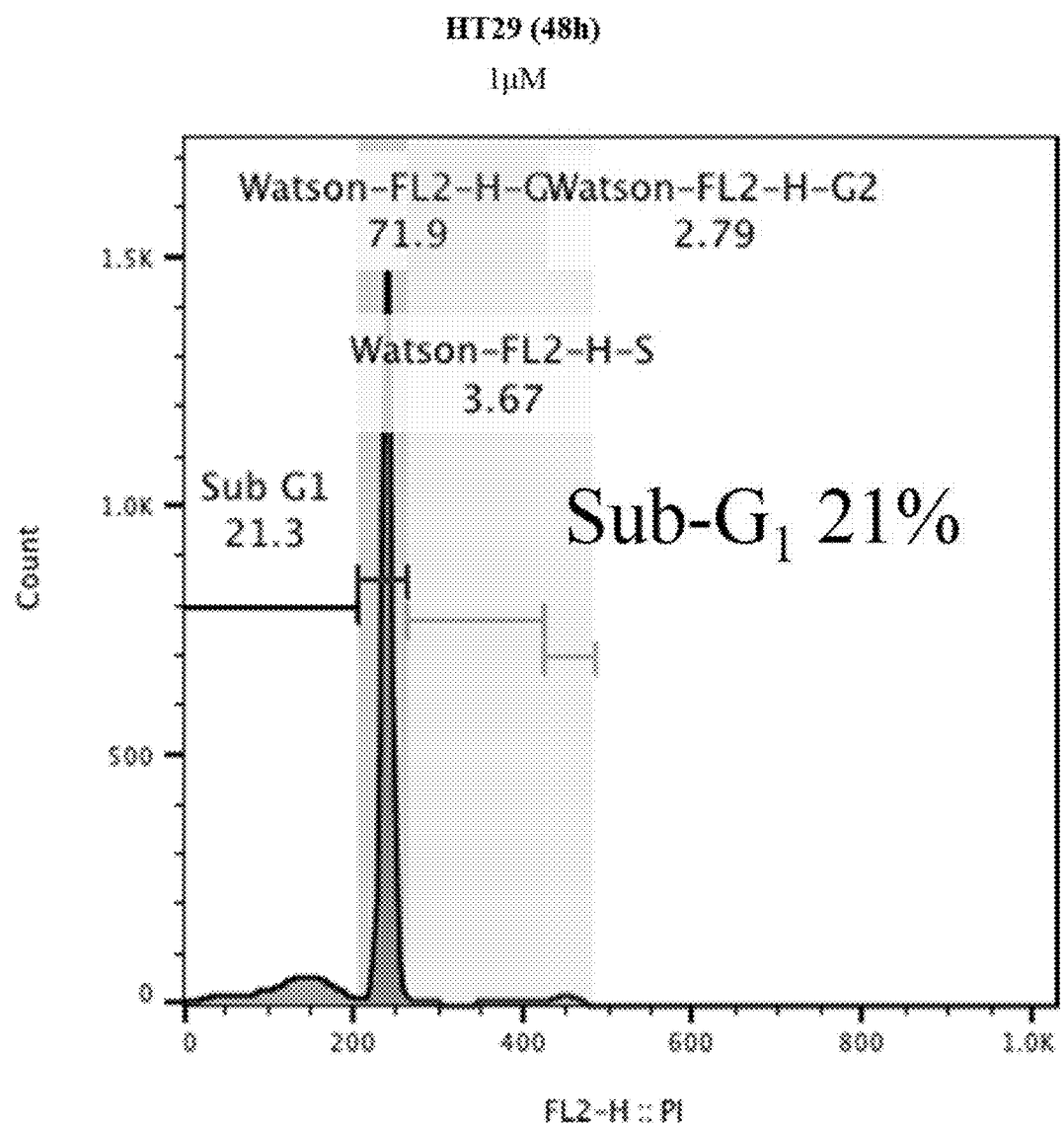
Figure 86:
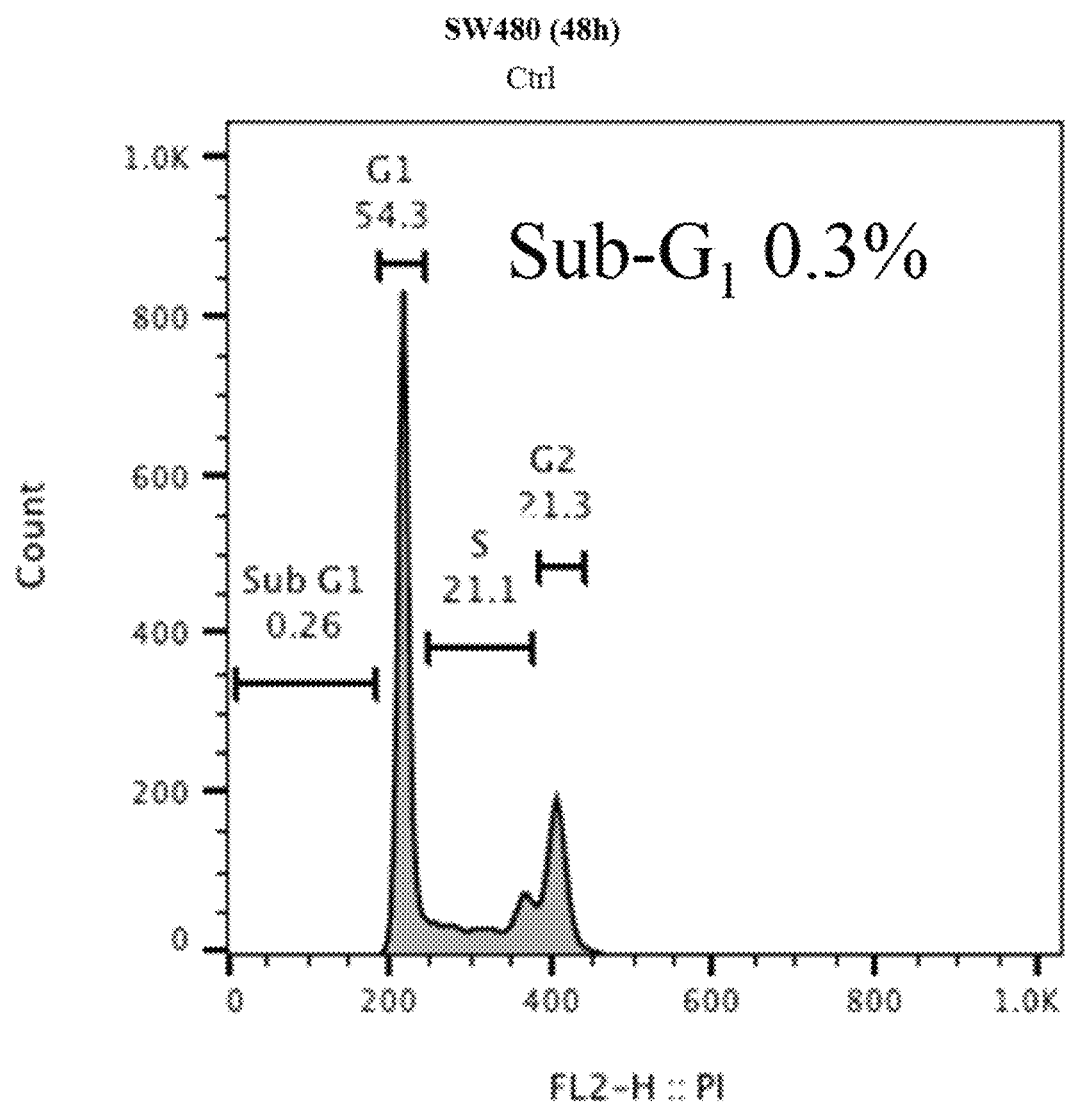
Figure 86:
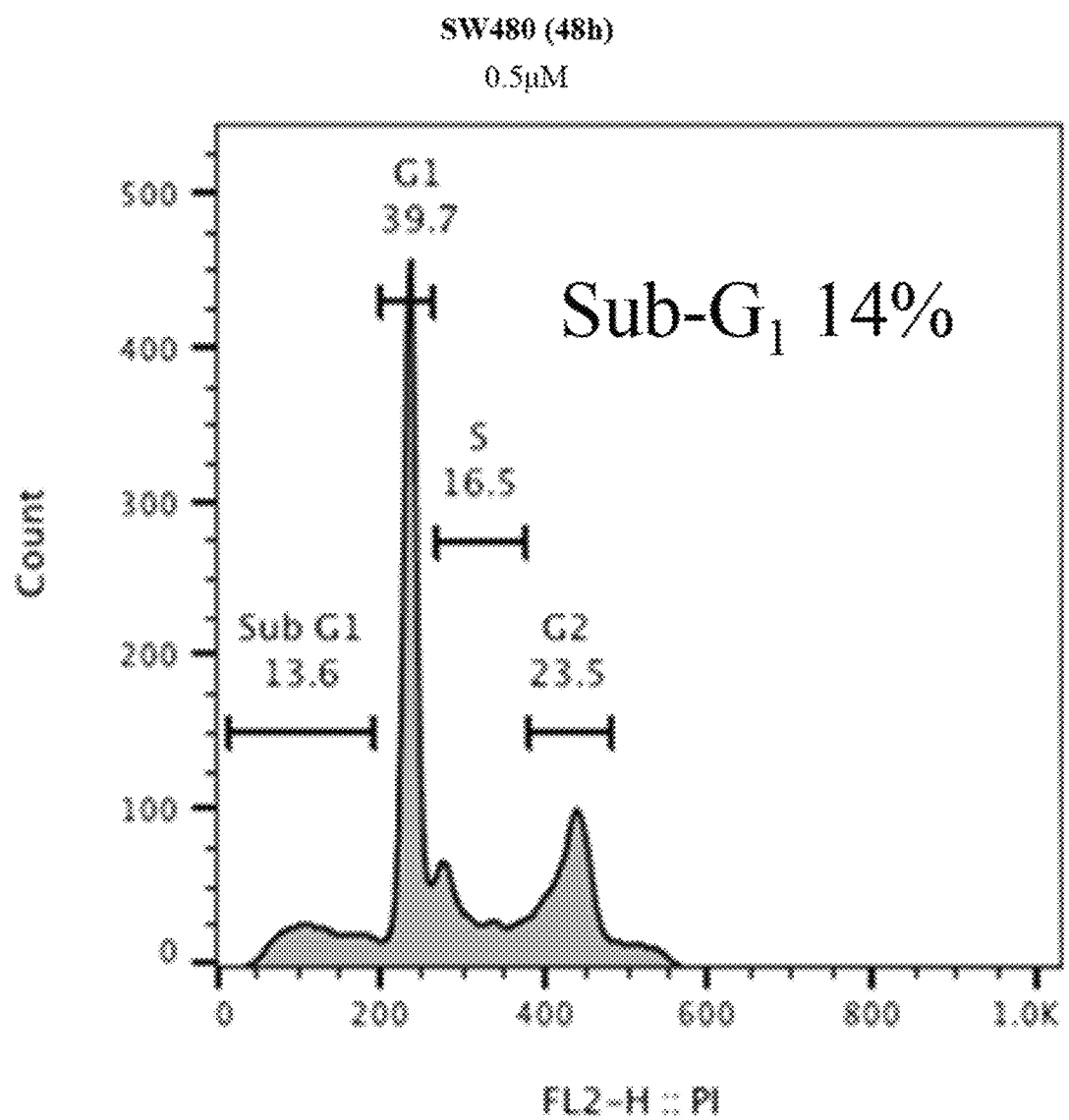
Figure 86:
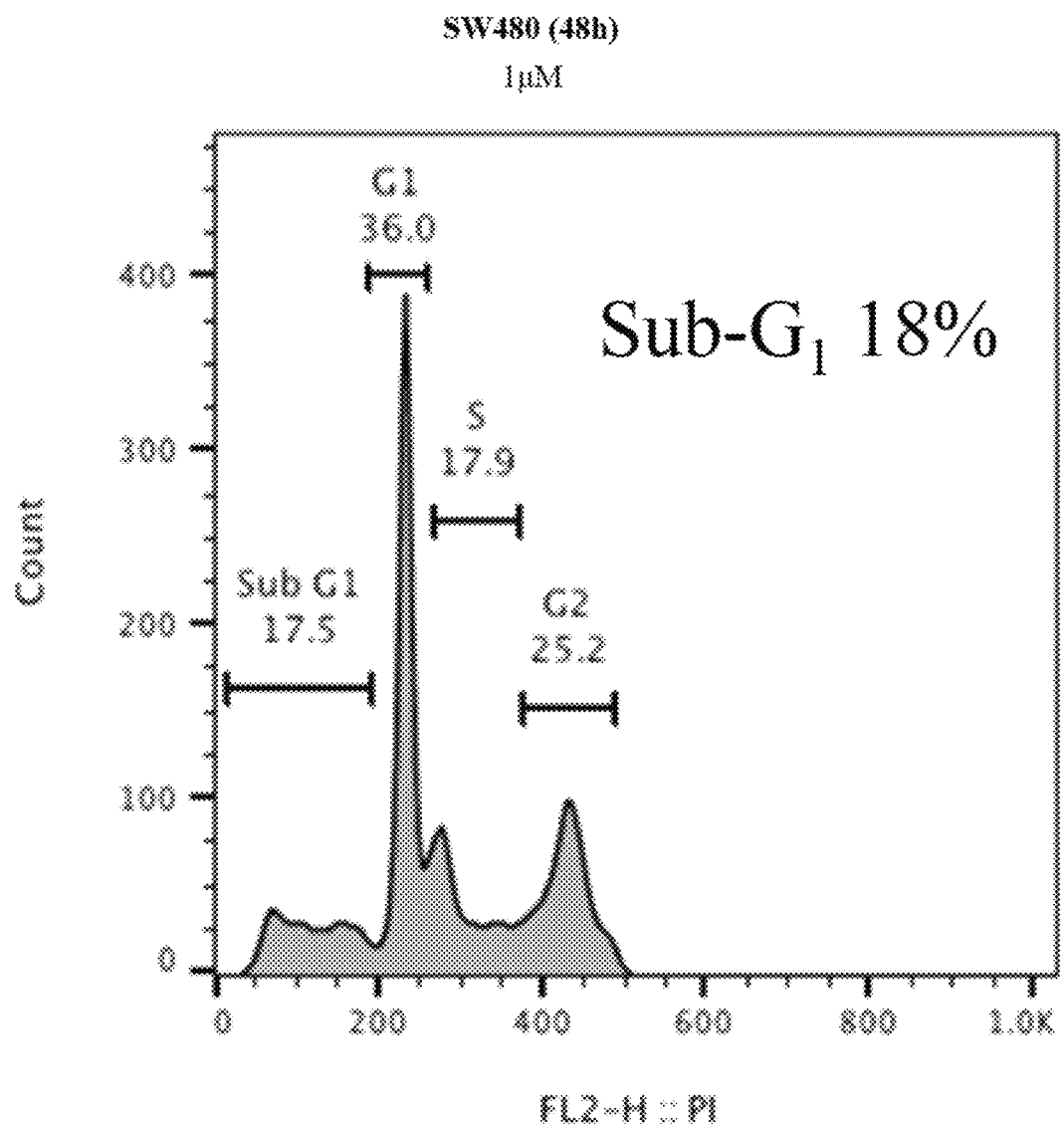
Figure 87:
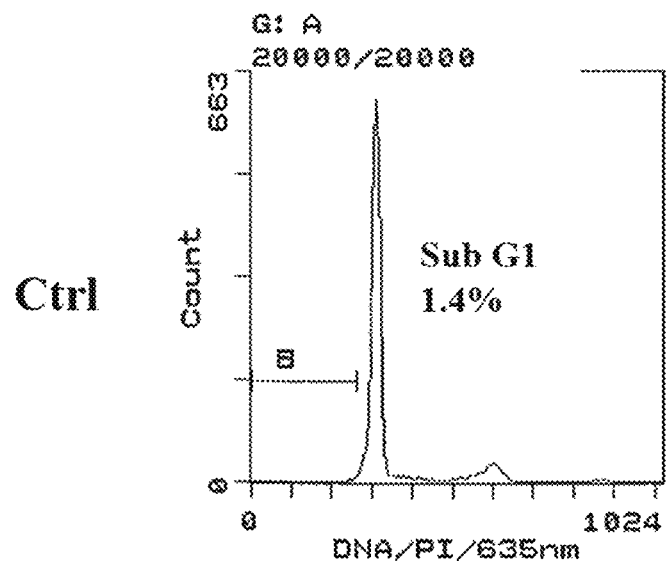
FIG. 87 shows cell-cycle profiles after PG3-Oc treatment and apoptosis analyzed by nuclear PI-staining using flow cytometry.
Figure 87:
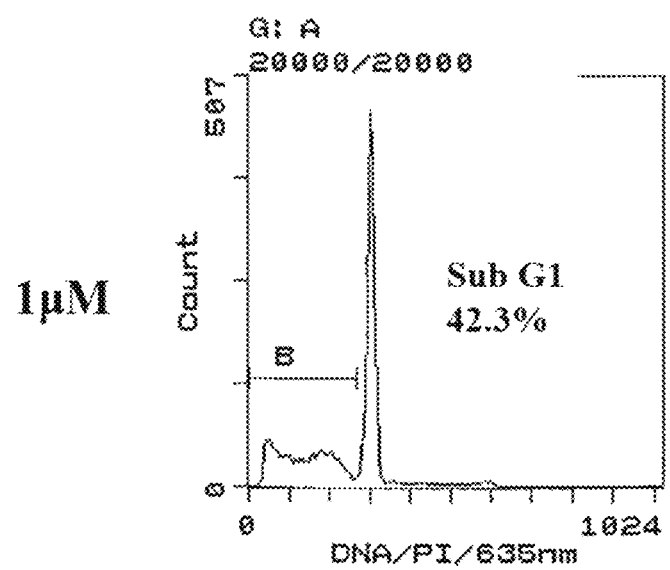
Figure 87:
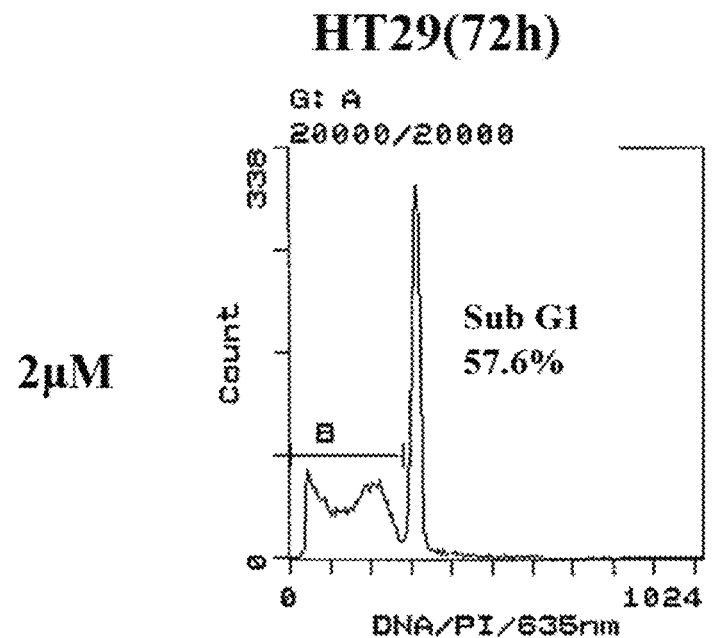
Figure 87:
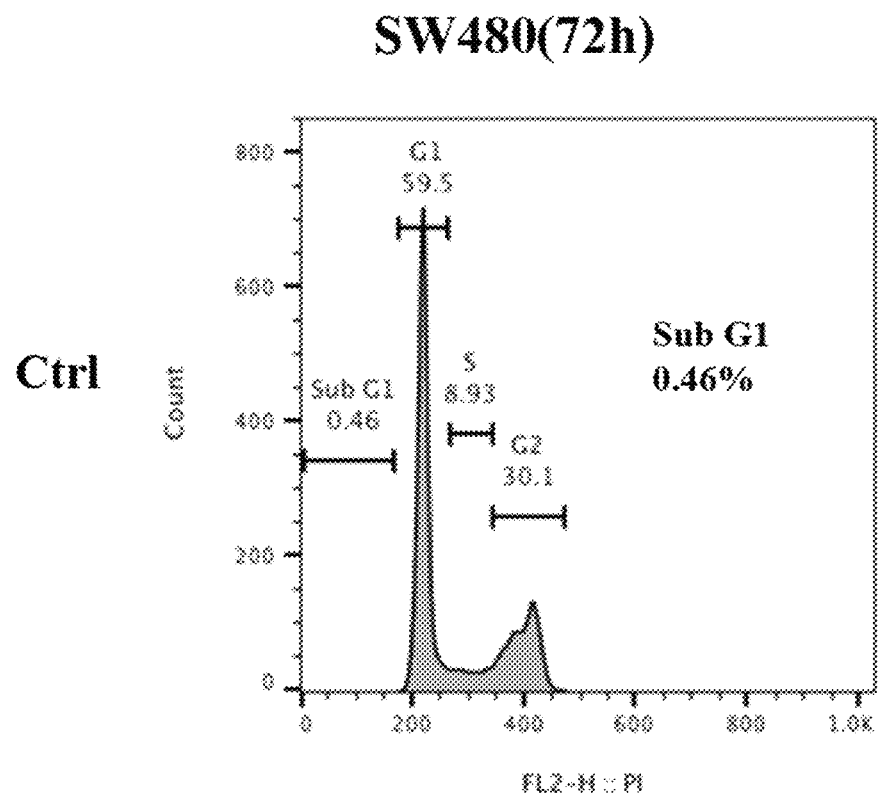
Figure 87:
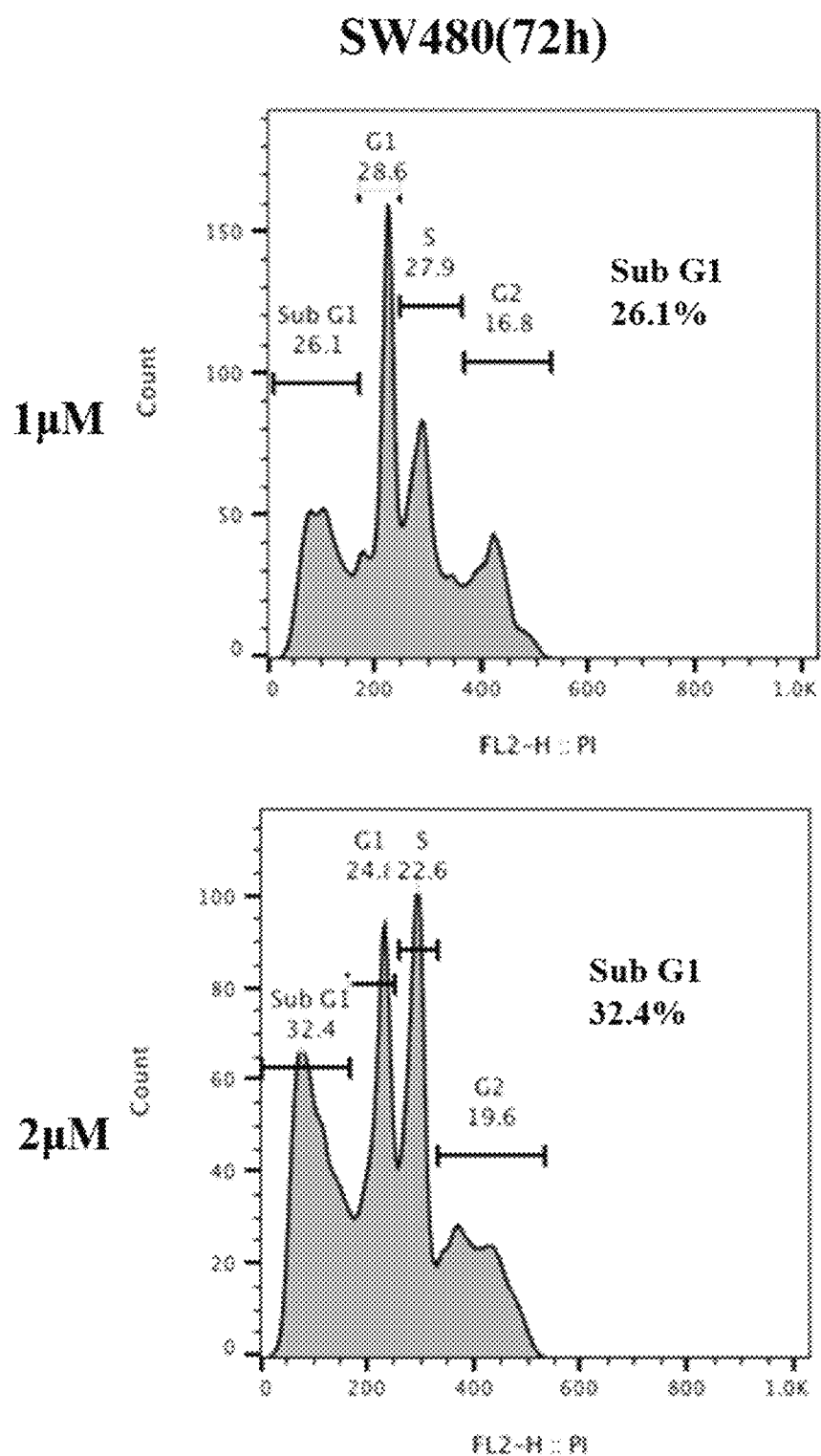

It was determined that PG3-Oc induced cell death in mutant p53-expressing cell lines. Treatment of colorectal cancer cell lines HT29 and SW480 with PG3-Oc induced cancer cell death in dose-and-time dependent manner demonstrated by sub-G1 analysis (FIG. 42, and FIGS. 86 and 87).

To evaluate if the cell death was caspase-dependent, apoptosis markers were analyzed by western blot. As seen in FIG. 29B, as low as 0.5 μM PG3-Oc was sufficient to activate cleaved caspase-8 and -3 and cleaved-PARP. Time-course experiments indicated that PUMA protein was first induced at 16 hours post PG3-Oc treatment and this induction was sustained even at 48 hours. At 48 hours, it was noted that induction of cleaved PARP, as well as cleaved caspase-8 and -3 occurred in both HT29 and SW480 cells (FIGS. 29A and 29C). These data also clearly indicated that PG3-Oc induces upregulation of PUMA and DR5 in a dose- and time-dependent manner.

Figure 27E:
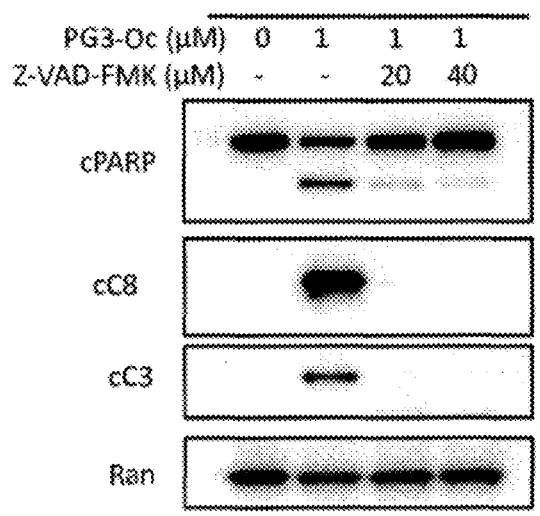

Caspase-dependent induction of apoptosis was further confirmed by the pan-caspase inhibitor (Z-VAD-FMK) co-treatment experiments with PG3-Oc. As seen in FIG. 27C, 20 μM Z-VAD-FMK completely blocked the formation of a sub-G1 population as compared to the untreated control. Under the same experimental conditions, western blot analysis showed that Z-VAD-FMK completely inhibited the cleavage of caspase-8 and caspase-3 in both HT29 (FIG. 27D) and SW480 cells (FIG. 27E). Caspase 3/7 activity was also measured. Treatment with PG3-Oc induced a 2-fold increase in caspase 3/7 activity as compared to untreated cells using mutant p53-expressing and p53-null cancer cells (FIG. 27B). PG3-Oc's apoptotic activity was found to be p73-independent as evident by the comparable caspase 3/7 activity in both DLD-1 and DLD1-p73$^{-/-}$ cells post PG3-Oc treatment (FIG. 27B). Taken together, these data suggest that PG3-Oc treatment induces capase-8 and caspase-3 activation in colorectal cancer cell lines, and caspase activation is needed for PG3-Oc-induced cell death.

TABLE 1

IC$_{50}$ values for different cancer cell lines with various mutant p53 status

| Tumor/Tissue Type | Cell Line | IC$_{50}$ (nM) | P53 status |
|---|---|---|---|
| Colorectal Cancer | HT29 | 66.3 | R273H |
| | SW480 | 95.3 (4-fold) | R273, P309S |
| | DLD1 | 54 | S241F |
| | HCT116 p53$^{-/-}$ | 41.1 (9 fold) | Null |
| Non-transformed colorectal epithelial cells | CCD 841 Con | 375.2 | WT |
| Head & neck squamous cell carcinoma | FaDu | 66 | R248L |
| | CAL-27 | 33.9 | H193L |
| Pancreatic Cancer | PANC-1 | 135.5 | R273H |
| | ASPC-1 | 39.2 | Frameshift |
| Breast Cancer | MDA-MB-231 | 242.3 | R280K |
| | MDA-MB-468 | 97.6 | R273H |
| Glioblastoma Multiforme | U251 | 100.2 | R273H |
| NSCLC | H1975 | 190.4 | R273H |

Example 6: PG3-Oc Restores p53 Pathway Signaling without Genotoxic Effects

Figure 44:
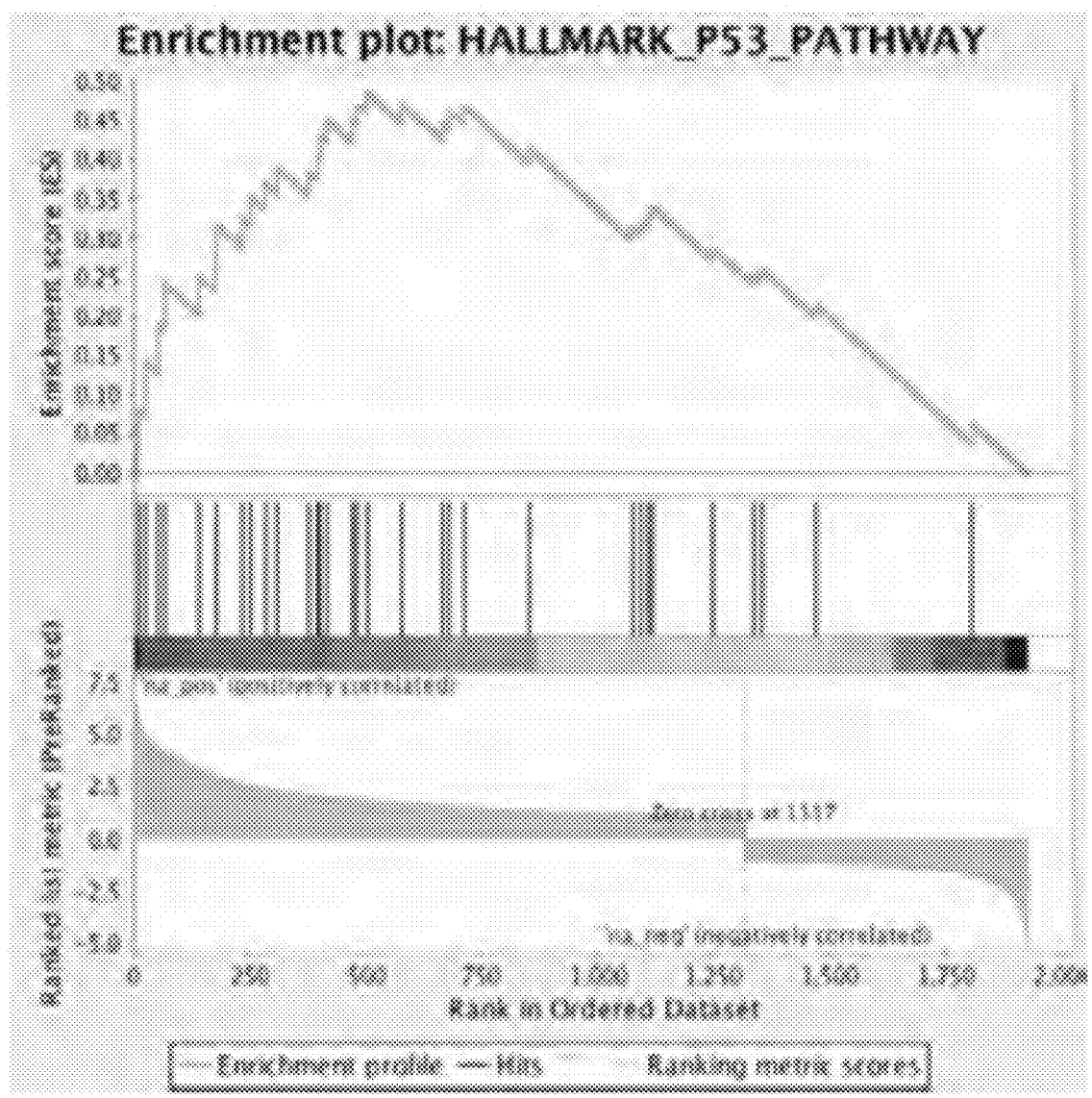
FIG. 44 shows the GSEA plot: Representative gene set from 1867 differential expression genes showing specific responses to the p53 pathway.
Figure 49:
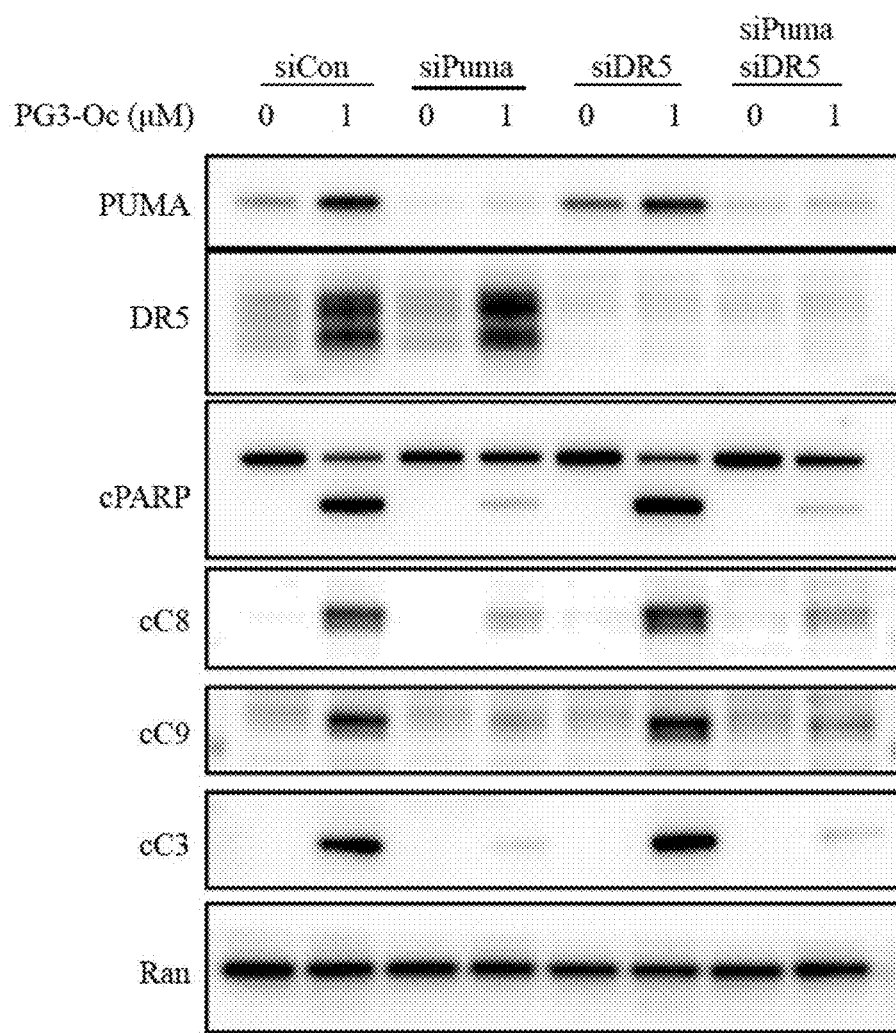
FIG. 49 shows HT29 cells were transfected with Control, PUMA, DR5 and PUMA/DR5 siRNAs.
Figure 88:
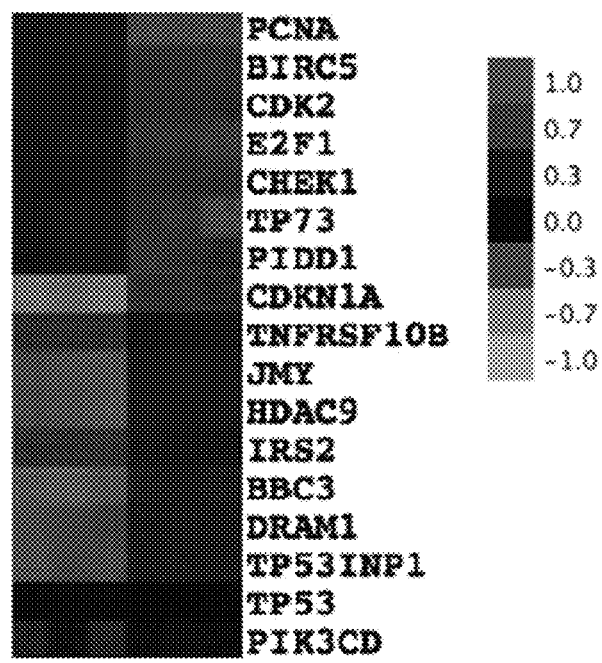
FIG. 88 shows a heat-map depicting differential gene expression of genes in the p53 pathway in PG3-Oc treated cells as identified by IPA analysis.
Figure 89:
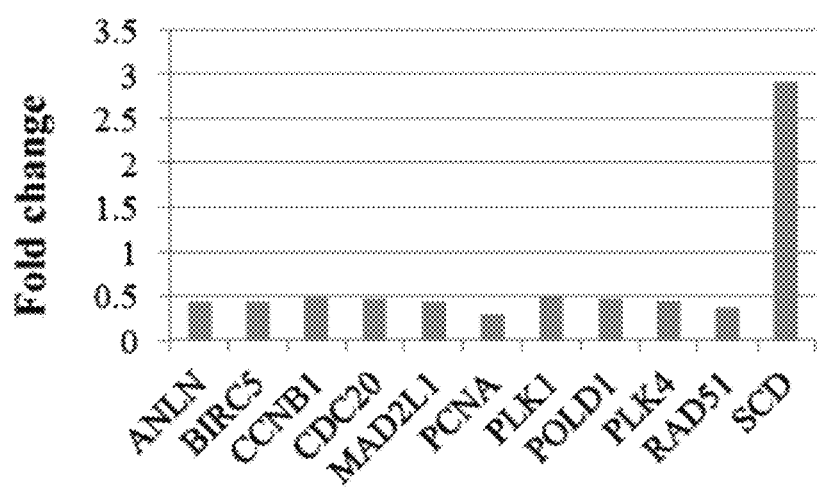
FIG. 89 shows a subset of p53 negatively regulated target genes, besides SCD, was significantly downregulated by PG3-Oc.
Figure 90:
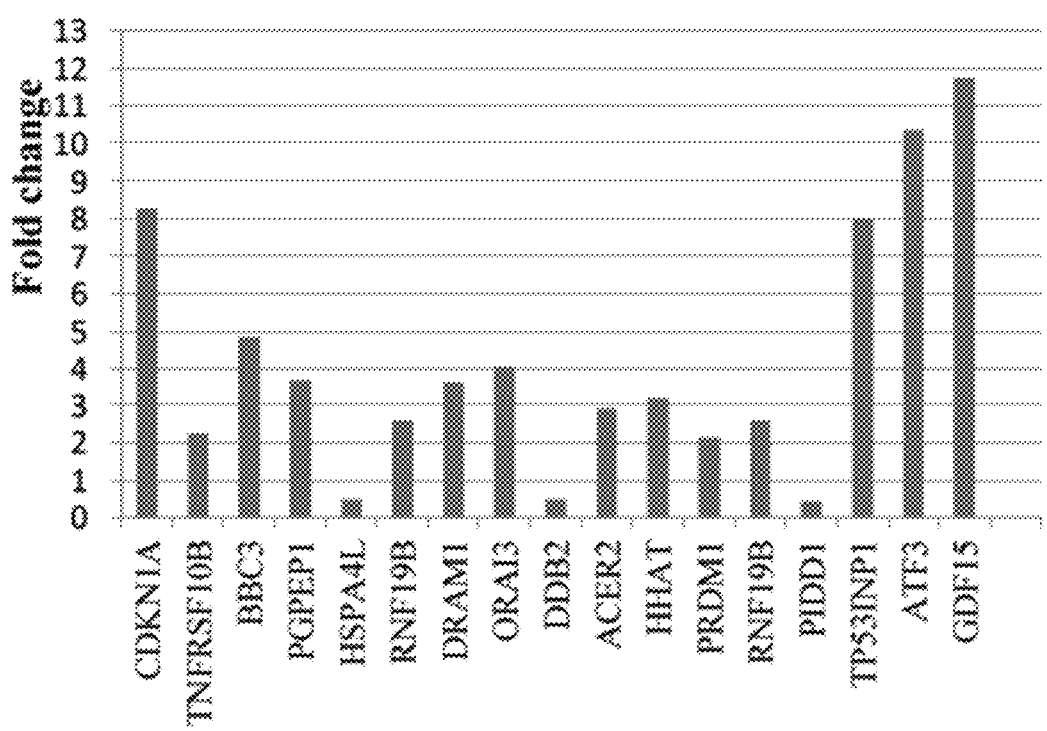
FIG. 90 shows a subset of p53 positively regulated target genes, besides HSPA4L, DDB2 and PIDD1, was significantly upregulated by PG3-Oc.

Having confirmed that PG3-Oc induces apoptosis in multiple p53-expressing mutant cancer cell lines, whether this small molecule restored p53 pathway signaling was investigated in HT29 cells after treatment with 1 μM PG3-Oc for 24 hours. For this purpose, gene profiling was performed by RNA-Seq and bioinformatics analysis, such as IPA (Ingenuity pathway analysis), GSEA (gene set enrichment analysis) and GO (gene ontology) (See details at Methods and Materials). IPA analysis of 1867 altered genes revealed that among of 284 known p53 target genes (Fischer, Oncogene, 2017, 36(28), 3943-3956), 35 genes were up-regulated and 24 genes were down-regulated (FIG. 49). Key p53 target gene CDKN1A (p21) that negatively regulate cell cycle and other p53 target genes that regulate apoptosis such as, TNFRSF10B (DR5), BBC3 (PUMA), BIRC5 (Survivin), TP53INP1 (Teap) were identified in canonical p53 pathway analysis. Pro-apoptotic p21, DR5, PUMA and Teap were potently induced and anti-apoptotic Survivin was significantly downregulated (FIG. 88). p53 target gene PMAIP1 (Noxa) underwent a 1.9-fold increase as compared to control, however the cutoff for the bioinformatics analysis was 2, hence, it was not shown in the IPA analysis. To verify that the behavior of regulation of p53 target genes by PG3-Oc is similar to p53 protein, based on published data (Fischer, Oncogene, 2017, 36(28), 3943-3956), genes directly repressed (FIG. 89) and activated (FIG. 90) by the p53 transcription factor were selected. It was observed that PG3-Oc treatment potently inhibited gene expression of p53 negatively-regulated genes besides SCD, and strongly upregulated gene expression of p53 positively-regulated genes besides HSPA4L, DDB2, and PIDD1 (FIGS. 89 and 90). This implicates that PG3-Oc is able to restore the p53 pathway. This observation was further supported by GSEA analysis which indicated that PG3-Oc-induced differential expression of genes was enriched in the p53 pathway, suggesting PG3-Oc has a significant impact to restore the p53 pathway and network (FIG. 44).

Figure 45:
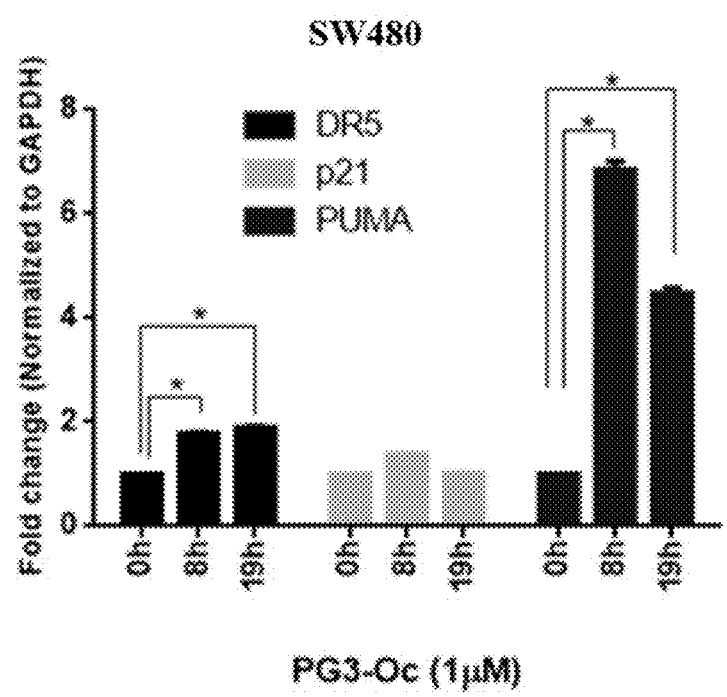
FIG. 45 shows cells treated with 1 µM PG3-Oc for 8 and 18 h.

HT29 cells were treated with 1 μM PG3-Oc at different time points followed by qRT-PCR analysis. Time-dependent induction of DR5, p21 and PUMA transcripts was observed (FIG. 28C). This is consistent with the RNA-Seq data (FIGS. 88 and 90). Importantly, PG3-Oc very strongly induced upregulation of PUMA mRNA in all three cell lines at the 8- or 19-hour time points (FIGS. 28C, 28D and 45). Over 3-fold induction of p21 mRNA was observed at 8 and 19 hours post-treatment in HT29 and HCT116 p53$^{-/-}$ cells, but no significant change was observed in SW480 cells. Of note, p21 protein level was potently upregulated in SW480 (FIG. 28A). For the DR5 mRNA level, about 2-fold upregulation at 19 hours post-treatment was observed in HT29 and SW480 cells, but not in HCT116 p53$^{-/-}$ cells (FIGS. 28C, 28D and 45). Interestingly, DR5 protein level was potently upregulated in HCT116 p53$^{-/-}$ cells (FIG. 28B). These data suggest PG3-Oc treatment may lead to p21 or DR5 protein stabilization depending on the cell type.

Western blot analysis of p53 mutant DLD1, SW480, HT29 cells, and p53-null HCT116 colon cancer cells showed strong upregulation of DR5, p21, PUMA and Noxa in a time- and dose-dependent manner (FIGS. 29B, 29A and 29C; FIGS. 31A, 28A and 28B). Further, the magnitude of induction of p53 target genes was higher in PG3-Oc treated SW480 and HCT116 p53$^{-/-}$ cells as compared to prodigiosin, especially for PUMA and p21 (FIGS. 28A and 28B).

Figure 61:
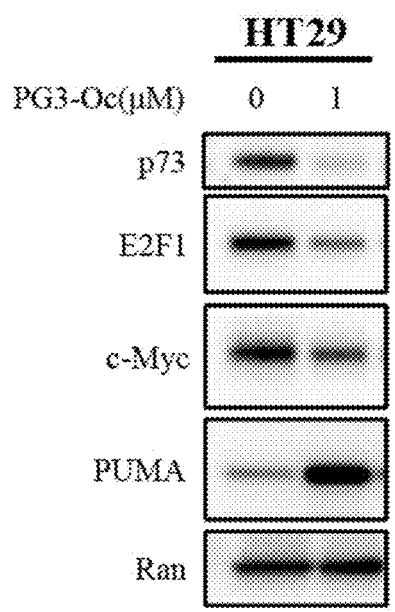
FIG. 61 shows HT29 cells treated with 1 µM PG3-Oc for 24 h.

It was observed that PG3-Oc treatment led to downregulation of p73 both at the protein level (FIG. 31A and FIG. 61) and the mRNA level (FIGS. 88 and 89). Consistent with this, induced upregulation of DR5, p21, PUMA and Noxa showed no significant differences compared to the p73 stable-knockdown DLD1 cell line (FIG. 31A). In addition, caspase3/7 activity assay also showed no significant difference between DLD1 and DLD1-p73$^{-/-}$ cell lines (FIG. 27B). Thus, the upregulation of the p53 pathway by PG3-Oc was independent of p73. Taken together, these data suggest that PG3-Oc can restore the p53 pathway in mutant p53-expressing cancer cell lines at the transcriptional level, with especially high induction observed for PUMA.

Figure 46:
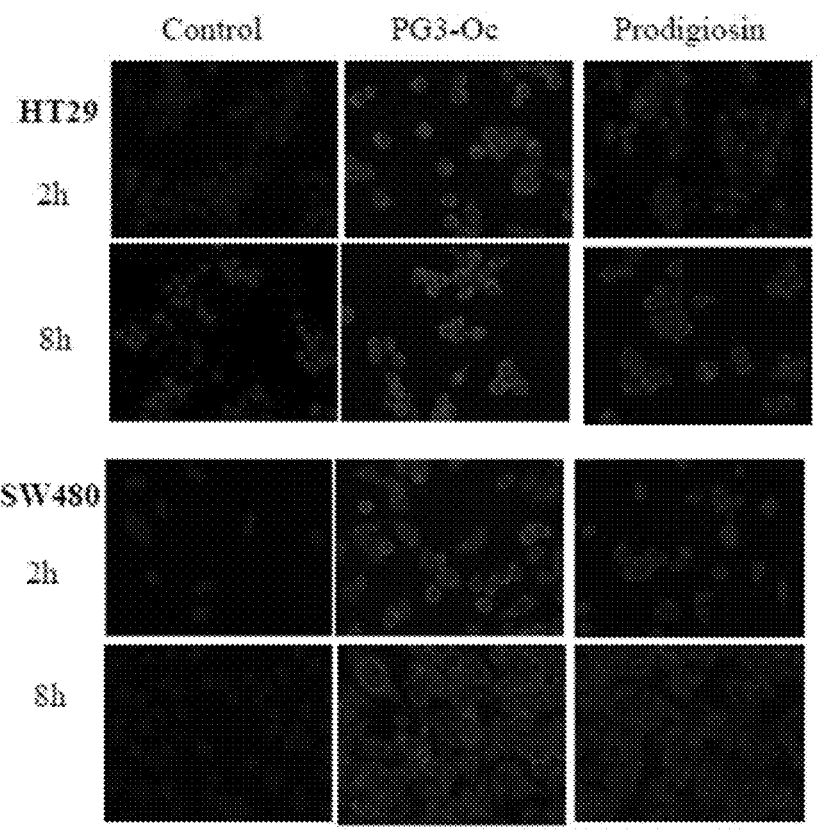
FIG. 46 shows fluorescence microscopy localization of PG3-Oc and prodigiosin in HT29 and SW480 cells.
Figure 47:
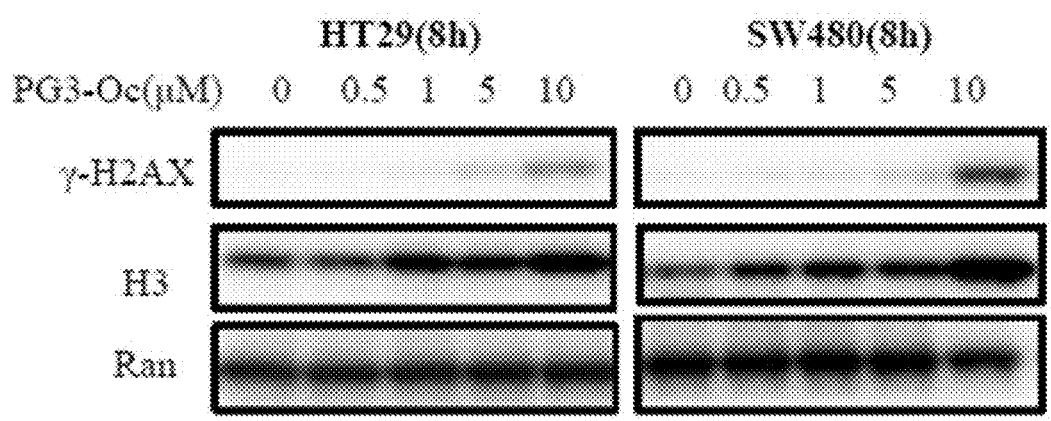
FIG. 47 shows PG3-Oc did not induce DNA damage.
Figure 48:
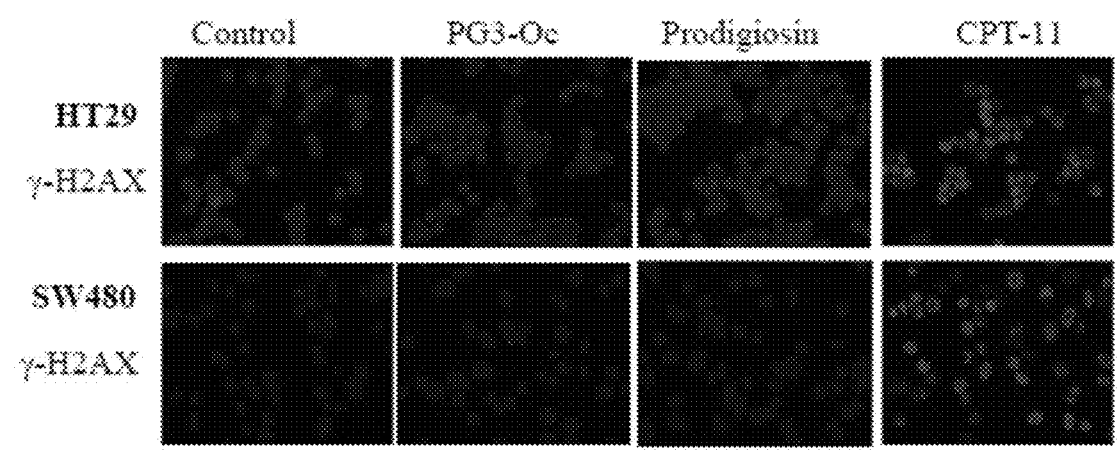
FIG. 48 shows immunofluorescence staining for γ-H2AX foci.

DNA damage induces the p53 pathway and leads to cell apoptosis. To study whether the p53 pathway restoration by compound PG3-Oc is due to DNA damage, the uptake and localization of PG3-Oc was investigated in cells. PG3-Oc and prodigiosin are red fluorescent compounds, and their localization in live cells can be monitored by fluorescence microscopy. PG3-Oc and prodigiosin rapidly entered cells within 2 hours of incubation and remained in the cytosol at the 8-hour time point in HT29 and SW480 cells (FIG. 46). Since it was already observed that 1 µM PG3-Oc treatment for 8 hours can prominently induce the upregulation of PUMA mRNA (FIGS. 28C, 28D and 45) in HT29, SW480 and HCT116 p53$^{-/-}$ cells, DNA damage marker γ-H2AX (phospho Ser 139-histone H2AX) expression was investigated after the treatment for 8 hours. Western blot analysis showed that PG3-Oc and prodigiosin did not induce γ-H2AX in HT29 and SW480 cells at lower doses required for p53 pathway activation (FIG. 47). Immunofluorescence staining showed that 1 µM PG3-Oc and prodigiosin did not induce γ-H2AX foci formation after the 8-hour treatment. By comparison, DNA damage chemotherapeutic drug CPT-11 was used as a positive control, and significantly induced γ-H2AX foci in HT29 and SW480 cells (FIG. 47). Both western blot and immunofluorescence staining data were consistent with the cytoplasmic localization of PG3-Oc. A previous publication also indicated that 1 µM prodigiosin did not induce γ-H2AX in SW480 cells and HCT116 p53$^{-/-}$ cells (Hong et al., Cancer Res, 2014, 74, 1153-1165). These results are also consistent with other group's results. Baldino, et al. reported that prodigiosin localized to the cytoplasm, but not within the nucleus, and no γ-H2AX signal was detected in A549 cancer cells (Baldino et al., Bioorg Med Chem Lett, 2006, 16, 701-704). One paper reported opposite results (Montaner et al., Toxicol Sc, 2005, 85, 870-879). However, those experiments were conducted under very different conditions. For example, MCF7 cells were pre-treated with Cupric acetate (2 µM) and PARP inhibitor DPQ (30 µM) for 30 minutes, and then treated with prodigiosin (2 µM) for 3 hours (Montaner et al., Toxicol Sc, 2005, 85, 870-879). This set of conditions probably is not physiologically relevant. The data presented herein indicate that the restoration of the p53 pathway by PG3-Oc at low concentrations did not show genotoxic effects in mutant p53-expressing cancer cells.

Figure 50:
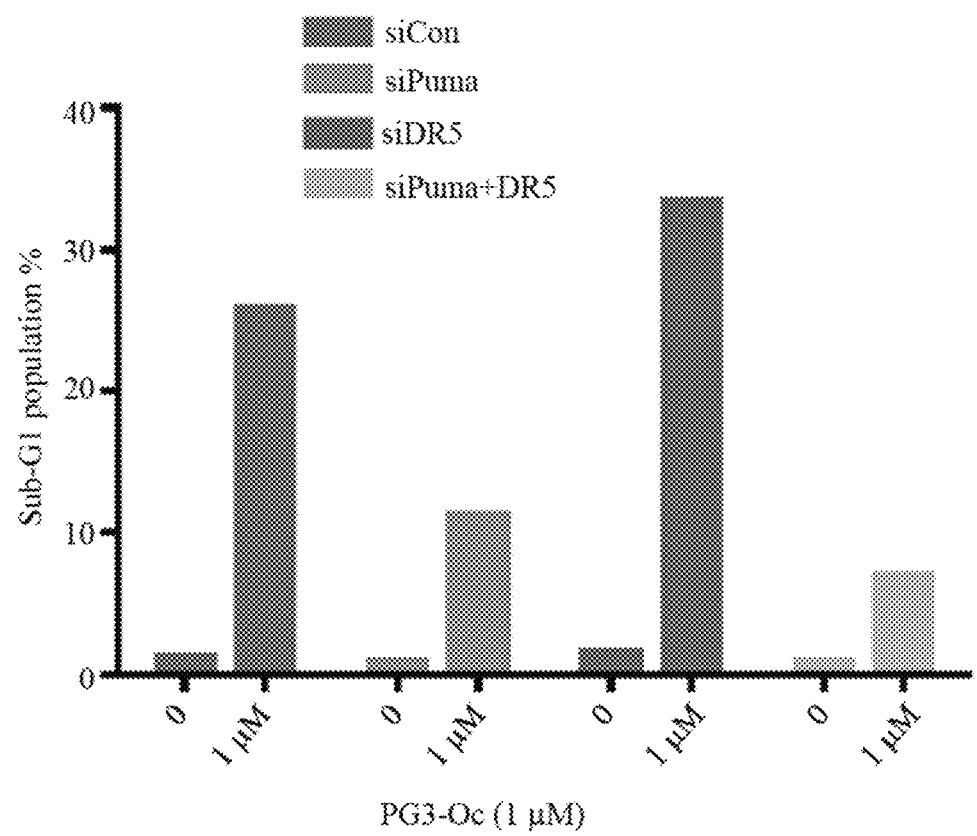
FIG. 50 shows cell death analyzed by nuclear PI-staining using flow cytometry.

Example 7: PUMA is Required for PG3-Oc Mediated Cell Death, and PG3-Oc-Induced Upregulation of DR5 is Through ATF4/CHOP Axis Whether PUMA and DR5 are dispensable for PG3-Oc mediated cell death in mutant p53-expressing cells was evaluated. As shown in FIG. 49, when PUMA was knocked down, alone or together with DR5, using siRNA, there was complete blunting of PARP cleavage and cleavage of caspases after PG3-Oc treatment. However, DR5 knockdown alone had no impact on the same apoptotic markers under the experimental conditions. Similar results were seen when knockdown of PUMA by siRNA reduced the sub-G1 population to 11.1% as compared to 25.8% in siControl, in PG3-Oc treated cells. However, knockdown of DR5 by siRNA did not protect cells from death induced by PG3-Oc (FIGS. 49 and 50 and FIG. 29D).

Figure 51:
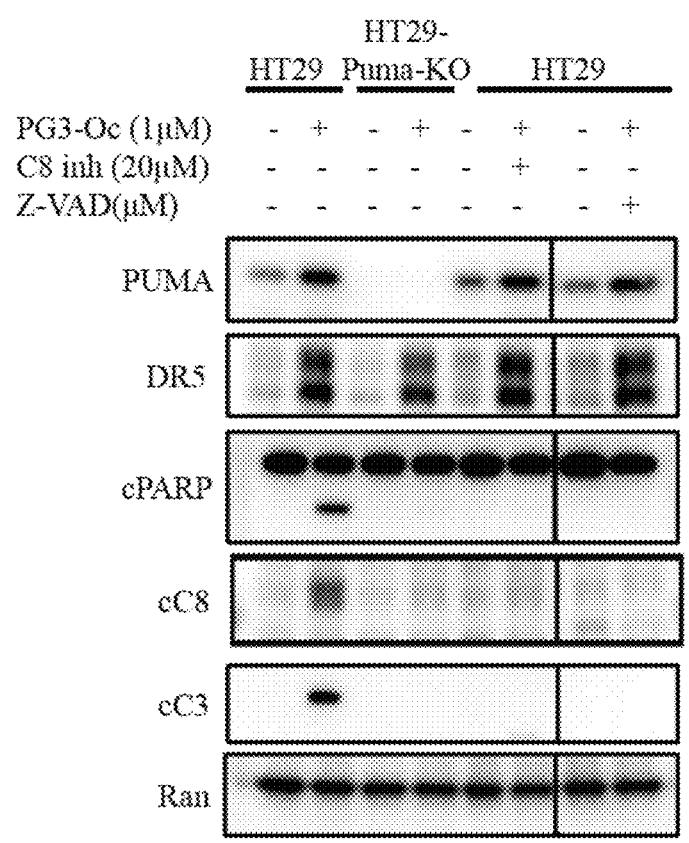
FIG. 51 shows cleavage of caspases and PARP were detected by western blotting using the indicated antibodies.
Figure 52:
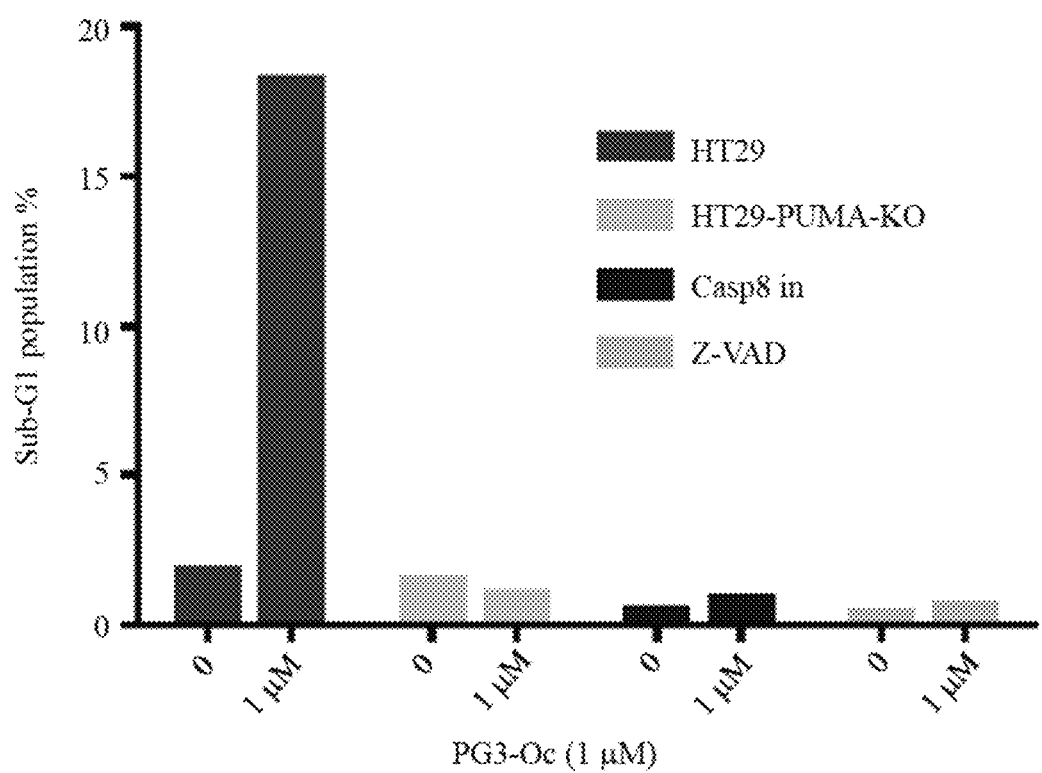
FIG. 52 shows sub G1 populations analyzed by flow cytometry.
Figure 91:
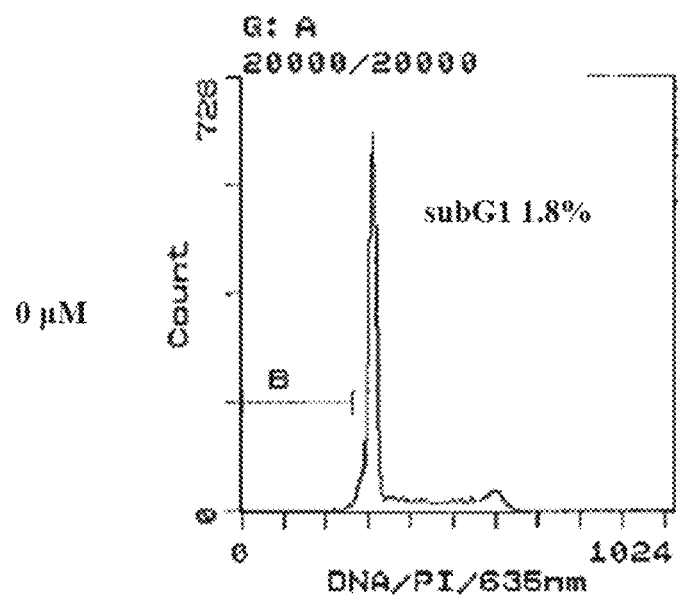
FIG. 91 shows HT29 and HT29-PUMA-KO cells treated with PG3-Oc or co-treated with caspase 8 inhibitor (cas8 inh) and pan-caspase (Z-VAD-FMK) inhibitor for 48 hours.
Figure 91:
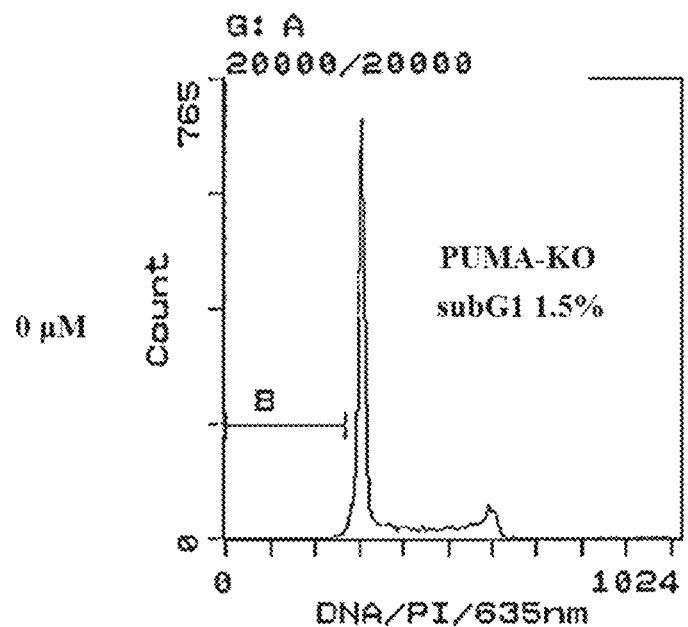
Figure 91:
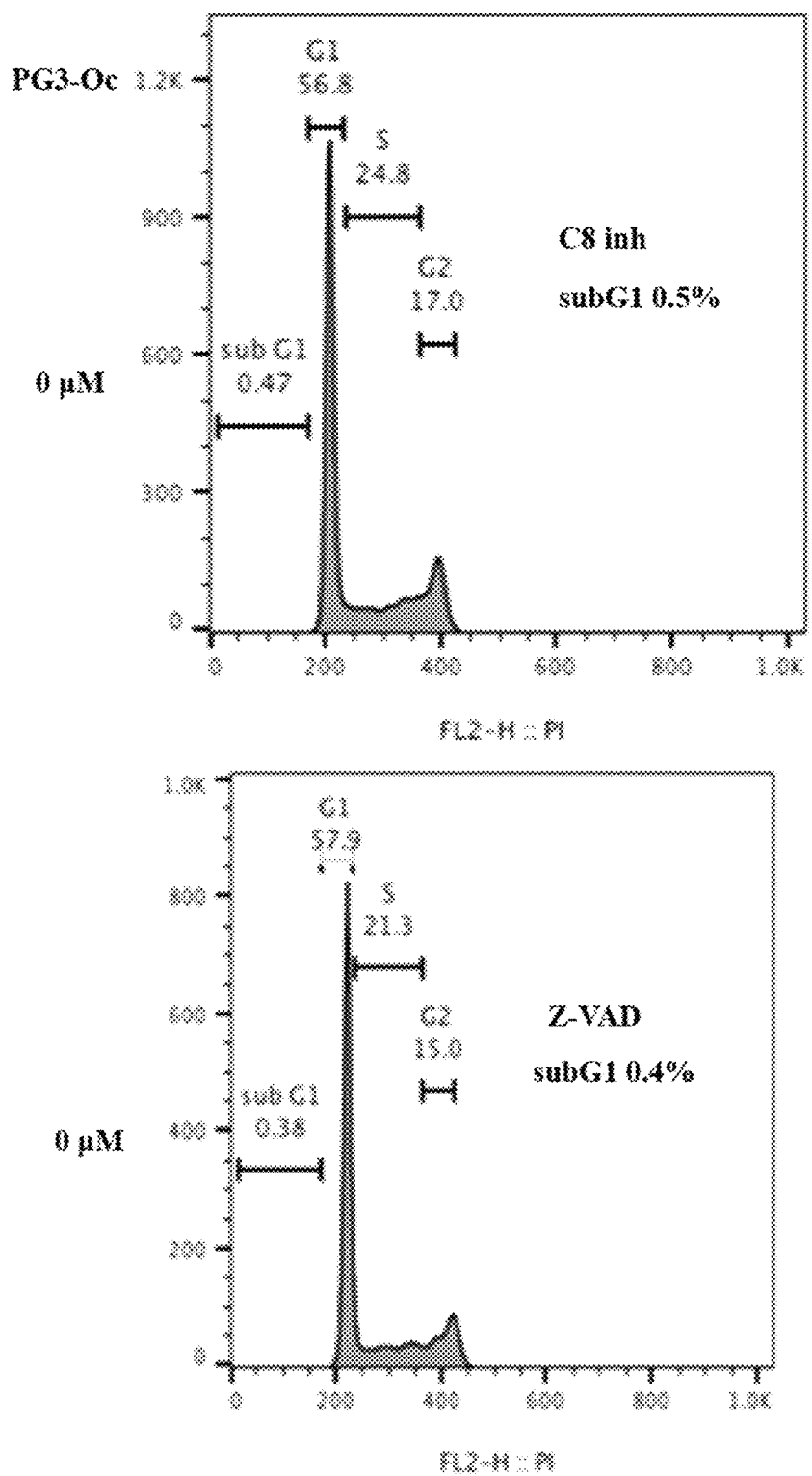
Figure 91:
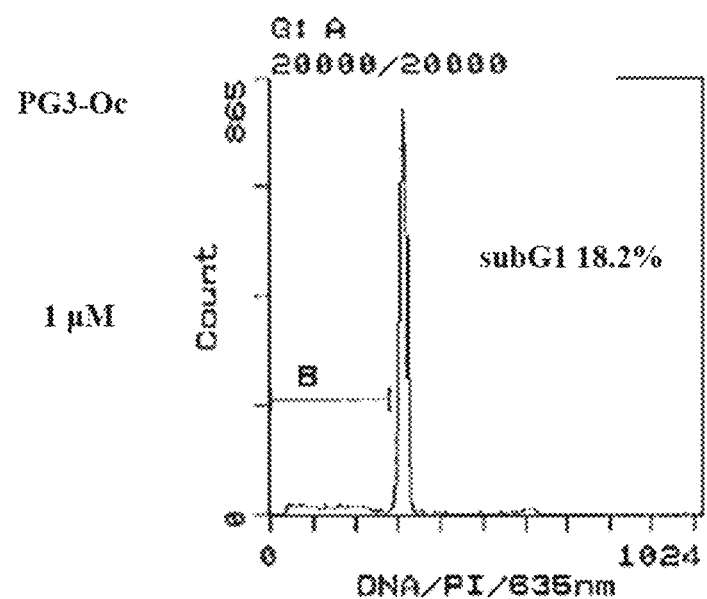
Figure 91:
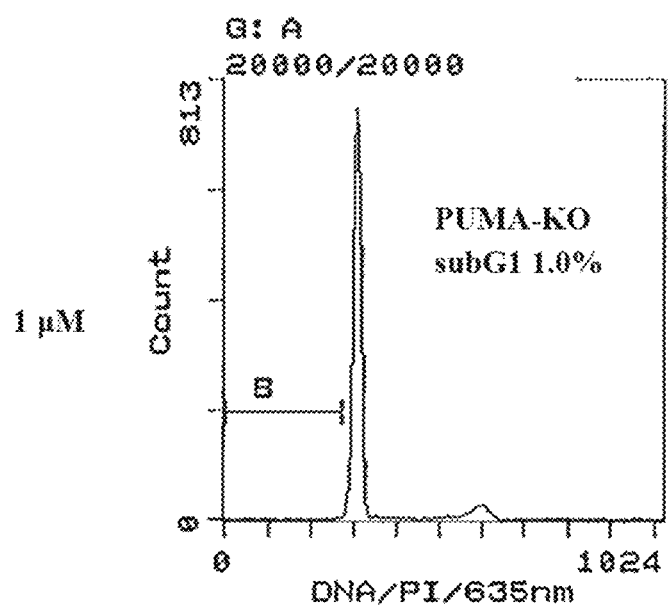
Figure 91:
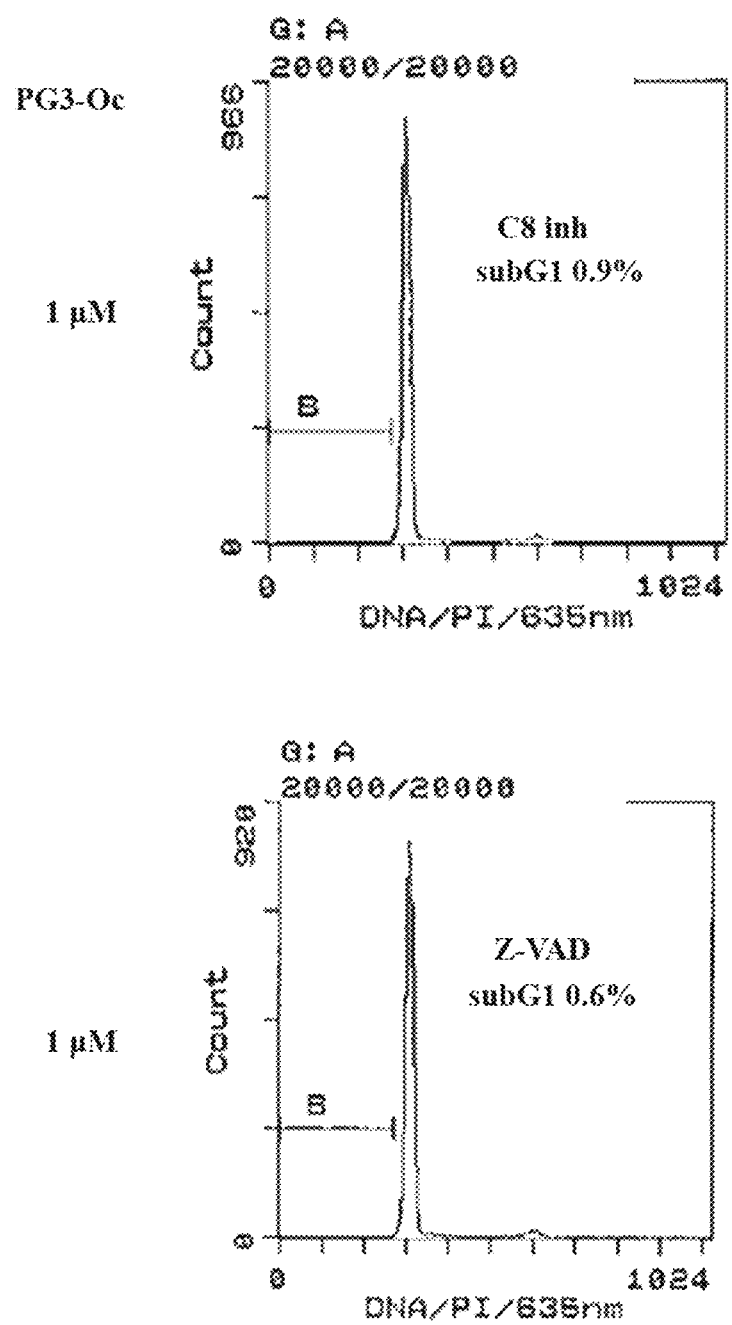
Figure 92:
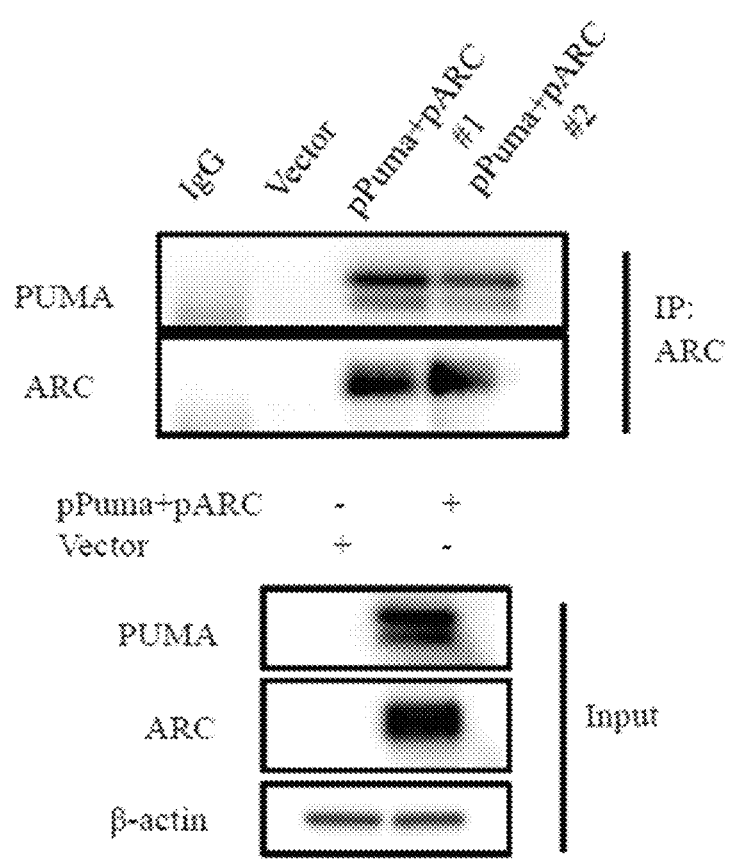
FIG. 92 shows HEK293 cells transfected to the control dish.

PUMA siRNA studies were validated by creating PUMA gene knockout HT29 cells via CRISPR/Cas9 gene-editing technology (FIGS. 30A-30D and 95-96) (For details see Materials and Methods). The gRNA was designed to target the DNA sequence that encodes amino-acid residues for the BH3-domain of PUMA (FIG. 30A). Knockout of the PUMA gene was found to abolish PG3-Oc-induced cleavage of PARP and caspase-8, -3 and sub-G1 population were the same as the positive control caspase-8 inhibitor Z-IETD-fmk and the pan-caspase inhibitor Z-VAD (FIGS. 51 and 52 and FIG. 91). Taken together, these data suggest that DR5 is dispensable for PG3-Oc mediated cell death. However, PUMA protein is required and is a key player in cell death induced by PG3-Oc treatment in HT29 cancer cells.

Of note, both knockdown and knockout of PUMA gene abolished caspase-8 and caspase-3 cleavage/activation and PARP cleavage after PG3-Oc treatment (FIGS. 49 and 51). Further, the caspase-8 inhibitor Z-IETD-fmk not only inhibited caspase-8 cleavage, but also resulted in inhibition of caspase-3 and PARP cleavage. These data suggest that the induced PUMA is able to feedback to mediate the activation of caspase-8 through an unknown mechanism.

Figure 53:
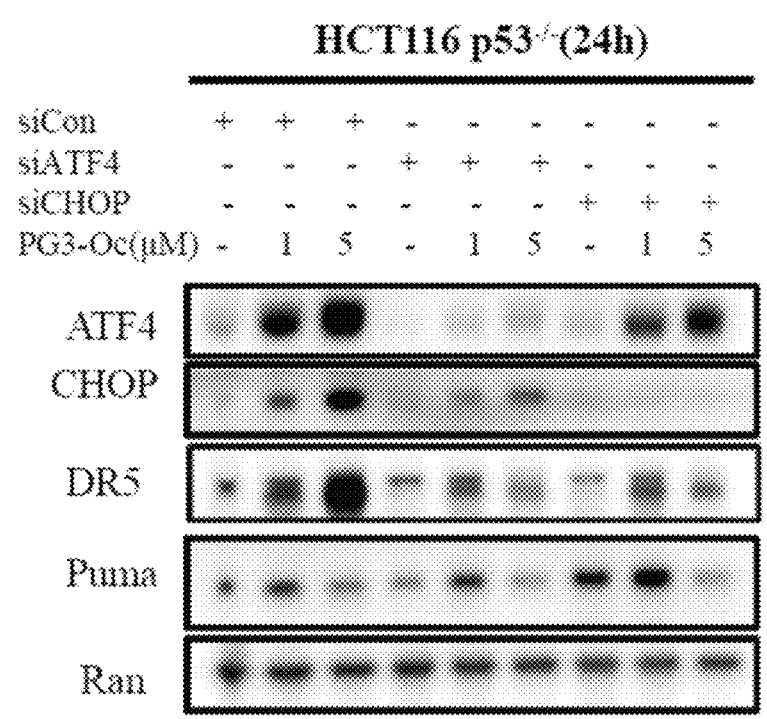
FIG. 53 shows HCT116 p53−/− cells transfected with the indicated siRNAs.

PG3-Oc-induced upregulation of DR5 was of interest in terms of mechanism and function. First of all, Western blotting data indicated the PG3-Oc treatment potently induced upregulation of ATF4 and CHOP, but the level of phosph-Ser-eIF2a did not increase compared to untreated controls (FIG. 33D and FIG. 33C), suggesting that PG3-Oc induced upregulation of ATF4 and CHOP might not go through ER stress or the integrated stress response pathway. siRNA knockdown of ATF4 led to potent blockage of CHOP and DR5 induction, but not PUMA. Knockdown of CHOP blocked DR5 upregulation, but not ATF4 and PUMA (FIG. 53). Taken together, these data indicated that PG3-Oc-induced upregulation of DR5 is through ATF4/CHOP axis, and ATF4 or CHOP did not mediate the induction of PUMA.

Figure 54:
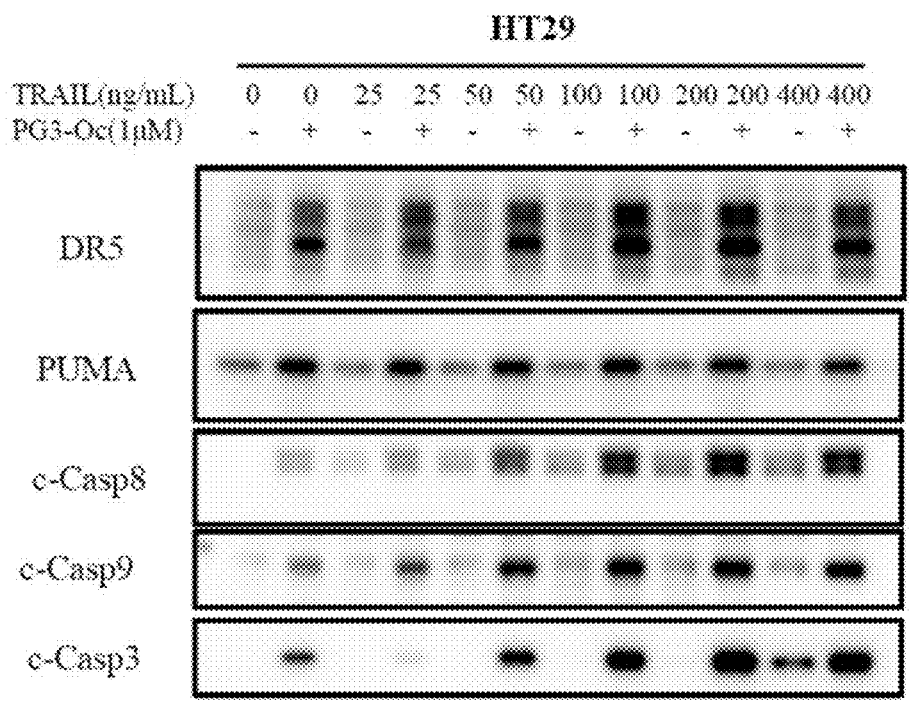
FIG. 54 shows HT29 cell western blots performed using the indicated antibodies.
Figure 55:
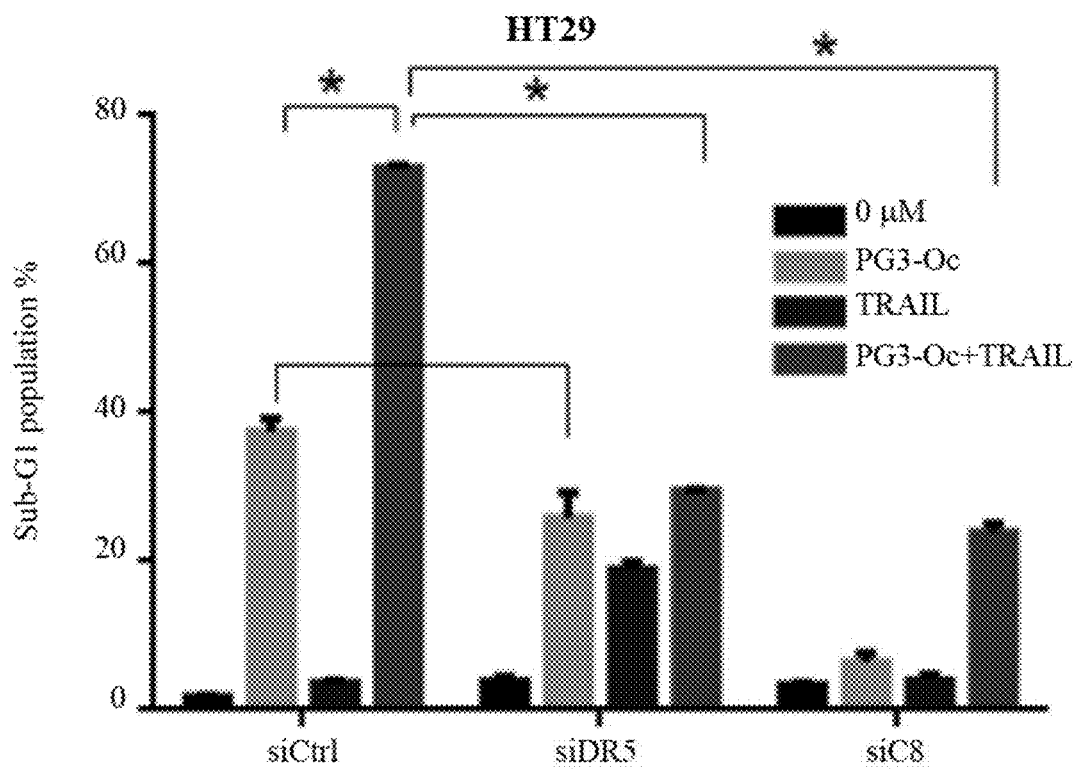
FIG. 55 shows HT29 cells transfected with the indicated siRNAs.
Figure 56:
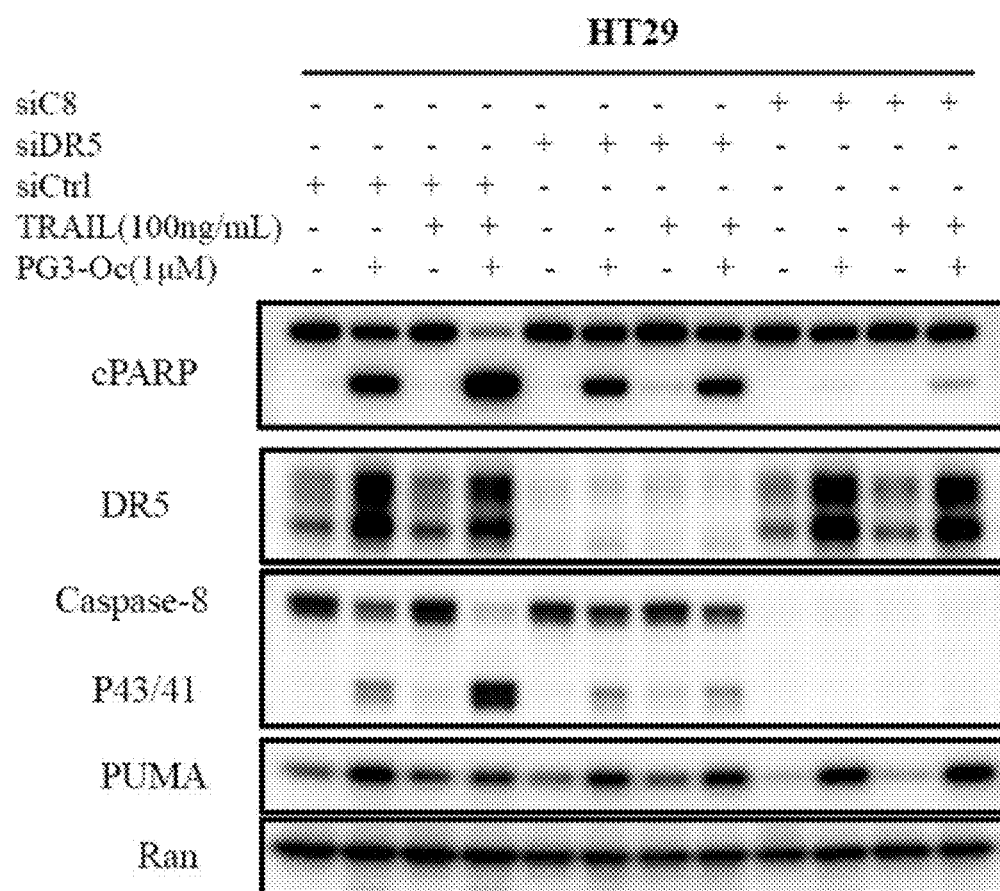
FIG. 56 shows HT29 cells transfected with the indicated siRNAs.

HT29 is a TRAIL-resistant cell line. Cells were pre-treated with 1 µM PG3-Oc to allow DR5 induction, and then TRAIL was added to the medium at different doses for an additional 5 hours. Cleaved capase-8, -9 and -3 were dramatically increased in a dose response manner compared with TRAIL treatment alone (FIG. 54). siRNA knockdown of DR5 potently reduced the sub-G1 populations of co-treatment with PG3-Oc and TRAIL from 72.9% to 29.5% (FIG. 55). Corresponding western blot data showed that knockdown of DR5 reduced the level of co-treatment-induced caspase-8 cleavage to the level of PG3-Oc treatment alone. Knockdown of caspase-8 is a positive control in both experiments (FIGS. 55 and 56). These data indicate that DR5 upregulation is required to sensitize HT29 cells to TRAIL treatment.

Figure 57:
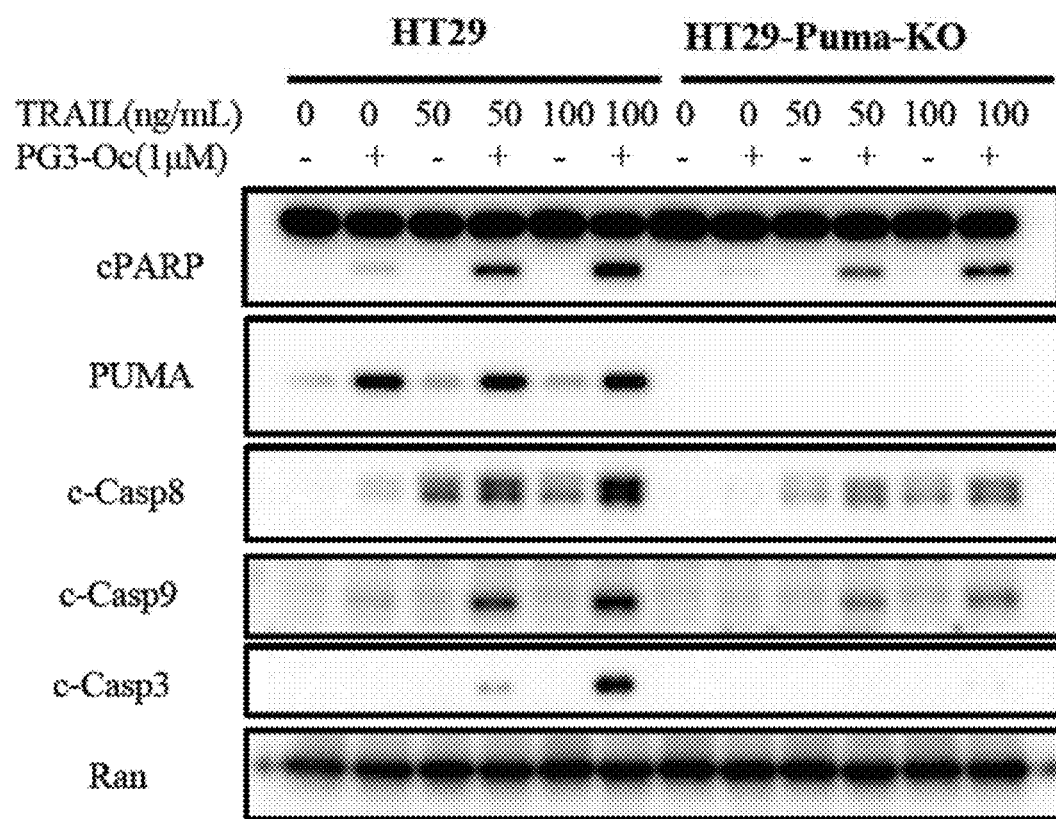
FIG. 57 shows HT29 and HT29-PUMA-KO cell western blots using the indicated antibodies.
Figure 58:
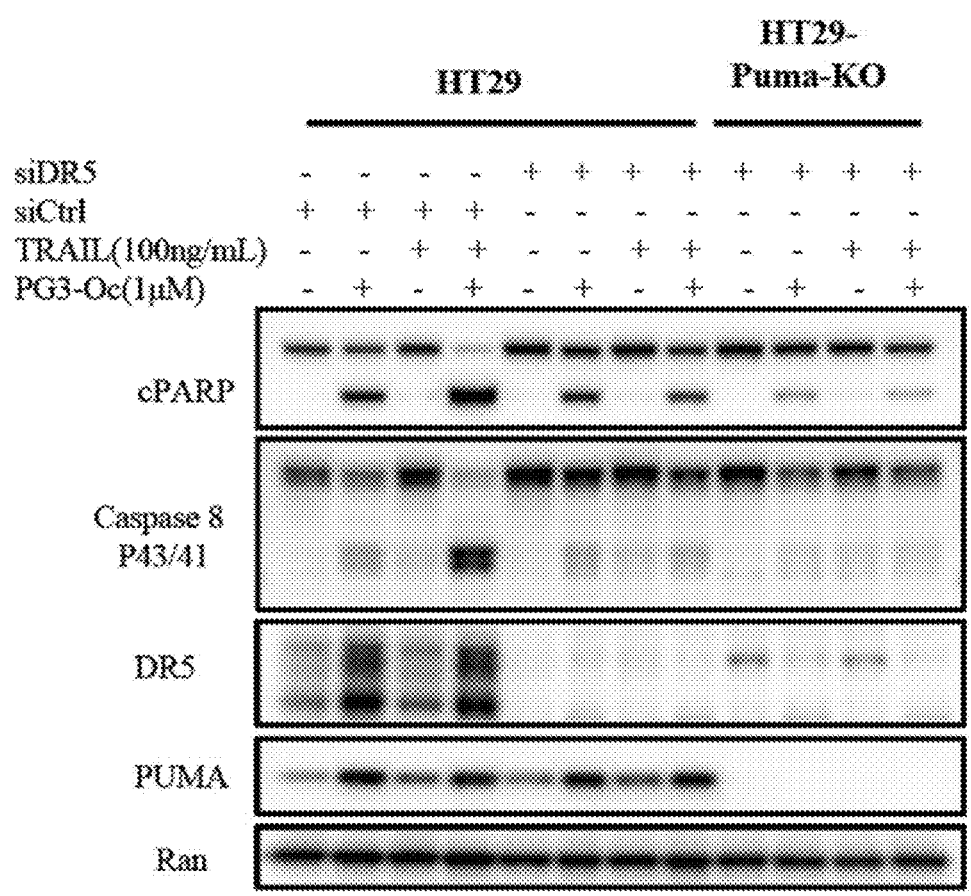
FIG. 58 shows HT29 and HT29-PUMA-KO cells transfected with indicated siRNAs.
Figure 59:
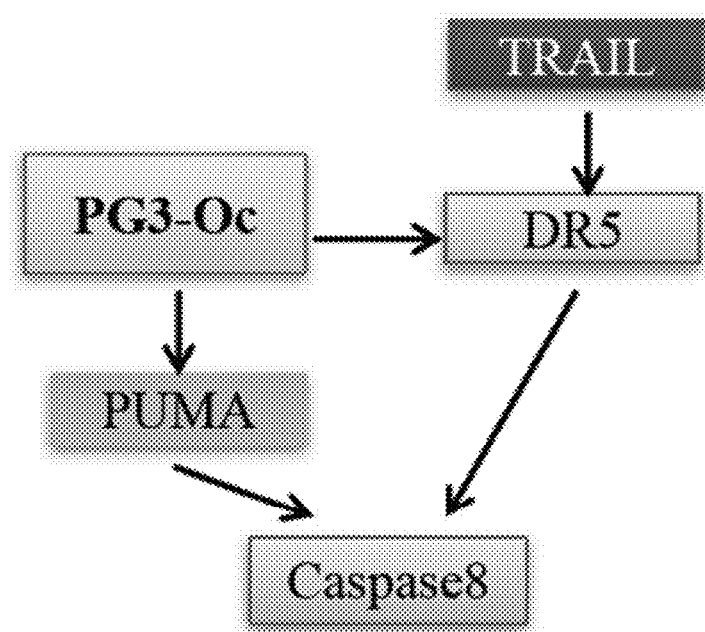
FIG. 59 shows suggested model of PG3-Oc induced upregulation of PUMA and DR5.

Knockout of the PUMA gene blunted cleavage of caspsase-8, -9, -3 and PARP induced by PG3-Oc and TRAIL co-treatment (FIG. 57). Depletion of both DR5 and PUMA further reduced caspase-8 activation induced by PG3-Oc and TRAIL co-treatment, as compared to knockdown of DR5 alone (FIG. 58). Taken together, these results indicated PUMA-mediated caspase-8 activation also contributes to sensitization to TRAIL treatment. In summary, a model as shown in FIG. 59 is proposed.

Example 8: PG3-Oc Dependent Repression of c-Myc Upregulates PUMA

Transcription factors p'73, p63, ATF4, CHOP, FOXO3a, NF-κB, and JNK/c-Jun can regulate PUMA gene expression in a p53-independent manner depending on cell types and stimuli (Zhang et al., Cancer Res, 2015, 75, 3842-3852; Hong et al., Cancer Res, 2014, 74, 1153-1165; Prabhu et al., Cancer Res, 2016, 76, 1989-1999; Sun et al., Oncogene, 28, 2348-2357; Dudgeon et al., Mol Cancer Ther, 2010, 9, 2893-2902; Qing et al., Cancer Cell, 2012, 22, 631-644; Cazanave et al., Am J Physiol Gastrointest Liver Physiol, 2010, 299, G236-G243; Ghosh et al., PLos ONE, 2012, 7, e39586; Dudgeon et al., Oncogene, 2012, 31, 4848-4858; Zhao et al., Biochem J, 2012, 444, 291-301; Zhang et al., Oncogene, 2014, 33, 1548-1557; Chen et al., Clin Cancer Res, 2014, 20, 3472-3484; Gao et al., Cell Death Differ, 2010, 17, 699-709). In addition, c-Myc is known to repress PUMA gene expression (Amente et al., Nucleic Acids Res, 2011, 39, 9498-9507 and Yun et al., Blood, 2016, 127, 2711-2722). A candidate approach was taken and checked which of these factors mediates PUMA upregulation in PG3-Oc treated cells.

Figure 93:
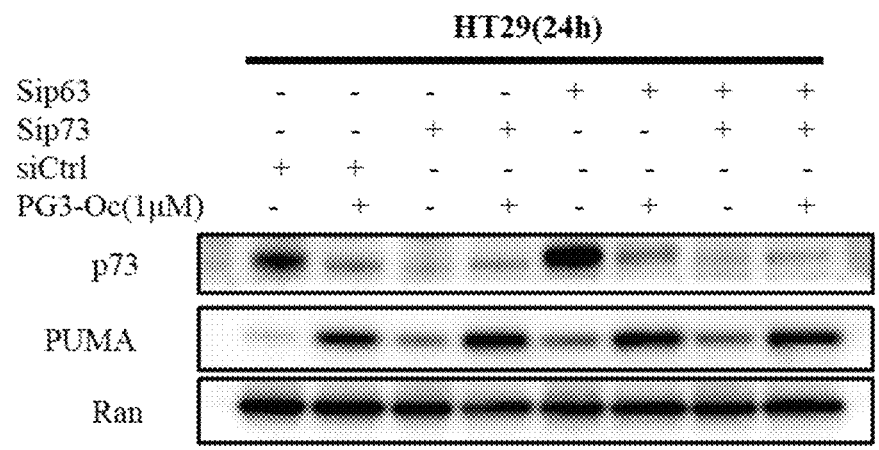
FIG. 93 shows HT29 cells transfected with p73 and p63 siRNAs.
Figure 94:
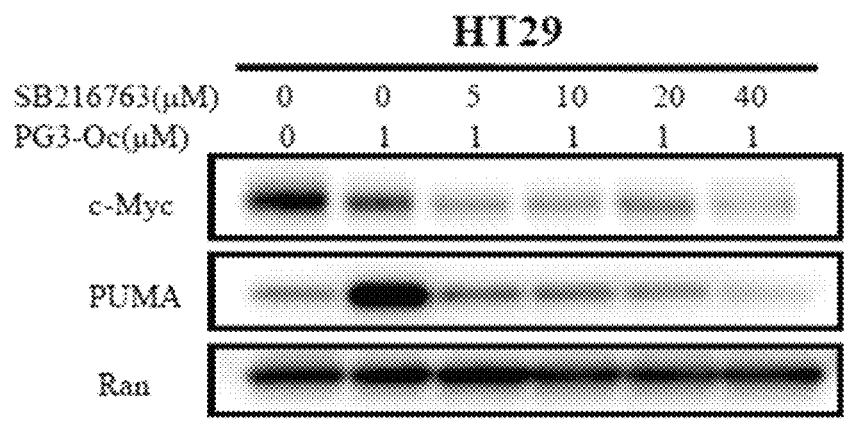
FIG. 94 shows HT29 cells treated with 1 µM PG3-Oc or co-treated with SB216763.

Stable knockdown of p73 or siRNA knockdown of p73 and/or p63 did not attenuate PG3-Oc-induced upregulation of PUMA in either DLD1 or HT29 cells (FIG. 31A and FIG. 93). These are consistent with the observation of PG3-Oc-treatment resulting in downregulation of p73 protein levels in DLD1 and HT29 cells (FIG. 31A, FIG. 61, FIG. 88 and FIG. 93), and also with PG3-Oc-induced caspase3/7 activity showing no significant difference between DLD1 and DLD1p73$^{-/-}$ cells (FIG. 27B). Knockdown of transcription factors FOXO3a and NF-κB (p65) respectively, or inhibition of JNK/c-Jun signaling by JNK inhibitor SP600125 did not blunt PG3-Oc-induced upregulation of PUMA (FIGS. 31D and 31E). Knockdown of ATF4 or CHOP also did not attenuate upregulation of PUMA by PG3-Oc (FIG. 53). These data suggest that p73, p63, ATF4, CHOP, NF-κB, FOXO3a, and JNK/c-Jun are not involved in the regulation of PUMA in PG3-Oc treated cells.

Figure 60:
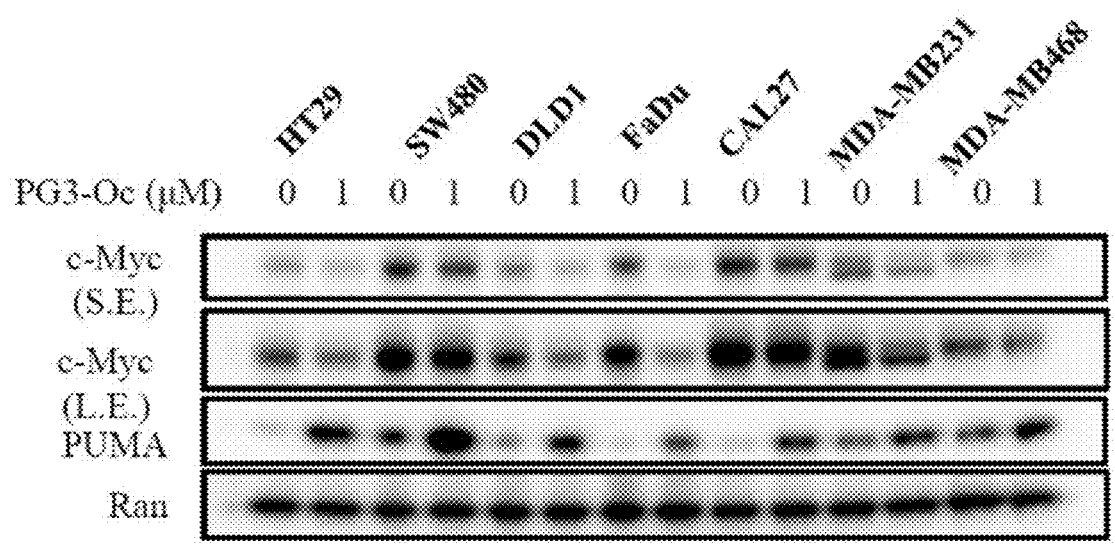
FIG. 60 shows various mutant p53-expressing cancer cell lines treated with PG3-Oc for 24 hours.
Figure 63:
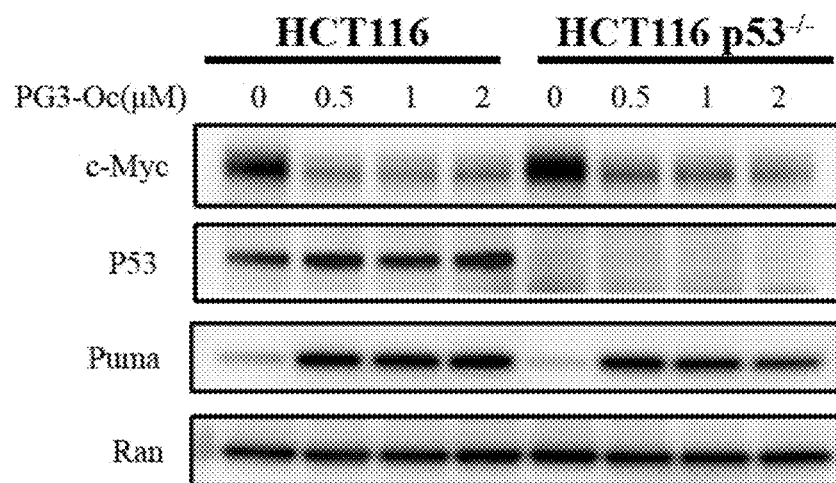
FIG. 63 shows HCT116 and HCT116 p53−/− cells treated with PG3-Oc at the indicated doses for 24 h.

PG3-Oc-induced significant downregulation of c-Myc and upregulation of PUMA protein levels was observed in a panel of p53 mutant cell lines, such as HT29, DLD1, FaDu, MDA-MB-231, MDA-MB-468, SW480 and CAL27 (FIG. 60). Experiments in isogenic HCT116 cells with wild-type p53 or p53-null showed no significant differences in induction of PUMA or downregulation of c-Myc by PG3-Oc (FIG. 63). These data suggest that PG3-Oc-induced downregulation of c-Myc and upregulation of PUMA is not limited to a specific cell line or p53 mutation, and is independent of p53 status.

Figure 62:
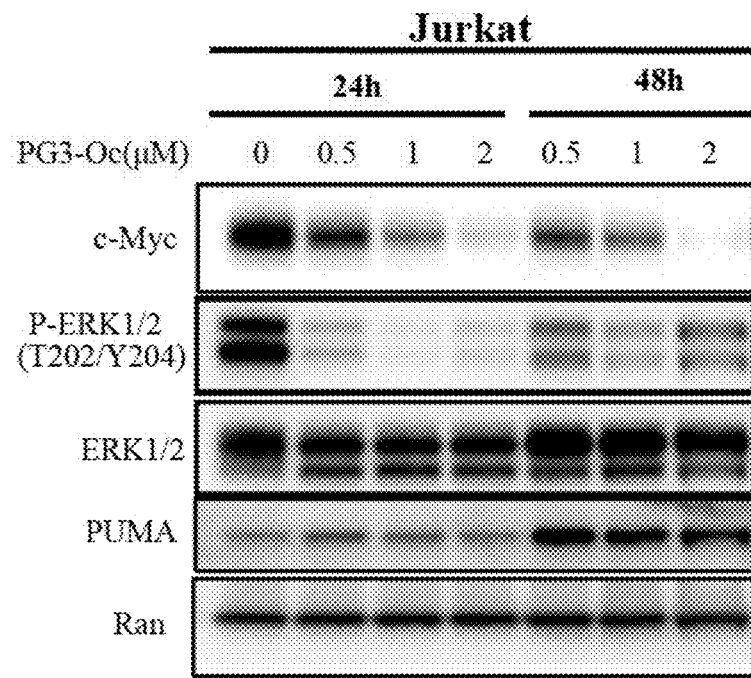
FIG. 62 shows Jurkat cells treated with PG3-Oc at the indicated doses and time points.
Figure 64:
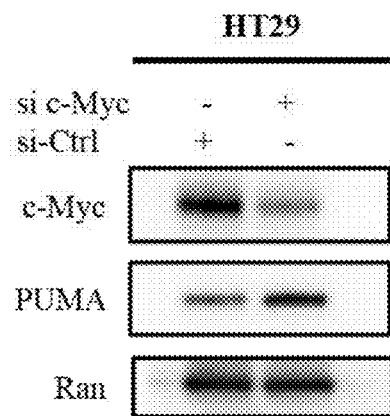
FIG. 64 shows cells transfected with c-Myc siRNAs and control siRNAs.
Figure 65:
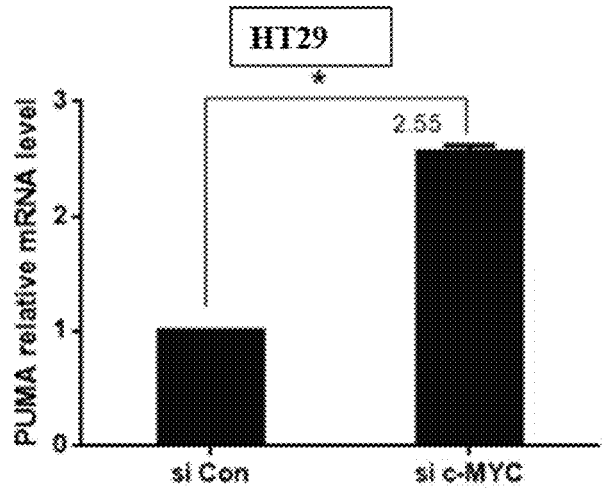
FIG. 65 shows mRNAs extracted for qRT-PCR analysis.
Figure 66:
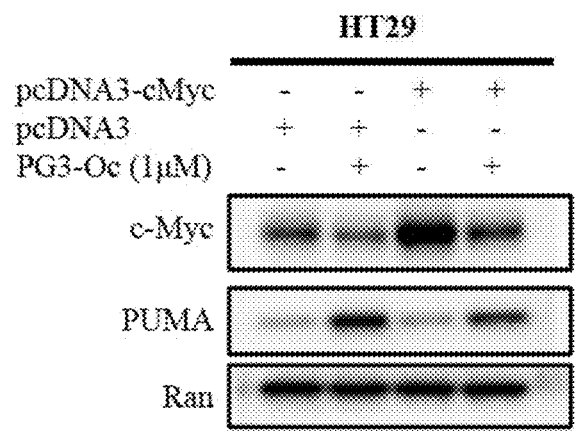
FIG. 66 shows HT29 cells transfected with the vector pcDNA3 and pcDNA3-cMyc.
Figure 67:
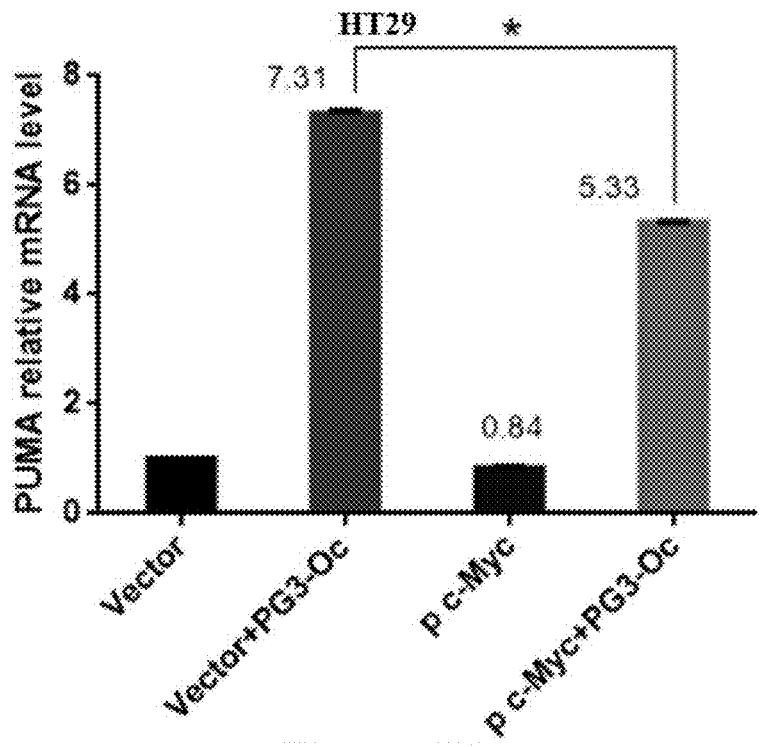
FIG. 67 shows mRNA extracted for qRT-PCR analysis.
Figure 68:
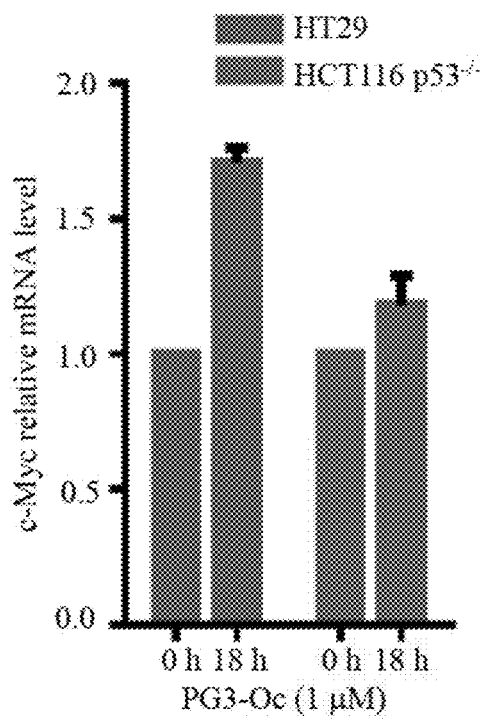
FIG. 68 shows HT29 and HCT115 p53−/− cells treated with PG3-Oc for 18 hours.
Figure 69:
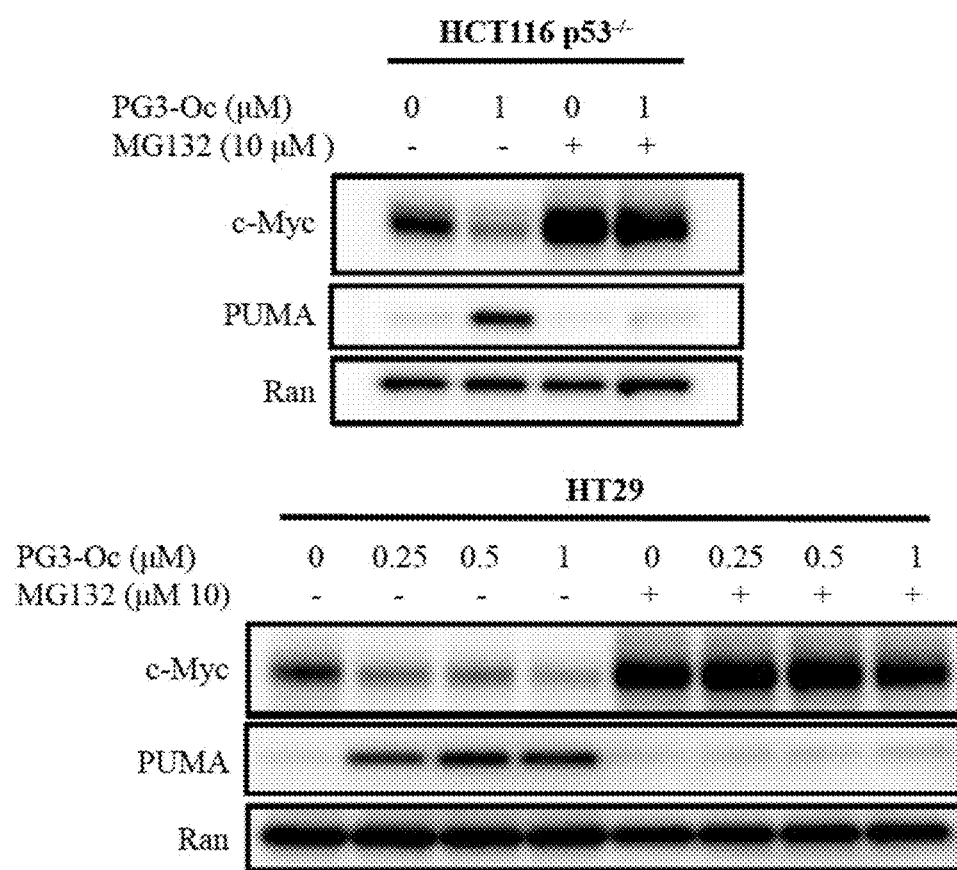
FIG. 69 shows cells co-treated with the proteasome inhibitor MG132.

Of the different candidates tested, it was found that PG3-Oc treatment potently downregulated c-Myc in colorectal cancer cell lines (FIGS. 61 and 63) and c-Myc addicted acute T cell leukemia Jurkat cells that carry multiple p53 mutations (FIG. 62). Interestingly, c-Myc downregulation and PUMA upregulation simultaneously occurred upon treatment with PG3-Oc, suggesting c-Myc might negatively regulate PUMA expression. Basal PUMA levels were modestly de-repressed on knockdown of c-Myc, both at the protein and mRNA levels (FIGS. 64 and 65). Over-expression of c-Myc led to attenuation of PUMA induction at both the protein and mRNA levels (FIGS. 66 and 67) post PG3-Oc treatment. To study whether endogenous c-Myc can inhibit PG3-Oc-induced upregulation of PUMA or not, HCT116 p53$^{-/-}$ and HT29 cells were co-treated with PG3-Oc and proteasome inhibitor MG132. MG132 blocked c-Myc degradation and led to accumulation of endogenous c-Myc that abolished PG3-Oc-induced upregulation of PUMA (FIG. 69).

qPCR data indicated that PG3-Oc treatment did not significantly change c-Myc mRNA levels in either HT29 or HCT116 p53$^{-/-}$ cell lines (FIG. 68). Proteasome inhibitor MG132 was able to rescue PG3-Oc-induced degradation of c-Myc protein in both HT29 and HCT116 p53$^{-/-}$ cells (FIG. 69). Taken together, these data indicate that degradation of c-Myc is through proteasome pathway in PG3-Oc treated tumor cells.

Figure 70:
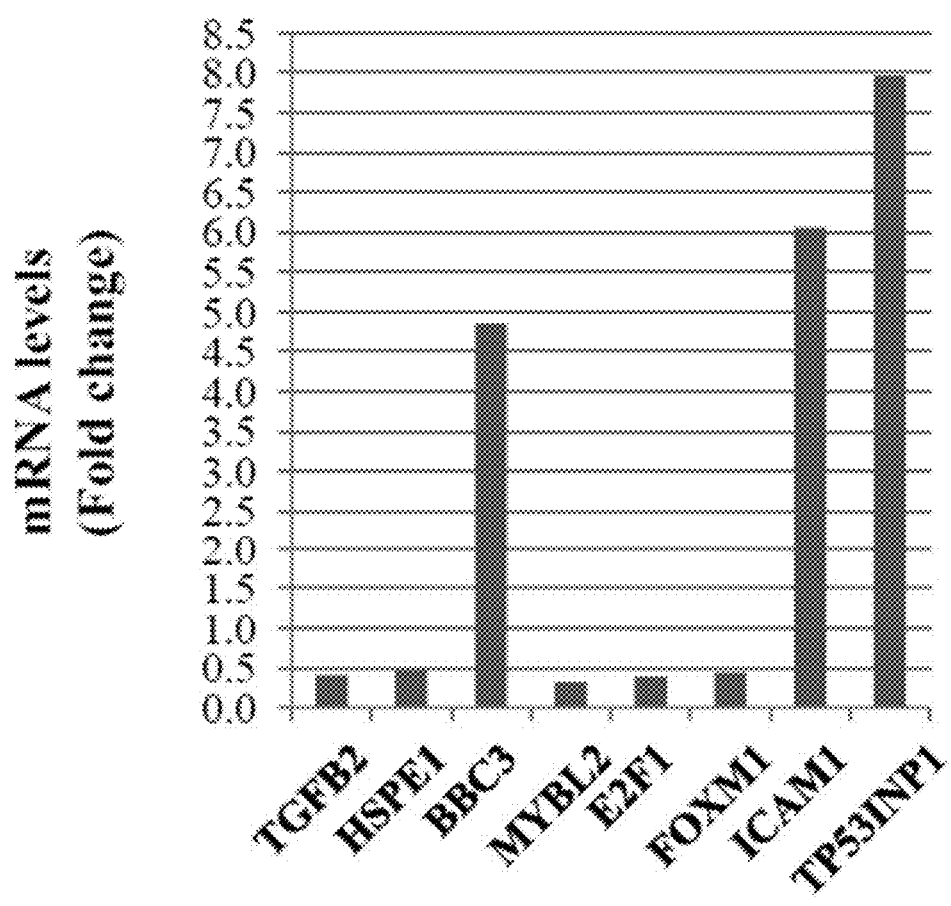
FIG. 70 shows analysis of c-Myc target genes from RNA-Seq analysis with differential gene expression induced by 1 µM PG3-Oc in HT29 cells.
Figure 71:
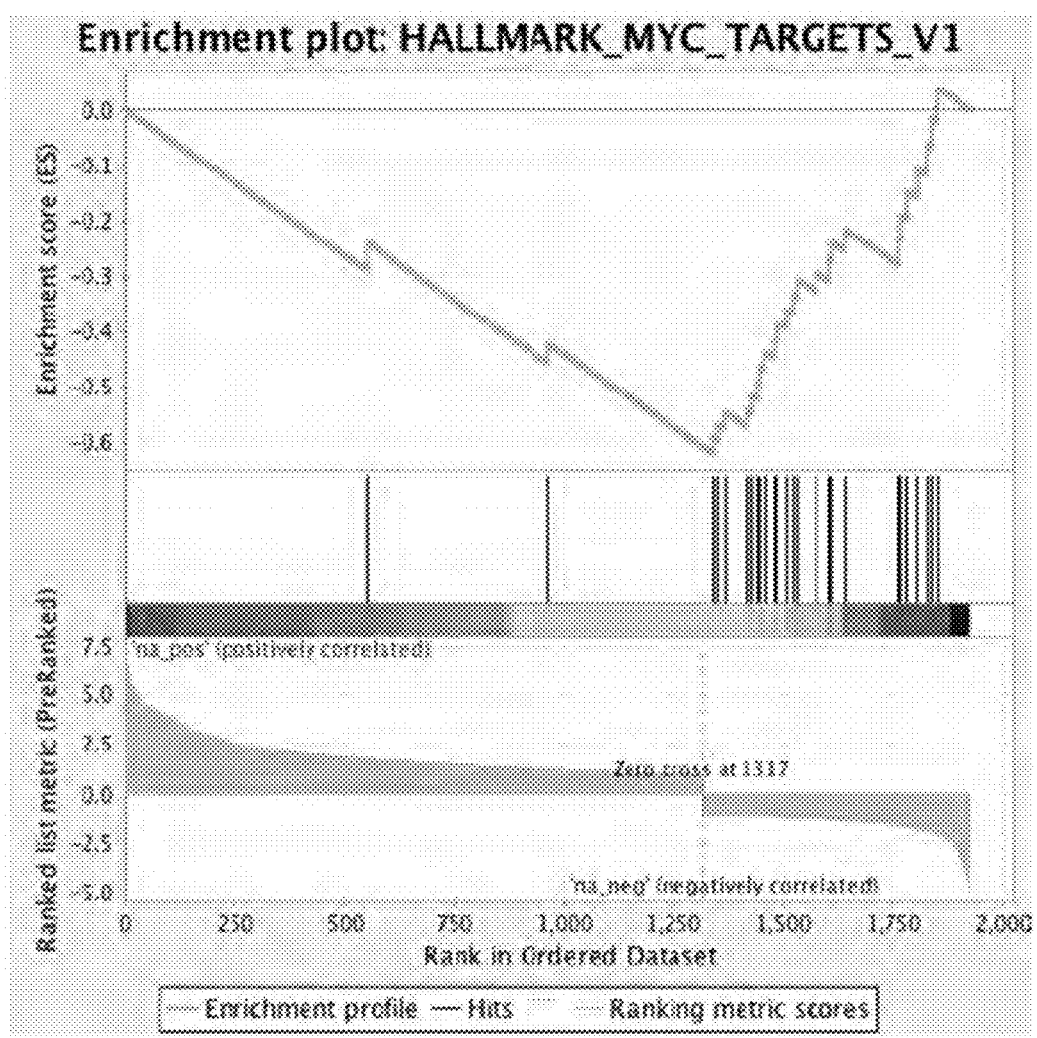
FIG. 71 shows a GSEA plot.

A subset of c-Myc target genes was selected (Fernandez et al., Genes Dev, 2003, 17, 1115-1129), and their expression was altered based on RNA-Seq data analysis in PG3-Oc treated cells (FIG. 70). c-Myc positively regulates TGFB2 (TGFβ-2), HSPE1 (Hsp10), MYBL2 (B-Myb), E2F1 (E2F1) and FOXM1 (FOXM1) (Fernandez et al., Genes Dev, 2003, 17, 1115-1129). Downregulation of these genes is consistent with PG3-Oc-induced degradation and inhibition of c-Myc (FIGS. 61 and 70). c-Myc negatively regulates BBC3 (PUMA), ICAM1 (ICAM1) and TP53INP1 (TP53INP1) (Amente et al., Nucleic Acids Res, 2011, 39, 9498-9507; Yun et al., Blood, 2016, 127, 2711-2722; Florea et al., PLoS ONE, 2013, 8, e73146). Upregulation of PUMA, ICAM1 and TP53INP1 is also consistent with the inhibition of c-Myc by PG3-Oc (FIG. 70). GSEA analysis indicated that downregulation of genes was enriched in the c-Myc pathway and network, suggesting PG3-Oc has significant impact on the c-Myc pathway and network (FIG. 6L).

Example 9: ERK1/2 Mediates PG3-Oc-Induced Degradation of c-Myc

Figure 97:
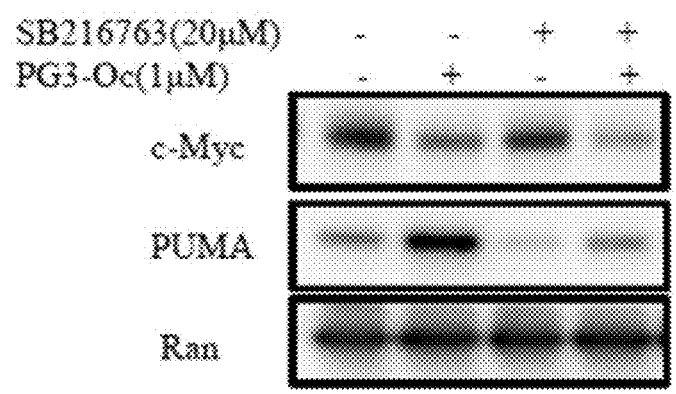
FIG. 97 shows PG3-Oc co-treatment with SB216763.
Figure 98:
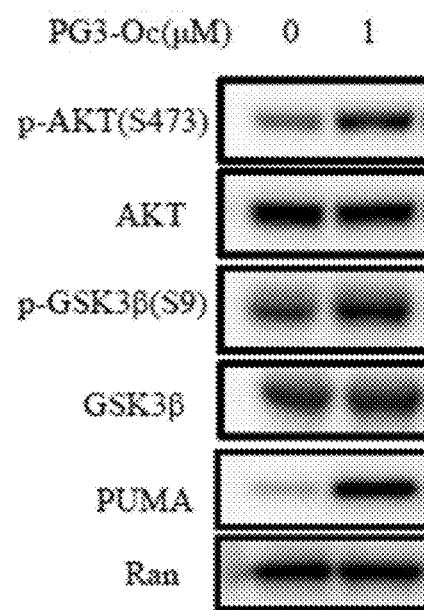
FIG. 98 shows cells treated with PG3-Oc for 24 hours.
Figure 99:
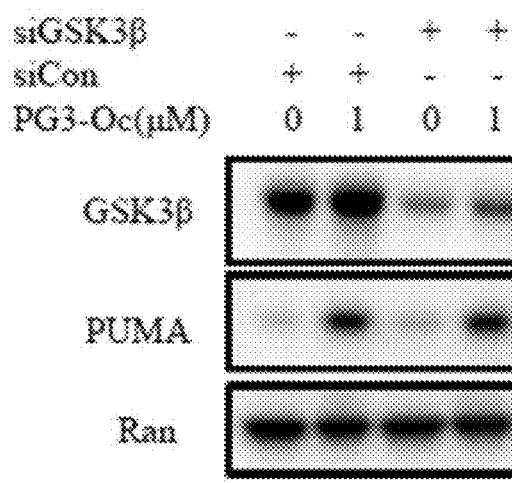
FIG. 99 shows cells transfected with control siRNA or GSK3β siRNA.
Figure 100:
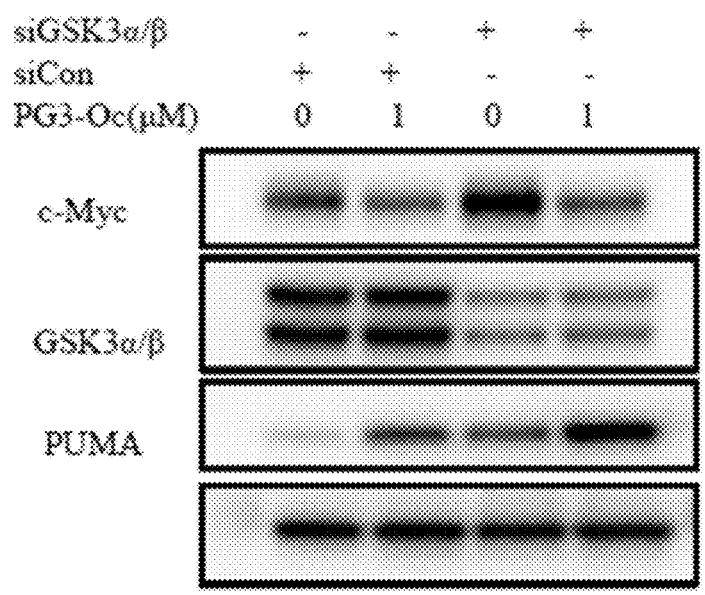
FIG. 100 shows cells transfected with control siRNA or GSK3α/β siRNA.

SB216763 is a GSK3α/β inhibitor. It has been reported that regorafenib-induced and GSK3β-dependent NF-κB (p65) activation mediates upregulation of PUMA in a p53-independent manner in several colorectal cancer cell lines, and upregulation of PUMA can be inhibited by SB216763 (Chen et al., Clin Cancer Res, 2014, 20, 3472-3484). SB216763 did block PG3-Oc-mediated upregulation of PUMA, but was permissive for the degradation of c-Myc protein (FIG. 97). Surprisingly, it was found that PG3-Oc treatment led to activation of AKT and inhibition of GSK3β, indicated by increased inhibitory phosphorylation of GSK3β at Ser9 (FIG. 98). Furthermore, knockdown of GSK3β did not have any effect on PG3-Oc-induced upregulation of PUMA (FIG. 99), which is consistent with that GSK3β was inhibited by PG3-Oc, and the knockdown of NF-κB subunit p65 did not prevent PUMA from induction by PG3-Oc (FIG. 31D). Because SB216763 inhibits both GSK3α/β, therefore, both GSK3α/β, which again did not prevent c-Myc from degradation and PUMA were knocked down from induction by PG3-Oc (FIG. 100). Taken together, these data suggest that GSK3β is inhibited by PG3-Oc, and is not involved in the degradation of c-Myc protein in PG3-Oc treated cells, and SB216763 blunted the induction of PUMA possibly through off-target inhibition of unknown targets which are required for c-Myc-downregulation-mediated upregulation of PUMA.

Figure 72:
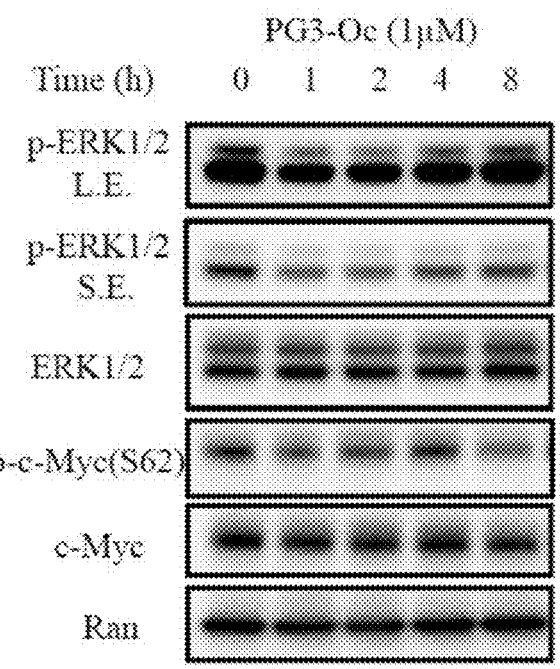
FIG. 72 shows HT29 cells treated with 1 µM PG3-Oc for the indicated time points.

It was found that PG3-Oc potently blocked phosphorylation of ERK1/2 in a time- and dose-dependent manner in Jurkat cells (FIG. 62). PG3-Oc treatment resulted in rapid dephosphorylation of ERK1/2, and simultaneous dephosphorylation of their direct target, c-Myc, at Ser 62 in HT29 cells (FIG. 72), indicating inhibition of ERK1/2. However, the levels of the phosphorylation of ERK1/2 gradually increased with time (FIG. 72). That is possibly because growth factors in the culture medium can stimulate the phosphorylation of ERK1/2. While phosphorylation of ERK1/2 was more evident at 8 (FIG. 72) and 24 hours (FIG. 73), in contrast, the level of phospho-c-Myc at the 8-hour time point was significantly decreased, and was undetectable at 24 hours as compared to the untreated control, suggesting that PG3-Oc also inhibits the function of phospho-ERK1/2.

Figure 73:
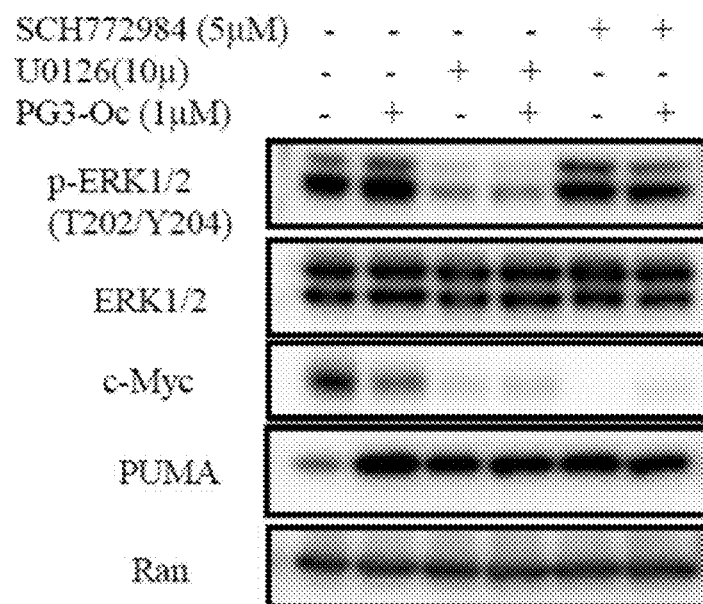
FIG. 73 shows HT29 cells treated with PG3-Oc, SCH772984 or U0126 respectively, or co-treatment with PG3-Oc/SCH772984 or PG3-Oc/U0126.

Hence, it was hypothesized that inhibition of ERK1/2 by PG3-Oc can lead to the dephosphorylation of c-Myc at Ser62 and subsequent degradation of c-Myc. To test this hypothesis, two ERK1/2 inhibitors that act by different mechanisms were used. U0126 is an indirect ERK1/2 inhibitor. It inhibits MEK1 kinase and blocks the phosphorylation of ERK1/2. SCH772984 directly binds to ATP-binding pockets of ERK1/2 and inhibits ERK1/2 regardless of the phosphorylation status of ERK1/2, and is a potent and highly selective ERK1/2 inhibitor (Chaikuad et al., Nat Chem Biol, 2014, 10, 853-860). As seen in FIG. 73, both inhibitors potently induced the downregulation of c-Myc and the upregulation of PUMA in HT29 cells, which phenocopied PG3-Oc treatment in the degradation of c-Myc and the upregulation of PUMA, indicating that ERK1/2 is an important mediator in the control of both c-Myc stability and PUMA induction. Consistent with a previous publication (Choi et al., Genes Dev, 2010, 24, 1236-1241), SCH772984 can inhibit ERK1/2 function after ERK1/2 is phosphorylated (FIG. 73), and the same is observed for PG3-Oc (FIG. 73). Co-treatments indicated that neither U0126 nor SCH772984 enhanced PG3-Oc-induced upregulation of PUMA compared to PG3-Oc alone (FIG. 73), suggesting that PG3-Oc and SCH772984 share the same target ERK1/2.

Figure 74:
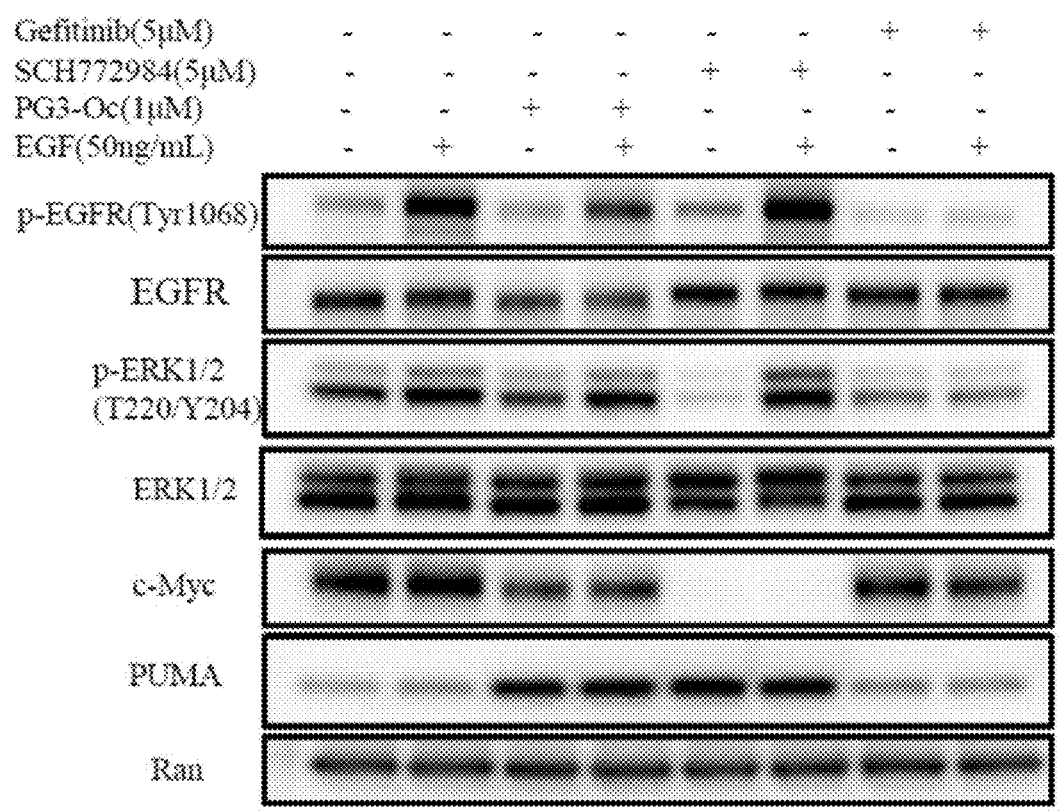
FIG. 74 shows HT29 cells pre-treated with PG3-Oc, SCH772984 or gefitinib.

EGFR signaling pathway activation can lead to the phosphorylation and the activation of ERK1/2. Hence, this pathway was chosen as a model to further verify this observation, that is, PG3-Oc inhibits phosphorylated ERK1/2. HT29 cells were cultured in charcoal-stripped medium so that ERK1/2 is maintained at a low phosphorylation status due to the removal of growth factors. Pre-treatment of cells with PG3-Oc, SCH772984 and EGFR inhibitor gefitinib respectively, was followed by addition of EGF to activate the EGFR pathway. PG3-Oc treatment resulted in a decrease of phosphorylation of ERK1/2 and downregulation of c-Myc. Subsequent addition of EGF stimulated the increase of ERK1/2 phosphorylation, but this did not rescue c-Myc from degradation (FIG. 74). Same result was observed for SCH772984 and it was more potently than PG3-Oc (FIG. 74). These data confirm that PG3-Oc is able to inhibit phospho-ERK1/2. In contrast, EGFR inhibitor gefitinib did not induce degradation of c-Myc and upregulation of PUMA, and was able to completely block EGF-stimulated phosphorylation of ERK1/2, suggesting that PG3-Oc inhibits ERK1/2 not through inhibition of EGFR (FIG. 74).

Figure 75:
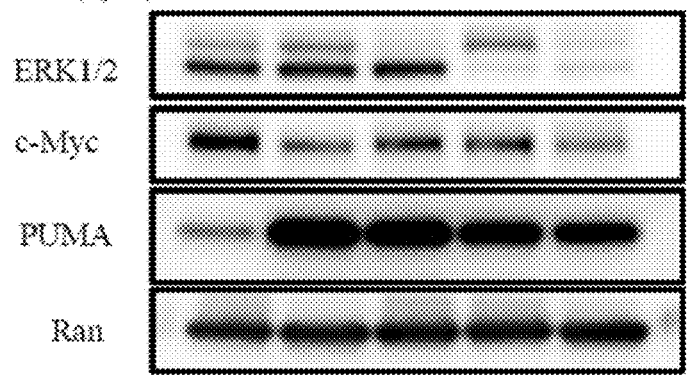
FIG. 75 shows HT29 cells transfected with control siRNA.

To further confirm the role of inhibition of ERK1/2 in regulating c-Myc and PUMA, siRNA knockdown of ERK1, ERK2 and both ERK1/2 respectively, was performed which led to potent downregulation of c-Myc and upregulation of PUMA (FIG. 75). Taken together, these data suggest that PG3-Oc inhibits ERK1/2 and leads to degradation of c-Myc and upregulation of PUMA.

Figure 76:
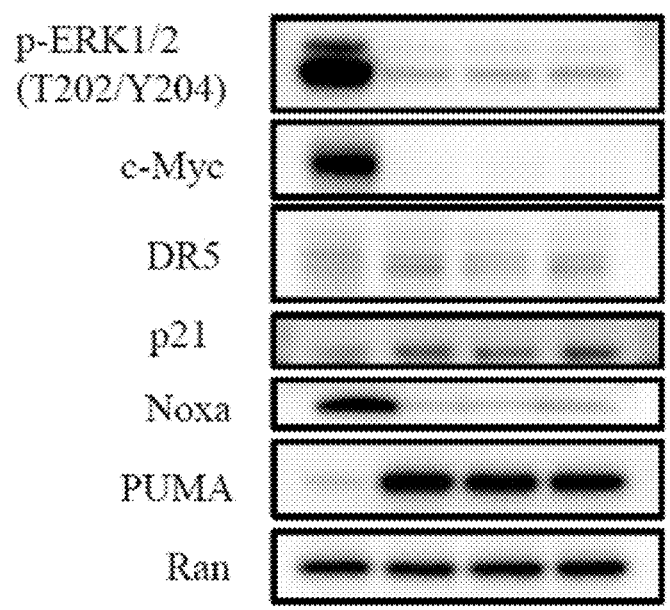
FIG. 76 shows HT29 cells treated with SCH772984.

Besides PUMA, PG3-Oc treatment also induces upregulation of DR5, p21 and Noxa (FIGS. 28C, 28D, 45, 31A, 28A and 28B). It is interesting to know whether SCH772984 also has impact on those p53 target genes. As shown in FIG. 76, SCH772984 did not induce DR5, shown mild upregulation of p21 and suppressed Noxa expression. Thus PG3-Oc has unique effects in p53 pathway restoration that go beyond effects on ERK1/2 and Puma induction.

Figure 77:
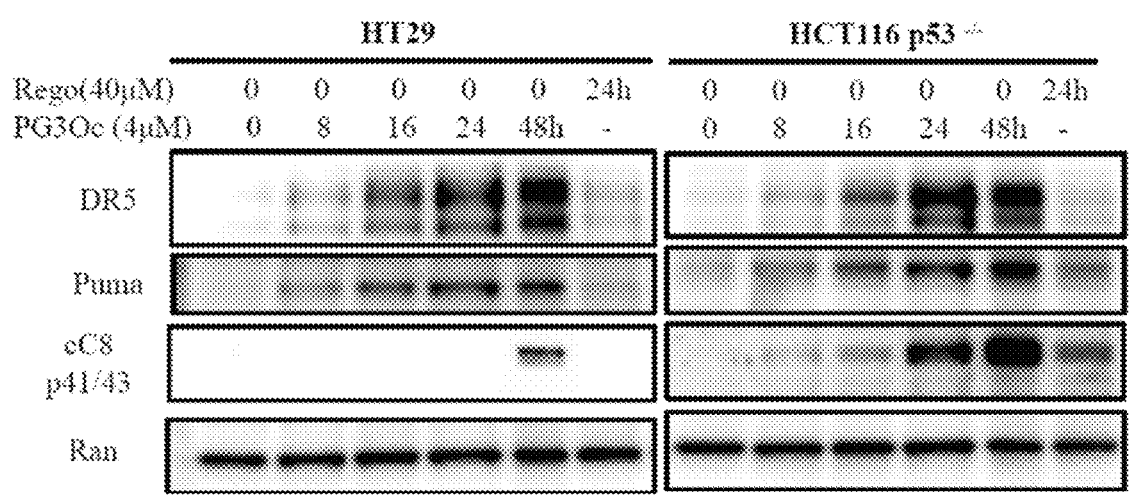
FIG. 77 shows HT29 and HCT116 p53−/− cells treated with 4 µM PG3-Oc and regorafenib.

Regorafenib is an FDA-approved drug for treatment of metastatic colorectal cancer, advanced gastrointestinal stromal tumors and hepatocellular carcinoma. Regorafenib inhibits ERK and leads to the induction of PUMA through the GSK3β/NF-κB axis and induces PUMA-mediated apoptosis in colon cancer cell lines (Chen et al., Clin Cancer Res, 2014, 20, 3472-3484). PG3-Oc was compared with regorafenib in the induction of PUMA and DR5. Regorafenib (40 µM and 24 hours treatment) was used as a control, as previously reported (Chen et al., Clin Cancer Res, 2014, 20, 3472-3484). As shown in FIG. 77, 4 µM PG3-Oc induced a much higher level of PUMA and DR5 in both HT29 and HCT116 p53$^{-/-}$ cell lines at the 24-hour time point compared to 40 µM regorafenib. In addition, the level of cleaved caspase-8 was also significantly higher with PG3-Oc than regorafenib in HCT116 p53$^{-/-}$ cells (FIG. 77) at the 24-hour time point.

Figure 78:
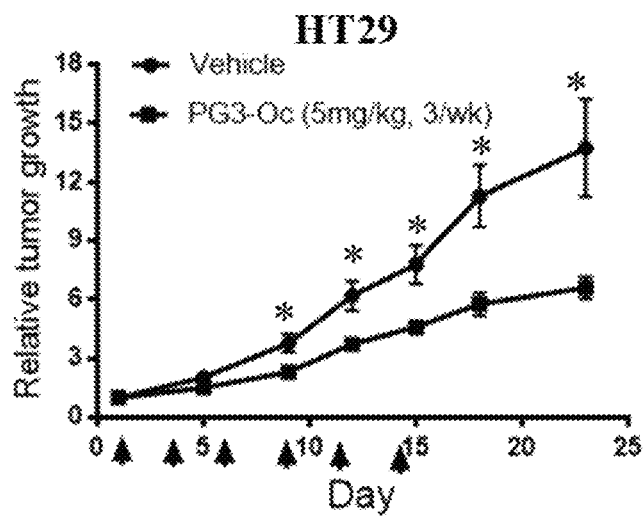
FIG. 78 shows the relative tumor growth is normalized tumor size to the tumor size of day 1 before the treatment (*, p<0.05 by an unpaired t test).
Figure 79:
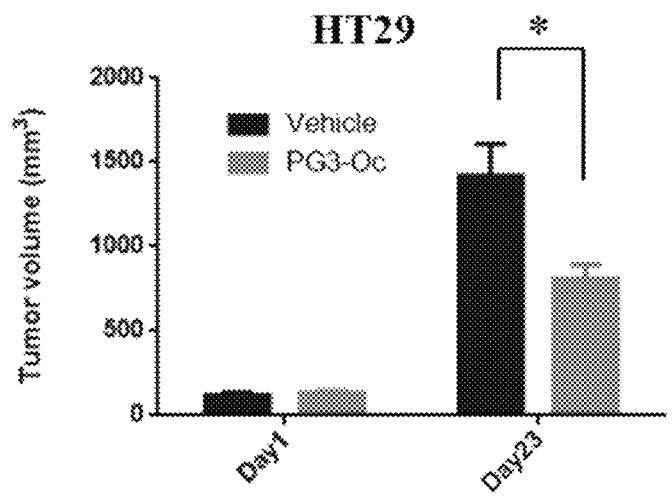
FIG. 79 shows the mean tumor volume before and after treatment (*, p<0.05 by an unpaired t test).
Figure 80:
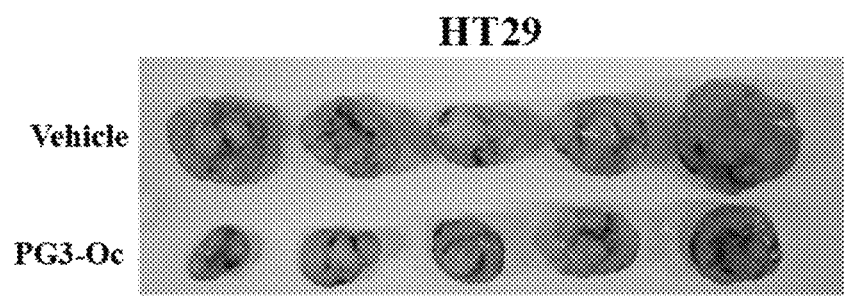
FIG. 80 shows images of 5 representative tumors from vehicle control and treated groups.
Figure 81:
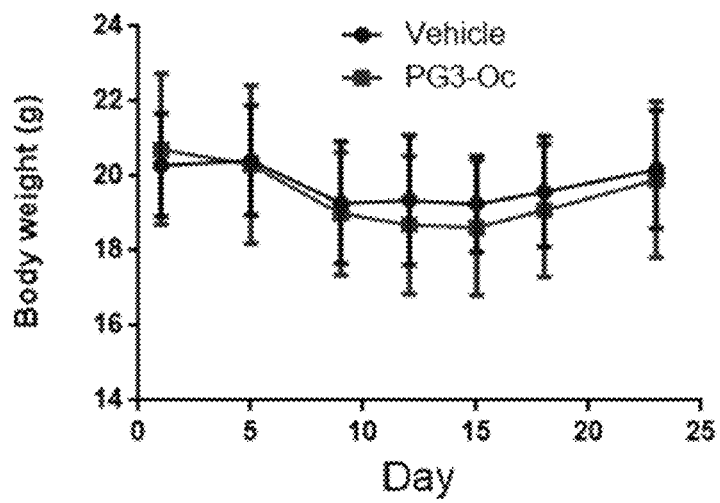
FIG. 81 shows body weight changes of nude mice during treatment period (*, p<0.05 by an unpaired t test).
Figure 82:
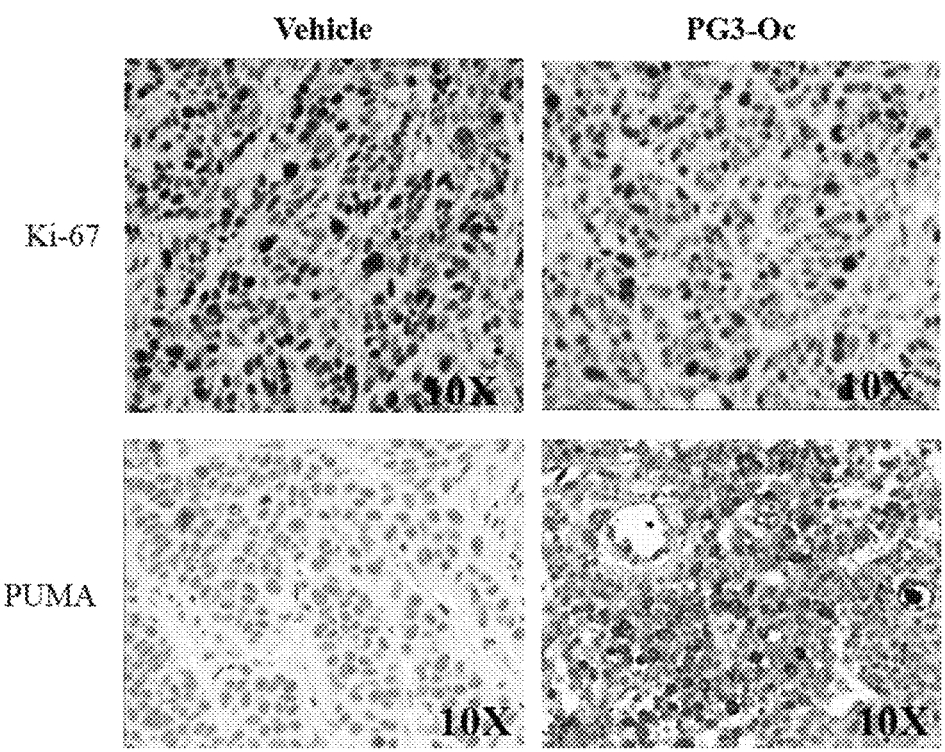
FIG. 82 shows Ki-67 and PUMA antibody staining.

Example 10: Inhibition of Tumor Growth In Vivo in HT29 Tumor Xenografts by PG3-Oc To evaluate the antitumor effects of PG3-Oc in vivo, a human tumor xenograft model was established by subcutaneous injection of human colon cancer cells into nude mice. After the tumor volume reached approximately 50 mm$^3$, mice were treated by i.p. injection with vehicle or PG3-Oc at 5 mg/kg 3 times weekly for 2 weeks. With HT29 xenografts, tumor volume in PG3-Oc-treated mice appeared to be significantly reduced as compared with vehicle-treated mice (FIGS. 78, 79 and 80). Ki-67 expression was found to be significantly decreased in PG3-Oc-treated tumors as compared with the vehicle group (FIG. 82). PUMA was significantly induced in PG3-Oc-treated tumors as compared with controls (FIG. 82). No significant difference in body weight was observed between PG3-Oc and the vehicle treatment groups (FIG. 81). These results indicate that PG3-Oc inhibits tumor growth in the HT29 mouse xenograft model.

Figure 83:
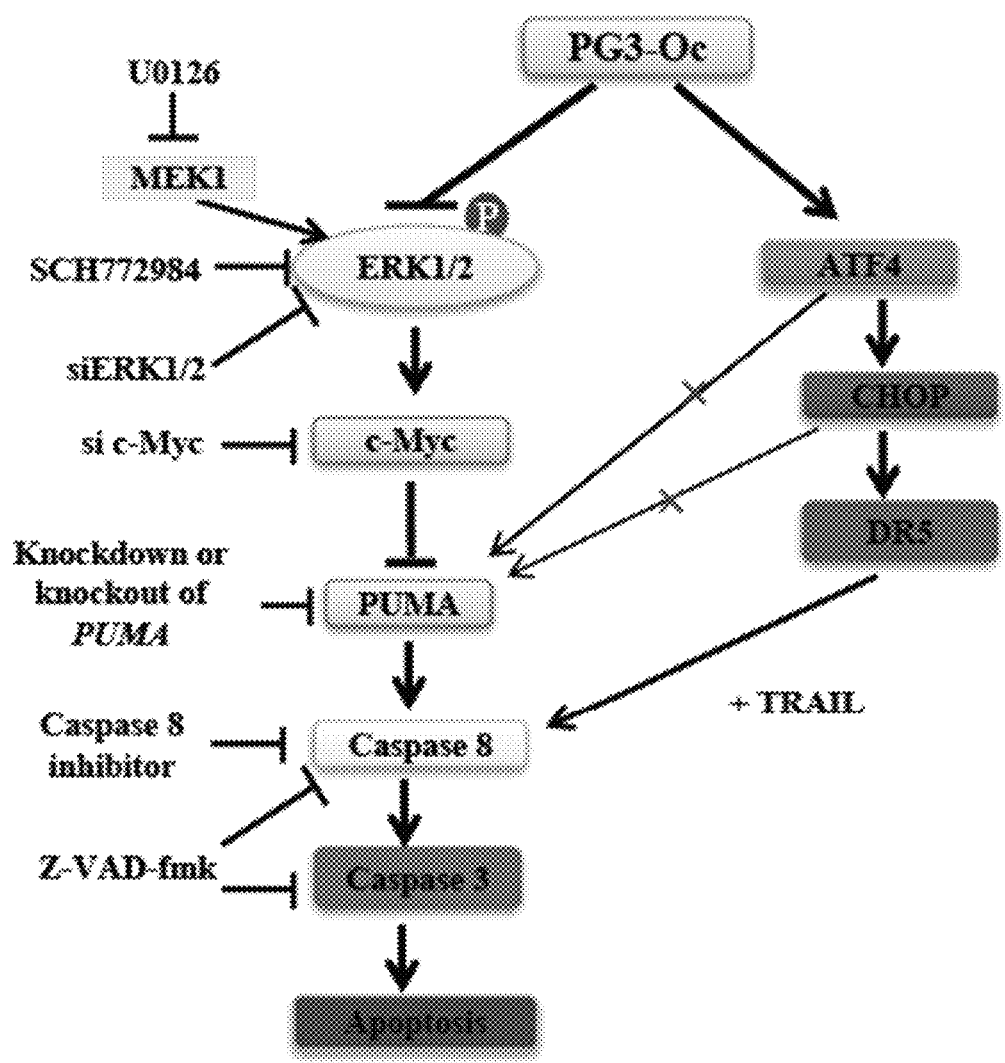
FIG. 83 shows the proposed mechanism of PG3-Oc-induced upregulation of PUMA through ERK1/2/c-Myc/PUMA pathway, and upregulation of DR5 through ATF4/CHOP axis.

In summary, evidence is provided for a novel prodigiosin analog PG3-Oc which has potent anti-tumor activity both in vitro and in vivo in a diverse panel of mutant p53 cancer lines. A model in which inhibition of ERK1/2 by PG3-Oc results in destabilization and degradation c-Myc is proposed, which leads to upregulation of PUMA. PUMA-mediated activation of caspase8 causes cell apoptosis (FIG. 83). PG3-Oc treatment also leads to upregulation of DR5 through the ATF4/CHOP axis, which sensitizes TRAIL-resistant cells to TRAIL treatment (FIG. 83).

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

The claims are not limited to the embodiments described and exemplified above, but is capable of variation and modification within the scope of the appended claims.

What is claimed is:

1. A compound of Formula XIV:

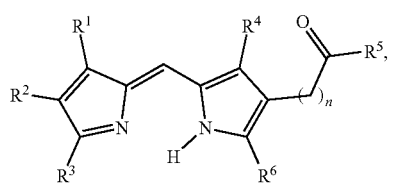

(XIV)

wherein:
$R^1$ and $R^2$ are, independently, selected from the group consisting of H, OH, halogen, $-C_{1-6}$alkyl, $-C_{1-6}$fluoroalkyl, $-CN$, $-NO_2$, $-OR^7$, $-SR^7$, $-S(=O)R^7$, $-S(=O)R^7$, $-NHS(=O)_2 R^7$, $-C(=O)R^7$, $-OC(=O)R^7$, $-CO_2R^7$, $-OCO_2 R^7$, $-CH(R^7)_2$, $-N(R^7)_2$, $-C(=O)N(R^7)_2$, $-NHC(=O)NHR^7$, $-NHC(=O)R^7$, $-NHC(=O)OR^7$, $-C(OH)(R^7)_2$, and $-C(NH_2)(R^7)_2$;

each $R^7$ is, independently, H, halogen, or $C_1$-$C_6$ alkyl, wherein the alkyl group is optionally substituted by 1, 2, 3, 4, or 5 substituents independently selected from halogen, OH, CN, and $NO_2$;

$R^3$ is an optionally substituted aryl or an optionally substituted heteroaryl;

$R^4$, $R^5$, and $R^6$ are, independently, OH, $-C_{1-10}$ alkyl, $-OC_{1-10}$-alkyl, or $-SC_{1-10}$alkyl, wherein each alkyl group is, independently, optionally substituted by 1, 2, 3, 4, or 5 substituents independently selected from halogen, OH, CN, and $NO_2$; and n is an integer from 0 to 5;
or a tautomer or solvate thereof, or a pharmaceutically acceptable salt thereof;
provided that:
if n is 0, then $R^3$ is not an optionally substituted pyrrolyl; and
if n is 2, then the compound is not

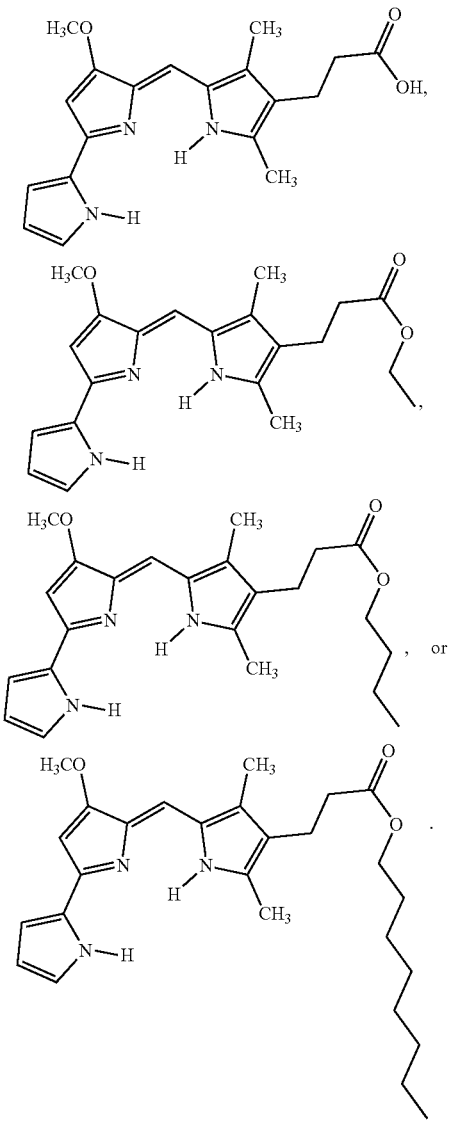

2. The compound according to claim 1, or tautomer or solvate thereof, or pharmaceutically acceptable salt thereof, wherein $R^1$ and $R^2$ are, independently, selected from the group consisting of H, halogen, —$C_{1-6}$ alkyl, —$C_{1-6}$ fluoroalkyl, —$OR^7$, —$SR^7$, —S(=O)$R^7$, —C(=O)$R^7$, —OC(=O)$R^7$, —$CO_2R^7$, —$OCO_2R^7$, —CH($R^7$)$_2$, —C(=O)N($R^7$)$_2$, —C(OH)($R^7$)$_2$, and —C($NH_2$)($R^7$)$_2$.

3. The compound according to claim 1, or tautomer or solvate thereof, or pharmaceutically acceptable salt thereof, wherein each $R^7$ is, independently, H, halogen, or $C_1$-$C_6$ alkyl.

4. The compound according to claim 1, or tautomer or solvate thereof, or pharmaceutically acceptable salt thereof, wherein $R^1$ is —$OCH_3$ and $R^2$ is H.

5. The compound according to claim 1, or tautomer or solvate thereof, or pharmaceutically acceptable salt thereof, wherein $R^3$ is an optionally substituted heteroaryl.

6. The compound according to claim 1, or tautomer or solvate thereof, or pharmaceutically acceptable salt thereof, wherein $R^3$ is an optionally substituted heteroaryl selected from the group consisting of pyridyl, pyrimidinyl, pyrazinyl, pyridazinyl, pyridinyl, triazinyl, furyl, quinolyl, isoquinolyl, thienyl, imidazolyl, thiazolyl, indolyl, pyrryl, oxazolyl, pyrazolyl, isoxazolyl, triazolyl, tetrazolyl, indazolyl, isothiazolyl, purinyl, carbazolyl, isoxazolyl, indolinyl, pyranyl, pyrazolyl, triazolyl, oxadiazolyl, thianthrenyl, indolizinyl, isoindolyl, pyrrolyl, and xanthenyl.

7. The compound according to claim 1, or tautomer or solvate thereof, or pharmaceutically acceptable salt thereof, wherein $R^4$, $R^5$, and $R^6$ are, independently, OH, —$C_{1-6}$ alkyl or —$OC_{1-10}$alkyl, wherein each alkyl group is, independently, optionally substituted by 1, 2, or 3 substituents independently selected from halogen, OH, CN, and $NO_2$.

8. The compound according to claim 1, or tautomer or solvate thereof, or pharmaceutically acceptable salt thereof, wherein n is an integer from 1 to 3.

9. The compound according to claim 1, or tautomer or solvate thereof, or pharmaceutically acceptable salt thereof, wherein:

$R^1$ and $R^2$ are, independently, selected from the group consisting of H, halogen, —$C_{1-6}$alkyl, —$C_{1-6}$ fluoroalkyl, —$OR^7$, —$SR^7$, —S(=O)$R^7$, —C(=O)$R^7$, —OC(=O)$R^7$, —$CO_2R^7$, —$OCO_2R^7$, —CH($R^7$)$_2$, —C(=O)N($R^7$)$_2$, —C(OH)($R^7$)$_2$, and —C($NH_2$)($R^7$)$_2$;

each $R^7$ is, independently, H, halogen, or $C_1$-$C_6$alkyl;

$R^3$ is an optionally substituted heteroaryl;

$R^4$, $R^5$, and $R^6$ are, independently, OH, —$C_{1-6}$alkyl or —$OC_{1-10}$ alkyl, wherein each alkyl group is, independently, optionally substituted by 1, 2, or 3 substituents independently selected from halogen, OH, CN, and $NO_2$; and n is an integer from 1 to 3;

provided that:

if n is 2, then the compound is not

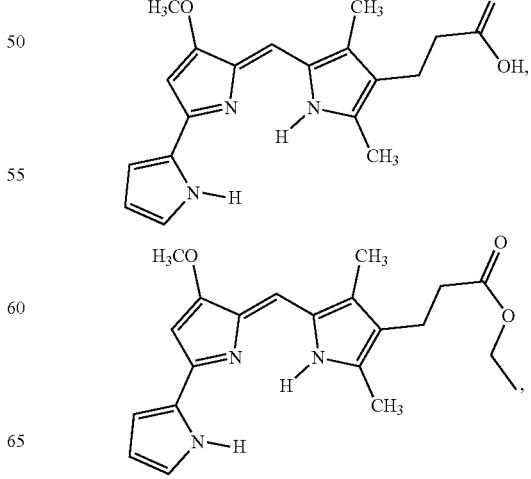

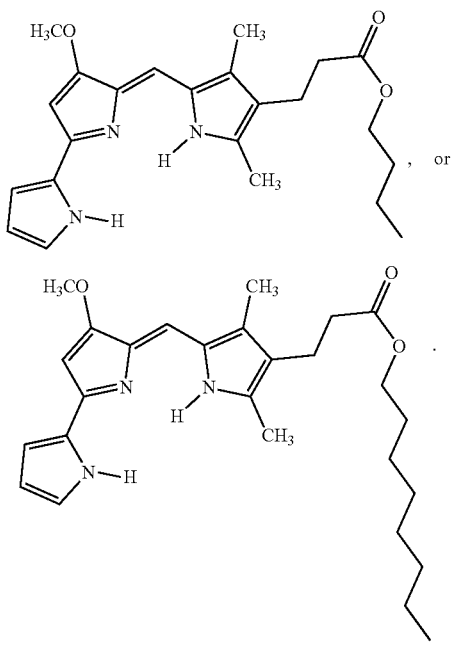

, or .

10. The compound according to claim 1, or tautomer or solvate thereof, or pharmaceutically acceptable salt thereof, wherein:

R$^1$ and R$^2$ are, independently, selected from the group consisting of H, halogen, —C$_{1-6}$alkyl, —OR$^7$, —S(=O)R$^7$, —C(=O)R$^7$, —OC(=O)R$^7$, —CO$_2$R$^7$, —OCO$_2$R$^7$, —CH(R$^7$)$_2$, and —C(OH)(R$^7$)$_2$;

each R$^7$ is, independently, H, halogen, or C$_1$-C$_3$alkyl;

R$^3$ is an optionally substituted heteroaryl selected from the group consisting of pyridyl, pyrimidinyl, pyrazinyl, pyridazinyl, pyridinyl, furyl, thienyl, imidazolyl, thiazolyl, indolyl, pyrryl, oxazolyl, pyrazolyl, isoxazolyl, indazolyl, isothiazolyl, purinyl, carbazolyl, isoxazolyl, indolinyl, pyranyl, pyrazolyl, oxadiazolyl, and pyrrolyl;

R$^4$, R$^5$, and R$^6$ are, independently, OH, —C$_{1-6}$alkyl or —OC$_{1-8}$alkyl, wherein each alkyl group is, independently, optionally substituted by 1 or 2 substituents independently selected from halogen and OH; and n is an integer from 1 to 3;

provided that:

if n is 2, then the compound is not

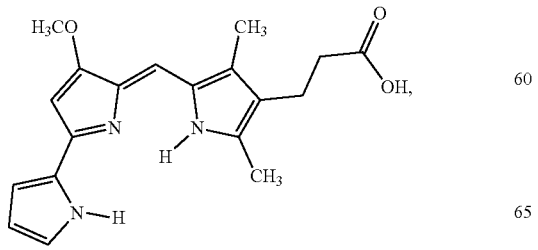

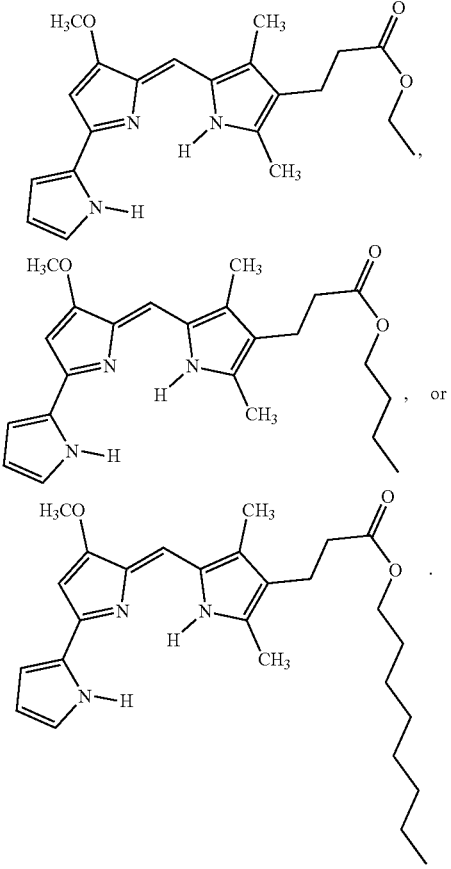

, or .

11. The compound according to claim 1, or tautomer or solvate thereof, or pharmaceutically acceptable salt thereof, wherein:

R$^1$ and R$^2$ are, independently, selected from the group consisting of H, —C$_{1-6}$ alkyl, —OR$^7$, —C(=O)R$^7$, and —OC(=O)R$^7$;

each R$^7$ is, independently, halogen or C$_1$-C$_3$alkyl;

R$^3$ is an optionally substituted heteroaryl selected from the group consisting of pyridyl, pyrimidinyl, pyrazinyl, pyridazinyl, pyridinyl, furyl, thienyl, imidazolyl, indolyl, pyrryl, purinyl, pyranyl, pyrazolyl, oxadiazolyl, and pyrrolyl;

R$^4$ and R$^6$ are, independently, —C$_{1-3}$alkyl, and R$^5$ is OH or —OC$_{1-8}$ alkyl, wherein each alkyl group is, independently, optionally substituted by 1 or 2 halogens; and n is 2 or 3;

provided that:

if n is 2, then the compound is not

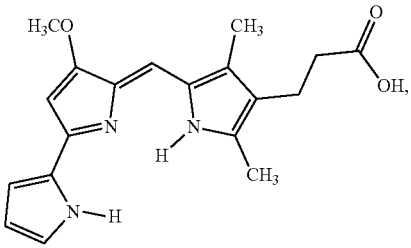

-continued

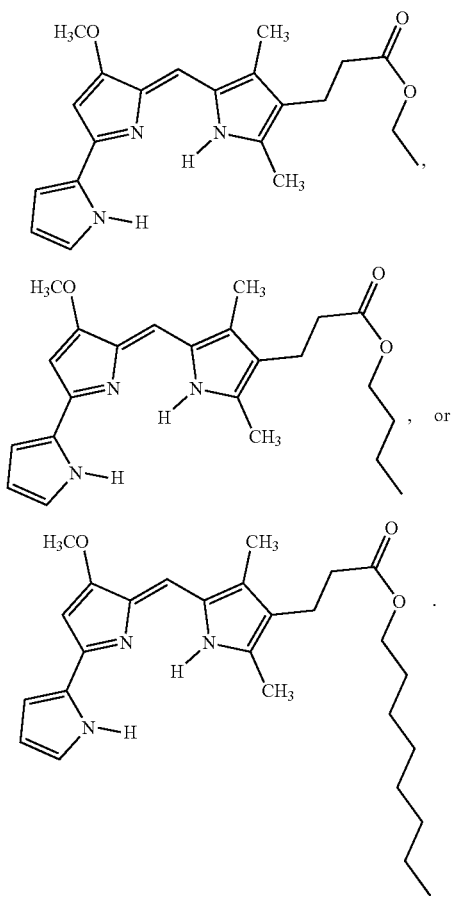

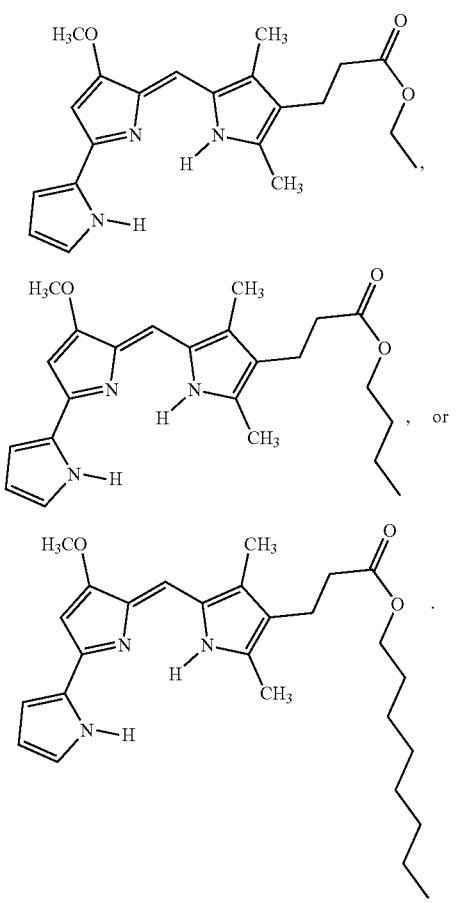

12. The compound according to claim 1, or tautomer or solvate thereof, or pharmaceutically acceptable salt thereof, wherein:

$R^1$ and $R^2$ are, independently, selected from the group consisting of H, —$C_{1-6}$ alkyl, and —$OR^7$;

each $R^7$ is, independently, halogen or $C_1$-$C_3$alkyl;

$R^3$ is an optionally substituted heteroaryl selected from the group conisisting of pyridyl, pyrimidinyl, pyridinyl, imidazolyl, indolyl, pyrryl, purinyl, pyranyl, and pyrrolyl;

$R^4$ and $R^6$ are, independently, —$C_{1-3}$alkyl;

$R^5$ is OH or —$OC_{6-8}$alkyl; and n is 2 or 3;

provided that:

if n is 2, then the compound is not

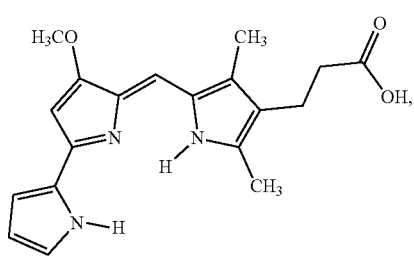

13. The compound according to claim 1, or tautomer or solvate thereof, or pharmaceutically acceptable salt thereof, wherein:

$R^1$ is —$OR^7$, wherein $R^7$ is halogen or $C_1$-$C_3$alkyl;

$R^2$ is H;

$R^3$ is an optionally substituted heteroaryl selected from the group consisting of pyridyl, pyrimidinyl, pyridinyl, pyrryl, and pyrrolyl;

$R^4$ and $R^6$ are, independently, —$C_{1-3}$alkyl;

$R^5$ is —$OC_{6-8}$alkyl; and n is 2;

provided that:

the compound is not

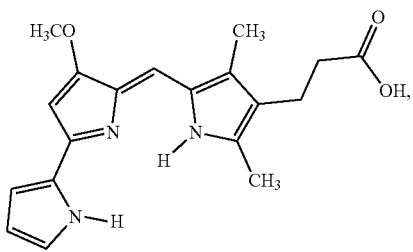

61

-continued

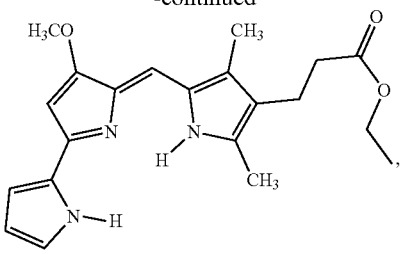

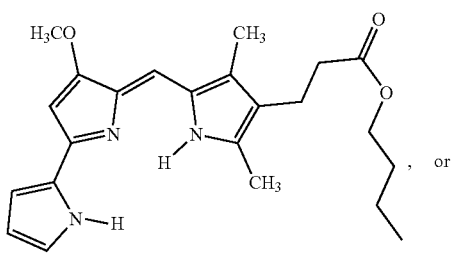
, or

62

-continued

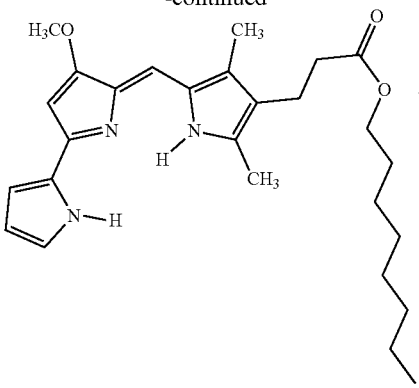
.

14. A pharmaceutical composition comprising the compound according to claim 1, or a tautomer or solvate thereof, or a pharmaceutically acceptable salt thereof, and a pharmaceutically acceptable carrier.

15. The pharmaceutical composition according to claim 14, further comprising an anti-cancer agent.

16. A method of treating cancer in a subject comprising administering to the subject in need thereof the compound, or tautomer or solvate thereof, or pharmaceutically acceptable salt thereof, according to claim 1, wherein the cancer is colorectal cancer, head and neck cancer, pancreatic cancer, breast cancer, colon cancer, lung cancer, or glioblastoma cancer.

17. The method according to claim 16, further comprising administering to the subject another anti-cancer therapy.

18. The method according to claim 17, wherein the another anti-cancer therapy is radiation therapy, chemotherapy, or immunotherapy, or any combination thereof.

* * * * *

SEQUENCE LISTING

```
<160> NUMBER OF SEQ ID NOS: 12

<210> SEQ ID NO 1
<211> LENGTH: 20
<212> TYPE: DNA
<213> ORGANISM: artificial sequence
<220> FEATURE:
<223> OTHER INFORMATION: PUMA primer forward
```

<400> SEQUENCE: 1
gacgacctca acgcacagta                                               20

<210> SEQ ID NO 2
<211> LENGTH: 22
<212> TYPE: DNA
<213> ORGANISM: artificial sequence
<220> FEATURE:
<223> OTHER INFORMATION: PUMA primer reverse

<400> SEQUENCE: 2
aggagtccca tgatgagatt gt                                            22

<210> SEQ ID NO 3
<211> LENGTH: 21
<212> TYPE: DNA
<213> ORGANISM: artificial sequence
<220> FEATURE:
<223> OTHER INFORMATION: DR5 primer forward

<400> SEQUENCE: 3
acagttgcag ccgtagtctt g                                             21

<210> SEQ ID NO 4
<211> LENGTH: 20
<212> TYPE: DNA
<213> ORGANISM: artificial sequence
<220> FEATURE:
<223> OTHER INFORMATION: DR5 primer reverse

<400> SEQUENCE: 4
ccaggtcgtt gtgagcttct                                               20

<210> SEQ ID NO 5
<211> LENGTH: 24
<212> TYPE: DNA
<213> ORGANISM: artificial sequence
<220> FEATURE:
<223> OTHER INFORMATION: GAPDH primer forward

<400> SEQUENCE: 5
tcgacagtca gccgcatctt cttt                                          24

<210> SEQ ID NO 6
<211> LENGTH: 24
<212> TYPE: DNA
<213> ORGANISM: artificial sequence
<220> FEATURE:
<223> OTHER INFORMATION: GAPDH primer reverse

<400> SEQUENCE: 6
accaaatccg ttgactccga cctt                                          24

<210> SEQ ID NO 7
<211> LENGTH: 24
<212> TYPE: DNA
<213> ORGANISM: artificial sequence
<220> FEATURE:
<223> OTHER INFORMATION: Guide1 DNA forward

<400> SEQUENCE: 7
caccggcggg cggtcccacc cagg                                          24

<210> SEQ ID NO 8

```
<211> LENGTH: 24
<212> TYPE: DNA
<213> ORGANISM: artificial sequence
<220> FEATURE:
<223> OTHER INFORMATION: Guide1 DNA reverse

<400> SEQUENCE: 8
aaaccctggg tgggaccgcc cgcc                                              24

<210> SEQ ID NO 9
<211> LENGTH: 24
<212> TYPE: DNA
<213> ORGANISM: artificial sequence
<220> FEATURE:
<223> OTHER INFORMATION: Guide 2 DNA forward

<400> SEQUENCE: 9
caccgccgct cgtactgtgc gttg                                              24

<210> SEQ ID NO 10
<211> LENGTH: 24
<212> TYPE: DNA
<213> ORGANISM: artificial sequence
<220> FEATURE:
<223> OTHER INFORMATION: Guide 2 DNA reverse

<400> SEQUENCE: 10
aaaccaacgc acagtacgag cggc                                              24

<210> SEQ ID NO 11
<211> LENGTH: 20
<212> TYPE: DNA
<213> ORGANISM: artificial sequence
<220> FEATURE:
<223> OTHER INFORMATION: PUMA primer forward

<400> SEQUENCE: 11
cacagtctct ggccttctgg                                                   20

<210> SEQ ID NO 12
<211> LENGTH: 17
<212> TYPE: DNA
<213> ORGANISM: artificial sequence
<220> FEATURE:
<223> OTHER INFORMATION: PUMA primer reverse

<400> SEQUENCE: 12
agctgccgca catctgg                                                      17
```